United States Patent
Sikes Johnson et al.

(10) Patent No.: US 12,287,336 B2
(45) Date of Patent: Apr. 29, 2025

(54) PROTEIN FOR RAPID, EFFICIENT CAPTURE OF ANTIGENS

(71) Applicant: Massachusetts Institute of Technology, Cambridge, MA (US)

(72) Inventors: Hadley Sikes Johnson, Arlington, MA (US); Eric Alexander Miller, Somerville, MA (US); Ki-Joo Sung, Minneapolis, MN (US)

(73) Assignee: Massachusetts Institute of Technology, Cambridge, MA (US)

( * ) Notice: Subject to any disclaimer, the term of this patent is extended or adjusted under 35 U.S.C. 154(b) by 6 days.

(21) Appl. No.: 18/330,411

(22) Filed: Jun. 7, 2023

(65) Prior Publication Data
US 2023/0305002 A1  Sep. 28, 2023

Related U.S. Application Data

(62) Division of application No. 16/158,506, filed on Oct. 12, 2018, now Pat. No. 11,740,236.

(60) Provisional application No. 62/572,392, filed on Oct. 13, 2017.

(51) Int. Cl.
| | | |
|---|---|---|
| G01N 33/566 | (2006.01) |
| C07K 14/195 | (2006.01) |
| C07K 14/33 | (2006.01) |
| C07K 16/06 | (2006.01) |
| C07K 16/28 | (2006.01) |
| G01N 33/569 | (2006.01) |

(52) U.S. Cl.
CPC ........ G01N 33/566 (2013.01); C07K 14/195 (2013.01); C07K 14/33 (2013.01); C07K 16/065 (2013.01); C07K 16/28 (2013.01); G01N 33/56911 (2013.01); C07K 2319/20 (2013.01); C07K 2319/24 (2013.01); C07K 2319/60 (2013.01); G01N 2400/26 (2013.01)

(58) Field of Classification Search
CPC ........ G01N 2400/26; G01N 33/56911; G01N 33/566; C07K 14/33; C07K 14/195; C07K 2319/20
See application file for complete search history.

(56) References Cited

U.S. PATENT DOCUMENTS

| | | | |
|---|---|---|---|
| 5,856,201 A | 1/1999 | Shoseyov et al. | |
| 2005/0118729 A1* | 6/2005 | Morag | G01N 33/6842 436/518 |
| 2017/0252417 A1 | 9/2017 | Irvine et al. | |
| 2023/0305002 A1* | 9/2023 | Sikes Johnson | C07K 14/33 |

OTHER PUBLICATIONS

Traxlmayr et al. "Strong Enrichment of Aromatic Residues in Binding Sites from a Charge-neutralized Hyperthermostable Sso7d Scaffold Library", published online Aug. 30, 2016, Journal of Biological Chemistry, vol. 291(43), p. 22496-22508. (Year: 2016).*

(Continued)

Primary Examiner — Gary B Nickol
Assistant Examiner — Amelia Nicole Dickens
(74) Attorney, Agent, or Firm — Wolf, Greenfield & Sacks, P.C.

(57) ABSTRACT

The present disclosure relates to proteins comprising a target-binding domain for detection of a target of interest, methods, compositions and kits thereof.

18 Claims, 108 Drawing Sheets

Specification includes a Sequence Listing.

(56) References Cited

OTHER PUBLICATIONS

Zhang et al. "Phage display selection of tight specific binding variants from a hyperthermostable Sso7d scaffold protein library", Feb. 2, 2016, The FEBS Journal, vol. 283, Issue 7, pp. 1351-1367. (Year: 2016).*
"Alexa Fluor 647 NHS Ester", accessed Aug. 2, 2024, PubChem, National Library of Medicine, 8 pgs. (Year: 2024).*
Hirabayashi et al. "Effect of amino acid substitution by sited-directed mutagenesis on the carbohydrate recognition and stability of human 14-kDa beta-galactoside-binding lectin", Dec. 15, 1991, Journal of Biological Chemistry, vol. 266 Issue 35, pp. 23648-23653 (Year: 1991).*
Miller et al. "Activity-based assessment of an engineered hyperthermophilic protein as a capture agent in paper-based diagnostic tests" Jun. 29, 2016, Molecular Systems Design & Engineering, vol. 1 No. 4, p. 377-381. (Year: 2016).*
International Search Report and Written Opinion for PCT/US2018/055582, mailed on Mar. 14, 2019.
International Preliminary Report on Patentability for PCT/US2018/055582, mailed on Apr. 23, 2020.
Invitation to Pay Additional Fees for PCT/US2018/055582 mailed Jan. 15, 2019.
Hirabayashi et al., Effect of amino acid substitution by sited-directed mutagenesis on the carbohydrate recognition and stability of human 14-kDa beta-galactoside-binding lectin. J Biol Chem. Dec. 15, 1991;266(35):23648-53.
Miller et al., Activity-based assessment of an engineered hyperthermophilic protein as a capture agent in paper-based diagnostic tests. Mol Syst Des Eng. Dec. 1, 2016;1(4):377-381. doi: 10.1039/C6ME00032K. Epub Jun. 29, 2016. PMID: 28451464; PMCID: PMC5403157.
Miller et al., Paper-based diagnostics in the antigen-depletion regime: High-density immobilization of rcSso7d-cellulose-binding domain fusion proteins for efficient target capture. Biosens Bioelectron. Apr. 15, 2018;102:456-463. doi: 10.1016/j.bios.2017.11.050. Epub Nov. 20, 2017. PMID: 29182928; PMCID: PMC5983361.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. doi: 10.1074/jbc.M116.741314. Epub Aug. 30, 2016. PMID: 27582495.
Ackerman et al., Highly avid magnetic bead capture: an efficient selection method for de novo protein engineering utilizing yeast surface display. Biotechnol Prog. May-Jun. 2009;25(3):774-83.
Almeida et al., A biomolecular recognition approach for the functionalization of cellulose with gold nanoparticles. J Mol Recognit. Sep. 2017;30(9). doi: 10.1002/jmr.2634. Epub Apr. 17, 2017.
Care et al., Solid-binding peptides for immobilisation of thermostable enzymes to hydrolyse biomass polysaccharides. Biotechnol Biofuels. Feb. 2, 2017;10:29.
Dai et al., A colorimetric paper sensor for lactate assay using a cellulose-binding recombinant enzyme. Sensors Act B Chem. 2017;238:138-144.
Holstein et al., Immobilizing affinity proteins to nitrocellulose: a toolbox for paper-based assay developers. Anal Bioanal Chem. Feb. 2016;408(5):1335-46. doi: 10.1007/s00216-015-9052-0. Epub Oct. 1, 2015.
Hussack et al., Multivalent anchoring and oriented display of single-domain antibodies on cellulose. Sensors (Basel). 2009;9(7):5351-67. doi: 10.3390/s90705351. Epub Jul. 7, 2009.
Hyre et al., Cooperative hydrogen bond interactions in the streptavidin-biotin system. Protein Sci. Mar. 2006; 15(3):459-67. doi: 10.1110/ps.051970306. Epub Feb. 1, 2006.
Kelley et al., Advancing the speed, sensitivity and accuracy of biomolecular detection using multi-length-scale engineering. Nat Nanotechnol. Dec. 2014;9(12):969-80.
Kosugi et al., Hydrophilic domains of scaffolding protein CbpA promote glycosyl hydrolase activity and localization of cellulosomes to the cell surface of Clostridium cellulovorans. J Bacteriol. Oct. 2004;186(19):6351-9.
Kozak, Initiation of translation in prokaryotes and eukaryotes. Gene. Jul. 8, 1999;234(2):187-208.
McBee, The characteristics of Clostridium thermocellum. J Bacteriol. Apr. 1954;67(4):505-6.
Miller et al., Activity-based assessment of an engineered hyperthermophilic protein as a capture agent in paper-based diagnostic tests. Mol Syst Des Eng. Dec. 1, 2016;1(4):377-381. doi: 10.1039/C6ME00032K. Epub Jun. 29, 2016.
Napolitano et al., Identification of Mycobacterium tuberculosis ornithine carboamyltransferase in urine as a possible molecular marker of active pulmonary tuberculosis. Clin Vaccine Immunol. Apr. 2008;15(4):638-43. doi: 10.1128/CVI.00010-08. Epub Feb. 27, 2008.
Ricci et al., Using Nature's "Tricks" To Rationally Tune the Binding Properties of Biomolecular Receptors. Acc Chem Res. Sep. 20, 2016;49(9):1884-92. doi: 10.1021/acs.accounts.6b00276. Epub Aug. 26, 2016.
Ryu et al., Translation initiation mediated by nuclear cap-binding protein complex. BMB Rep. Apr. 2017;50(4):186-193.
Sabathe et al., Characterization of the CipA scaffolding protein and in vivo production of a minicellulosome in Clostridium acetobutylicum. J Bacteriol. Feb. 2003;185(3):1092-6.
Seker et al., Material binding peptides for nanotechnology. Molecules. Feb. 9, 2011;16(2):1426-51.
Shen et al., Site-selective orientated immobilization of antibodies and conjugates for immunodiagnostics development. Methods. Mar. 1, 2017;116:95-111. doi: 10.1016/j.ymeth.2016.11.010. Epub Nov. 19, 2016.
Yaniv et al., Structure of a family 3a carbohydrate-binding module from the cellulosomal scaffoldin CipA of Clostridium thermocellum with flanking linkers: implications for cellulosome structure. Acta Crystallogr Sect F Struct Biol Cryst Commun. Jul. 2013;69(Pt 7):733-7. doi: 10.1107/S174430911301614X. Epub Jun. 27, 2013.
Yu et al., Biofunctional paper via the covalent modification of cellulose. Langmuir. Jul. 31, 2012;28(30):11265-73. doi: 10.1021/la301661x. Epub Jul. 20, 2012.
Zhao et al., Hyperthermostable binding molecules on phage: Assay components for point-of-care diagnostics for active tuberculosis infection. Anal Biochem. Mar. 15, 2017;521:59-71.
Zhu et al., Cellulose paper sensors modified with zwitterionic poly(carboxybetaine) for sensing and detection in complex media. Anal Chem. Mar. 18, 2014;86(6):2871-5. doi: 10.1021/ac500467c. Epub Mar. 5, 2014.

* cited by examiner rcSso7d.NS1.1
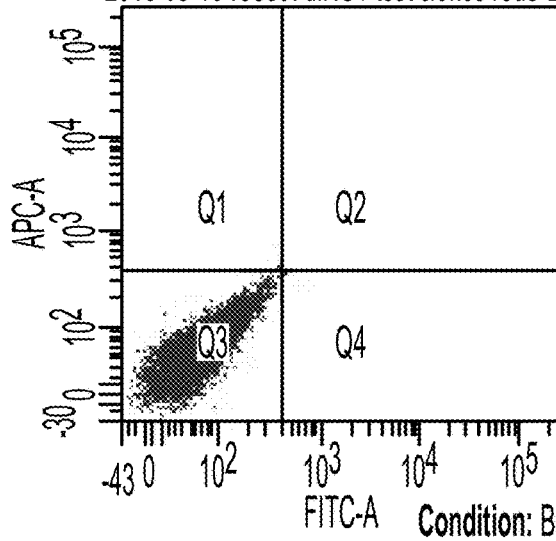
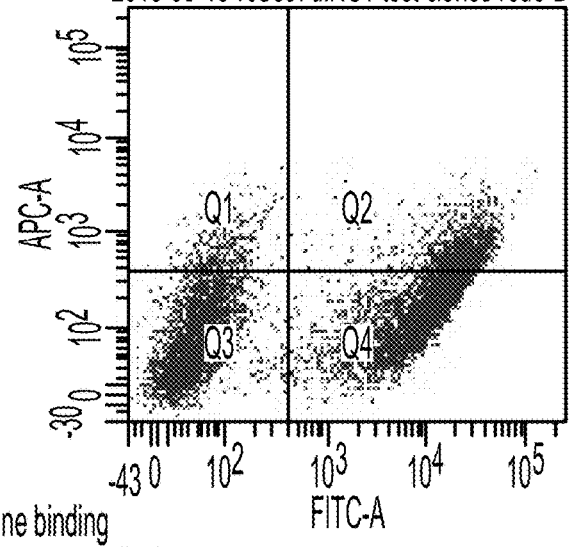
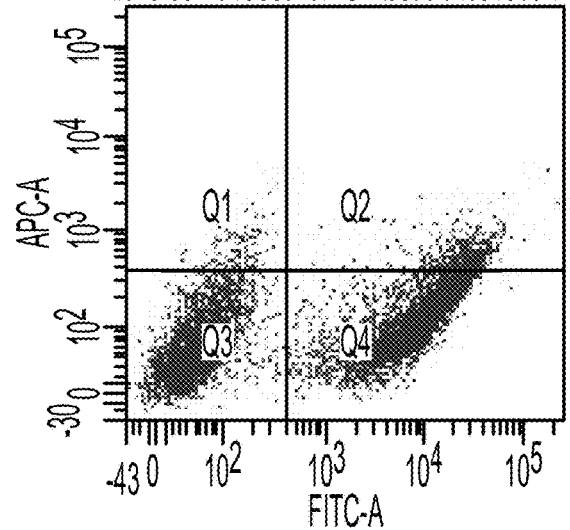
FIG. 20 rcSso7d.NS1.2
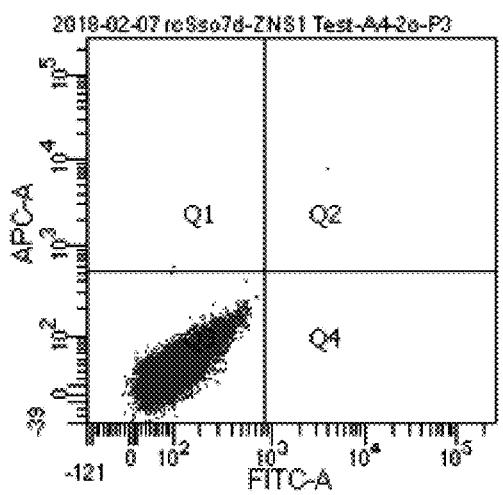
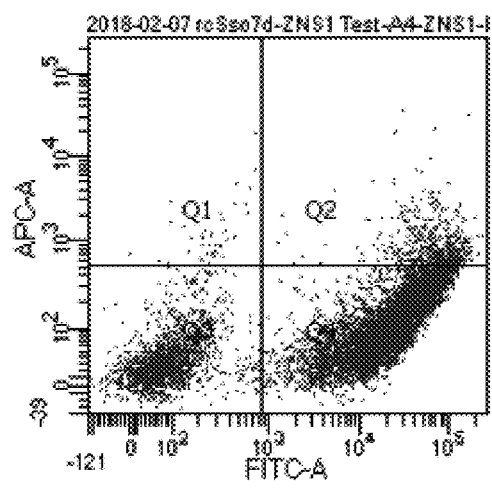
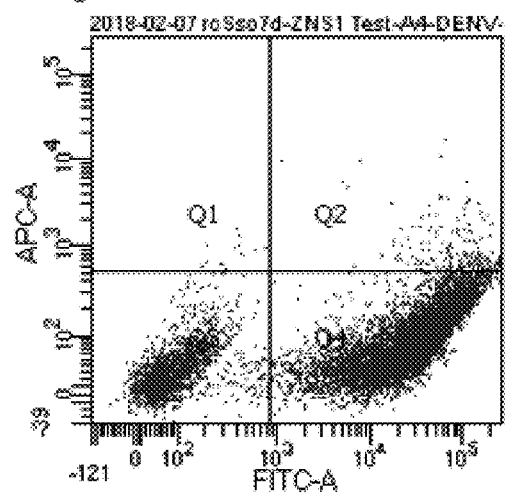
FIG. 21 rcSso7d.NS1.3
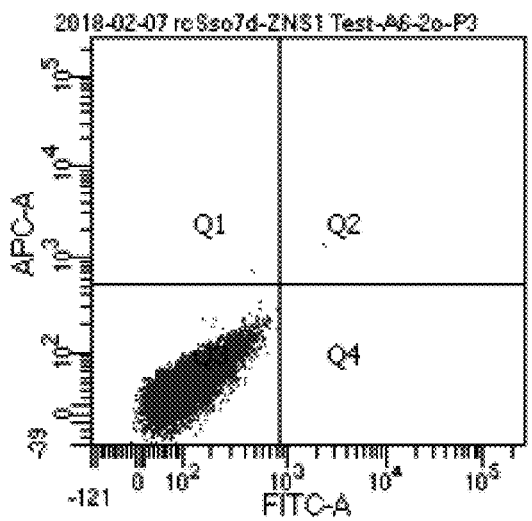
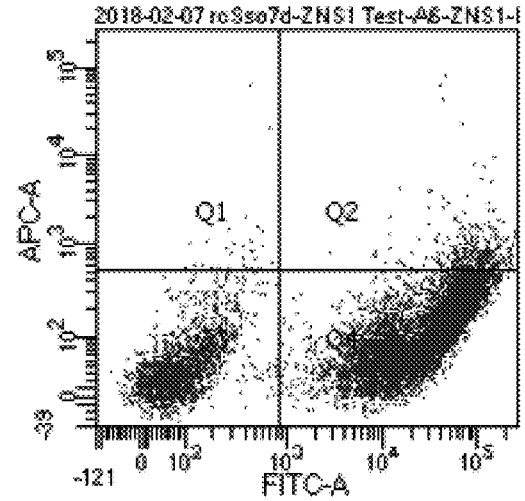
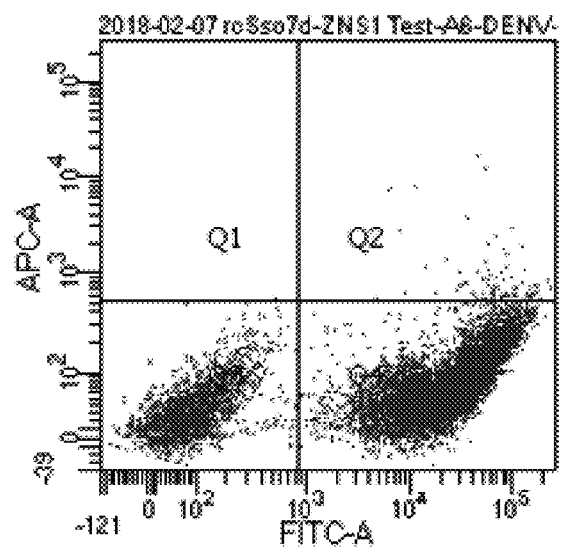
FIG. 22 rcSso7d.NS1.5

Condition: Secondary control
Antigen (Ag): N/A
Ag pre-treatment: N/A
Detection reagent: Mouse anti-His/ goat anti-mouse AF647

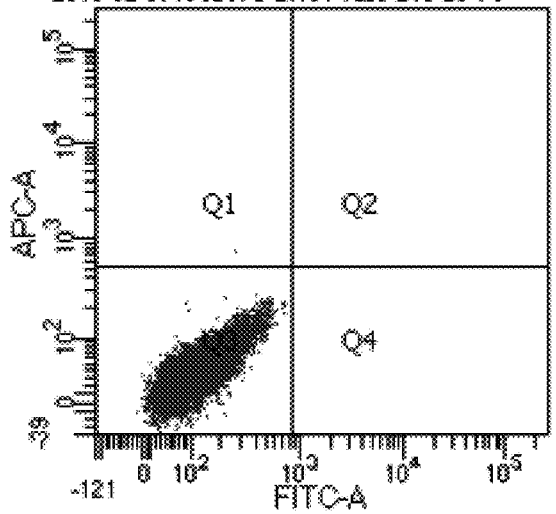

Condition: Baseline binding
Antigen (Ag): 200 nM ZIKV NS1
Ag pre-treatment: 0.1% BSA, 4°C
Detection reagent: Mouse anti-His/ goat anti-mouse AF647

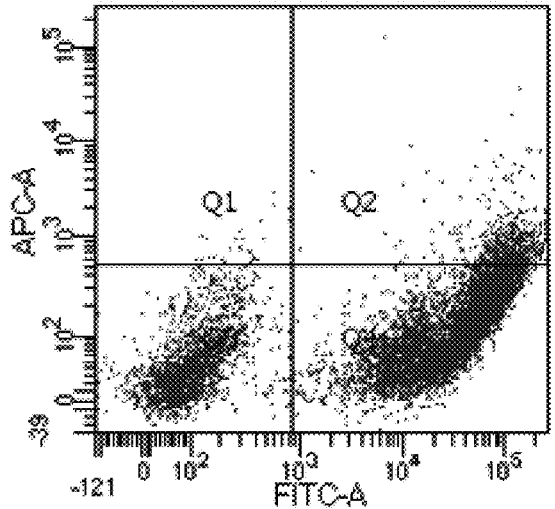

Condition: Condition: Baseline binding
Antigen (Ag): 200 nM DENV2 NS1
Ag pre-treatment: 0.1% BSA, 4°C
Detection reagent: Mouse anti-His/ goat anti-mouse AF647

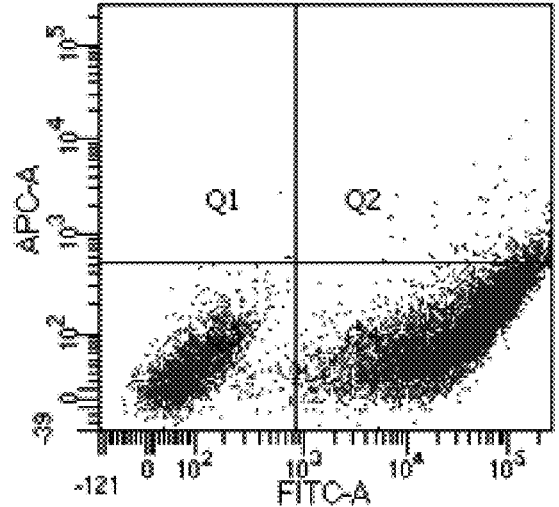

FIG. 24 rcSso7d.NS1.6
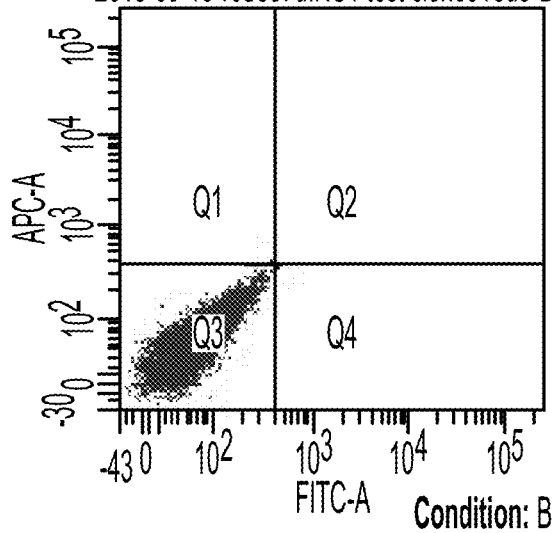
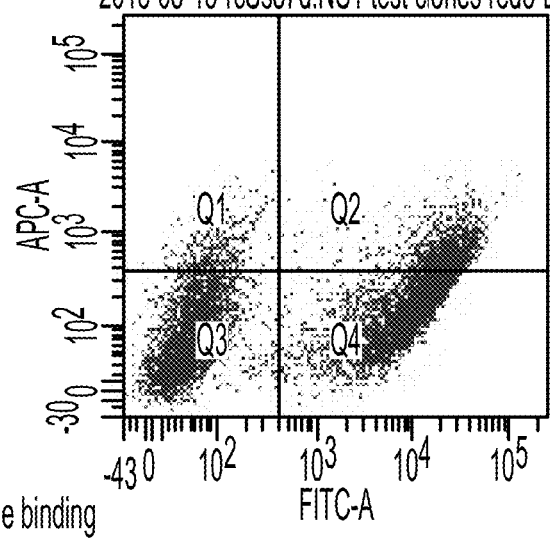
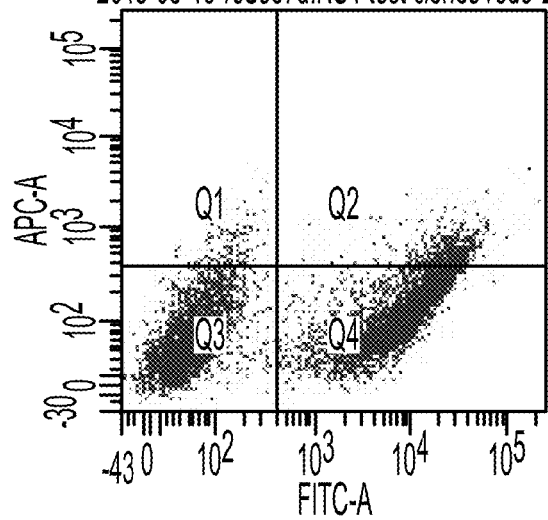
FIG. 25 rcSso7d.IL6.2
Condition: Three-component negative control (antigen absent)
Antigen (Ag): N/A
Ag pre-treatment: N/A
Detection reagent: Mouse anti-His/ goat anti-mouse AF647
Condition: Baseline binding
Antigen (Ag): 0.25 nM human IL-6
Ag pre-treatment: 0.1% BSA, 4°C
Detection reagent: Mouse anti-His/ goat anti-mouse AF647
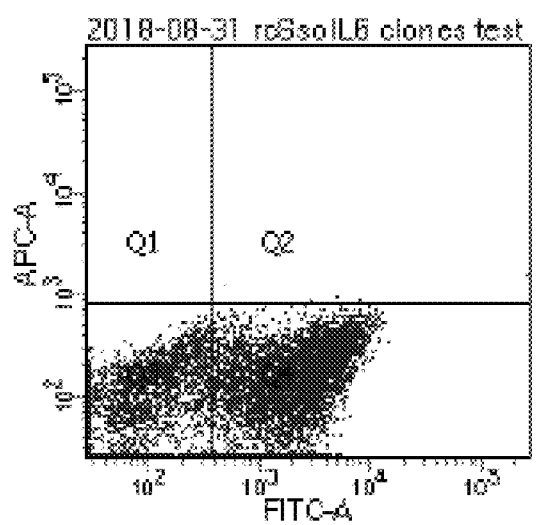
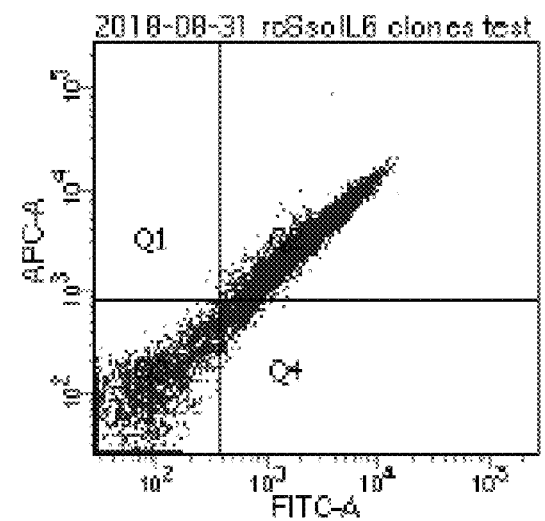
FIG. 27 rcSso7d.IL6.6
Condition: Three-component negative
control (antigen absent)
Antigen (Ag): N/A
Ag pre-treatment: N/A
Detection reagent: Mouse anti-His/
goat anti-mouse AF647
Condition: Baseline binding
Antigen (Ag): 0.25 nM human IL-6
Ag pre-treatment: 0.1% BSA, 4°C
Detection reagent: Mouse anti-His/
goat anti-mouse AF647
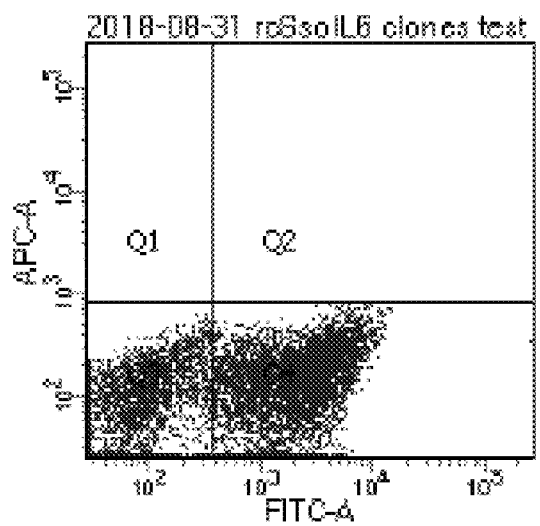
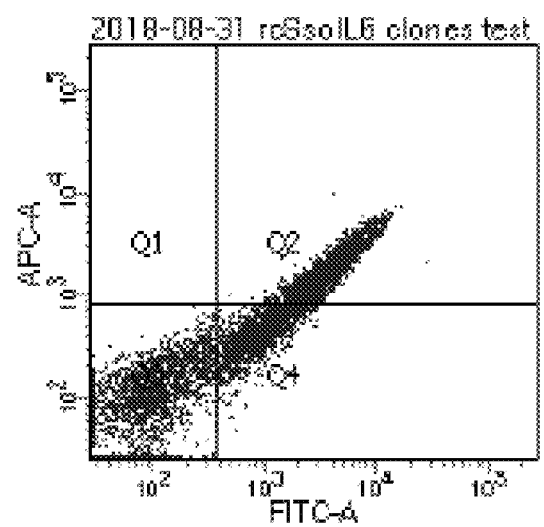
FIG. 31

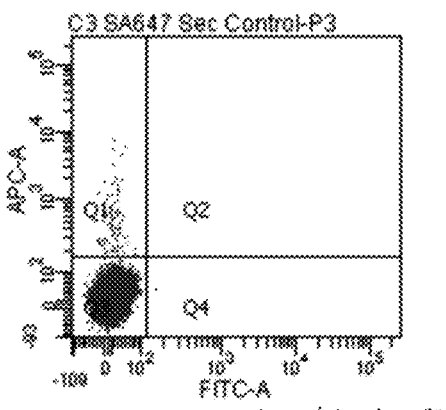
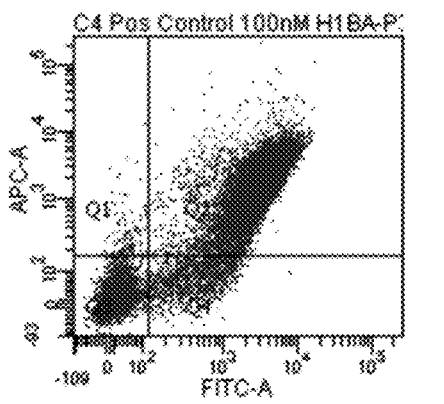
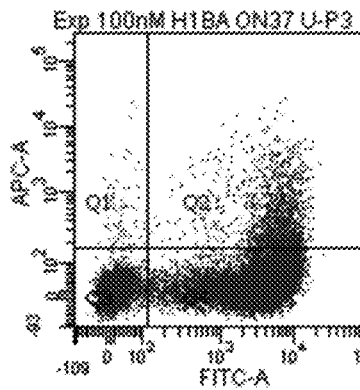
FIG. 40A

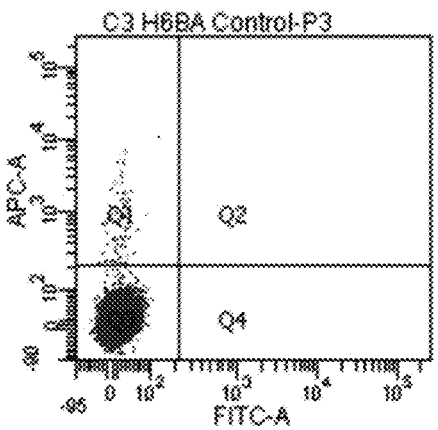
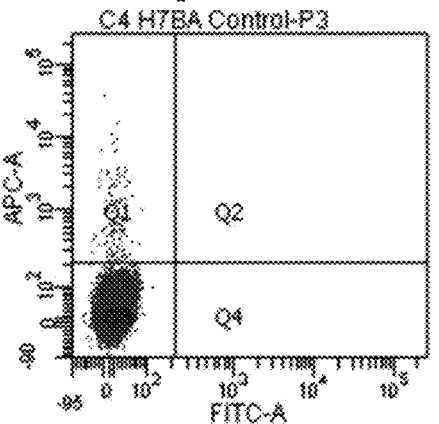
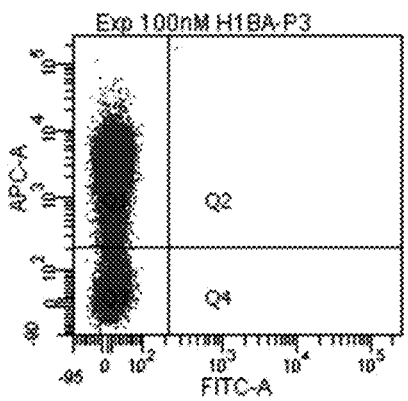
FIG. 40C rcSso7d.H1BA.4
Condition: Secondary control
Antigen (Ag): N/A
Ag pre-treatment: 0.1% BSA, 4°C
Pre-treatment time: N/A
Detection reagent: SA AF647
Condition: Baseline binding
Antigen (Ag): 100 nM H1bx
Ag pre-treatment: 0.1% BSA, 4°C
Pre-treatment time: N/A
Detection reagent: SA AF647
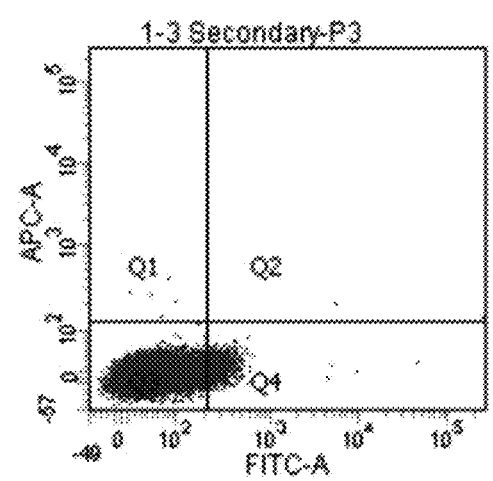
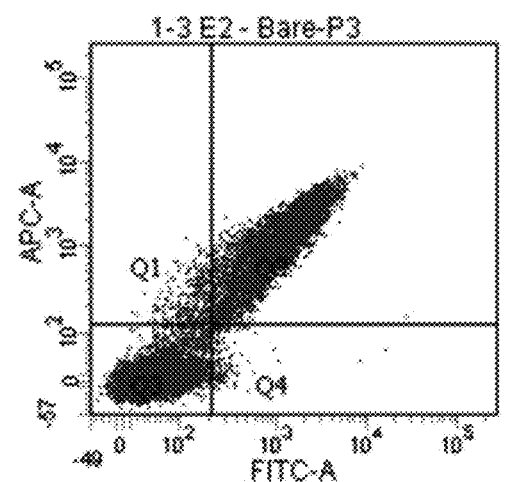
FIG. 41 rcSso7d.H1BA.5
Condition: Secondary control
Antigen (Ag): N/A
Ag pre-treatment: 0.1% BSA, 4°C
Pre-treatment time: N/A
Detection reagent: SA AF647
Condition: Baseline binding
Antigen (Ag): 100 nM H1BA
Ag pre-treatment: 0.1% BSA, 4°C
Pre-treatment time: N/A
Detection reagent: SA AF647
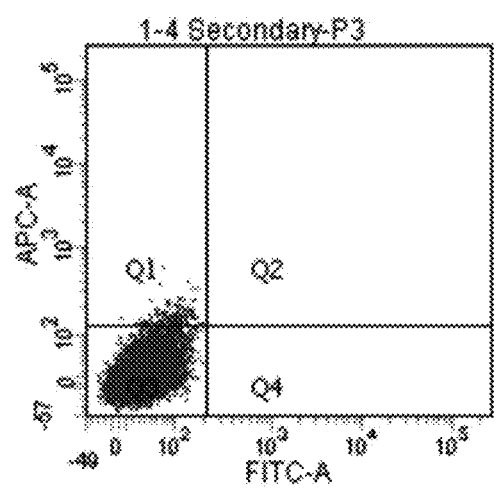
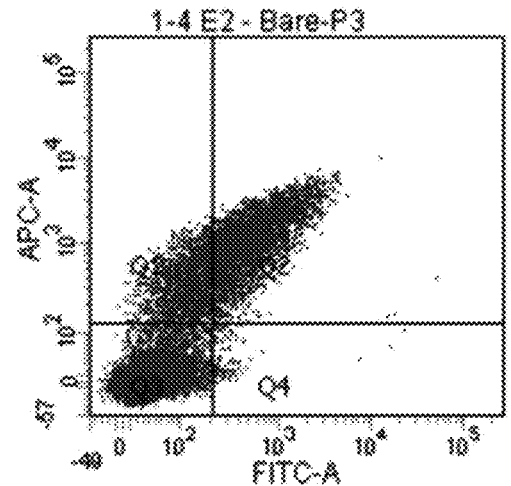
FIG. 42

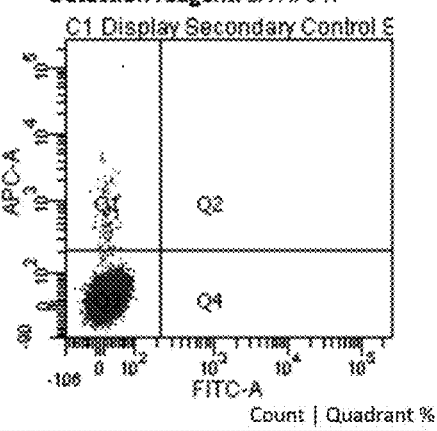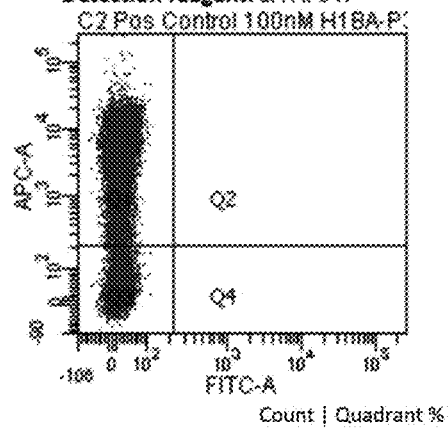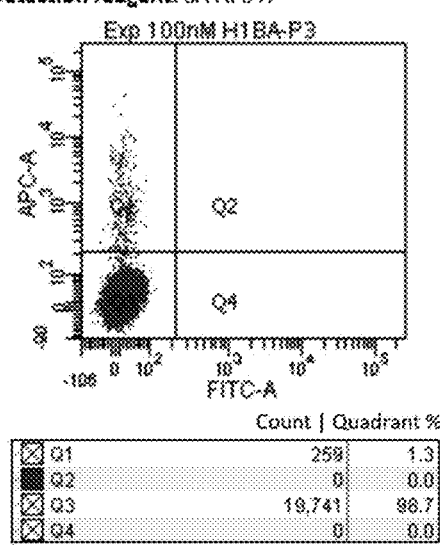
FIG. 43 rcSso7d.H2BA.1
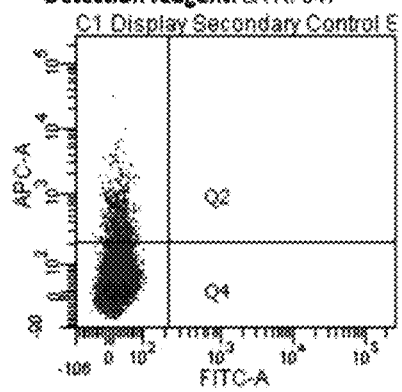
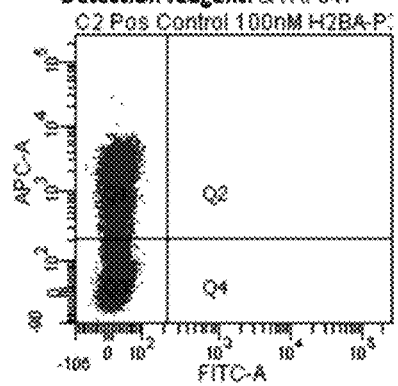
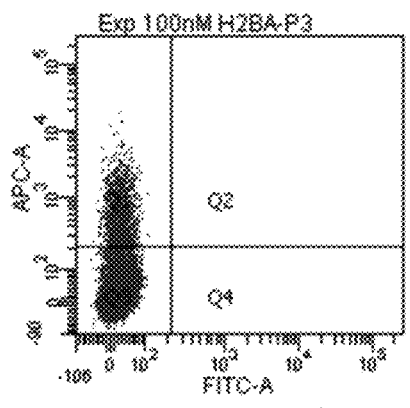
FIG. 45 rcSso7d.H4.1

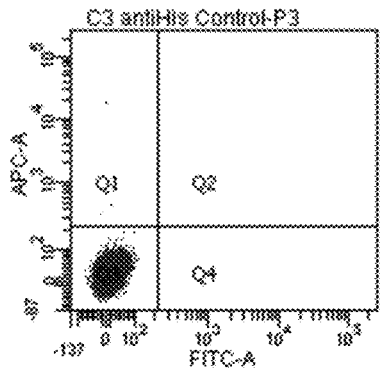

Condition: Secondary control
Antigen (Ag): N/A
Ag pre-treatment: N/A
Pre-treatment time: N/A
Detection reagent: Mouse anti-His/ goat anti-mouse AF647

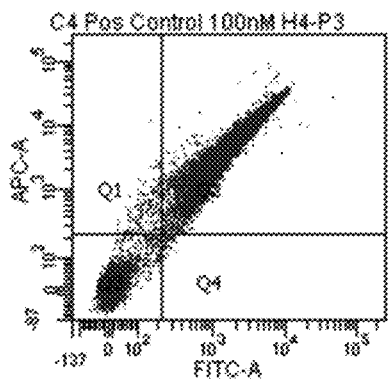

Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647

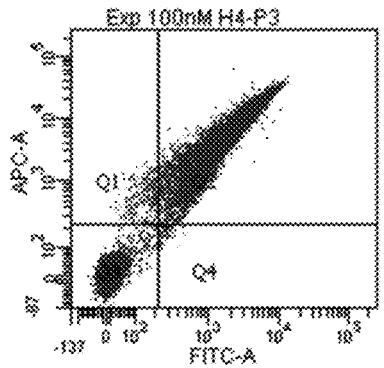

Condition: Condition: Overnight heat/ urine inactivation
Antigen (Ag): 100 nM H4
Ag pre-treatment: Urine, 37°C
Pre-treatment time: Overnight
Detection reagent: Mouse anti-His/ goat anti-mouse AF647

FIG. 47 rcSso7d.H4.2

Condition: Secondary control
Antigen (Ag): N/A
Ag pre-treatment: N/A
Pre-treatment time: N/A
Detection reagent: Mouse anti-His/ goat anti-mouse AF647

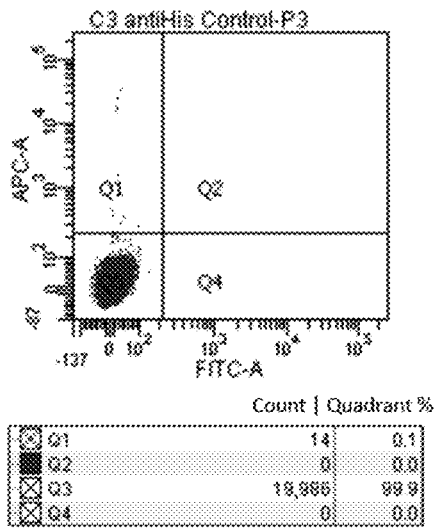

Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647

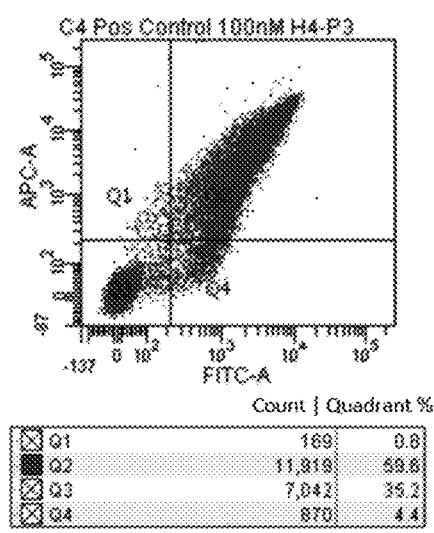

Condition: Overnight heat/ urine inactivation
Antigen (Ag): 100 nM H4
Ag pre-treatment: Urine, 37°C
Pre-treatment time: Overnight
Detection reagent: Mouse anti-His/ goat anti-mouse AF647

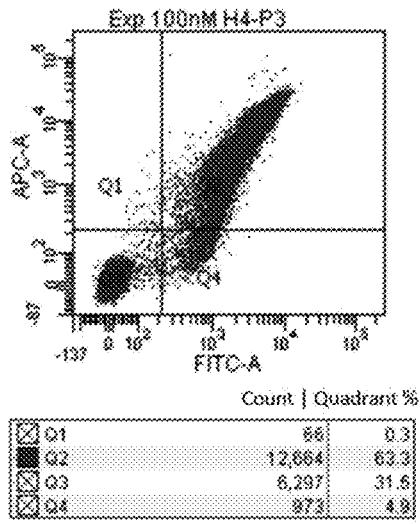

FIG. 48 rcSso7d.H4.3
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
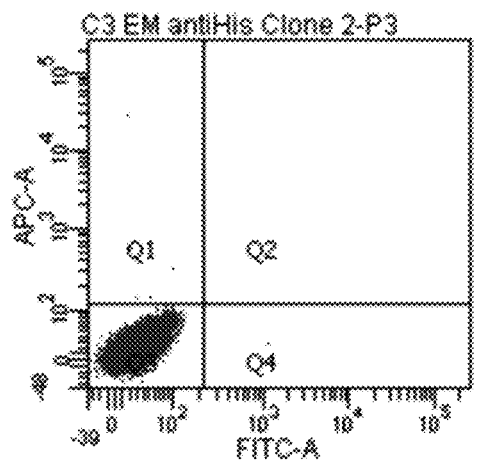
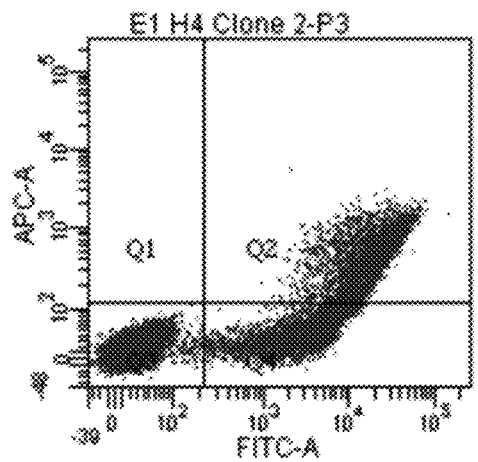
FIG. 49 rcSso7d.H4.4
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
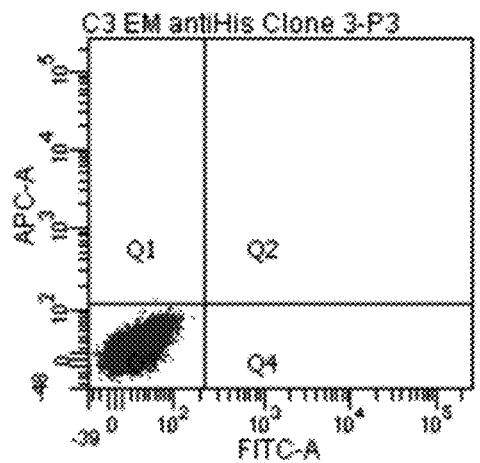
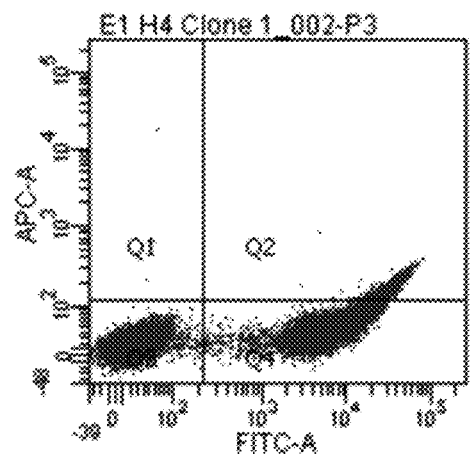
FIG. 50 rcSso7d.H4.5
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
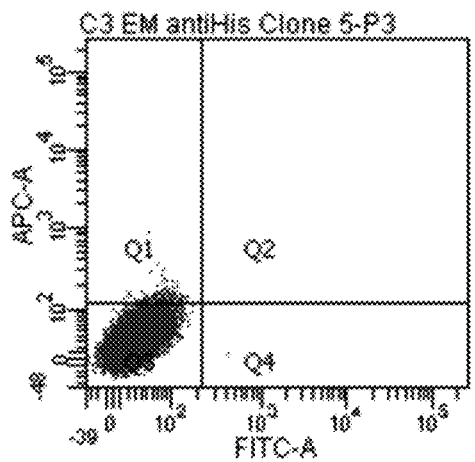
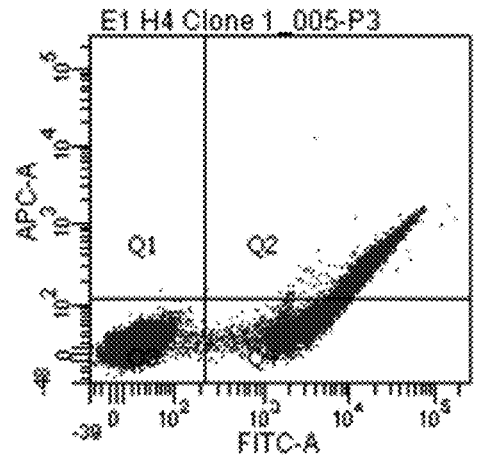
FIG. 51 rcSso7d.H4.6
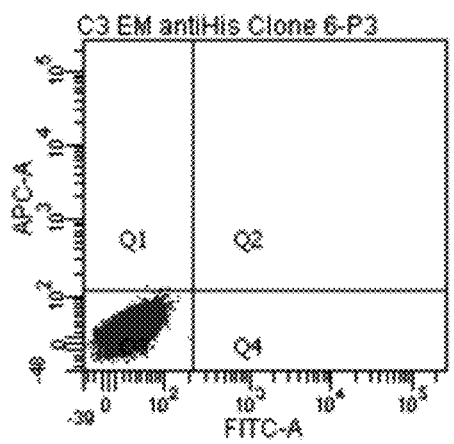
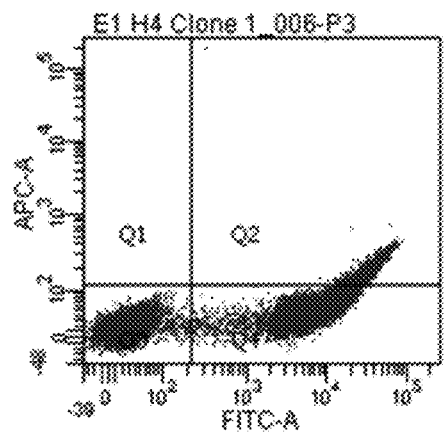
FIG. 52 rcSso7d.H4.7
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
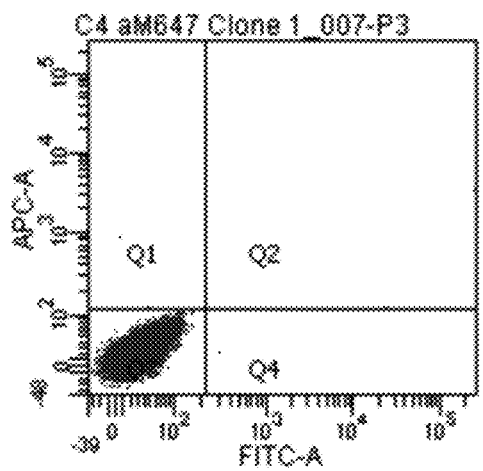
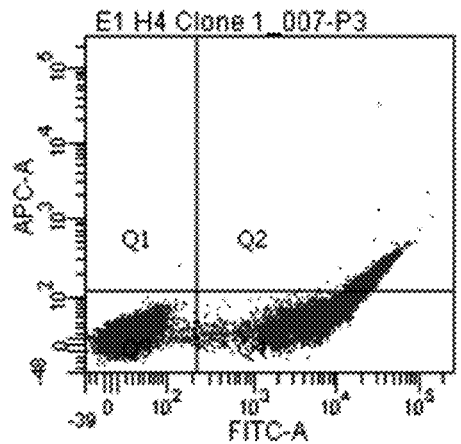
FIG. 53 rcSso7d.H4.8
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
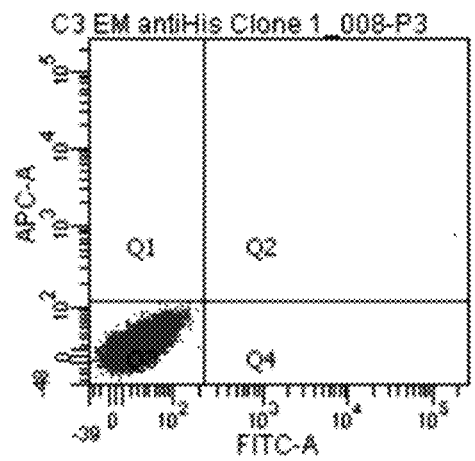
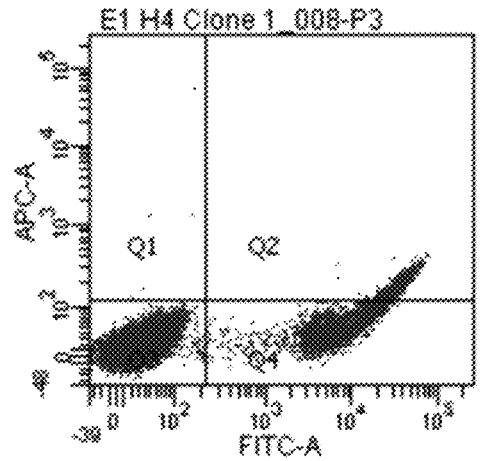
| | Count | Quadrant % |
|---|---|---|
| Q1 | 0 | 0.0 |
| Q2 | 1 | 0.0 |
| Q3 | 19,999 | 100.0 |
| Q4 | 0 | 0.0 |
| | Count | Quadrant % |
|---|---|---|
| Q1 | 5 | 0.0 |
| Q2 | 706 | 3.5 |
| Q3 | 16,891 | 84.5 |
| Q4 | 2,398 | 12.0 |
FIG. 54 rcSso7d.H4.9
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
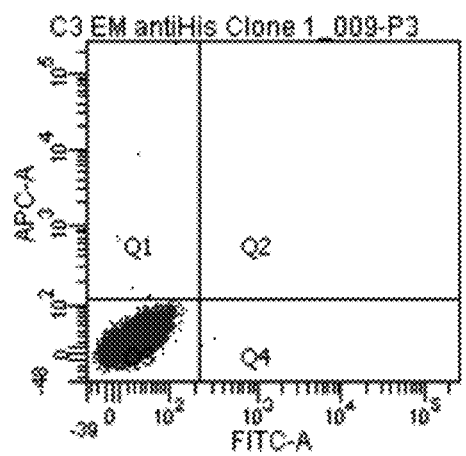
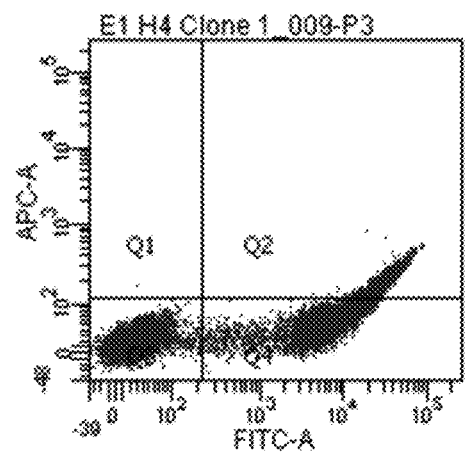
| | Count | Quadrant % |
|---|---|---|
| Q1 | 8 | 0.0 |
| Q2 | 0 | 0.0 |
| Q3 | 19,989 | 99.9 |
| Q4 | 3 | 0.0 |
| | Count | Quadrant % |
|---|---|---|
| Q1 | 1 | 0.0 |
| Q2 | 3,924 | 19.6 |
| Q3 | 8,693 | 43.5 |
| Q4 | 7,382 | 36.9 |
FIG. 55 rcSso7d.H4.2/H4/BA-MBP-rcSso7d.H4.1

Condition: Secondary control
Antigen (Ag): N/A
Ag pre-treatment: N/A
Pre-treatment time: N/A
Detection reagent: Avidin-purified BA-MBP-rcSso7d.H4.1/SA AF647

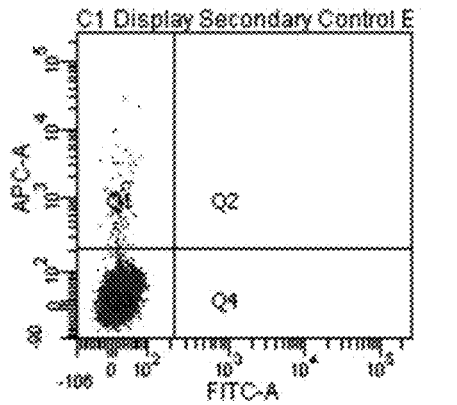

Condition: Baseline binding
Antigen (Ag): 100 nM H4
Ag pre-treatment: 0.1% BSA, 4°C
Pre-treatment time: N/A
Detection reagent: Avidin-purified BA-MBP-rcSso7d.H4.1/SA AF647

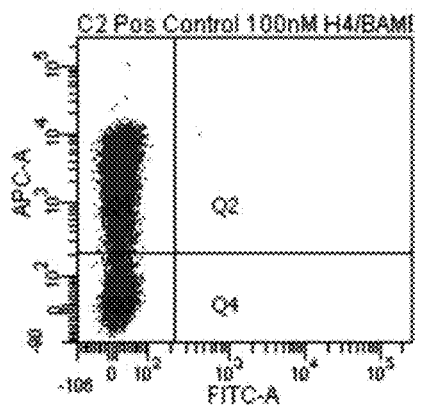

Condition: Condition: Overnight heat/ urine inactivation
Antigen (Ag): 100 nM H4
Ag pre-treatment: Urine, 37°C
Pre-treatment time: Overnight
Detection reagent: Avidin-purified BA-MBP-rcSso7d.H4.1/SA AF647

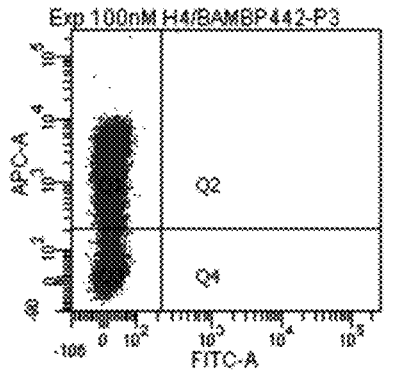

FIG. 56A rcSso7d.H4.2/H4/BA-MBP-rcSso7d.H4.1

Condition: Secondary control
Antigen (Ag): N/A
Ag pre-treatment: N/A
Pre-treatment time: N/A
Detection reagent: Avidin-purified BA-MBP-rcSso7d.H4.2/SA AF647

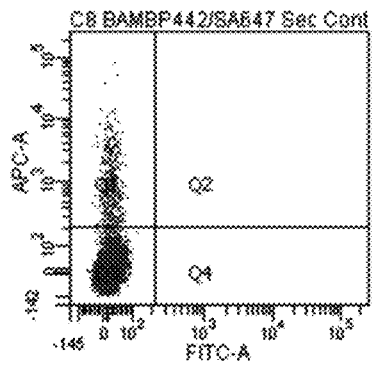

| | Count | Quadrant % |
|---|---|---|
| Q1 | 457 | 2.3 |
| Q2 | 0 | 0.0 |
| Q3 | 19,543 | 97.7 |
| Q4 | 0 | 0.0 |

Condition: Baseline binding
Antigen (Ag): 100 nM H4
Ag pre-treatment: 0.1% BSA, 4°C
Pre-treatment time: N/A
Detection reagent: Avidin-purified BA-MBP-rcSso7d.H4.2/SA AF647

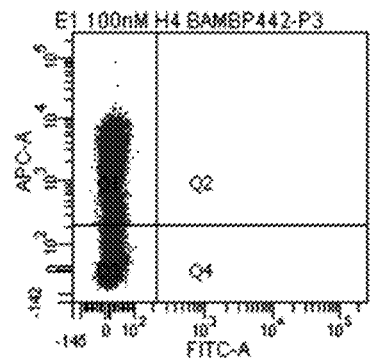

| | Count | Quadrant % |
|---|---|---|
| Q1 | 12,448 | 62.2 |
| Q2 | 0 | 0.0 |
| Q3 | 7,552 | 37.8 |
| Q4 | 0 | 0.0 |

Condition: Condition: Weeklong heat/urine inactivation
Antigen (Ag): 100 nM H4
Ag pre-treatment: Urine, 37°C
Pre-treatment time: 1 week
Detection reagent: Avidin-purified BA-MBP-rcSso7d.H4.2/SA AF647

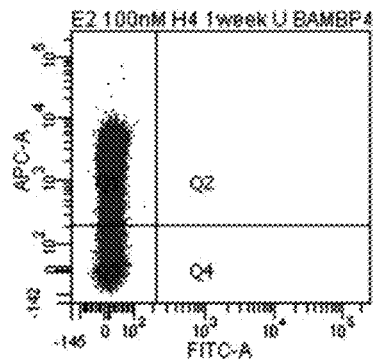

| | Count | Quadrant % |
|---|---|---|
| Q1 | 11,481 | 57.4 |
| Q2 | 0 | 0.0 |
| Q3 | 8,519 | 42.6 |
| Q4 | 0 | 0.0 |

FIG. 56B

H6BA
38.1 kDa rcSso7d.H6BA.1

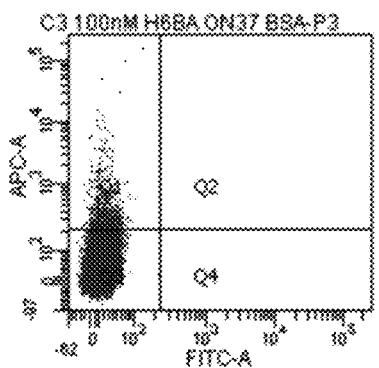
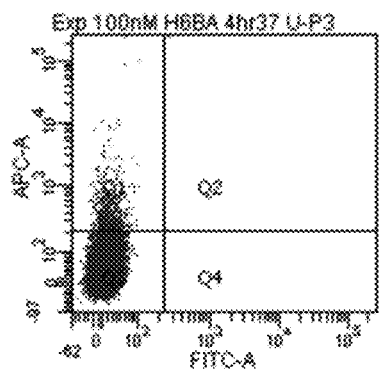
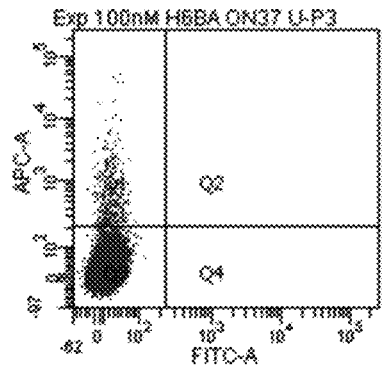
FIG. 58B rcSso7d.H6BA.2

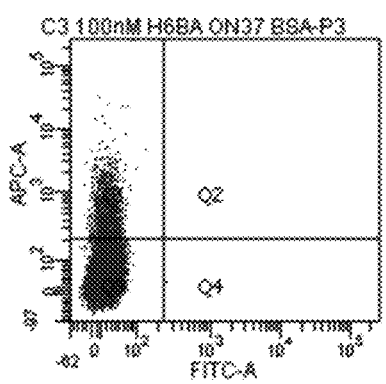

Condition: Heat inactivation
Antigen (Ag): H6BA
Ag pre-treatment: 0.1% BSA, 37°C
Pre-treatment time: Overnight
Detection reagent: SA AF647

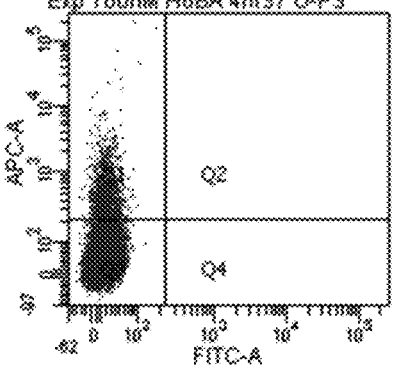

Condition: Short-time heat/urine inactivation
Antigen (Ag): H6BA
Ag pre-treatment: Urine, 37°C
Pre-treatment time: 4 hours
Detection reagent: SA AF647

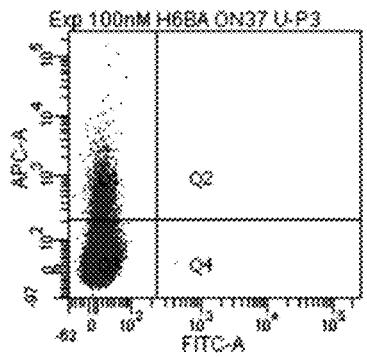

Condition: Overnight heat/urine inactivation
Antigen (Ag): H6BA
Ag pre-treatment: Urine, 37°C
Pre-treatment time: Overnight
Detection reagent: SA AF647

FIG. 59B

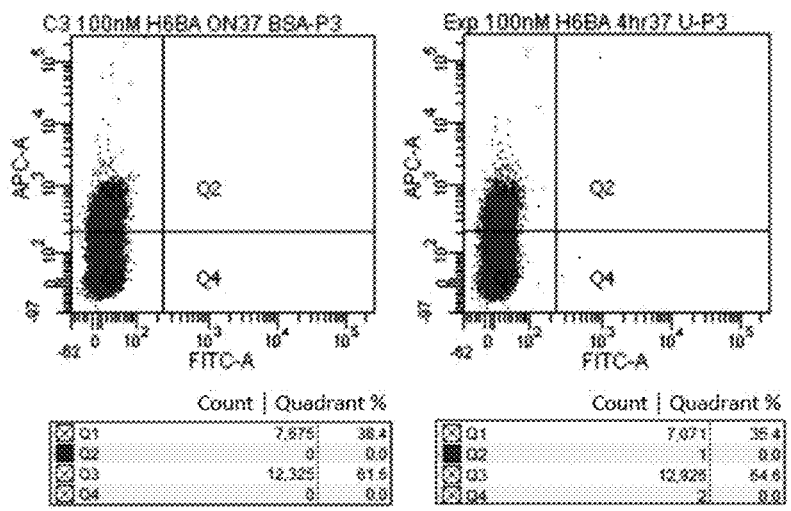
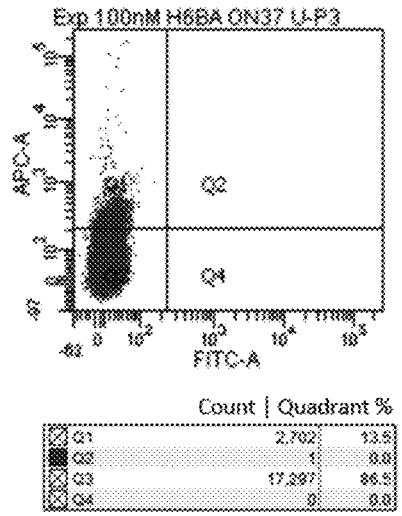
FIG. 60B rcSso7d.H7.1

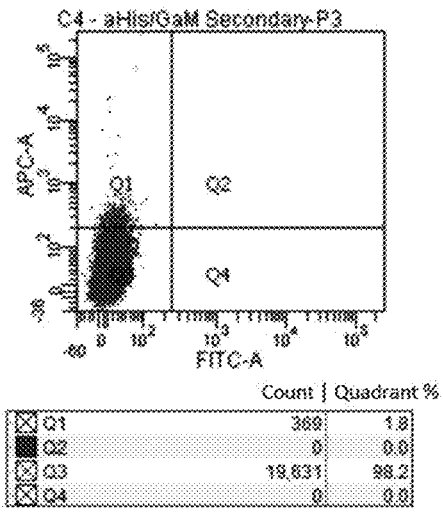

Condition: Secondary control
Antigen (Ag): N/A
Ag pre-treatment: N/A
Pre-treatment time: N/A
Detection reagent: Mouse anti-His/ goat anti-mouse AF647

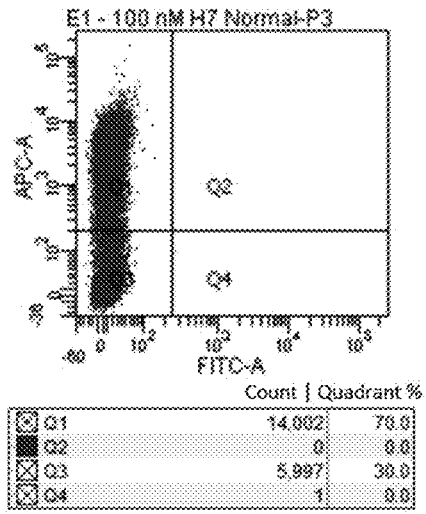

Condition: Baseline binding
Antigen (Ag): 100 nM H7
Ag pre-treatment: 0.1% BSA, 4°C
Pre-treatment time: N/A
Detection reagent: Mouse anti-His/ goat anti-mouse AF647

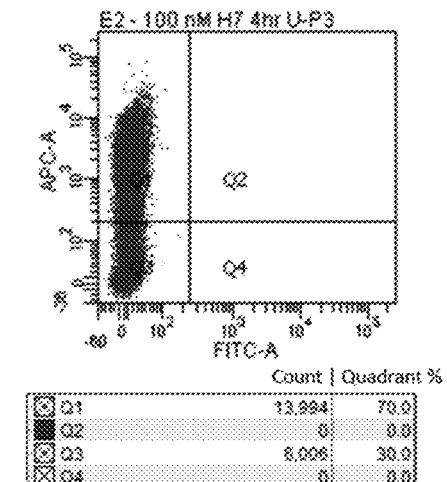

Condition: Short-term heat/ urine inactivation
Antigen (Ag): 100 nM H7
Ag pre-treatment: Urine, 37°C
Pre-treatment time: 4 hours
Detection reagent: Mouse anti-His/ goat anti-mouse AF647

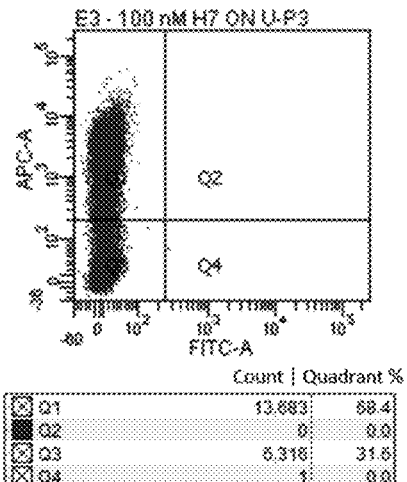

Condition: Condition: Overnight heat/ urine inactivation
Antigen (Ag): 100 nM H7
Ag pre-treatment: Urine, 37°C
Pre-treatment time: Overnight
Detection reagent: Mouse anti-His/ goat anti-mouse AF647

FIG. 62

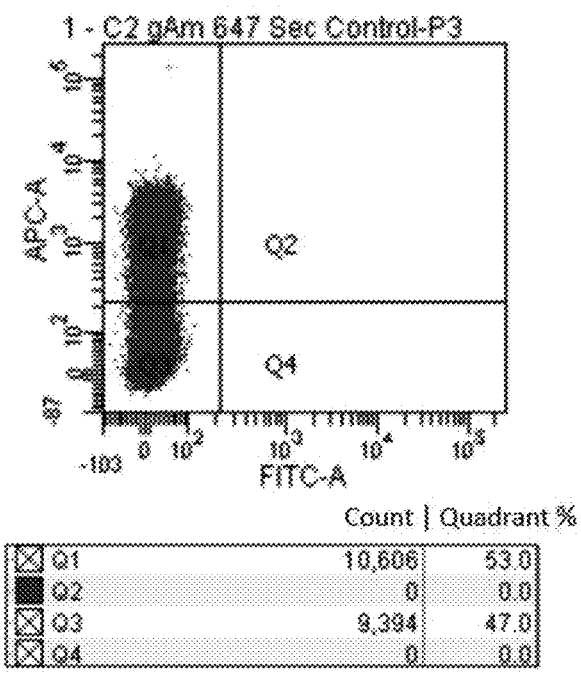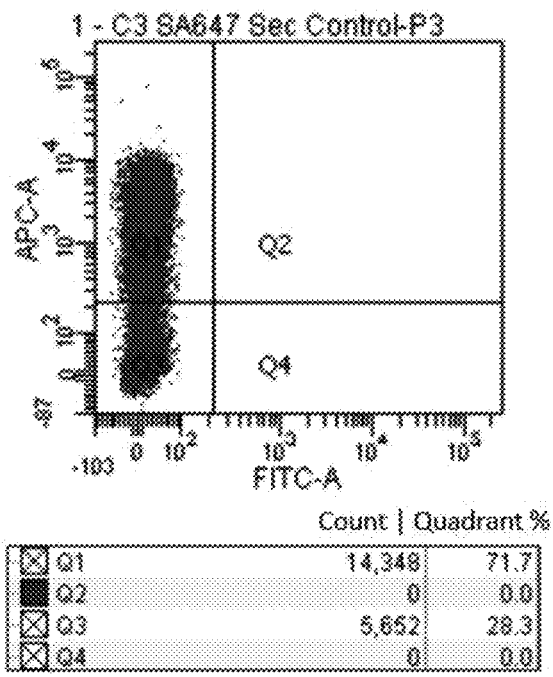
FIG. 63 rcSso7d.H4.5-CBD
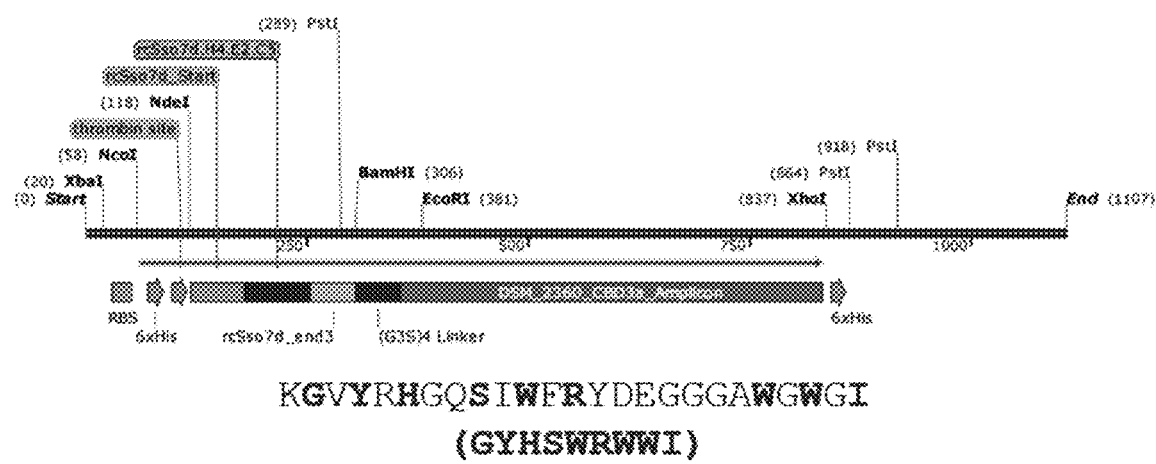
KGVYRHGQSIWFRYDEGGGAWGWGI
(GYHSWRWWI)
FIG. 65A

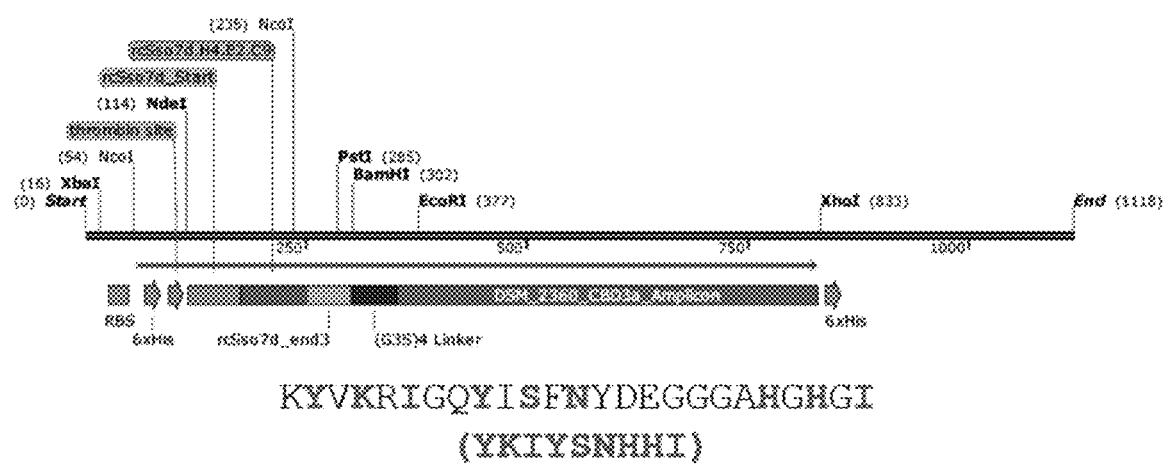
KYVKRIGQYISFNYDEGGGAHGHGI
(YKIYSNHHI)
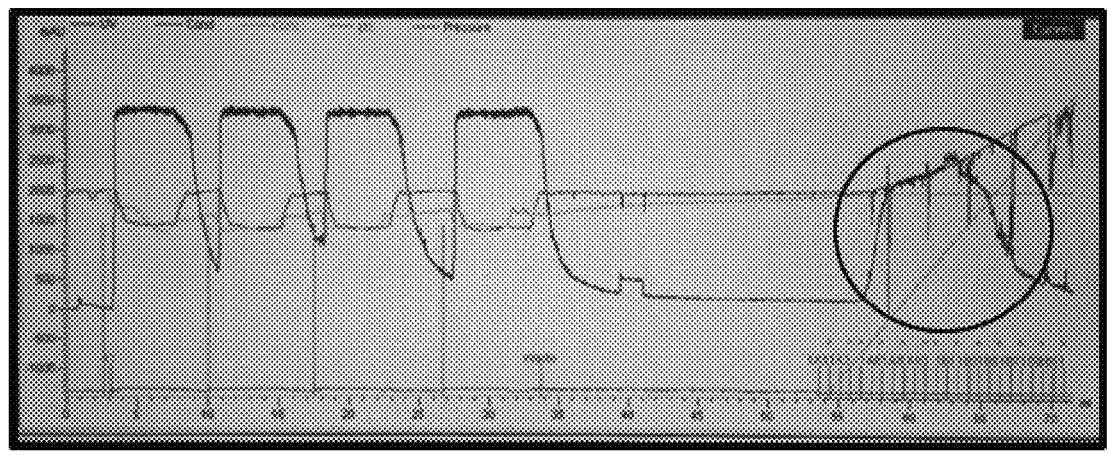
FIG. 65B rcSso7d.SA-CBD
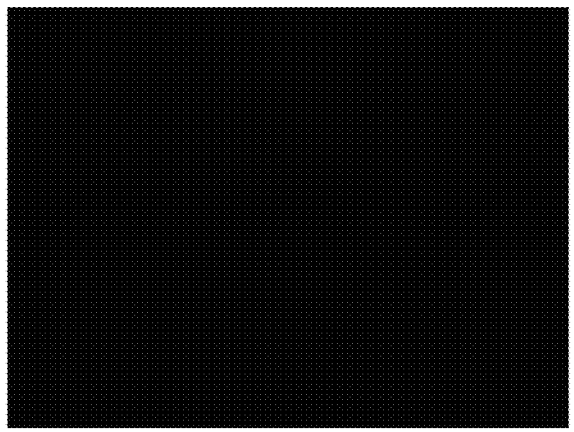
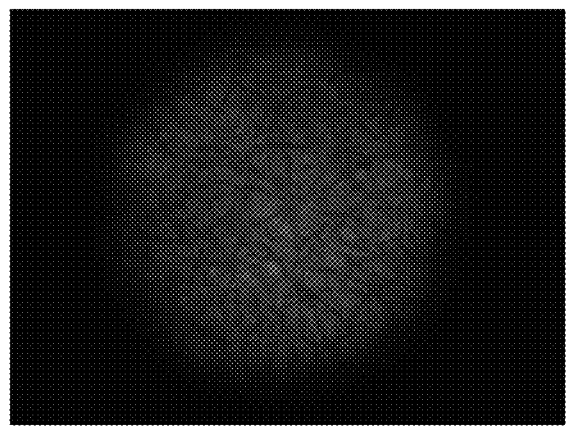
Negative control            Positive control
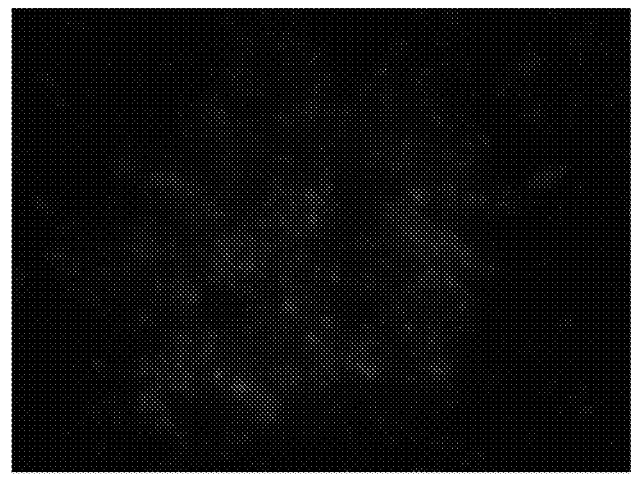
Experimental sample
FIG. 69

PROTEIN FOR RAPID, EFFICIENT CAPTURE OF ANTIGENS

RELATED APPLICATIONS

This application is a divisional of U.S. application Ser. No. 16/158,506, filed Oct. 12, 2018, which claims priority under 35 U.S.C. § 119(e) to U.S. Provisional Application No. 62/572,392, filed Oct. 13, 2017, each of which is incorporated herein by reference in its entirety.

REFERENCE TO AN ELECTRONIC SEQUENCE LISTING

The contents of the electronic sequence listing (M065670429US02-SUBSEQ-JRV.xml; Size: 178,263 bytes; and Date of Creation: Oct. 21, 2024) is herein incorporated by reference in its entirety.

FIELD

Methods and compositions for detecting targets of interest are disclosed herein.

BACKGROUND

Under the antigen-dilute conditions of a typical diagnostic assay, every target molecule that goes uncaptured represents a loss in potential binding signal, and directly diminishes diagnostic sensitivity. (Kelley et al., 2014; Rissin et al., 2013) Given that the signal-to-noise ratio for an immunoassay is directly proportional to the molar abundance of bound analyte, general strategies must be developed to enhance the efficiency of target capture, in order to boost the maximum achievable sensitivity for any given diagnostic platform.

SUMMARY

In some aspects, the present disclosure relates to the development of a general strategy for enhancing the efficiency of target capture in immunoassays, using a bifunctional fusion protein construct which incorporates a substrate-anchoring moiety (e.g., a cellulose binding domain (CBD)) for the high-abundance immobilization of an antigen-binding protein (e.g., Sso7d, reduced charge Sso7d (rcSso7d)). The approach utilizes a pseudo first-order rate constant model and was tested in a paper-based assay format using a fusion construct consisting of an rcSso7d binding protein and a CBD (rcSso7d-CBD fusion protein). The rcSso7d-CBD fusion proteins described herein enable oriented, high-density, and rapid adsorption of the antigen-binding protein (e.g., rcSso7d) to a cellulose-containing substrate.

According to some aspects, a bifunctional fusion protein including a cellulose binding domain (CBD) or a carbohydrate-binding module (CBM) and an engineered reduced-charge Sso7d (rcSso7d) antigen-binding protein is provided herein.

In some embodiments, the C-terminus of the engineered rcSso7d antigen-binding protein is linked to the N-terminus of the CBD.

In some embodiments, the engineered rcSso7d antigen-binding protein is linked to the CBD through a linker. In some embodiments, the linker is a Gly-Ser linker.

In some embodiments, the engineered rcSso7d antigen-binding protein comprises a streptavidin-binding domain. In some embodiments, the rcSso7d antigen-binding protein comprises a tuberculosis antigen-binding domain, a Flavivirus non-structural 1 (NS1) binding domain, an interleukin-6 (IL-6) binding domain, or a fluorophore binding domain. In some embodiments, the tuberculosis antigen-binding domain comprises a Rv1656-binding domain.

In some embodiments, the rcSso7d antigen-binding protein comprises at least 85% of the amino acid sequence of SEQ ID NO: 3 from *Sulfolobus solfataricus*.

In some embodiments, the CBD is a type 3a CBD or a type 1 dimerized cellulose binding domain (dCBD). In some embodiments, the type 3a CBD is a domain of the protein CipA from *Clostridium thermocellum*.

According to some aspects, a method for detecting an antigen of interest is provided herein. In some embodiments, the method includes contacting any of the bifunctional fusion proteins described herein with a cellulose-containing substrate for a time sufficient for the bifunctional fusion protein to bind the cellulose-containing substrate; contacting the bifunctional fusion protein bound to the cellulose-containing substrate with a sample that includes an antigen of interest; and detecting the antigen of interest bound by the engineered rcSso7d antigen-binding protein.

In some embodiments, the bifunctional fusion protein is in solution. In some embodiments, the solution comprises a buffer.

In some embodiments, the sample is a biological sample.

In some embodiments, the bifunctional fusion protein is in molar excess of the antigen of interest. In some embodiments, the bifunctional fusion protein is in at least 10-fold molar excess of the antigen of interest. In some embodiments, the antigen of interest is a tuberculosis antigen. In some embodiments, the antigen of interest is Rv1656 or streptavidin.

In some embodiments, at least 50% of the antigen of interest is depleted from the sample.

In some embodiments, the cellulose-containing substrate is paper or nitrocellulose. In some embodiments, the cellulose-containing substrate is chromatography paper. In some embodiments, the chromatography paper is unmodified.

In some embodiments, the method further includes rinsing the cellulose-containing substrate with a buffer solution before detecting the antigen of interest bound by the engineered rcSso7d antigen-binding protein.

In some embodiments, the sample is a biological sample from a subject. In some embodiments, the subject is a mammal. In some embodiments, the subject is a human.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

According to some aspects, methods for detecting an antigen of interest are provided herein. In some embodiments, the method includes contacting any of the bifunctional fusion proteins described herein with a sample including an antigen of interest, wherein the antigen of interest binds to the bifunctional fusion protein and forms a complex; contacting the complex with a cellulose-containing substrate for a time sufficient for the complex to bind to the cellulose-containing substrate; and detecting the antigen of interest bound by the engineered rcSso7d antigen-binding protein.

In some embodiments, the bifunctional fusion protein is in solution. In some embodiments, the solution comprises a buffer.

In some embodiments, the sample is a biological sample.

In some embodiments, the bifunctional fusion protein is in molar excess of the antigen of interest. In some embodiments, the bifunctional fusion protein is in at least 10-fold molar excess of the antigen of interest. In some embodiments, the antigen of interest is a tuberculosis antigen. In some embodiments, the antigen of interest is Rv1656 or streptavidin.

In some embodiments, at least 50% of the antigen of interest is depleted from the sample.

In some embodiments, the cellulose-containing substrate is paper or nitrocellulose. In some embodiments, the cellulose-containing substrate is chromatography paper. In some embodiments, the chromatography paper is unmodified.

In some embodiments, the method further includes rinsing the cellulose-containing substrate with a buffer solution before detecting the antigen of interest bound by the engineered rcSso7d antigen-binding protein.

In some embodiments, the sample is a biological sample from a subject. In some embodiments, the subject is a mammal. In some embodiments, the subject is a human.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

According to some aspects, methods for assessing the presence or amount of an antigen of interest is a sample are provided herein. In some embodiments, the method includes contacting the sample with any of the bifunctional fusion proteins described herein and measuring the presence or amount of the antigen of interest in the sample.

In some embodiments, the bifunctional fusion protein is in solution. In some embodiments, the solution comprises a buffer.

In some embodiments, the sample is a biological sample.

In some embodiments, the bifunctional fusion protein is in molar excess of the antigen of interest. In some embodiments, the bifunctional fusion protein is in at least 10-fold molar excess of the antigen of interest. In some embodiments, the antigen of interest is a tuberculosis antigen. In some embodiments, the antigen of interest is Rv1656 or streptavidin.

In some embodiments, at least 50% of the antigen of interest is depleted from the sample.

In some embodiments, the bifunctional fusion protein is bound to a cellulose-containing substrate. In some embodiments, the cellulose-containing substrate is paper or nitrocellulose. In some embodiments, the cellulose-containing substrate is chromatography paper. In some embodiments, the chromatography paper is unmodified.

In some embodiments, the sample is a biological sample from a subject. In some embodiments, the subject is a mammal. In some embodiments, the subject is a human.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

According to some aspects, compositions are provided herein. In some embodiments, the composition includes any of the bifunctional fusion proteins described herein bound to a cellulose-containing substrate.

In some embodiments, the cellulose-containing substrate is paper, nitrocellulose or cellulose powder. In some embodiments, the cellulose-containing substrate is chromatography paper. In some embodiments, the chromatography paper is unmodified.

According to some aspects, kits for assessing a presence or amount of an antigen are provided herein. In some embodiments, the kit includes a container containing any of the bifunctional fusion proteins described herein. In some embodiments, the kit includes a container containing any of the target binding proteins or domains disclosed herein, wherein the target binding protein or domain is not part of a bifunctional fusion protein disclosed herein.

In some embodiments, the kit further includes a cellulose-containing substrate.

In some embodiments, the bifunctional fusion protein is bound to the cellulose-containing substrate. In some embodiments, the bifunctional fusion protein is not bound to the cellulose-containing substrate. In some embodiments, the cellulose-containing substrate is paper, nitrocellulose or cellulose powder. In some embodiments, the cellulose-containing substrate is chromatography paper. In some embodiments, the chromatography paper is unmodified.

According to some aspects, methods for assaying an antigen of interest are provided herein. In some embodiments, the method includes contacting an antigen with any of the bifunctional fusion proteins described herein bound to a cellulose-containing substrate, wherein the bifunctional fusion protein is bound to the cellulose-containing substrate at an at least 10-fold or greater molar excess or at an at least 10-fold or greater volume-average concentration excess to the antigen of interest. In some embodiments, the bifunctional fusion protein is in at least 60-fold molar excess of the antigen of interest.

In some embodiments, the antigen of interest is a tuberculosis antigen. In some embodiments, the antigen of interest is Rv1656 or streptavidin.

In some embodiments, the cellulose-containing substrate is paper or nitrocellulose. In some embodiments, the cellulose-containing substrate is chromatography paper. In some embodiments, the chromatography paper is unmodified.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

In some embodiments, any of the bifunctional fusion proteins disclosed herein comprise at least 2, 3, 4, 5, 6, 7, 8, 9 or 10 rcSso7d antigen-binding proteins or antigen-binding domains. In some embodiments, the at least 2, 3, 4, 5, 6, 7, 8, 9 or 10 rcSso7d antigen-binding proteins are genetically fused together. In some embodiments, the at least 2, 3, 4, 5, 6, 7, 8, 9 or 10 rcSso7d antigen-binding proteins are directly or indirectly linked to the CBM or CBD.

In some embodiments, the cellulose powder is in solution to capture a soluble analyte, antigen or antigen of interest.

According to another aspect, engineered reduced-charge Sso7d (rcSso7d) antigen-binding proteins or domains are contemplated herein.

In some embodiments, the rcSso7d antigen-binding protein is directly or indirectly linked to a maltose binding protein (MBP).

In some embodiments, the rcSso7d further comprises a biotin acceptor.

According to another aspect, methods for detecting an antigen of interest are contemplated herein.

In some embodiments, the method includes contacting an antigen of interest with an oxidized cellulose substrate for a time sufficient for the antigen of interest to bind to the oxidized cellulose substrate, contacting the antigen of interest bound to the oxidized cellulose substrate of with an engineered rcSso7d antigen-binding protein disclosed herein for a time sufficient for the antigen of interest to bind to an engineered rcSso7d antigen-binding protein disclosed herein, and detecting the antigen of interest bound to the engineered rcSso7d antigen-binding protein.

In some embodiments, the antigen of interest is detected with a streptavidin conjugated to a fluorophore.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

(FIG. 2A) Ligand capture efficiency at equilibrium for the analytical and PFORC models. Curves represent the proportion of free ligand that is bound at equilibrium for varying initial concentrations of ligand and receptor. (FIG. 2B) Calculated time required to achieve 99% of equilibrium binding in the analytical and PFORC models. All plots were generated using a KD of $5.5 \times 10^{-10}$ M. Colored triangles denote the points where the receptor concentration is equivalent to the associated ligand concentration, to highlight the local changes near these values.

(FIG. 5A) SA-E titration curves for various applied soluble concentrations of rcSso7d.SA-CBD. Sets of non-functionalized cellulose test zones were prepared with a range of soluble rcSso7d.SA-CBD concentrations. All test zones were contacted for 30 s and washed, and were then treated for 30 minutes with a serial dilution of SA-E ranging from 256 nM to 0.25 nM. Samples were imaged in the TEXAS RED® channel using an exposure time of 1000 ms. Datasets were fit with a second-order polynomial. Error bars represent the standard deviation of four independent replicates. (FIG. 5B) Limits of detection for various applied concentrations of rcSso7d.SA-CBD. The measured MFI values for all negative control samples (with [SA-E]ranging from 256 nM to 0.25 nM) were averaged to calculate a conservative three-sigma detection threshold of 167.8 AU. Second-order polynomial lines of best fit were used to calculate the antigen concentration corresponding to this LOD for each sample set treated with a different applied rcSso7d.SA-CBD concentration. Second-order polynomial lines of best fit were also used to plot the upper and lower bounds of each data point (determined by the standard deviation), and these bounding trendlines were used to generate bounds on the limits of detection, represented by the error bars.

FIG. 31 shows flow cytometry data indicating the specific binding activity of Human IL-6 protein binder rcSso7d.IL6.6.

FIG. 33A shows a schematic representation of the rcSso7d.NS1.1-CBD construct immobilized to cellulose following with incubations of Zika virus NS1 (at various concentrations), biotinylated anti-Zika virus NS1 antibody, and streptavidin-AF 647.

FIG. 33B shows binder performance of rcSso7d.NS1.1-CBD in cellulose paper-based assay.

FIGS. 40A-40C show flow cytometry data indicating the specific binding activity of H1 binder rcSso7d.H1BA.3.

FIG. 41 shows flow cytometry data indicating the specific binding activity of binder rcSso7d.H1BA.4 (1.E2.3).

FIG. 42 shows flow cytometry data indicating the specific binding activity of H1 binder rcSso7d.H1BA.5 (1.E2.4).

FIG. 43 shows flow cytometry data indicating the specific binding activity of H1 binder rcSso7d.H1BA.6.

FIG. 45 shows flow cytometry data indicating the specific binding activity of H2 binder rcSso7d.H2BA.1.

FIG. 47 shows flow cytometry data indicating the specific binding activity of H4 binder rcSso7d.H4.1.

FIG. 48 shows flow cytometry data indicating the specific binding activity of H4 binder rcSso7d.H4.2.

FIG. 49 shows flow cytometry data indicating the specific binding activity of H4 binder rcSso7d.H4.3.

FIG. 50 shows flow cytometry data indicating the specific binding activity of H4 binder rcSso7d.H4.4.

FIG. 51 shows flow cytometry data indicating the specific binding activity of H4 binder rcSso7d.H4.5.

FIG. 52 shows flow cytometry data indicating the specific binding activity of H4 binder rcSso7d.H4.6.

FIG. 53 shows flow cytometry data indicating the specific binding activity of H4 binder rcSso7d.H4.7.

FIG. 54 shows flow cytometry data indicating the specific binding activity of H4 binder rcSso7d.H4.8.

FIG. 55 shows flow cytometry data indicating the specific binding activity of H4 binder rcSso7d.H4.9.

FIGS. 56A-56B show flow cytometry data indicating the specific binding activity of H4 binders rcSso7d.H4.2/H4/BA-MBP-rcSso7d.H4.1.

FIGS. 58A-58B show flow cytometry data indicating the specific binding activity of H6 binder rcSso7d.H6BA.1.

FIGS. 59A-59B show flow cytometry data indicating the specific binding activity of H6 binder rcSso7d.H6BA.2.

FIGS. 60A-60B show flow cytometry data indicating the specific binding activity of H6 binder rcSso7d.H6BA.3.

FIG. 62 shows flow cytometry data indicating the specific binding activity of H7 binder rcSso7d.H7.1.

FIG. 63 shows flow cytometry data indicating the specific binding activity of AF647 binder rcSso7d.AF647.1.

FIGS. 65A-65B show cloning and purification data of rcSso7d.H4.5-CBD (FIG. 65A) and rcSso7d.H4.9-CBD (FIG. 65B). The sequences is FIG. 65A correspond to SEQ ID NOs: 122 and 98, top to bottom. The sequences is FIG. 65B correspond to SEQ ID NOs: 123 and 102, top to bottom.

FIGS. 66A-66B show H4 binding activity of selected clones. FIG. 66C shows positive rcSso7d.H4.E1-BA controls. FIG. 66D shows schematic representations of the constructs in the assay rcSso7d.H4.2-CBD Full (1) and rcSso7d.H4.2-CBD with pre-incubation of the rcSso7d.H4.E1-BA and SA-AF647 species (4).

FIG. 68A is a multimer schematic. FIG. 68B shows a 12% SDS-PAGE demonstrating the purity of the 1×-, 2×-, and 3×-CBD variants following purification with immobilized metal affinity chromatography. FIG. 68C shows binder performance of the immobilized rcSso7d-CBD variants in antigen-capture assays, using streptavidin ALEXA FLUOR®647 as the analyte.

FIG. 69 shows the immobilization of rcSso7d.SA-CBD on cellulose powder for combing through large volumes. Images show the results of the negative control, positive control, and experimental sample.

$$y = \frac{A - B}{\left(1 + \left(\frac{x}{C}\right)^D\right)^E} + B \quad \text{(Eq. S10)}$$

Figure 74A:
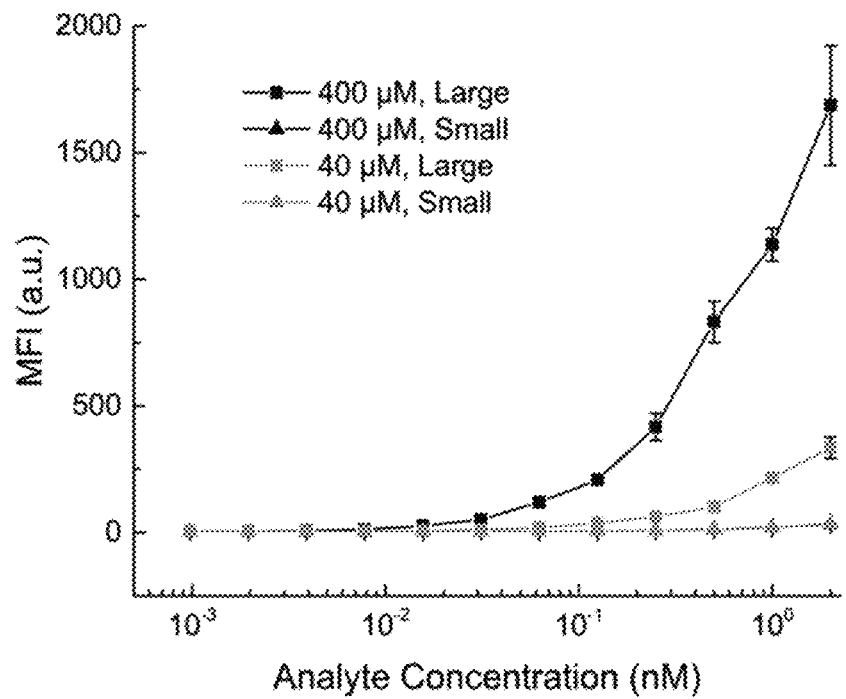
Figure 74B:
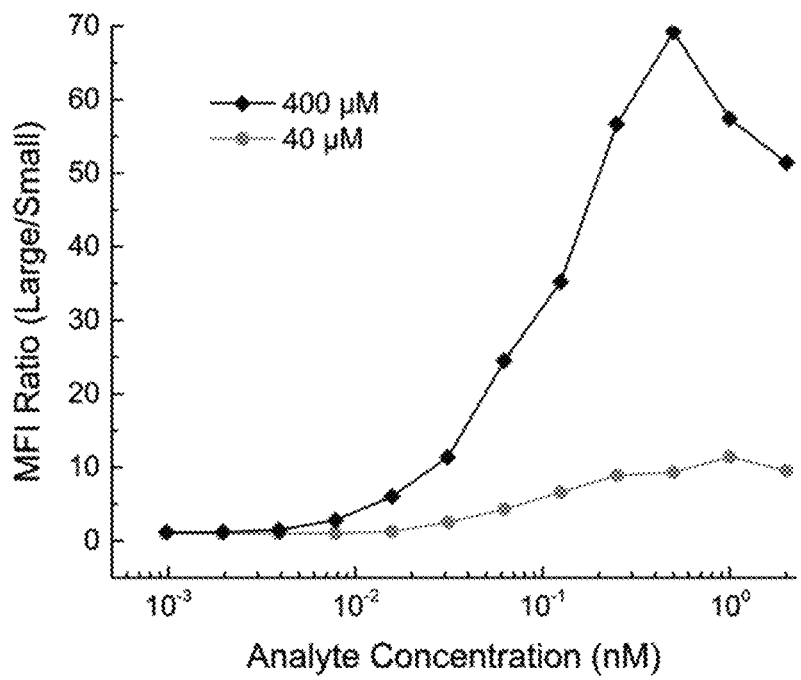
Figure 87:
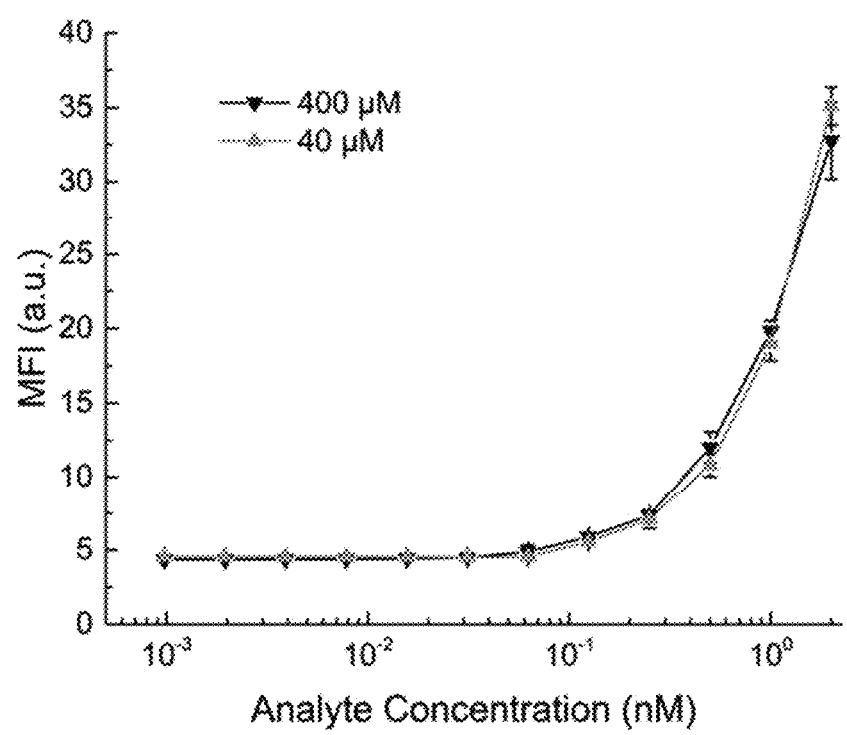

FIGS. 74A-74B show a comparison between analyte titration curves for rcSso7d-CBD at varying local concentrations. FIG. 74A shows mean fluorescence intensity (MFI) observed at varying analyte concentrations for large-(10 mL) and small-volume (10 L) samples using test zones with local rcSso7d-CBD concentrations of 400 and 40 µM. Data points corresponding to the 400 µM/10 µL samples directly overlap with those corresponding to the 40 M/10 µL samples (FIG. 87). FIG. 74B shows fluorescence ratios comparing the corresponding large- and small-volume samples at local rcSso7d-CBD concentrations of 400 and 40 µM. Large-volume samples consist of 10 mL of analyte solution (5 mL min-1, 20 recirculations). Small-volume samples consisted of 10 µL incubated on the test zones for an equivalent 40 min period. Error bars represent the standard deviation of three (large-volume) or four (small-volume) independent replicates.

Figure 75A:
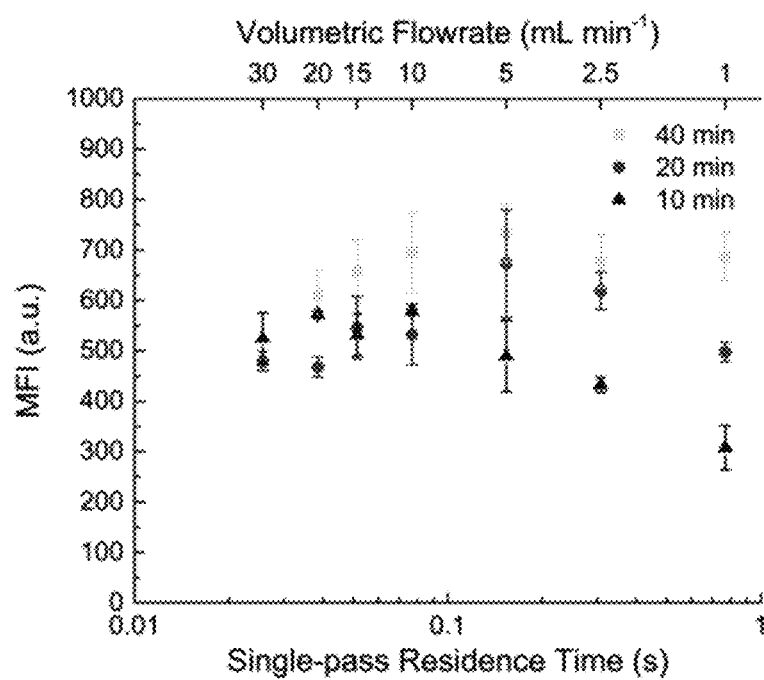
Figure 75B:
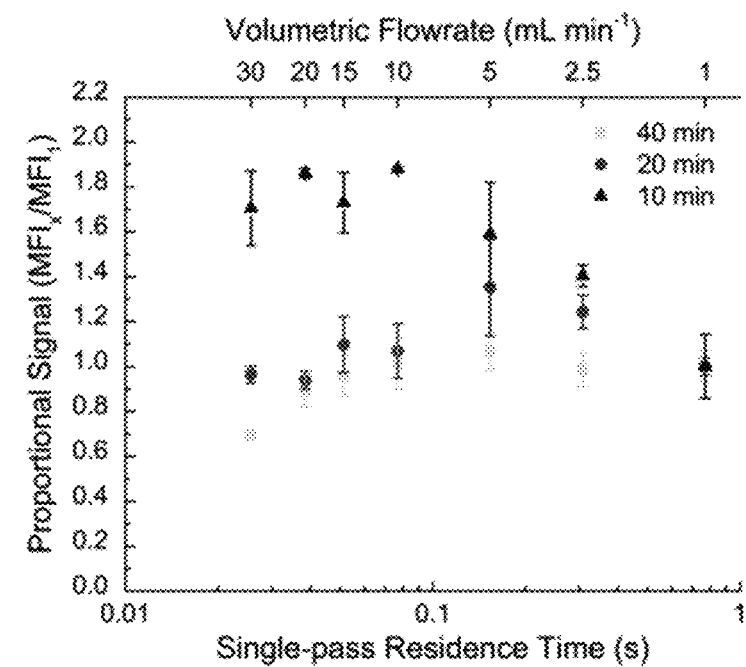
Figure 75C:
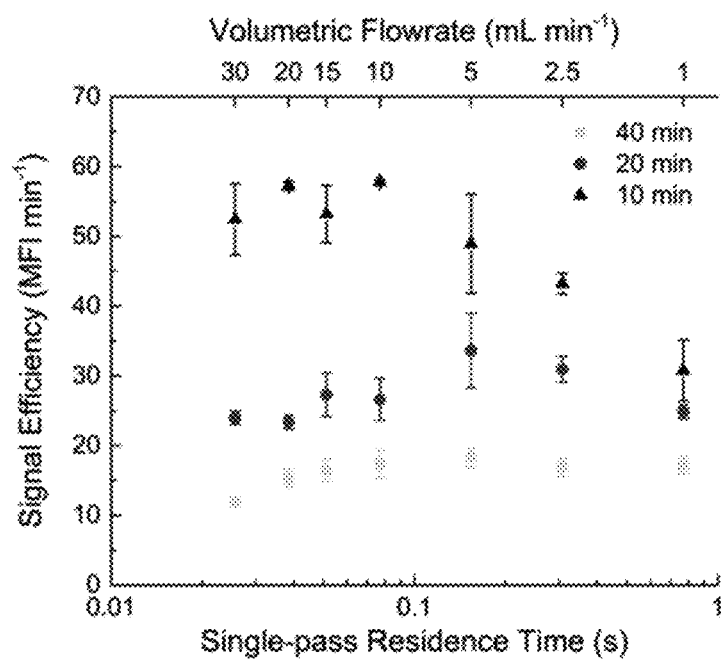
Figure 75D:
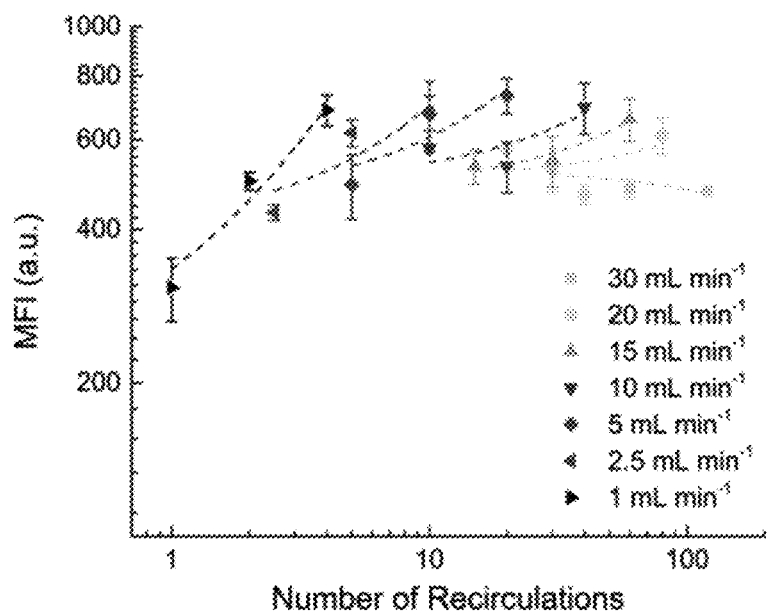

FIGS. 75A-75D show assay performance for varying flow rates and total processing times. FIG. 75A shows absolute mean fluorescence intensity (MFI), FIG. 75B shows proportional MFI (relative to samples processed for the same period of time at 1 mL min-1), and FIG. 75C shows signal development efficiency (MFI min-1) for varying single-pass residence times and total processing times. FIG. 75D shows signal development as a function of the number of recirculations. Linear trend lines indicate the performance of samples produced using a common volumetric flow rate (denoted in the legend). Sample specifications: 10 mL and 1 nM SA-AF647. Error bars represent the standard deviation of three independent replicates.

Figure 76:
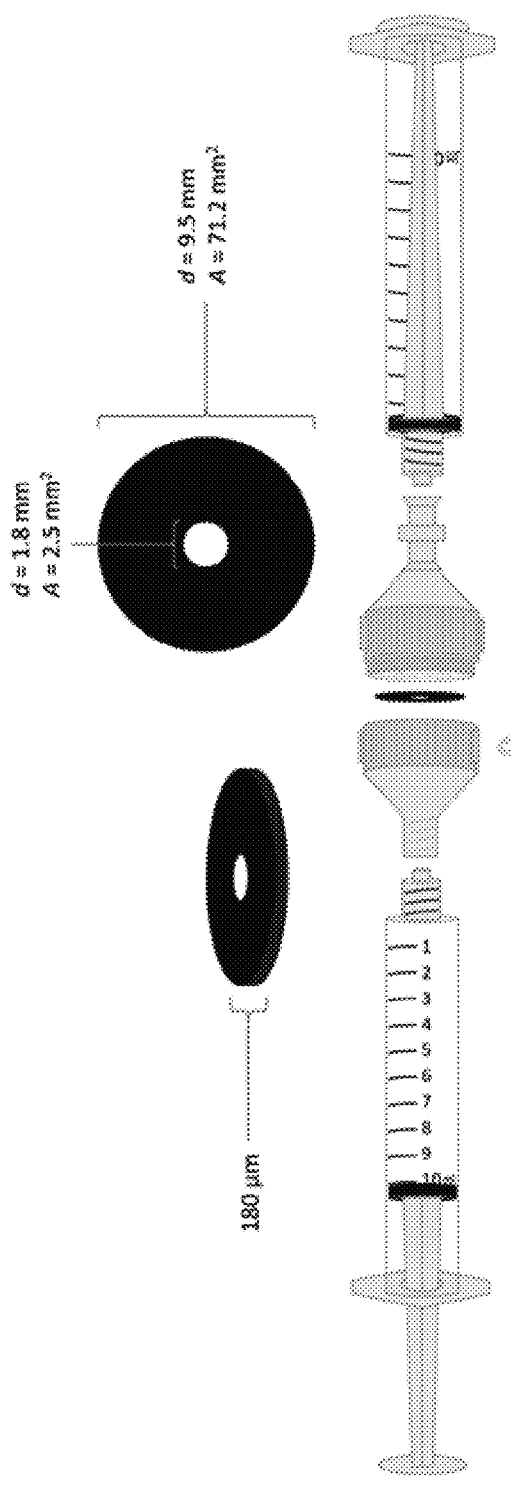

FIG. 76 shows a syringe-based assay format. Paper samples are excised and secured in a 13 mm Swinnex filter holder. A 10-mL syringe is connected upstream and used to pre-fill the filter holder with the analyte solution. A Qosina Female-to-Female Luer-Lok connector is used to join this cassette to a second syringe downstream, and any remaining air is bled from the system. In all cases, the top of the test zone (the surface to which the rcSso7d.SA-CBD solution was applied) is oriented so as to be the first side contacted by the analyte solution.

Figure 77A:
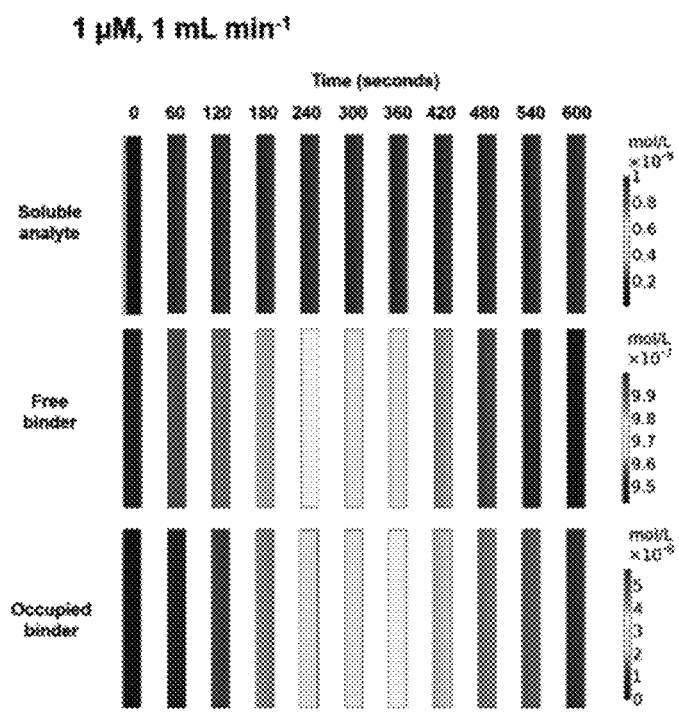
Figure 77B:
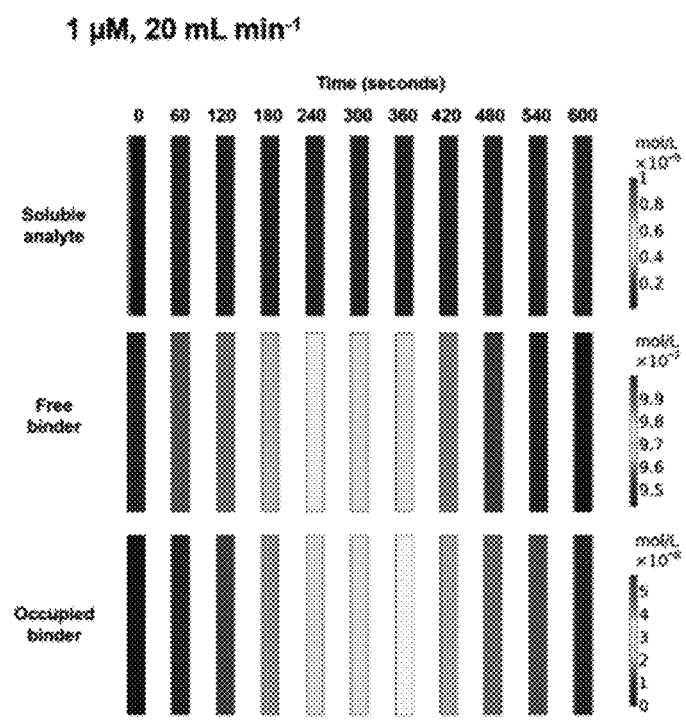
Figure 77C:
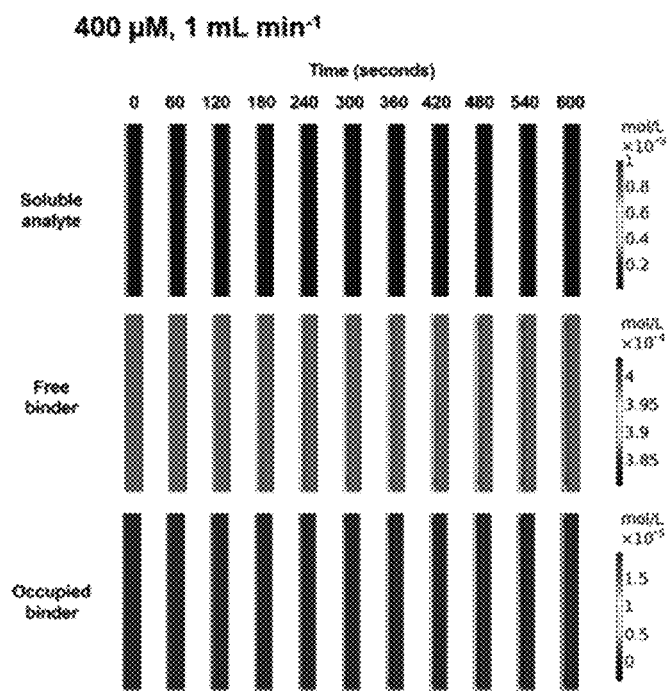
Figure 77D:
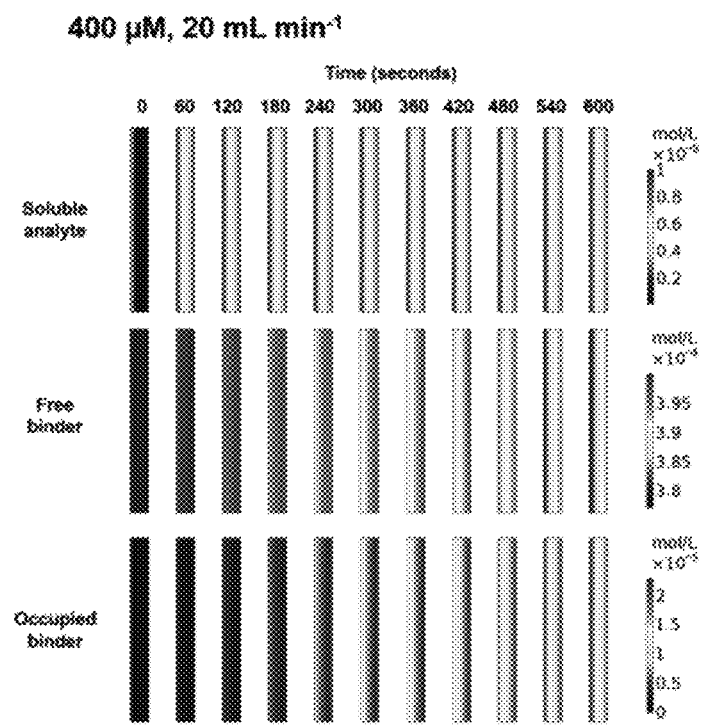

FIGS. 77A-77D show a set-up of COMSOL proportional analyte capture model. The test zone is modeled as a two dimensional reactor volume, throughout which the immobilized binder is homogeneously distributed. Depth=L=180 µm; width=2rtz=1.8 mm. Analyte concentration at the inlet (at left) is 1 nM. The binder concentration and volumetric flow rate for the sample sets are varied across the different subfigures: 1 µM, 1 mL min-1 (FIG. 77A), 1 µM, 20 mL min-1 (FIG. 77B), 400 µM, 1 mL min-1 (FIG. 77C), and 400 µM, 20 mL mini (FIG. 77D). Within each sub-figure, the rows of test snapshots correspond to the soluble analyte, free binder, and the occupied binder (from top to bottom). Test zone snapshots are captured every sixty seconds, at time-points denoted along the top of each sub-figure. Legends at right denote the concentrations of the relevant species for the corresponding row of cross-sectional snapshots. In order to capture system dynamics, color-bars are scaled relative to the relevant species for each set of operating conditions, rather than representing a universal concentration scale.

Figure 78:
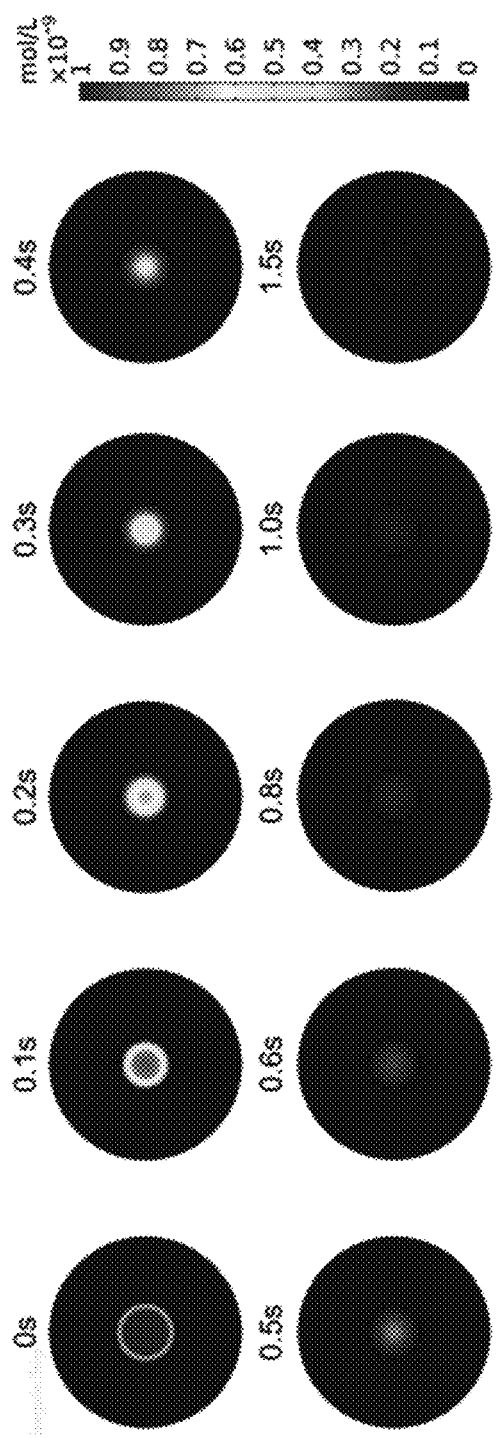

FIG. 78 shows a set-up of COMSOL diffusion model. An idealized circular pore (r=5.5 µm) is initialized with an analyte concentration of 1 nM. The surrounding matrix represents a binder-functionalized fibrous network, at an average binder concentration of 40 mM. Analyte diffusion and capture is allowed to proceed over the course of 2 seconds, to model diffusive capture over a range of different sample residence times. Each snapshot represents a different time-point, denoted above the pore image, and the color-bar represents the concentration of the soluble analyte.

Figure 79:

FIG. 79 shows the confirmation of fluid flow across the entire assay cross-sectional area. Insoluble cellulose powder (50 µm diameter) was added to the sample volume in order to track the fluid flow as the sample was recirculated across the test zone. Rather than focusing solely within the hydrophilic region, the powder distributes across the entire cross-sectional area, indicating that the hydrophobic region permits fluid flow once it becomes sufficiently wetted. Thus, the relevant flow volume is 12.81 µL, rather than that associated strictly with the binder-functionalized region (0.45 µL).

Figure 80:
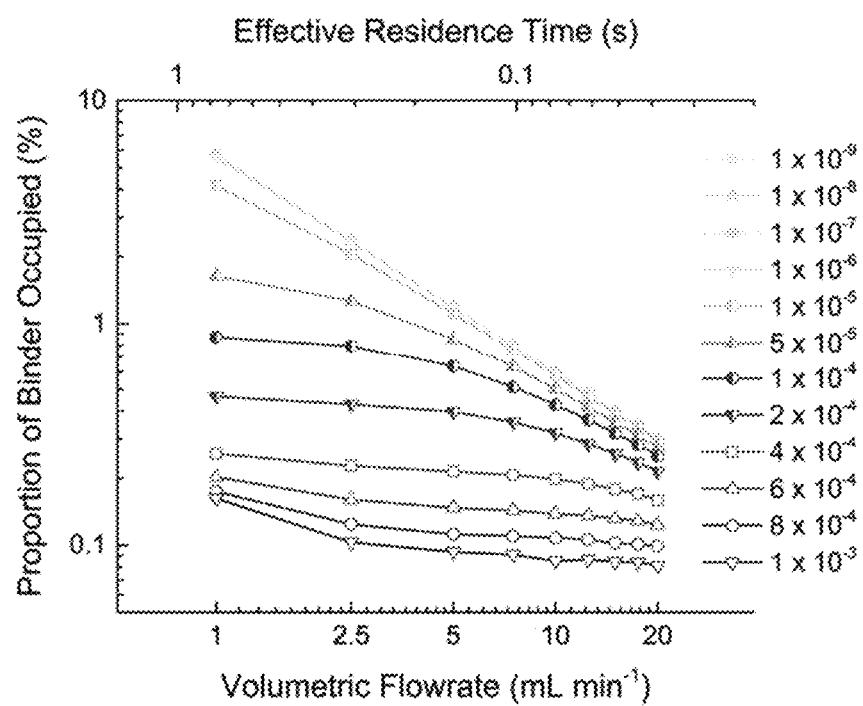

FIG. 80 shows proportional binder occupancy at varying concentrations and volumetric flow rates. Each line plot represents operation at a different local binder concentration (denoted in the legend). For all data sets, analyte was introduced at a concentration of 1 nM, and data was collected immediately following a single simulated 10-mL recirculation.

Figure 81A:
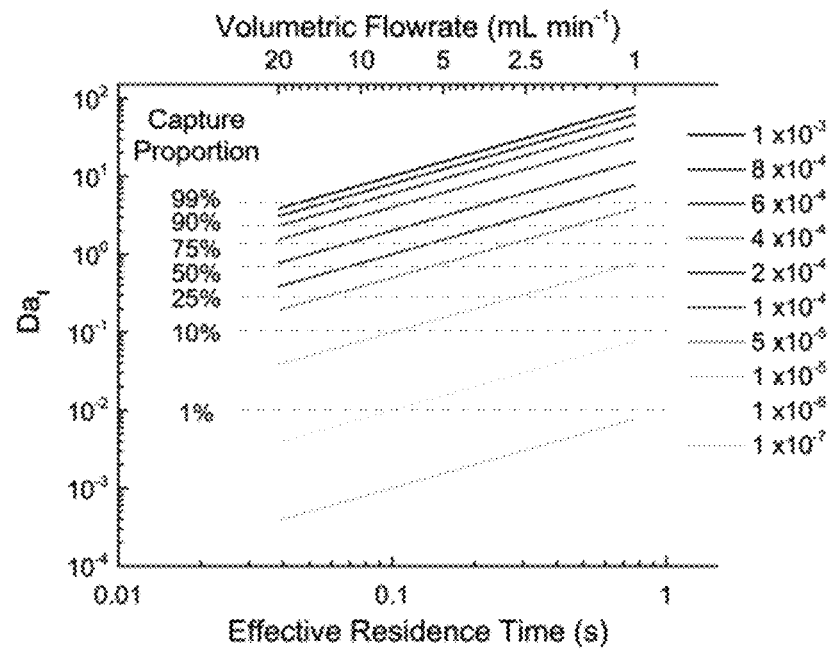
Figure 81B:
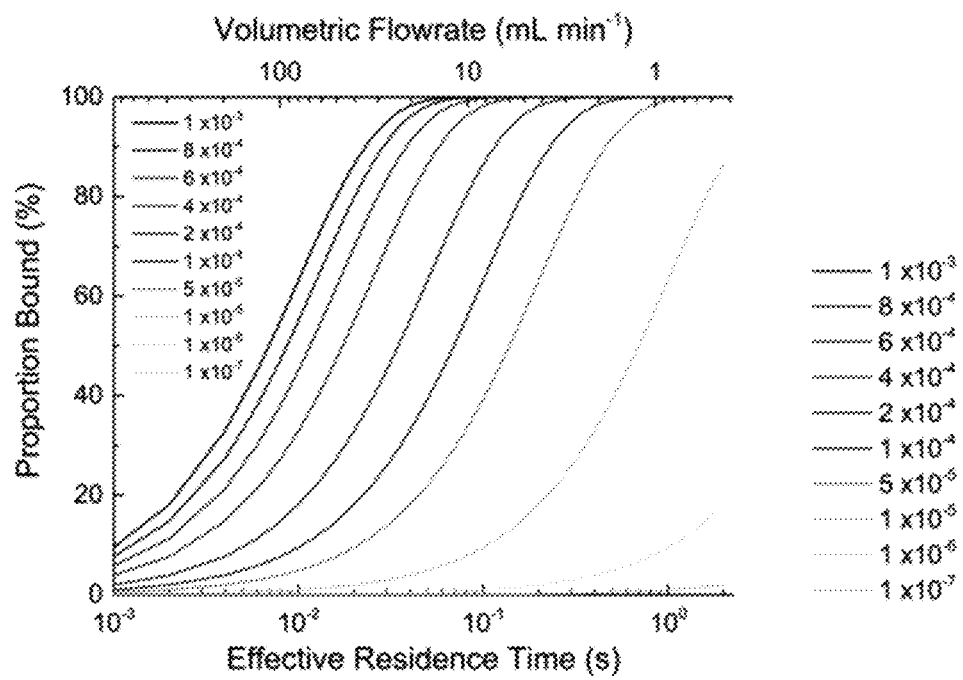

FIGS. 81A-81B show the correlation of flow rate, binder concentration, analyte capture, and DaI. FIG. 81A shows standard curves correlating volumetric flow rate, binder concentration (mol L$^{-1}$), and Damköhler number, as well as rates of proportional analyte capture predicted by the pseudo first-order rate model. FIG. 81B shows predicted proportional binding curves for varying local concentrations of immobilized binder.

Figure 82A:
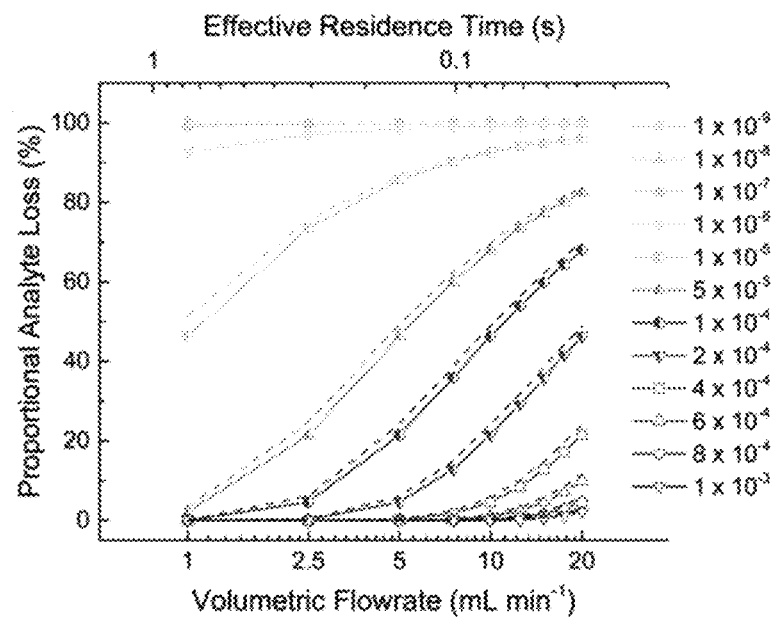
Figure 82B:
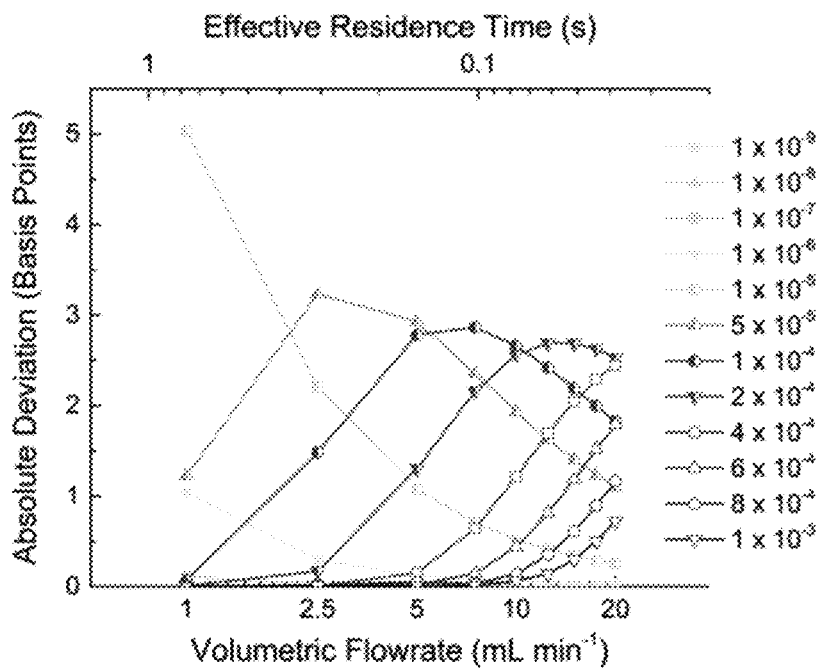

FIGS. 82A-82B show deviation between finite-element analysis and PFORC model. FIG. 82A shows a comparison of the finite element model of analyte binding in the non-diffusive limit (dashed lines) and the pseudo first-order rate constant model (solid lines).

FIG. 82B shows the absolute basis point deviation between the FEA model and PFORC model for all processing conditions. The greatest deviation between the predictive models is observed in regions of dynamic signal change.

Figure 83:
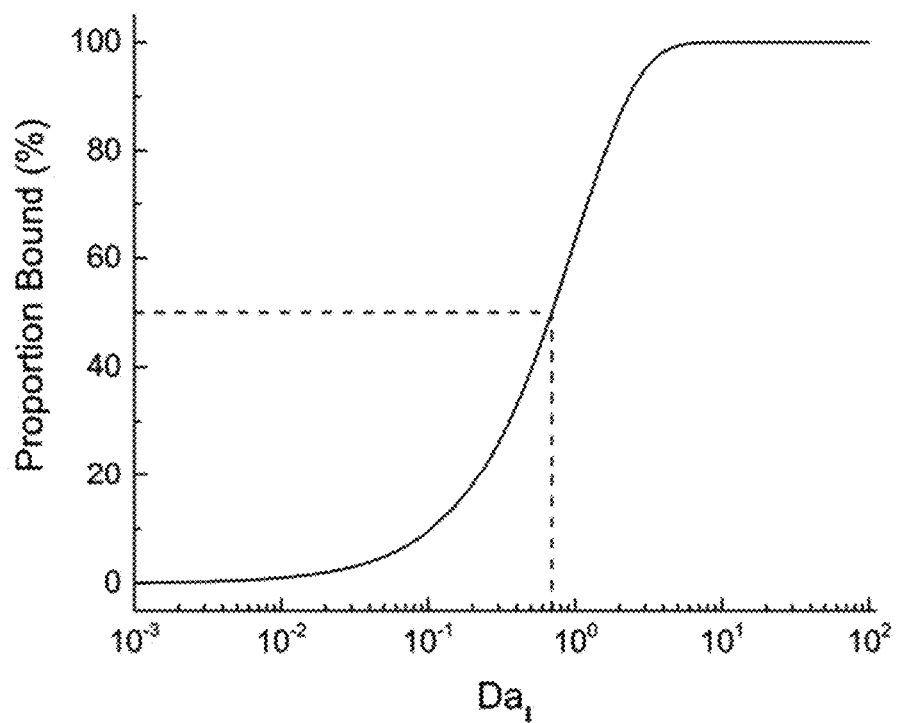

FIG. 83 shows a Damköhler master curve. All dimensional binding curves generated via the pseudo first-order rate model collapse onto a single dimensionless binding curve describing system performance. This relation is valid for all cases in which the immobilized binder is in significant molar excess (>10x) of the soluble analyte. Dashed lines highlight the value of the Damköhler number at which 50% of the analyte is captured.

Figure 84:
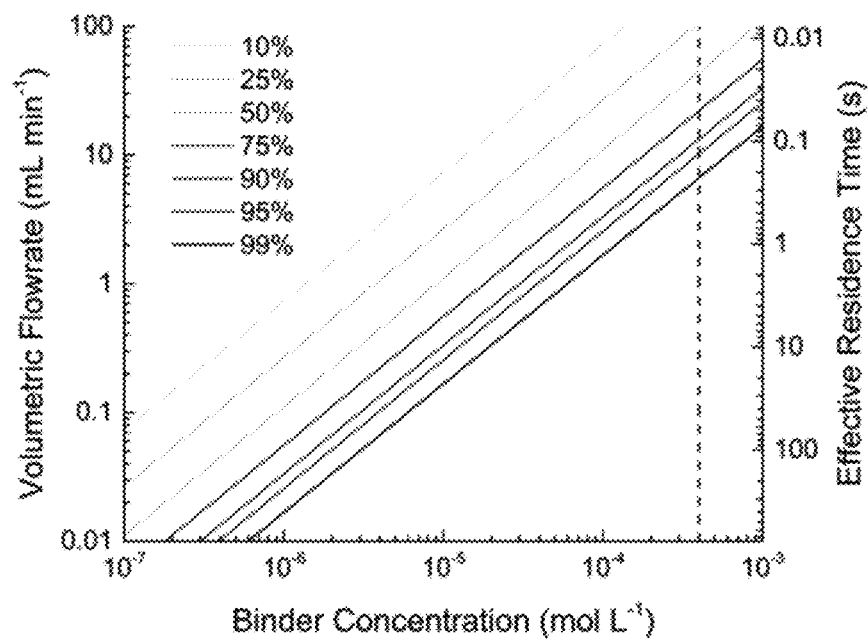

FIG. 84 shows binding isotherms. Curves denote the theoretical proportional analyte capture observed for a given volumetric flow rate (or residence time) at varying concentrations of immobilized binder. The dashed line indicates the operating regime of the standard rcSso7d-CBD system (CB=400 µM).

Figure 85:
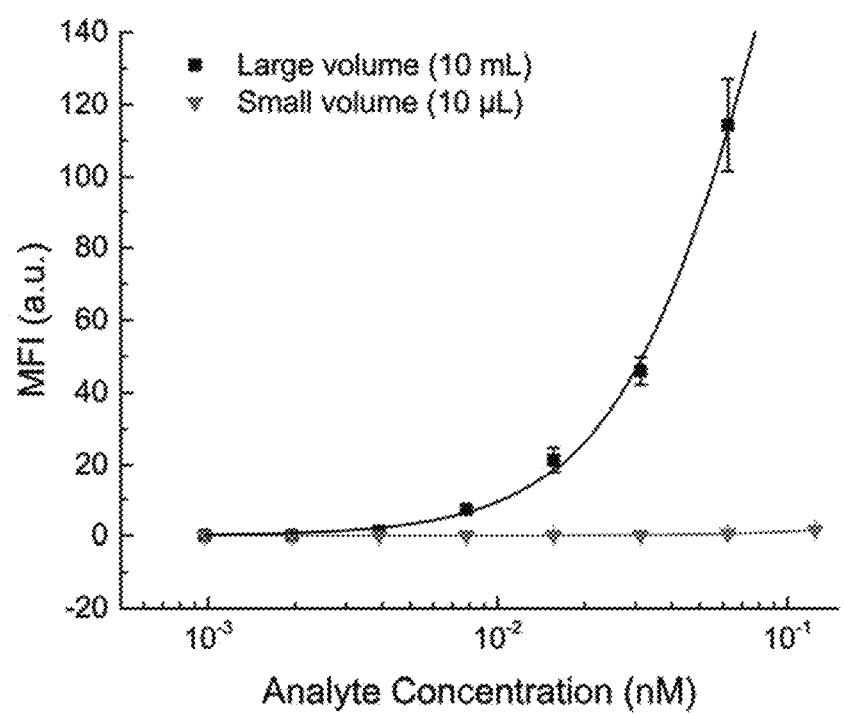

FIG. 85 shows titration curves near the point of signal onset. All large-volume samples consisted of 10 mL sample volumes, driven across the test zone at 5 mL min-1 for 20 recirculations. All small-volume samples consisted of 10 µL sample volumes, applied directly to the test zones and allowed to incubate for an equivalent 40-minute period. Dataset is identical to that seen in FIG. 73. Error bars represent the standard deviation of three (large-volume) or four (small-volume) independent replicates.

Figure 86A:
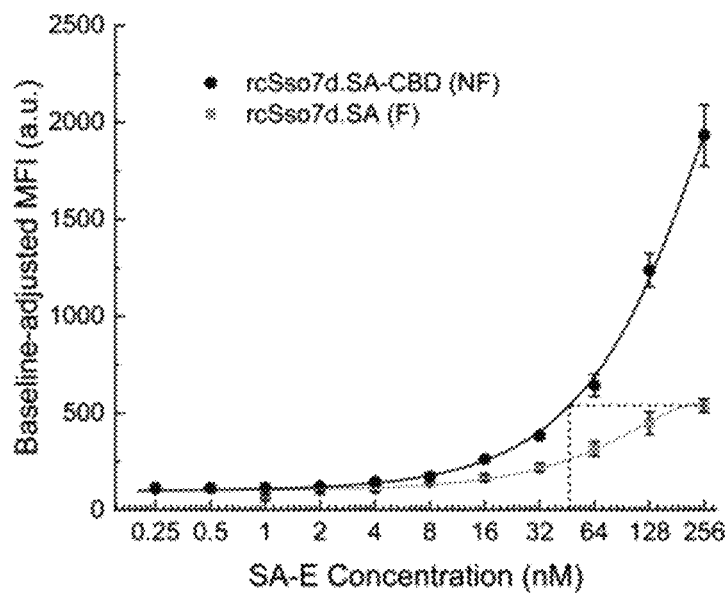
Figure 86B:
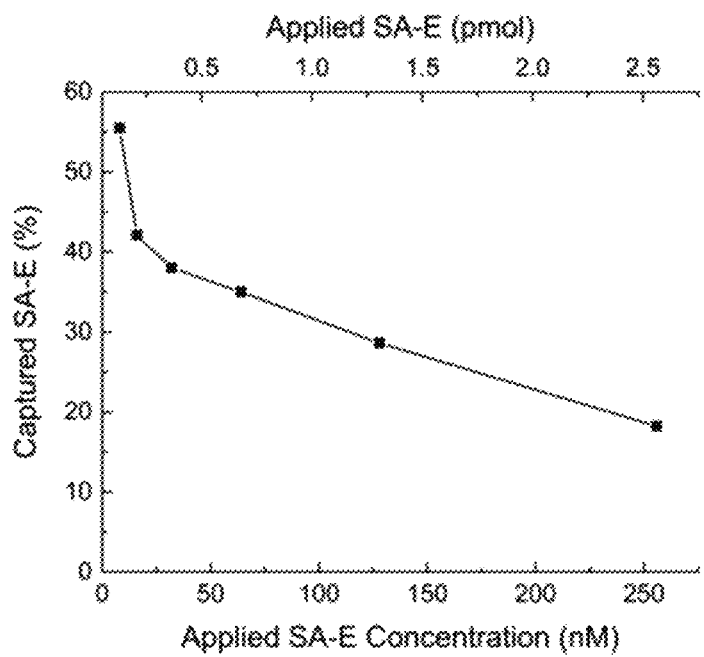

FIGS. 86A-86B show the calculation of immobilized protein abundance on functionalized paper. FIG. 86A shows titration data for rcSso7d.SA-CBD applied to non-functionalized paper (black) and rcSso7d.SA applied to aldehyde-functionalized paper (red), for streptavidin-eosin (SA-E) concentrations ranging from 0.25 nM to 256 nM and 10 µL sample volumes. FIG. 86B shows proportional analyte capture at varying applied analyte concentrations. Analysis is conducted for all applied concentrations wherein there is an appreciable difference between signals observed for the functionalized and non-functionalized samples. All tests were incubated with the analyte solution for thirty minutes. Error bars represent the standard deviation of four independent replicates.

FIG. 87 shows the comparison between small-volume titration curves for rcSso7d-CBD at local concentrations of 400 µM and 40 µM. Dataset is identical to that seen in FIG. 74A. Small-volume samples consisted of 10 µL incubated on the test zones for a 40-minute period. Error bars represent the standard deviation of four independent replicates.

Figure 88:
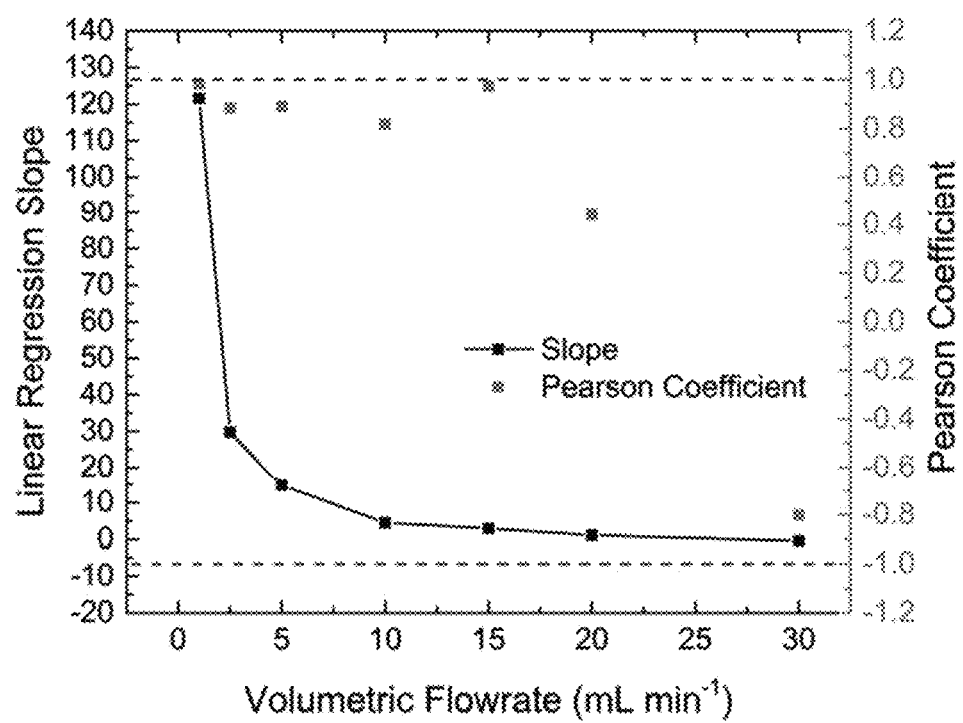

FIG. 88 shows linear regression slopes, which correlate the number of recirculations and the degree of signal development, decline with increasing volumetric flow rate. In nearly all cases, linear regression curves are observed to correlate well with the experimental data, as indicated by Pearson coefficients near ±1.

Figure 89:
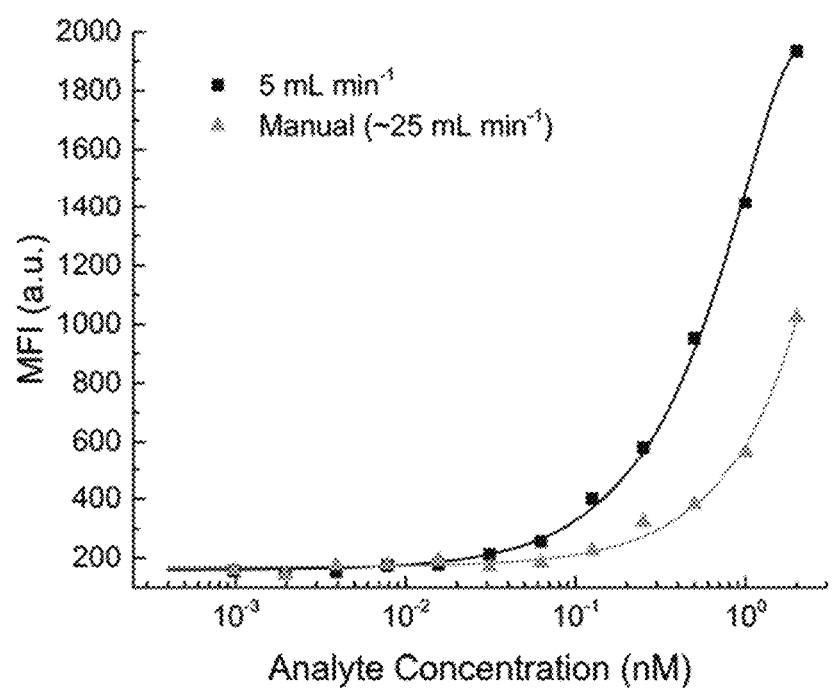

FIG. 89 shows a representative manual titration curve using streptavidin-eosin as the soluble analyte. Samples were processed for 20 recirculations each. Each data point represents a single assay replicate. Manual samples were processed at a flow rate that could be sustained without physical discomfort (~25 mL min−1). Samples were exposed for 1000 ms using a TXRED®-4040C filter set. Streptavidin-eosin was prepared as described in Reference 3.

Figure 90:
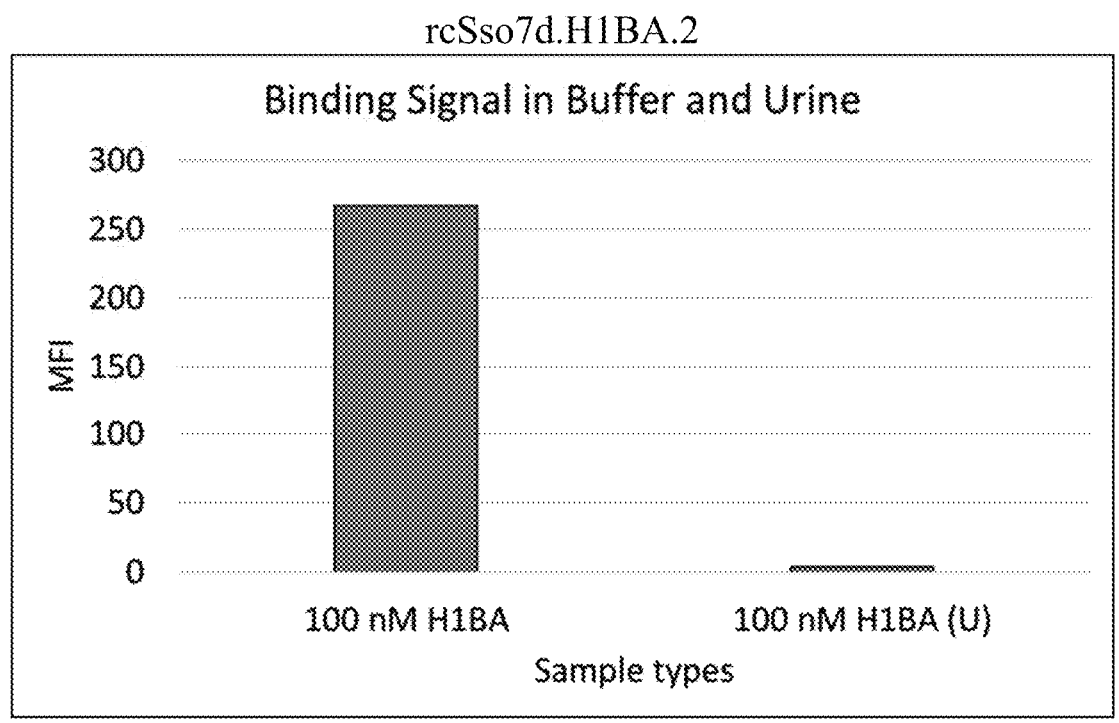

FIG. 90 shows the binding activity of rcSso7d.H1BA.2 binder against urine-treated analytes, quantified using the geometric mean fluorescence intensity, rather than population proportions.

Figure 91:
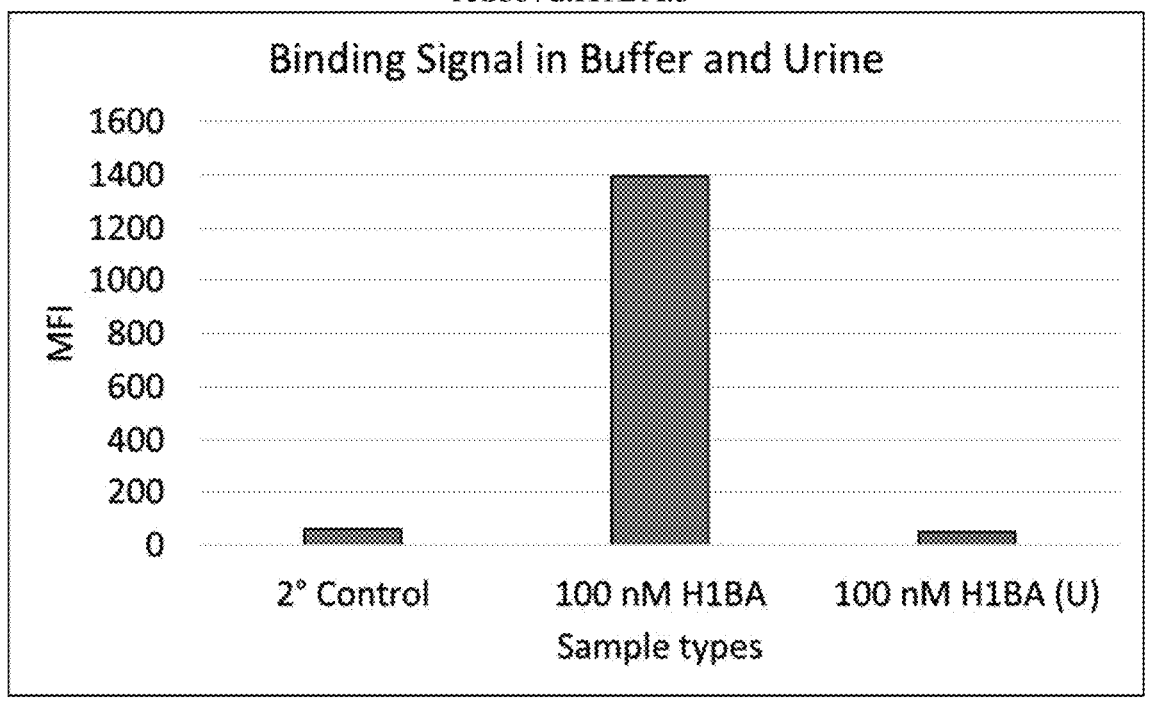

FIG. 91 shows the binding activity of rcSso7d.H1BA.3 binder against urine-treated analytes, quantified using the geometric mean fluorescence intensity, rather than population proportions.

Figure 92:
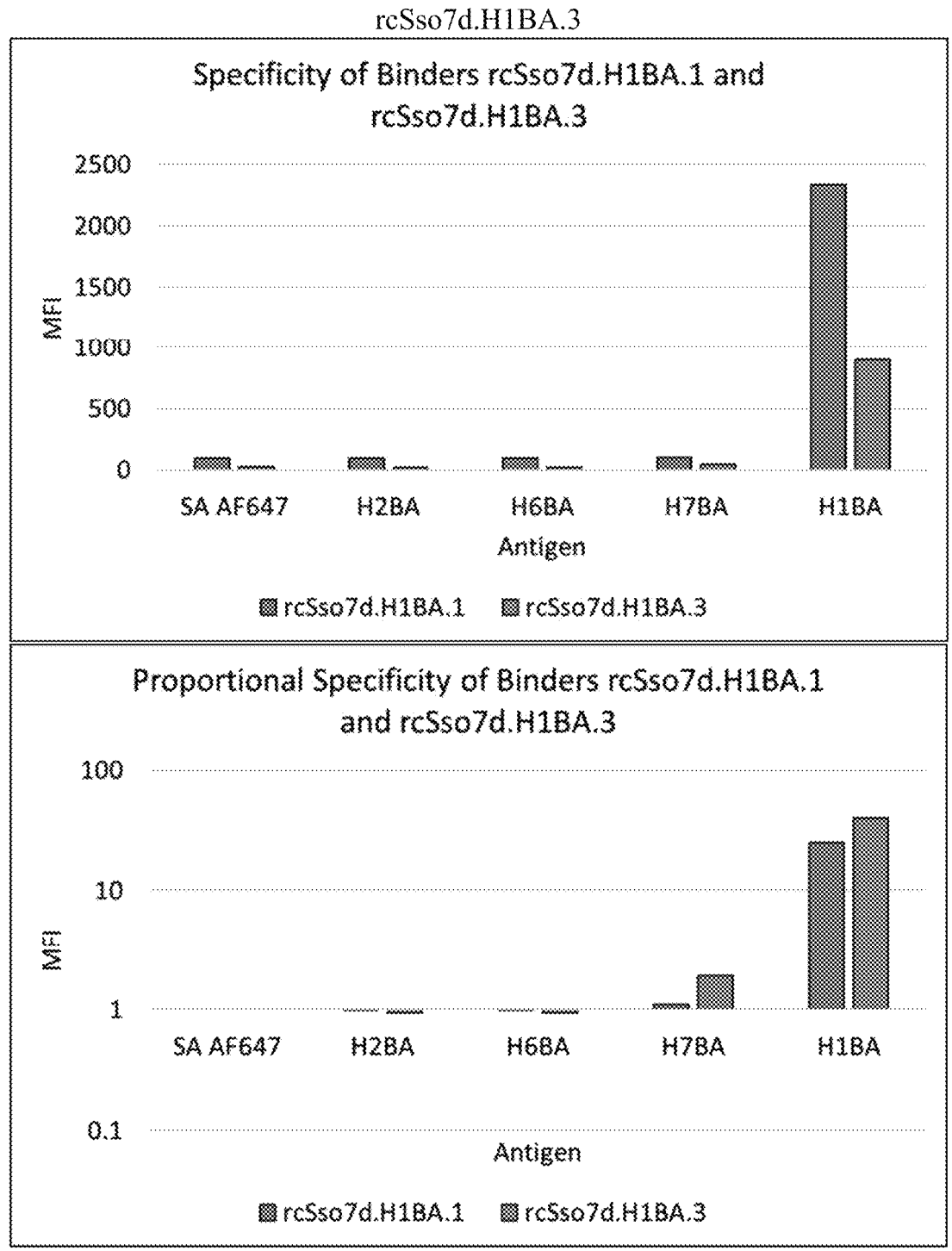

FIG. 92 shows the specificity and proportional specificity of binders rcSso7d.H1BA.1 and rcSso7d.H1BA.3.

Figure 93:
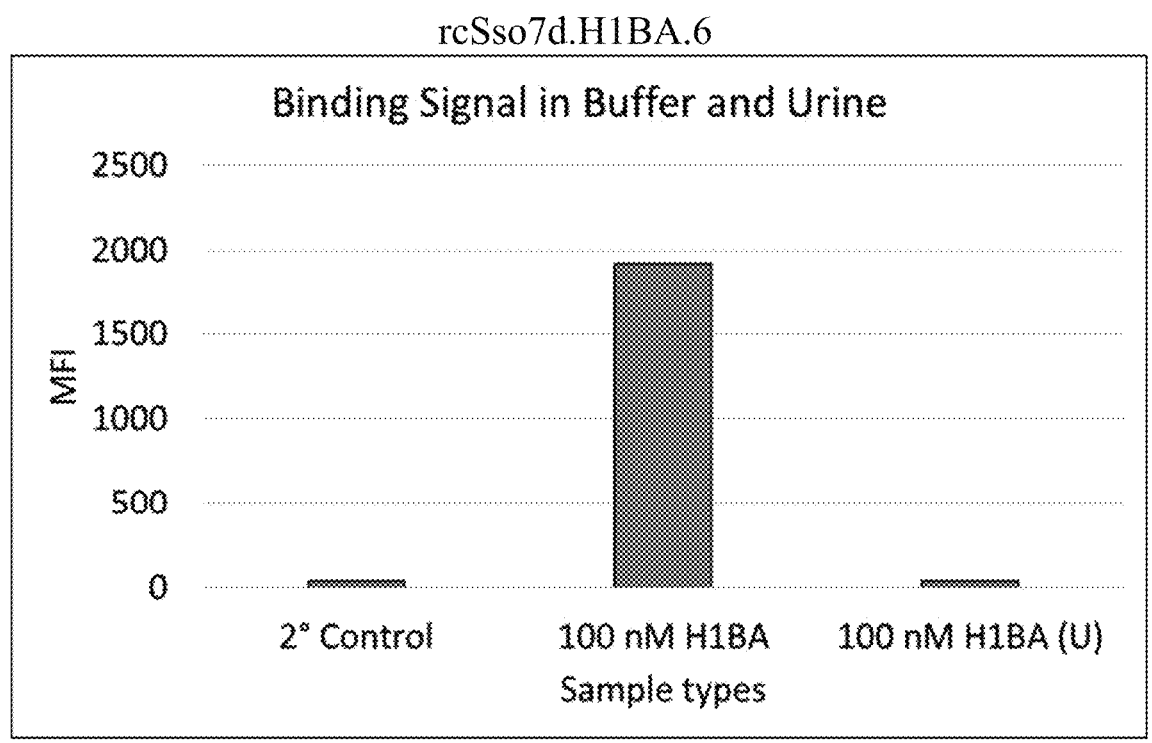

FIG. 93 shows the binding activity of rcSso7d.H1BA.6 binder against urine-treated analytes, quantified using the geometric mean fluorescence intensity, rather than population proportions.

Figure 94:
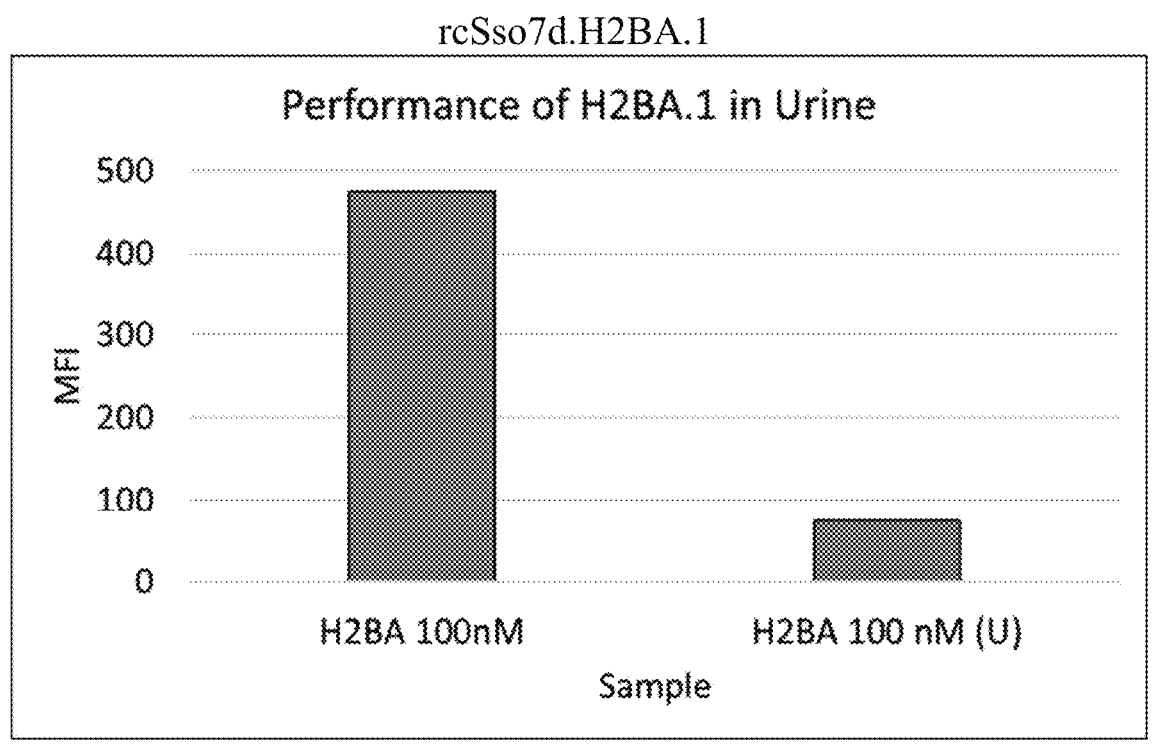

FIG. 94 shows the binding activity of rcSso7d.H2BA.1 binder against urine-treated analytes, quantified using the geometric mean fluorescence intensity, rather than population proportions.

Figure 95A:
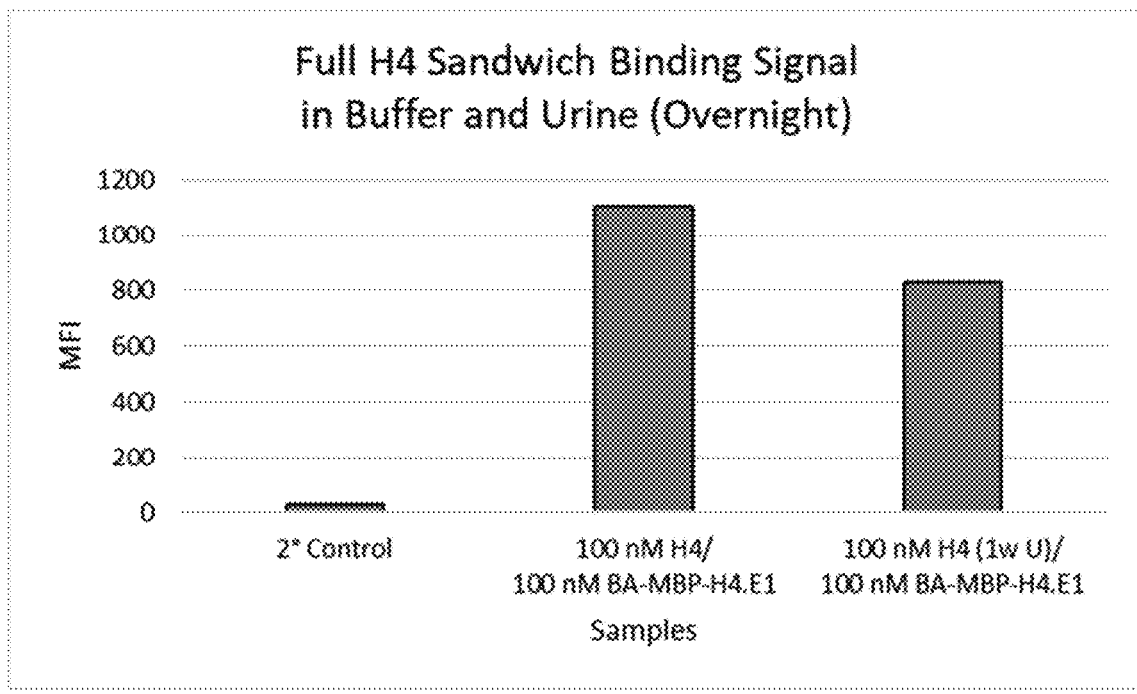
Figure 95B:
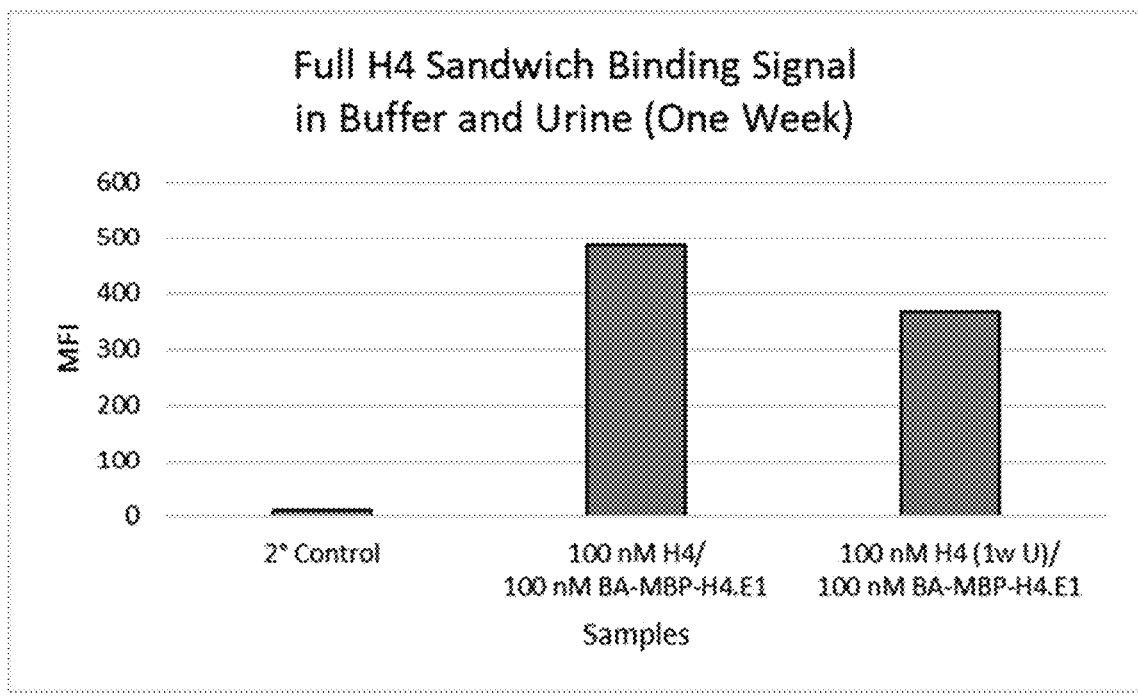

FIGS. 95A-95B show H4 full sandwich performance, overnight urine (FIG. 95A), and 1 week urine (FIG. 95B), against urine-treated analytes, quantified using the geometric mean fluorescence intensity, rather than population proportions.

Figure 96:
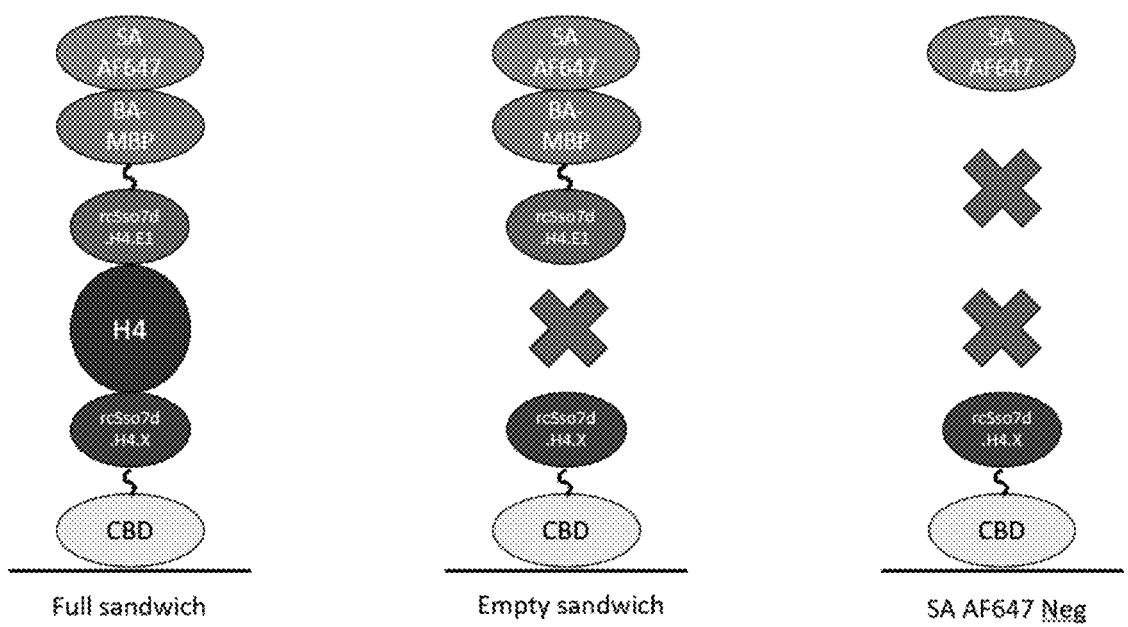

FIG. 96 is a schematic of H4 sandwich assays.

Figure 97:
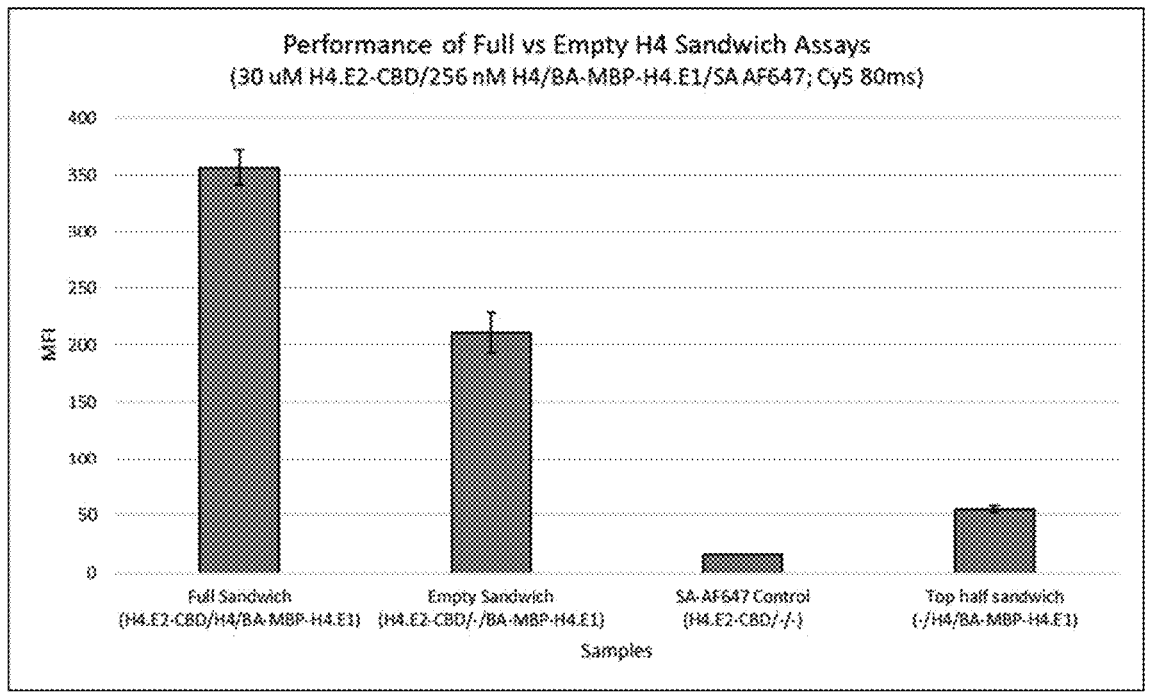

FIG. 97 shows the performance of full vs. empty H4 sandwich assays. BA-MBP-rcSso7d.H4.1 and rcSso7d.H4.2-CBD yield full sandwich.

Figure 98:
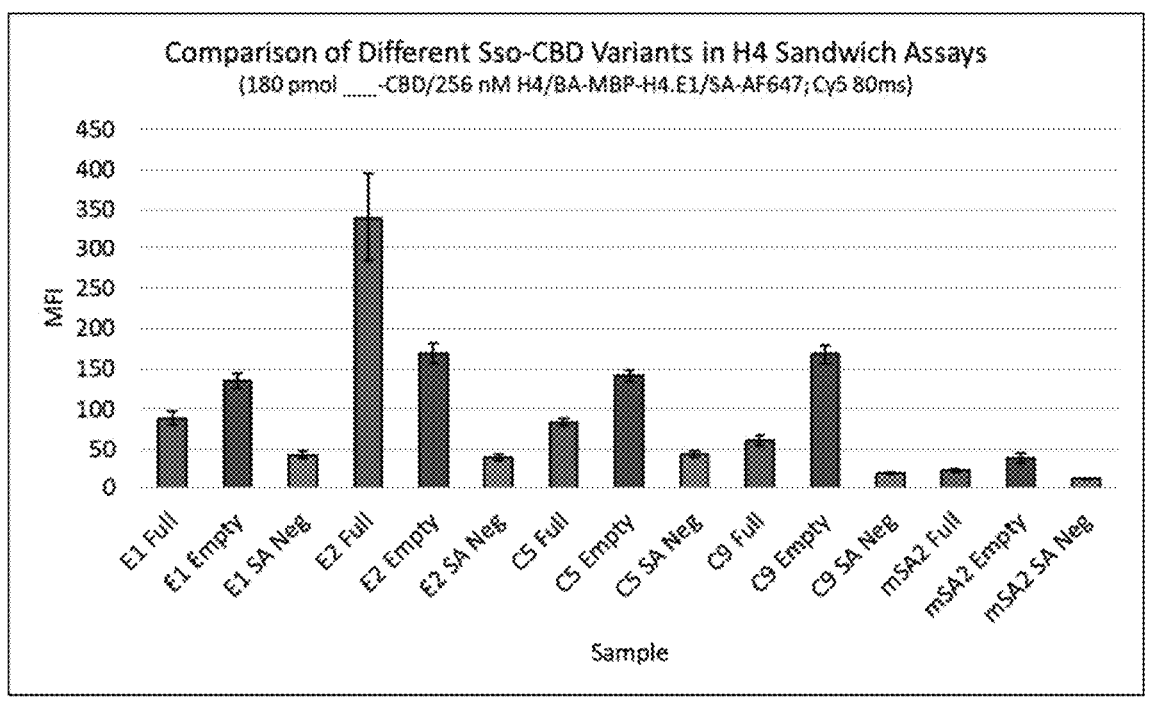

FIG. 98 shows a comparison of different Sso-CBD Variants in H4 sandwich assays. Only rcSso7d.H4.2-CBD yields full sandwich performance.

Figure 99:
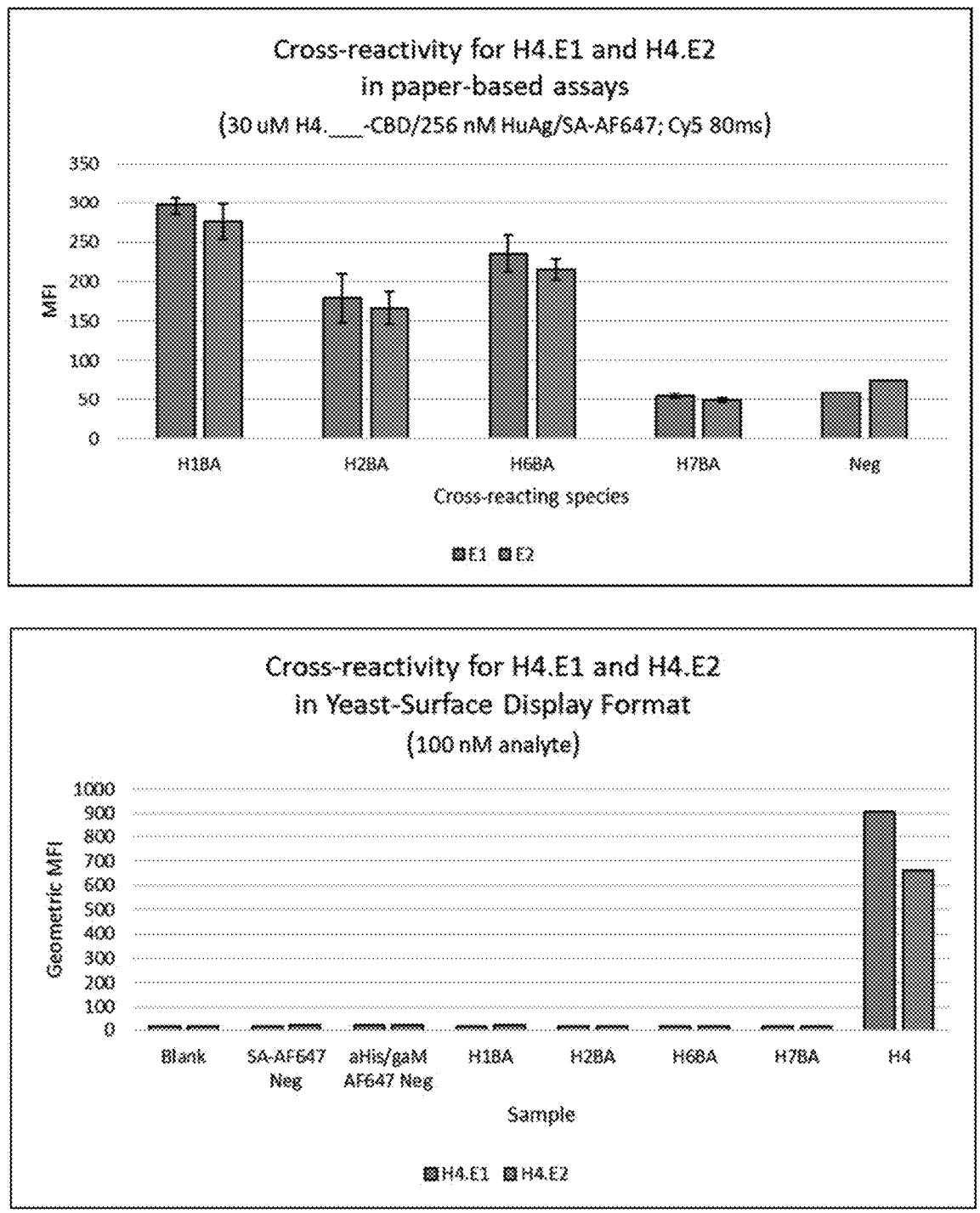

FIG. 99 shows cross-reactivity for H4.E1 and H4.E2 in paper-based assays and in yeast-surface display format.

Figure 100:
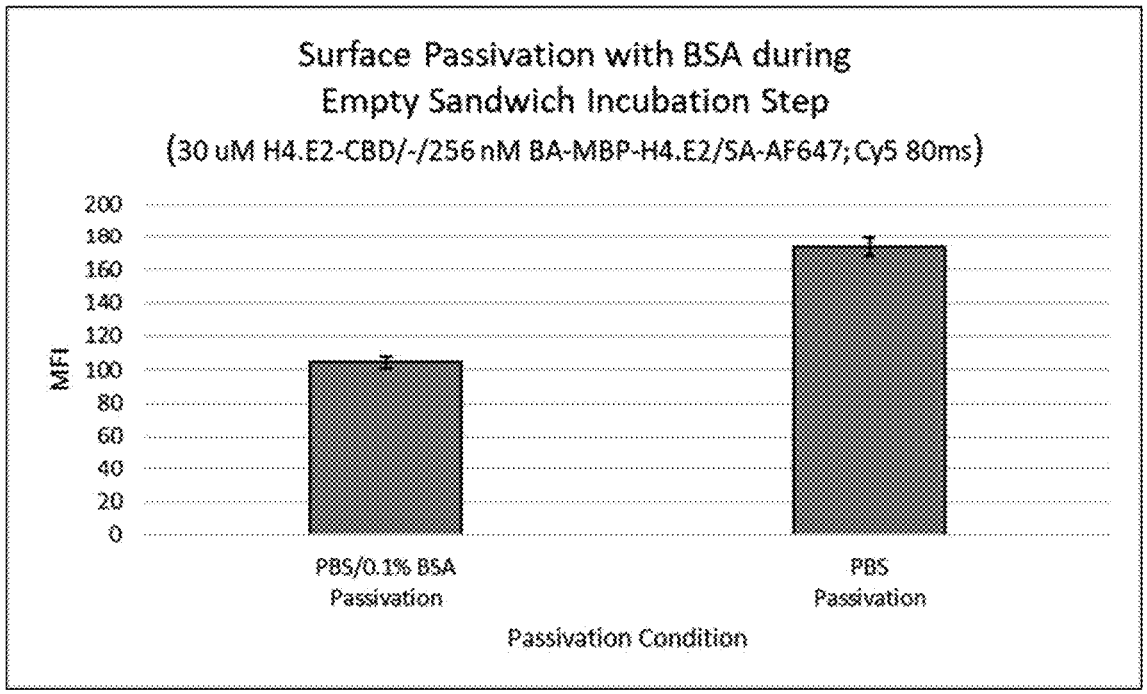

FIG. 100 shows the reduction of nonspecific binding via BSA passivation.

Figure 101:
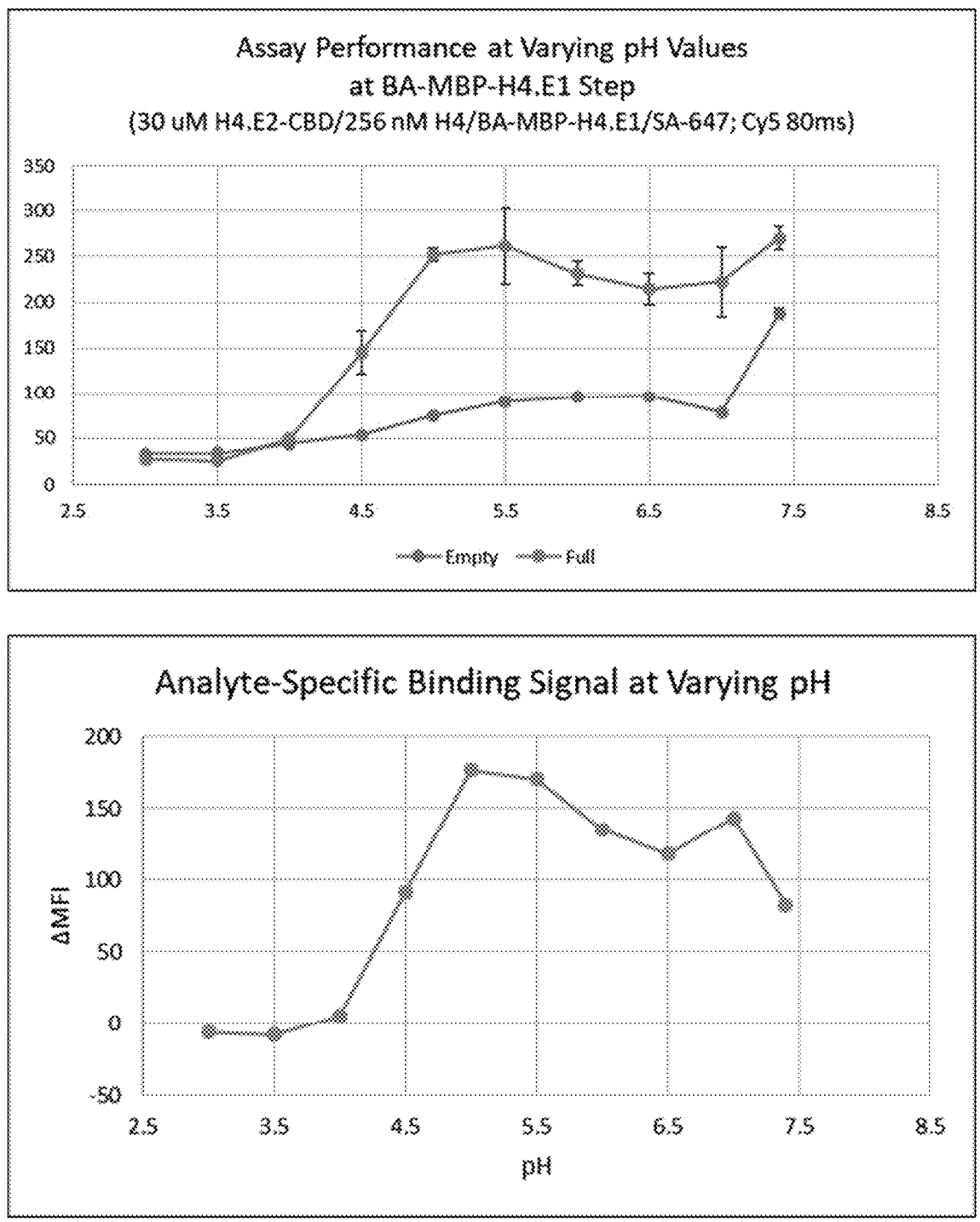

FIG. 101 shows assay performance and analyte-specific binding signal at varying pH values. The results indicate the reduction of non-specific detection reagent binding at pH 5.

Figure 102:
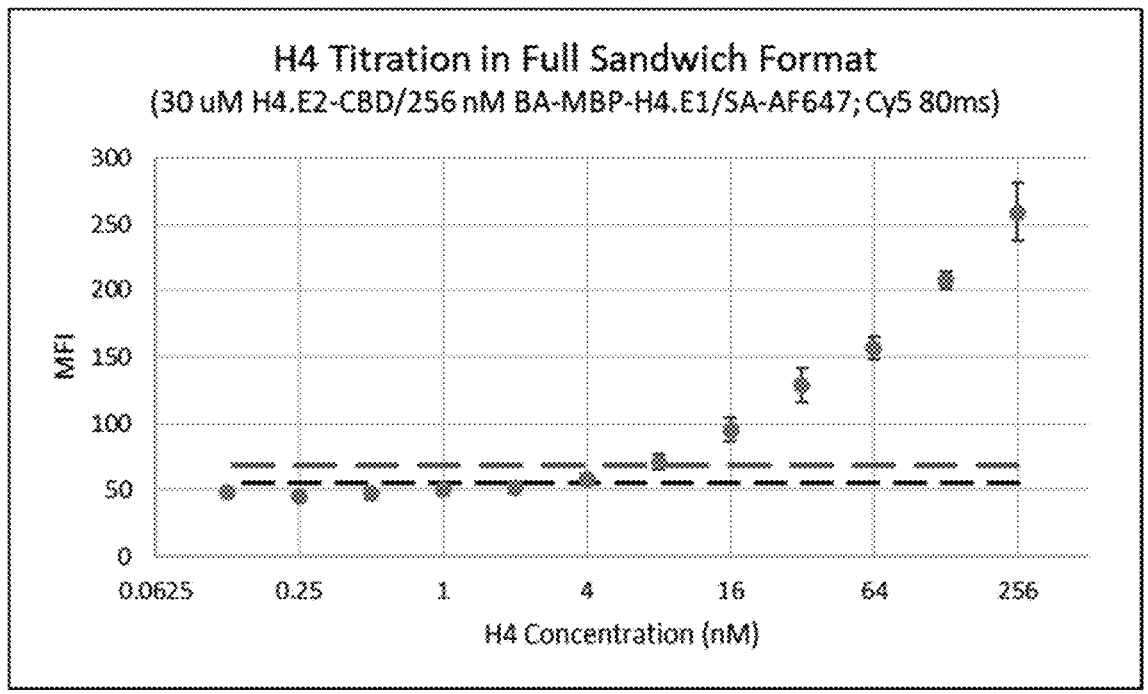

FIG. 102 depicts that H4 titration in full sandwich format with pH 5 wash shows LOD of 8 nM.

Figure 103:
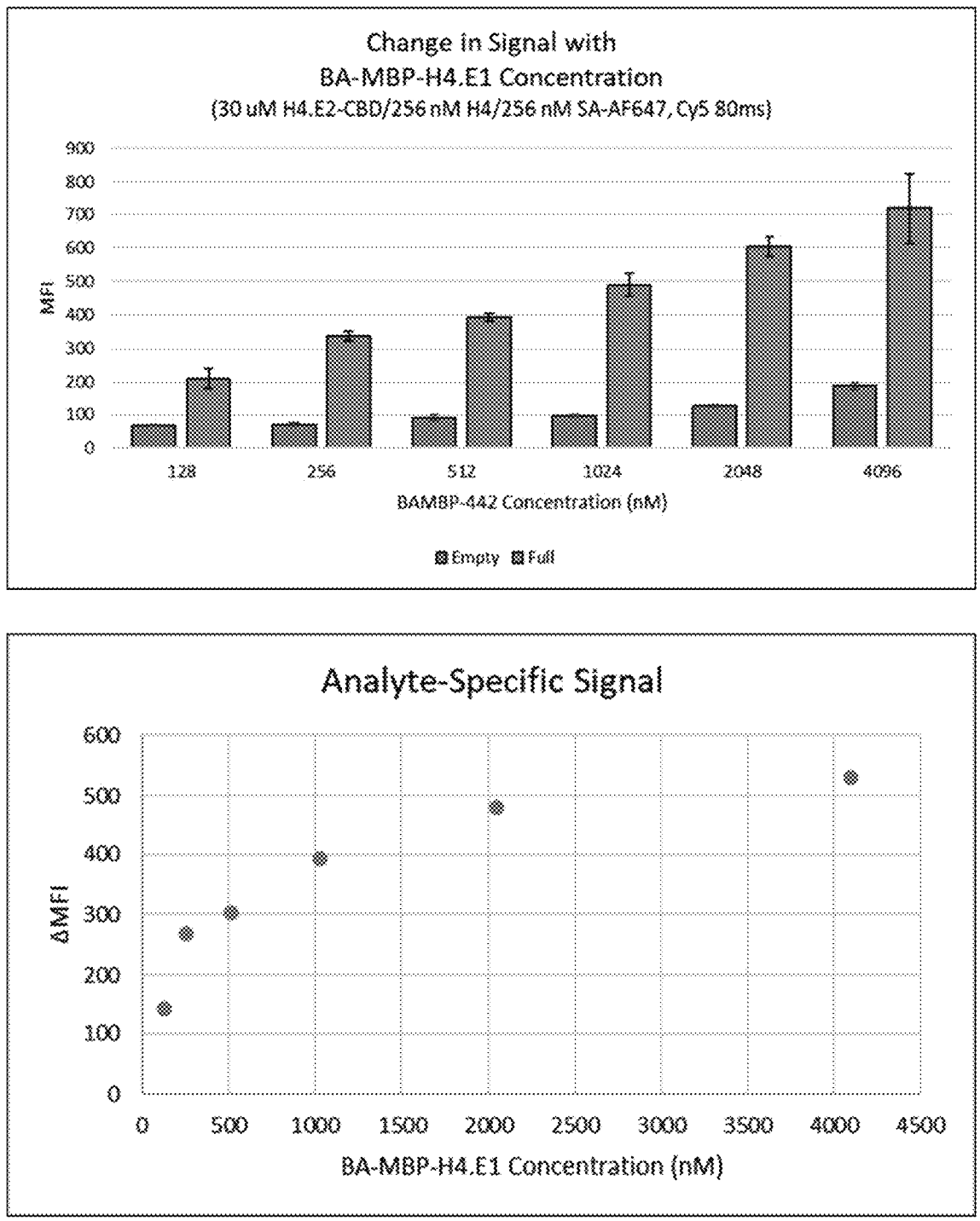

FIG. 103 shows change in signal with BA-MBP-H4.E1 concentration, and analyte-specific signal. The results show that increased signal was observed with increased BA-MBP-H4.1 concentration.

DETAILED DESCRIPTION

According to the law of mass action, the stoichiometry and kinetics of a target-binding interaction can be favorably influenced via three general approaches: i) increasing the molar abundance and concentration of the soluble antigen, ii) increasing the abundance and concentration of its surface-immobilized binding partner, or iii) enhancing the affinity of this binding interaction under relevant assay conditions. (Esteban et al., 2013) These guiding principles have been borne out in numerous experimental studies, which have demonstrated the advantageous impact of antigen pre-concentration (Ahmed et al., 2016; Giri et al., 2016; Tang et al., 2016) and enhanced binding affinity (Kaastrup et al., 2013; Ricci et al., 2016) upon target capture and assay sensitivity.

Previous studies have also explored the impact of the abundance of the surface-immobilized binding species upon the sensitivity of analyte detection. (Esteban et al., 2013; Parsa et al., 2008; Peluso et al., 2003) However, while these studies confirmed improved diagnostic sensitivity for assays conducted at a higher abundance of immobilized binder, only modest densities of surface-bound species (e.g., picomoles/cm$^2$) were achieved, and the target analyte was in molar excess of the immobilized binders. The implications of operating within the true target-depletion regime, wherein the binding protein is present in significant molar excess of the analyte, have not been thoroughly investigated.

In order to explore the consequences of enhanced binder immobilization upon target capture efficiency, a simplified binding model has been developed which employs a pseudo first-order rate constant (PFORC) to describe the antigen-binding interaction. This PFORC assumes a significant molar excess of the immobilized binding species, such that the abundance of available binder is effectively undiminished by the capture of soluble antigen. These modeling results indicate that within this high-abundance adsorption regime, the target antigen is rapidly and efficiently depleted from solution. Furthermore, this model suggests that at a large molar excess, the affinity of the immobilized binder has little effect upon the capture efficiency—so long as the local concentration of surface-bound species is at least ten-fold higher than the dissociation constant ($K_D$), the binding reaction will proceed to near-completion. Thus, if this molar excess can be achieved, protein engineering efforts need not be invested into the affinity maturation of selected binders—depending on the specific immobilized abundance, a modest binding affinity in the high nanomolar or even low micromolar range could be sufficient for efficient target capture.

Figure 1:
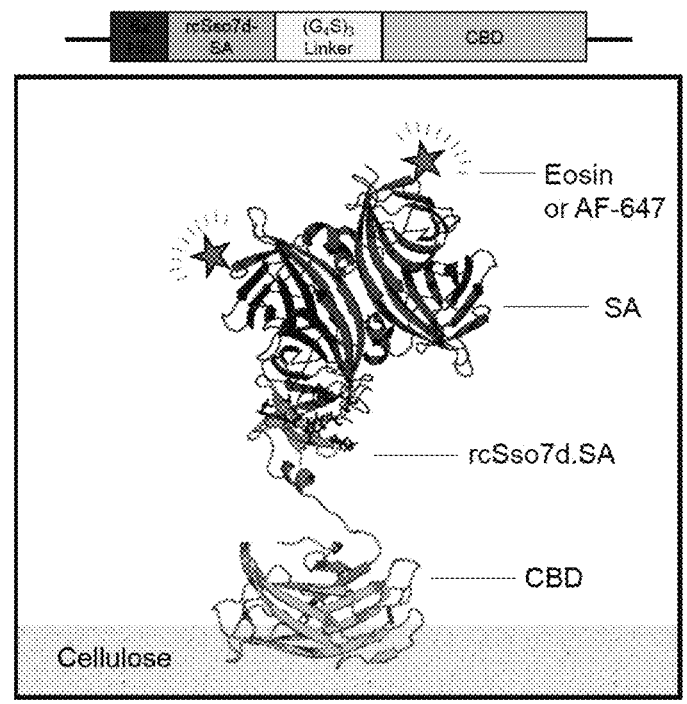
FIG. 1. Schematic representation of the rcSso7d.SA-CBD genetic construct, and the relevant binding complexes for this immunoassay format. CBD: cellulose binding domain; rcSso7d: reduced charge protein Sso7d from *Sulfolobus solfataricus*; SA: streptavidin; AF-647: ALEXA FLUOR®647. PDB Structures: 4JO5 (CBD); (Yaniv et al., 2013) 1SSO (Sso7d); (Baumann et al., 1994) 1MEP (SA). (Hyre et al., 2006)

The predictions of this PFORC model were validated experimentally using a bifunctional fusion protein construct that combines a Type 3a cellulose-binding domain (CBD) with a modular binding scaffold based on the thermostable rcSso7d protein (Miller et al., 2016; Traxlmayr et al., 2016) (FIG. 1). Previous studies have demonstrated the use of CBD fusion proteins for the bio-functionalization of cellulose substrates, in applications including protein purification, (Sugimoto et al., 2012; Tomme et al., 1998) textile manufacturing, (Levy and Shoseyov, 2002) and immunoassay development. (Dai et al., 2016; Holstein et al., 2016; Hussack et al., 2009; Kim et al., 2013) These studies have indicated that this CBD species adsorbs to cellulose in molar quantities which, in a standard diagnostic context, would yield a significant excess of immobilized protein relative to the soluble target. (Dai et al., 2016; Li et al., 2016) The experimental studies have confirmed that the use of this substrate-anchoring domain in a paper-based assay format permits the rapid and oriented adsorption of the antigen-binding protein (e.g., engineered reduced charge rcSso7d) on unmodified chromatography paper (e.g., WHATMAN® Grade 1 Qualitative Filtration Paper) in sufficient abundance to completely capture all of the antigen from solution and thereby deplete the antigen from the solution. In some embodiments, up to 0.5 nanomoles of antigen from solution were captured, thereby depleting all antigen from 10 µL of a 50 µM solution. For the sample volumes and antigen concentrations observed in typical diagnostic assays (i.e. microliters, and concentrations in the picomolar to low nanomolar range), this antigen-binding protein abundance may represent greater than a 1000-fold molar excess relative to the soluble target. The high local concentration of this immobilized CBD fusion protein within the paper substrate (~760 µM) also increases the rate of target capture, biasing the binding equilibrium toward the rapid depletion of the dilute antigen from solution. At this molar abundance, target antigens are captured from solution with nearly 100% efficiency, maximizing the attainable sensitivity for any given diagnostic system.

This surface-anchoring approach can be adapted to any substrate for which there is a known anchoring moiety, so long as the given bulk material features sufficient accessible surface area for the high-abundance immobilization of the binding construct, and is also structured so as to facilitate efficient transport of the antigen to the surface. For instance, solid-binding peptides have been used to immobilize biomolecules to a variety of substrates, ranging from metals and metal oxides to plastics, minerals, semiconductors, and carbon-based materials. (Care et al., 2017, 2015; Kumada, 2014; Seker and Demir, 2011) This strategy can also be extended to any immobilized target or class of binding domain which can interact with or be expressed as a genetic fusion to this anchoring moiety (e.g. antigens, antibodies and antibody fragments, non-antibody binding scaffolds, DNA oligonucleotides and aptamers, etc.). (Holstein et al., 2016; Hussack et al., 2009; Rosa et al., 2014).

Lastly, this system has also been shown to be generalizable across varying soluble targets—the enhanced capture efficiency of the rcSso7d-CBD fusion protein was confirmed using two different engineered rcSso7d antigen-binding protein variants. One engineered rcSso7d antigen-binding protein variant was raised against the 52.8-kDa model antigen streptavidin and attached to CBD (rcSso7d.SA-CBD). Thus, the rcSso7d.SA-CBD fusion protein contains a motif (e.g., amino acid sequence) that binds to or recognizes streptavidin. Another engineered rcSso7d antigen-binding protein variant was raised against the 33.1-kDa urine-based biomarker of active tuberculosis, Rv1656 (Napolitano et al., 2008) and attached to CBD (rcSso7d.Rv1656-CBD). Thus, the rcSso7d.Rv1656-CBD fusion protein contains a motif (e.g., amino acid sequence) that binds to or recognizes the antigen Rv1656.

Accordingly, aspects of the present disclosure relate to the development of a general strategy to enhance the capture of a target, such as a target molecule or antigen of interest, using a bifunctional fusion protein which includes an antigen-binding protein or antigen-binding domain and a substrate-anchoring domain, such as a cellulose binding domain (CBD) or a carbohydrate binding module (CBM).

Bifunctional Fusion Proteins

In some aspects, provided herein is a bifunctional fusion protein that incorporates a substrate-anchoring domain and a target-binding domain, such as an antigen-binding protein or an antigen-binding domain. In some embodiments, the substrate-anchoring domain is a CBM or CBD. In some embodiments the CBM has carbohydrate-binding activity. In some embodiments, the CBM is CBM1, CBM2, CBM3, CBM4, CBM5, CBM6, CBM9, CBM10, CBM11, CBM12, CBM14, CBM15, CBM17, CBM18, CBM19, CBM20, CBM21, CBM25, CBM27, CBM28, CBM32, CBM33, CBM48, or CBM49. The nucleic acid and amino acid sequences of CBMs contemplated herein have been described, such as those disclosed in www.cazypedia.org/index.php/Carbohydrate-binding_modules, and can be readily identified by one of ordinary skill in the art using a BLAST search.

In some embodiments, the substrate-anchoring domain is a CBD. Orthologs of CBDs have been described in various species, including, but not limited to *Micromonospora mirobrigensis* (GenBank ID: SCF42127.1), *Mycobacterium tuberculosis* (GenBank ID: CNE10097.1), *Micromonospora nigra* (GenBank ID: SCL15442.1), *Micromonospora mirobrigensis* (GenBank ID: SCF04121.1), Cellulomonas Fimi (PDB: 1EXH_A), *Mycobacterium kansasii* 732 (GenBank: EUA13076.1), *Ruminococcus albus* 8 (GenBank: EGC02462.1), *Leifsonia aquatic* (NCBI Reference Sequence: WP_021763186.1), *Schizosaccharomyces pombe* (NCBI Reference Sequence: NP_593986.1), *Desulfitobacterium hafniense* (GenBank: CDX04743.1). CBDs expressed in other species that are known to one of ordinary skill in the art, such as CBDs of families I, II, III and IV disclosed, for instance, in Tomme et al., *J Chromatogr B Biomed Sci Appl* (1998) 715(1):283-96, are also contemplated herein.

Different types of CBDs are also contemplated herein. In some embodiments, a type 1 CBD is contemplated herein and serves as the substrate-anchoring domain of a bifunctional fusion protein described herein. In some embodiments, the type 1 CBD is identified by SEQ ID NO: 10.

Amino acid sequence of type 1 CBD (SEQ ID NO: 10)

```
                                          (SEQ ID NO: 10)
AGPGANPPGTTTTSRPATTTGSSPGPQACSSVWGQCGGQNWSGPTCCASGS

TCVYSNDYYSQCLPGANPPGTTTTSRPATTTGSSPGPTQSHYGQCGGIGYS

GPTVCASGTTCQVLNPYYSQCL
```

Orthologs of type 1 CBDs have been described in various species, including, but not limited to *Trichoderma reesei* QM6a (NCBI Reference Sequence: XP_006969224.1); *Rhizopus oryzae* (GenBank: BAC53988.1); *Schizosaccharomyces japonicus* yFS275 (NCBI Reference Sequence: XP_002172247.1); *Trichoderma virens* Gv29-8 (NCBI Reference Sequence: XP_013954979.1); *Trichoderma viride* (GenBank: CAA37878.1) are also contemplated herein. Type 1 CBDs or orthologs thereof in other species known to one of ordinary skill in the art are also contemplated herein.

In some embodiments, a type 3a CBD is contemplated herein and serves as the substrate-anchoring domain of a bifunctional fusion protein described herein. In some embodiments, the type 3a CBD is a domain of the CipA protein from *Clostridium thermocellum* (Genbank: HF912725.1; UniProtKB/TrEMBL: N1JW75)

Amino acid sequence of CipA protein from *Clostridium thermocellum* (SEQ ID NO: 1)

```
                                         (SEQ ID NO: 1)
MRKVISMLLV VAMLTTIFAA MIPQTVSAAT MTVEIGKVTA

AVGSKVEIPI TLKGVPSKGM ANCDFVLGYD PNVLEVTEVK

PGSIIKDPDP SKSFDSAIYP DRKMIVFLFA EDSGRGTYAI

TQDGVFATIV ATVKSAAAAP ITLLEVGAFA DNDLVEISTT

FVAGGVNLGS SVPTTQPNVP SDGVVVEIGK VTGSVGTTVE

IPVYFRGVPS KGIANCDFVF RYDPNVLEII GIDPGDIIVD

PNPTKSFDTA IYPDRKIIVF LFAEDSGTGA YAITKDGVFA

KIRATVKSSA PGYITFDEVG GFADNDLVEQ KVSFIDGGVN

VGNATPTKGA TPTNTATPTK SATATPTRPS VPTNTPTNTP

ANTPVSGNLK VEFYNSNPSD TTNSINPQFK VTNTGSSAID

LSKLTLRYYY TVDGQKDQTF WCDHAAIIGS NGSYNGVTSN

VKGTFVKMSS STNNADTYLE ISFTGGTLEP GAHVQIQGRF

AKNDWSNYTQ SNDYSFKSAS QFVEWDQVTA YLNGVLVWGK

EPGGSVVPST QPVTTPPATT KPPATTIPPS DDPNAIKIKV

DTVNAKPGDT VNIPVRFSGI PSKGIANCDF VYSYDPNVLE

IIEIKPGELI VDPNPDKSFD TAVYPDRKII VFLFAEDSGT

GAYAITKDGV FATIVAKVKS GAPNGLSVIK FVEVGGFANN

DLVEQKTQFS DGGVNVGGTT VPTTPPASTT PTDDPNAIKI

KVDTVNAKPG DTVNIPVRFS GIPSKGIANC DFVYSYDPNV

LEIIEIKPGE LIVDPNPDKS FDTAVYPDRK IIVFLLTEDS

GTGAYAITKD GVFATIVAKV KSGAPNGLSV IKFVEVGGFA

NNDLVEQKTQ FFDGGVNVGD TTVPTTPTTP VTTPTDDPNA

VRIKVDTVNA KTGDTVRIPV RFSGIPSKGI ANCDFVYSYD

PNVLEIIEIE PGDIIVDPNP DKSFDTAVYP DRKIIVFLFA

EDSGTGAYAI TKDGVFATIV AKVKSGAPNG LSVIKFVEVG

GFANNDLVEQ KTQFFDGGVN VGDTTEPATP TTPVTTPTTT

DGLDAVRIKV DTVNAKPGDT VRIPVRFSGI PSKGIANCDF

VYSYDPNVLE IIEIEPGDII VDPNPDKSFD TAVYPDRKII

VFLFAEDSGT GAYAITKDGV FATIVAKVKS GAPNGLSVIK

FVEVGGFANN DLVEQRTQFF DGGVNVGDTT VPTTPTTPVT

TPTDDSNAVR IKVDTVNAKP GDTVRIPVRF SGIPSKGIAN

CDFVYSYDPN VLEIIEIEPG DIIVDPNPDK SFDTAVYPDR

KIIVFLFAED SGTGAYAITK DGVFATIVAK VKSGAPNGLS

VIKFVEVGGF ANNDLVEQKT QFFDGGVNVG DTTVPTTSPT

TTPPEPTIAP NKLTLKIGRA EGRPGDTVEI PVNLYGVPQK

GIASGDFVVS YDPNVLEIIE IEPGELIVDP NPTKSFDTAV

YPDRKMIVFL FAEDSGTGAY AITEDGVFAT IVAKVKEGAP

EGFSAIEISE FGAFADNDLV EVETDLINGG VLVTNKTVIE

GYKVSGYILP DFSFDATVAP LVKAGFKVEI VGTELYAVTD

ANGYFEITGV PANASGYTLK ISRATYLDRV IANVVVTGDT

SVSTSQAPIM MWVGDIVKDN SINLLDVAEV IRCFNATKGS

ANYVEELDIN RNGAINMQDI MIVHKHFGAT SSDY
```

In some embodiments, the underlined valine (V) residue of SEQ ID NO: 1 is an isoleucine (I), which corresponds to SEQ ID NO: 15.

Amino acid sequence of CipA protein from *Clostridium thermocellum* with an isoleucine in place of a valine (SEQ ID NO:15)

```
                                         (SEQ ID NO: 15)
MRKVISMLLV VAMLTTIFAA MIPQTVSAAT MTVEIGKVTA

AVGSKVEIPI TLKGVPSKGM ANCDFVLGYD PNVLEVTEVK

PGSIIKDPDP SKSFDSAIYP DRKMIVFLFA EDSGRGTYAI

TQDGVFATIV ATVKSAAAAP ITLLEVGAFA DNDLVEISTT

FVAGGVNLGS SVPTTQPNVP SDGVVVEIGK VTGSVGTTVE

IPVYFRGVPS KGIANCDFVF RYDPNVLEII GIDPGDIIVD

PNPTKSFDTA IYPDRKIIVF LFAEDSGTGA YAITKDGVFA

KIRATVKSSA PGYITFDEVG GFADNDLVEQ KVSFIDGGVN

VGNATPTKGA TPTNTATPTK SATATPTRPS VPTNTPTNTP

ANTPVSGNLK VEFYNSNPSD TTNSINPQFK VTNTGSSAID

LSKLTLRYYY TVDGQKDQTF WCDHAAIIGS NGSYNGITSN

VKGTFVKMSS STNNADTYLE ISFTGGTLEP GAHVQIQGRF

AKNDWSNYTQ SNDYSFKSAS QFVEWDQVTA YLNGVLVWGK

EPGGSVVPST QPVTTPPATT KPPATTIPPS DDPNAIKIKV

DTVNAKPGDT VNIPVRFSGI PSKGIANCDF VYSYDPNVLE

IIEIKPGELI VDPNPDKSFD TAVYPDRKII VFLFAEDSGT
```

-continued

```
GAYAITKDGV FATIVAKVKS GAPNGLSVIK FVEVGGFANN

DLVEQKTQFS DGGVNVGGTT VPTTPPASTT PTDDPNAIKI

KVDTVNAKPG DTVNIPVRFS GIPSKGIANC DFVYSYDPNV

LEIIEIKPGE LIVDPNPDKS FDTAVYPDRK IIVFLLTEDS

GTGAYAITKD GVFATIVAKV KSGAPNGLSV IKFVEVGGFA

NNDLVEQKTQ FFDGGVNVGD TTVPTTPTTP VTTPTDDPNA

VRIKVDTVNA KTGDTVRIPV RFSGIPSKGI ANCDFVYSYD

PNVLEIIEIE PGDIIVDPNP DKSFDTAVYP DRKIIVFLFA

EDSGTGAYAI TKDGVFATIV AKVKSGAPNG LSVIKFVEVG

GFANNDLVEQ KTQFFDGGVN VGDTTEPATP TTPVTTPTTT

DGLDAVRIKV DTVNAKPGDT VRIPVRFSGI PSKGIANCDF

VYSYDPNVLE IIEIEPGDII VDPNPDKSFD TAVYPDRKII

VFLFAEDSGT GAYAITKDGV FATIVAKVKS GAPNGLSVIK

FVEVGGFANN DLVEQRTQFF DGGVNVGDTT VPTTPTTPVT

TPTDDSNAVR IKVDTVNAKP GDTVRIPVRF SGIPSKGIAN

CDFVYSYDPN VLEIIEIEPG DIIVDPNPDK SFDTAVYPDR

KIIVFLFAED SGTGAYAITK DGVFATIVAK VKSGAPNGLS

VIKFVEVGGF ANNDLVEQKT QFFDGGVNVG DTTVPTTSPT

TTPPEPTIAP NKLTLKIGRA EGRPGDTVEI PVNLYGVPQK

GIASGDFVVS YDPNVLEIIE IEPGELIVDP NPTKSFDTAV

YPDRKMIVFL FAEDSGTGAY AITEDGVFAT IVAKVKEGAP

EGFSAIEISE FGAFADNDLV EVETDLINGG VLVTNKTVIE

GYKVSGYILP DFSFDATVAP LVKAGFKVEI VGTELYAVTD

ANGYFEITGV PANASGYTLK ISRATYLDRV IANVVVTGDT

SVSTSQAPIM MWVGDIVKDN SINLLDVAEV IRCFNATKGS

ANYVEELDIN RNGAINMQDI MIVHKHFGAT SSDY
```

The amino acid sequence of the type 3a CBD of CipA protein from *Clostridium thermocellum*, which corresponds to amino acids 364-522 of the CipA protein from *Clostridium thermocellum* corresponds to SEQ ID NO: 2.

```
                                           (SEQ ID NO: 2)
PVSGNLK VEFYNSNPSD TTNSINPQFK VTNTGSSAID LSKLTLRYYY

TVDGQKDQTF WCDHAAIIGS NGSYNGVTSN VKGTFVKMSS

STNNADTYLE ISFTGGTLEP GAHVQIQGRF AKNDWSNYTQ

SNDYSFKSAS QFVEWDQVTA YLNGVLVWGK EP
```

In some embodiments, the underlined valine (V) residue of SEQ ID NO: 2 is an isoleucine (I), which corresponds to SEQ ID NO: 16.

```
                                          (SEQ ID NO: 16)
PVSGNLK VEFYNSNPSD TTNSINPQFK VTNTGSSAID LSKLTLRYYY

TVDGQKDQTF WCDHAAIIGS NGSYNGITSN VKGTFVKMSS
```

-continued

```
STNNADTYLE ISFTGGTLEP GAHVQIQGRF AKNDWSNYTQ

SNDYSFKSAS QFVEWDQVTA YLNGVLVWGK EP
```

Orthologs of type 3a CBDs have been described in various species, including, but not limited to *Ruminiclostridium thermocellum* AD2 (GenBank: ALX08828.1), *Caldicellulosiruptor lactoaceticus* 6A (GenBank: AEM74847.1), *Niastella koreensis* GR20-10 (GenBank: AEV99440.1), *Actinobacteria bacterium* OV450 (GenBank: KPH97519), *Spirosoma linguale* DSM 74 (GenBank: ADB37689.1). Type 3 CBDs, including type 3a CBDs, from other species known to one of ordinary skill in the art are also contemplated herein.

In some embodiments, the CBD includes a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 1.

In some embodiments, the type 1 CBD includes a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 10.

In some embodiments, the type 3a CBD includes a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 2 or SEQ ID NO: 16.

In some embodiments, the CBD includes a variant which is shorter or longer than the amino acid sequence of SEQ ID NO: 1 or SEQ ID NO: 15 by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, by 200 amino acids, by 300 amino acids, by 400 amino acids, by 500 amino acids, 800 amino acids, 1000 amino acids, 1200 amino acids, 1400 amino acids or more.

In some embodiments, the type 1 CBD includes a variant which is shorter or longer than the amino acid sequence of a type 1 CBD of SEQ ID NO: 10 by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more.

In some embodiments, the type 3a CBD includes a variant which is shorter or longer than the amino acid sequence of a CBD of SEQ ID NO: 2 or SEQ ID NO: 16 by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more.

According to some aspects, the bifunctional fusion protein contains a target-binding domain, such as an antigen-binding protein or antigen-binding domain. In some embodiments, the antigen-binding protein is an engineered Sso7d antigen-binding protein. The Sso7d protein from the hyperthermophilic archaeon *Sulfolobus solfataricus* is a small protein (7 kDa) with high thermal stability ($T_m$ of 98° C.), which is highly positively charged since it is a DNA-binding protein. The high positive charges in Sso7d introduce a strong specificity constraint for binding epitopes and leads to nonspecific interaction with mammalian cell membranes. Charge-neutralized variants of Sso7d that maintain high thermal stability have been reported (Traxlmayr et al., *J Biol Chem* (2016) 291(43):22496-508).

In some embodiments, the Sso7d antigen-binding protein comprises the amino acid sequence of SEQ ID NO: 12, corresponding to the amino acid sequence of Sso7d from *Sulfolobus solfataricus* (UniProtKb: P39476; European Nucleotide Archive: AAK42212.1)

Amino acid sequence of Sso7d from *Sulfolobus solfataricus* (SEQ ID NO: 12):

```
                                       (SEQ ID NO: 12)
MATVKFKYKGEEKEVDISKIKKVWRVGKMISFTYDEGGGKTGRGAVSEKDA

PKELLQMLEKQKK
```

Orthologs of Sso7d have been described in various species, including *Sulfolobus islandicus* (NCBI Reference Sequence: WP_012713334.1), *Sulfolobus tokodaii* (NCBI Reference Sequence: WP_010978621.1), *Sulfolobus* sp. A20 (Sequence ID: WP_069284107.1), *Acidianus hospitalis* (NCBI Reference Sequence: WP_013777046.1), and *Acidianus manzaensis* (GenBank: ARM76167.1).

In some embodiments, the Sso7d antigen-binding protein is a reduced-charge variant of Sso7d (rcSso7d). In some embodiments, the rcSso7d antigen-binding protein comprises the amino acid sequence of SEQ ID NO: 3.

Amino acid sequence of rcSso7d from *Sulfolobus solfataricus* (SEQ ID NO: 3):

```
                                       (SEQ ID NO: 3)
MATVKFTYQGEEKQVDISKIKKVWRVGQMISFTYDEGGGATGRGAVSEKDA

PKELLQMLEKQ
```

In some embodiments, the engineered antigen-binding protein is Sso7a. In some embodiments, the Sso7a antigen-binding protein is from *Sulfolobus solfataricus* (UniProtKB: P61991; European Nucleotide Archive: AAK42090.1).

Amino acid sequence of Sso7a from *Sulfolobus solfataricus* (SEQ ID NO: 11):

```
                                       (SEQ ID NO: 11)
   MATVKFKYKG EEKQVDISKI KKVWRVGKMI SFTYDEGGGK

TGRGAVSEKD APKELLQMLE KQKK
```

In some embodiments, a reduced charge variant of Sso7a is contemplated herein.

In some embodiments, the antigen-binding protein is Sac7d from *Sulfolobus acidocaldarius* (UniProtKB: P13123). In some embodiments, the antigen-binding protein is a reduced-charge variant of Sac7d (rcSac7d).

Amino acid sequence of Sac7d from *Sulfolobus acidocaldarius* (SEQ ID NO: 13):

```
                                       (SEQ ID NO: 13)
   MVKVKFKYKG EEKEVDTSKI KKVWRVGKMV SFTYDDNGKT

GRGAVSEKDA PKELLDMLAR AEREKK
```

In some embodiments, the Sso7 antigen-binding protein is a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 3, SEQ ID NO: 11, SEQ ID NO: 12, or SEQ ID NO: 13.

In some embodiments, the Sso7 antigen-binding protein includes variants which are shorter or longer than amino acid sequence of SEQ ID NO: 3, SEQ ID NO: 11, SEQ ID NO: 12, or SEQ ID NO: 13 by about 5 amino acids, by about 10 amino acids, by about 15 amino acids, by about 20 amino acids, by about 25 amino acids, by about 30 amino acids, by about 40 amino acids, by about 50 amino acids, or more.

Any orthologs of the sequences described herein may be identified conducting a BLAST search of the sequence of interest.

In some embodiments, the bifunctional fusion protein incorporates a substrate-anchoring domain and a target-binding domain, in which the target-binding domain is expressed as a genetic fusion to the substrate-anchoring domain. In some embodiments, the target-binding domain is not expressed as a genetic fusion to the substrate-anchoring domain. In some embodiments, the target-binding domain interacts with the substrate-anchoring domain. Non-limiting examples of a target-binding domain includes, without limitation, antigens, enzymes, peptides, antibodies, antibody fragments, non-antibody binding scaffolds, DNA oligonucleotides, aptamers, etc. (See e.g., Care et al., *Trends Biotechnol* (2015) 33(5):259-68). Additional examples of a target-binding domain or a target-binding protein include, protein A, lipocalins, fibronectin domains, Ankyrin concensus repeat domains, scFv, and thioredoxin. (See e.g., Skerra et al., *Curr Opin Biotechnol* (2007) 18(4):295-304). Additional target-binding domains known to one of ordinary skill in the art are also contemplated herein.

The amino acid sequence of an exemplary rcSso7d.SA-CBD bifunctional fusion protein construct described herein can be represented as follows:

```
                                       (SEQ ID NO: 14)
MGSSHHHHHHSSGLVPRGSHMATVKFTYQGEEKQVDISKIKIVARDGQYI

DFKYDEGGGAYGYGWVSEKDAPKELLQMLEKQGGGGSGGGGSGGGGSPVS

GNLKVEFYNSNPSDTTNSINPQFKVTNTGSSAIDLSKLTLRYYYTVDGQK
```

-continued

DQTFWCDHAAIIGSNGSYNGITSNVKGTFVKMSSSTNNADTYLEISFTGG

TLEPGAHVQIQGRFAKNDWSNYTQSNDYSFKSASQFVEWDVTAYLNGVL

VWG*

The single underlined amino acids correspond to a histidine tag-thrombin site for purification. The double underlined amino acids correspond to the rcSso7d.SA (i.e., rcSso7d antigen binding protein variant that binds to streptavidin—SA). The dash underlined amino acids correspond to the (G$_4$S)$_3$ linker (SEQ ID NO: 125). The zig-zag underlined amino acids correspond to the CBD. In some embodiments, any of the bifunctional fusion protein constructs described herein have a similar arrangement, consisting of a purification tag and cleavage site, followed by the amino acid sequence of an antigen-binding protein contemplated herein, followed by a linker, and followed by the amino acid sequence of a CBD domain contemplated herein.

In some embodiments, the target-binding protein is an engineered rcSso7d antigen-binding protein, which binds to an antigen. As described herein, an "antigen" or "antigen of interest" refers to any molecule that can bind to the target-binding domain, such as the engineered rcSso7d antigen-binding protein. In some embodiments, an antigen is a molecule capable of inducing an immune response (to produce an antibody) in a host organism. In some embodiments, an antigen is a molecule which does not induce an immune response. In some embodiments, an antigen is an exogenous antigen, an endogenous antigen, an autoantigen, or a neoantigen (e.g., viral antigen, a tumor antigen, etc.).

In some embodiments, the antigen or antigen of interest is a tuberculosis antigen or tuberculosis molecule. A tuberculosis antigen or tuberculosis molecule is an antigen or molecule that is produced by *Mycobacterium tuberculosis* in either its active or latent form, or it may represent a biochemical response to the presence of the *M. tuberculosis* (in either its active or latent form) from the infected subject (e.g. disease-specific immunoglobulins, signaling cytokines, compound biomarkers representing a signature response across several biochemical entities, etc.). In some embodiments, the engineered rcSso7d antigen-binding protein includes a motif which recognizes and/or binds to a specific antigen of interest. In some embodiments, the engineered rcSso7d antigen-binding protein which recognizes and/or binds to the antigen of interest comprises an amino acid sequence that recognizes and/or binds to streptavidin (e.g., rcSso7d.SA or rcSso7d.SA-CBD), such as the amino acid sequence (SEQ ID NO: 4)
MATVKFTYQGEEKQVDISKIKIVARDGQYIDFKYDEGGGAYGYGWVSEKDA

PKELLQMLEKQ.

Additional non-limiting examples of engineered rcSso7d antigen-binding protein variants that bind to streptavidin or to the goat anti-chicken antibody AF488 are listed in Table 1.

TABLE 1

Engineered rcSso7d antigen-binding protein variants that bind to streptavidin or to the goat anti-chicken antibody

| rcSso7d Variant | SEQ ID NO | Amino Acid Sequence (N-terminus to C-terminus) |
|---|---|---|
| SA-AF647 | 17 | MATVKFTYQGEEKQVDISKIKYVYRWGHYIYFWYDEGGGASGWGWVSEKDAPKELLQ |
| | 18 | MATVKFTYQGEEKQVDISKIKHVRRWGQWIYFIYDEGGGARGNGYVSEKDAPKELLQ |
| | 19 | MATVKFTYQGEEKQVDISKIKRVRRYGQWIAFHYDEGGGAAGWGYVSEKDAPKELLQ |
| | 20 | MATVKFTYQGEEKQVDISKIKWVWRGGQGIIFWYDEGGGARGYGRVSEKDAPKELLQ |
| | 21 | MATVKFTYQGEEKQVDISKIKRVIRIGQYIYFWYDEGGGARGWGYVSEKDAPKELLQ |
| | 22 | MATVKFTYQGEEKQVDISKIKWVHRWGQRIRFWYDEGGGAAGNGKVSEKDAPKELLQ |
| | 23 | MATVKFTYQGEEKQVDISKIKWVIRWGQWIWFKYDEGGGASGWGYVSEKDAPKELLQ |
| | 24 | MATVKFTYQGEEKQVDISKIKRVRRWGQWIYFRYDEGGGAYGSGYVSEKDAPKELLQ |
| | 25 | MATVKFTYQGEEKQVDISKIKYVYRWGQWIYFWYDEGGGAWGRGYVSEKDAPKELLQ |
| Goat anti-Chicken antibody AF488 | 26 | MATVKFTYQGEEKQVDISKIKYVRRYGQYIGFIYDEGGGAWGKGYVSEKDAPKELLQ |
| | 27 | MATVKFTYQGEEKQVDISKIKHVRRYGQWIRFRYDEGGGASGWGIVSEKDAPKELLQ |
| | 28 | MATVKFTYQGEEKQVDISKIKSVKRSGQGIKFIYDEGGGAYGHGRVSEKDAPKELLQ |

In some embodiments, the engineered Sso7d antigen-binding protein (e.g., rcSso7d) which recognizes and/or binds to the antigen of interest comprises an amino acid sequence that recognizes and/or binds to a marker for tuberculosis, such as an antigen produced by active tuberculosis. In some embodiments, the engineered rcSso7d antigen-binding protein which recognizes and/or binds to the antigen of interest includes a sequence that recognizes and/or binds to the marker for tuberculosis Rv-1656 (e.g., rcSso7d.Rv-1656 or rcSso7d.Rv-1656-CBD), such as the amino acid sequence (SEQ ID NO: 5)
MATVKFTYQGEEKQVDISKIKWVRRYGQYIGFSYDEGGGAWGKGYVSEKDA

PKELLQMLEKQ.

In some embodiments, the engineered Sso7d antigen-binding protein (e.g., rcSso7d) which recognizes and/or binds to the antigen of interest comprises an amino acid sequence that recognizes and/or binds to a marker for tuberculosis, such as an antigen produced by active tuberculosis. In some embodiments, the marker for tuberculosis is Rv1656, Rv1681, Rv2392, Rv1729c or TBCG_03312.

Additional non-limiting examples of an antigen or antigen of interest produced in tuberculosis which can be recognized by or can bind to any of the bifunctional fusion proteins described herein include detection of the bacterium that causes tuberculosis (i.e., *Mycobacterium tuberculosis*), detection of specific regions of the genome of *M. tuberculosis*, such as regions detected by the GeneXpert MTB/RIF nucleic acid amplification test, antigens that are shed from *M. tuberculosis* into body fluids surrounding the one or more infected tissues, which can reach the blood circulation and be eliminated from the body of the subject, such as in urine. The antigen could be detected from both pulmonary tuberculosis or extrapulmonary tuberculosis (See e.g., Tucci et al., *Front Microbiol* (2014) 5(549):1-6). Lipoarabinomannan (LAM) is another antigen contemplated herein. LAM is a component of the outer cell wall of all Mycobacteria shed from metabolically active or degrading cells, which is cleared by the kidney and detectable in urine, which can be detected by the bifunctional fusion protein and methods described herein. (See e.g., Hunter et al. *J Biol Chem* (1986) 261(26):12345-51; Chan et al. *Infect Immun* (1991) 59(5): 1755-61). The bifunctional fusion protein that can detect LAM includes a target-binding protein, such as an engineered rcSso7d antigen-binding protein, that is selected for binding to the antigen of interest, LAM.

Additional non-limiting examples of antigens that can be detected using the bifunctional fusion protein and methods described herein to detect and diagnose tuberculosis are listed in Table 2 (See e.g., Tucci et al., *Front Microbiol* (2014) 5(549):1-6).

The bifunctional fusion protein described herein can be exemplified by the use of the rcSso7d.Rv1656-CBD bifunctional fusion protein bound to a cellulose-containing substrate, such as a chromatography paper (e.g., WHATMAN® Grade 1 Qualitative Filtration Paper). The bifunctional fusion protein bound to the cellulose-containing substrate can be contacted with a sample, such as a biological sample (e.g., urine), obtained from a subject, that contains an antigen of interest. The antigen of interest can be a urine-based biomarker of active tuberculosis obtained from a subject that has or is suspected of having tuberculosis, which, in some instances, may be used to determine whether the subject has tuberculosis. In some embodiments, the biomarker for tuberculosis is Rv1656, LAM, any of the biomarkers listed in Table 2 or any biomarkers for tuberculosis known to one of ordinary skill in the art.

Additional non-limiting examples of antigens or antigens of interest include antibodies, peptides, etc. In some embodiments, the antigen or antigen of interest is a biomarker for prostate cancer [e.g., prostate specific antigen (PSA)], a biomarker for cardiac arrest (e.g., troponin), neuro-filament light or a biomarker for traumatic brain injury, tau protein or a biomarker for Alzheimer's Disease, NS1 or a biomarker

TABLE 2

Exemplary antigens associated with *Mycobacterium tuberculosis*.

| Gene | Rv Number | Protein | Diagnosis |
| --- | --- | --- | --- |
| apa | Rv1860 | Alanine proline rich secreted protein APA | Tested in sputum and serum of active smear-positive tuberculosis patients (Chanteau et al., *Int J Tuberc Lung Dis* (2000) 4: 377-83). |
| esxA | Rv3875 | 6 kDa Early secretory antigen target ESXA. | Detected in cerebrospinal fluid (CSF) of tuberculous meningitis patients (Kashyap et al. *Infection* (2009) 37: 508-13). |
| fbpA | Rv3804c | Secreted antigen 85-A FBPA | Antigen 85 complex proteins have been detected in sputum (Wallis et al., *J Infect Dis* (1998) 178: 1115-21 and serum (Kashyap et al., *BMC Infect Dis* (2007) 7: 74) specimens of tuberculosis patients. |
| fbpB | Rv1886c | Secreted antigen 85-B FBPB | |
| fbpD | Rv3803c | Secreted MPT51/MPB51 antigen protein FBPD | |
| glcB | Rv1837c | Malate synthase G (GlcB) | Promising in cerebral spinal fluid in tuberculous meningitis (Haidar et al., *PLoS ONE* (2012) 7: e44630). |
| groEL2 | Rv0440 | 60 kDa chaperonin 2 GROEL2 | Promising in ELISA of serum samples of tuberculosis patients (Rajan et al., *Int J Tuberc Lung Dis* (2007) 11: 792-7). |
| hspX | Rv2031c | Heat shock protein HSPX | Assayed with promising results in CSF in tuberculous meningitis (Haidar et al., *PLoS ONE* (2012) 7: e44630). |
| moeX | Rv1681 | Possible molybdopterin biosynthesis protein MoeX | Identified by mass spectrometry in urine from active tuberculosis patients (Pollock et al., *J Clin Microbiol* (2013) 51: 1367-73). |
| mpt64 | Rv1980c | 24 kDa immunogenic protein MPT64 | A lateral flow assay was developed for the identification of *M. tuberculosis* complex in liquid culture media by using anti-MPB64 monoclonal antibodies (Akyar et al., *Indian J Med Microbiol* (2010) 28: 308-12). |
| pstS1 | Rv0934 | Periplasmic phosphate-binding lipoprotein PSTS1 | Assayed in cerebral spinal fluid in tuberculous meningitis (Haidar et al., *PLoS ONE* (2012) 7: e44630). |
| TB31.7 | Rv2623 | Universal stress protein family protein TB31.7 | Potential biomarker for the diagnosis of latent as well as active tuberculous meningitis infection. Assayed in CSF (Jain et al., *Dis Markers* (2013) 35: 311-6). | for Dengue Fever or a biomarker for Zika virus, pLDH, HRP2, aldolase, HSP70, or a biomarker for malaria, interferon-γ-inducible protein-10 (IP-10) or a biomarker for human immunodeficiency virus (HIV), Schistosome GST or a biomarker for Schistosomiasis, cancer antigen 125 (CA-125) or a biomarker for ovarian cancer, or outer surface protein A (ospA) or a biomarker for Lyme Disease.

In some embodiments, the antigen or antigen of interest is a non-tuberculosis antigen.

In some embodiments, the antigen or antigen of interest is one or more cytokines. In some embodiments, a cytokine is a hemokine, an interferon, an interleukin, a lymphokine, a tumor necrosis factor, a chemokine, a pro-inflammatory cytokine, or an anti-inflammatory cytokine. Non-limiting examples of cytokines include interleukins, such as interleukin (IL)-1α, interleukin (IL)-β, interleukin (IL)-2, interleukin (IL)-3, interleukin (IL)-4, interleukin (IL)-5, interleukin (IL)-6, interleukin (IL)-7, interleukin (IL)-8, interleukin (IL)-9, interleukin (IL)-10, interleukin (IL)-11, interleukin (IL)-12, interleukin (IL)-13, interleukin (IL)-18; interferons, such as interferon (IFN)-α, interferon (IFN)-β, interferon (IFN)-γ; macrophage inflammatory proteins, such as macrophage inflammatory protein (MIP)-1α, macrophage inflammatory protein (MIP)-1β; tumor necrosis factor (TNF)-β, stem cell factor (SCF), granulocyte-macrophage colony-stimulating factor (GM-CSF), granulocyte-colony stimulating factor (G-CSF), MIP-ly, leukemia inhibitory factor (LIF), c-kit ligand, thrombopoietin (TPO), CD40 ligand (CD40 μL), tumor necrosis factor-related activation-induced cytokine (TRANCE) or flt3 ligand (flt-3 μL). Other cytokines known to one of ordinary skill in the art (see e.g., Zhang et al. *Int Anesthesiology Clin* (2007) 45(2):27-7) are also contemplated herein.

In some embodiments, the antigen or antigen of interest is released or secreted by a member of the genus Flavivirus. In some embodiments, the member of the genus Flavivirus is West Nile virus (WNV), St. Louis encephalitis virus (SLEV), Japanese encephalitis virus (JEV), yellow fever virus (YFV), dengue virus (DENV) or Zika virus (ZIKV). (See e.g., Guzman et al. *Lancet* (2015) 385:453-65). Other members of the genus Flavivirus known to one of ordinary skill in the art are also contemplated herein. In some embodiments, the antigen or antigen of interest is Flavivirus non-structural 1 (NS1). In some embodiments, the NS1 antigen or antigen of interest is released by a member of the genus Flavivirus, such as WNV, SLEV, JEV, SLEV, JEV, YFV, DEVN or ZIKV. The nucleic acid and/or amino acid sequences of NS1 antigen or antigen of interest released by WNV, SLEV, JEV, SLEV, JEV, YFV, DEVN or ZIKV are known and/or can be readily identified by one of ordinary skill in the art. In some embodiments, the antigen or antigen of interest is released or secreted by the member of a genus that is not Flavivirus. In some embodiments, the antigen or antigen of interest is released or secreted by an organism that causes malaria, such as an organism that is known to one of ordinary skill in the art. In some embodiments, the antigen or antigen of interest is released or secreted by a member of the genus Plasmodium. In some embodiments, the antigen or antigen of interest is released or secreted by *Plasmodium falciparum, Plasmodium vivax, Plasmodium malariae, Plasmodium ovale*. In some embodiments, the antigen or antigen of interest is plasmodium lactate dehydrogenase (pLDH), histidine-rich protein 2 (HRP2), or plasmodium aldolase. The nucleic acid and/or amino acid sequences of an pLDH, HRP2 or plasmodium aldolase are known to one of ordinary skill in the art and could be readily identified using tools, such as a BLAST search.

In some embodiments, the antigen or antigen of interest is a detection reagent. In some embodiments, the detection reagent is a fluorophore. In some embodiments, the antigen or antigen of interest is a fluorophore, such as ALEXA FLUOR®647 (AF647). In some embodiments, the fluorophore is hydroxycoumarin, methoxycoumarin, aminocoumarin, CY2®, FAM, ALEXA FLUOR®405 (AF405), ALEXA FLUOR®488 (AF488), Fluorescein FITC, ALEXA FLUOR®430 (AF430), ALEXA FLUOR®532 (AF532), HEX, CY3®, TRITC, ALEXA FLUOR®546 (AF546), ALEXA FLUOR®555 (AF555), R-phycoerythrin (PE), RHODAMINE RED™-X, Tamara, CY3.5® 581, Rox, ALEXA FLUOR®568 (AF568), RED 613™, TEXAS RED®, ALEXA FLUOR®594 (AF594), ALEXA FLUOR®633 (AF633), Allophycocyanin, CY5®, ALEXA FLUOR®660 (AF660), CY5.5®, TruRed, ALEXA FLUOR®680 (AF680), CY7®, CY7.5® or any other fluorophores known to one of ordinary skill in the art (see e.g., www.biosyn.com/Images/ArticleImages/Comprehensive %20fluorophore %20list.pdf). In some embodiments, the fluorophore is a fluorescent protein or a chromophore, such as green fluorescent protein (GFP), chromoprotein from the coral *Acropora millepora* (amilCP), a chromoprotein from the coral *Acropora millepora* (amilGFP), a fluorescent protein from *Acropora millepora* (amilRFP), etc., or other species chemically linked to a detection reagent known to one of ordinary skill in the art. In some embodiments, one or more fluorophores could be used for the purification of chemically-labeled molecules to ensure 100% or near 100% labeling efficiency. In some embodiments, the antigen or antigen of interest is a molecule that emit a detectable signal. In some embodiments, the molecule is phycoerythrin. In some embodiments, the molecule that emits a detectable signal is a color-producing enzyme (e.g., beta-galactosidase), APEX2 for metal sequestration and high contrast electron microscopy (EM), or a chemiluminescent species. In some embodiments, any of the antigen-binding proteins disclosed herein, such as a multimeric rcSso7d binding protein associated or not associated with a substrate-anchoring domain includes a binding face that binds an analyte, antigen or antigen of interest and a second binding face that binds one or more of the detection reagents disclosed herein. Other detection reagents, fluorophores or molecules that emit a detectable signal known to one of ordinary skill in the art are also contemplated herein. In some embodiments, the detection reagent, fluorophore or molecule that emits a detectable signal is directly or indirectly linked to one or more of streptavidin, to IgG antibody (polyclonal or monoclonal), any of the biomarkers disclosed herein, any of the antigen-binding proteins disclosed herein [e.g., rcSso7d, rcSso7d-based detection reagents (e.g., BA-MBP-rcSso7d)], a nucleic acid (e.g., DNA, RNA, etc.), or an organic or inorganic nanoparticle (e.g., a nanoparticle comprising gold, carbon, latex, cellulose, etc.)

In some embodiments, the substrate-anchoring domain, such as a CBD, and the target-binding domain, such as an antigen-binding protein or an antigen-binding domain (e.g., an engineered rcSso7d antigen-binding protein) are directly attached. The substrate-anchoring domain, such as a CBD, can be directly attached to the target-binding protein or an antigen-binding domain (e.g., an engineered rcSso7d antigen-binding protein) through a peptide bond between the substrate-anchoring domain and the target-binding protein or antigen-binding domain. In some embodiments, the substrate-anchoring domain, such as a CBD, and the target-binding domain, such as an antigen-binding protein or an antigen-binding domain (e.g., engineered rcSso7d antigen-binding protein) are indirectly attached. In some embodiments, the engineered Sso7d antigen-binding protein (e.g., rcSso7d) is indirectly attached to the CBD through a linker (i.e., is linked). Non-limiting examples of linkers contemplated herein include a protein linker; a peptide linker, such as a Gly-Ser linker (e.g., a linker that includes the amino acid sequence GGGGSGGGGSGGGGS (SEQ ID NO: 125), known as $(G_4S)_3$). The Gly-Ser linker can be replicated n number of times, wherein n=1, 2, 3, 4, 5, 6, 7, 8, 9, 10, 15, 20, 25, or 30, for example. Additional non-limiting examples of linkers known to one of ordinary skill in the art, such as chemical linkers (e.g., crosslinkers, bifunctional linkers, trifunctional trilinkers), such as Bis[2-(N-succinimidyl-oxycarbonyloxy)ethyl]sulfone, 0,0'-Bis[2-(N-Succinimidyl-succinylamino)ethyl]polyethylene glycol 2,000, 0,0'-Bis[2-(N-Succinimidyl-succinylamino)ethyl]polyethylene glycol 3,000, 0,0'-Bis[2-(N-Succinimidyl-succinylamino)ethyl] polyethylene glycol 10,000, BS(PEG)5 (PEGylated bis (sulfosuccinimidyl)suberate), 4,4'-Diisothiocyanatostilbene-2,2'-disulfonic acid disodium salt hydrate, rromoacetic acid N-hydroxysuccinimide ester, maleimide-PEG2-succinimidyl ester, SBAP (succinimidyl 3-(bromoacetamido)propionate), 5-Azido-2-nitrobenzoic acid N-hydroxysuccinimide ester, etc.; flexible linkers (e.g., $(Gly)_6$ (SEQ ID NO: 126), $(Gly)_8$ (SEQ ID NO: 127), etc.), rigid linkers (e.g., $(EAAAK)_3$ (SEQ ID NO: 128), $A(EAAAK)_4ALEA$ $(EAAAK)_4A$ (SEQ ID NO: 129), PAPAP (SEQ ID NO: 130), etc.) and cleavable linkers (e.g., disulfide, VSQTSK-LTR↓JAETVFPDV (SEQ ID NO: 131), RVLJAEA (SEQ ID NO: 132); EDVVCCJSMSY (SEQ ID NO: 133); GGIEGRJGS (SEQ ID NO: 134); GFLGJ (SEQ ID NO: 135), etc.) naturally-occurring or synthetic, such as those disclosed in Chen et al., *Adv Drug Deliv Rev* (2013) 65(10): 1357-69, are also contemplated herein.

In some embodiments, the C-terminus of the engineered rcSso7d antigen-binding protein is either directly or indirectly attached to the N-terminus of the CBD. In some embodiments, the C-terminus of the engineered rcSso7d antigen-binding protein is directly attached to the N-terminus of the CBD. In some embodiments, the C-terminus of the engineered rcSso7d antigen-binding protein is indirectly attached to the N-terminus of the CBD through a linker. In some embodiments, the N-terminus of the engineered rcSso7d antigen-binding protein is either directly or indirectly attached to the C-terminus of the CBD. In some embodiments, the N-terminus of the engineered rcSso7d antigen-binding protein is directly attached to the C-terminus of the CBD. In some embodiments, the N-terminus of the engineered rcSso7d antigen-binding protein is indirectly attached to the C-terminus of the CBD through a linker.

Expression of Bifunctional Fusion Protein

Also disclosed herein are nucleic acids that encode for any of the bifunctional fusion proteins described herein, libraries that contain any of the nucleic acids and/or bifunctional fusion proteins described herein, and compositions that contain any of the nucleic acids and/or bifunctional fusion proteins described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences.

The development and selection of an antigen-binding protein described herein, such as the rcSso7d.SA or the rcSso7d.Rv1656 can be produced by methods disclosed in Miller et al., 2016. Briefly, an antigen-binding protein, such as rcSso7d.SA or the rcSso7d.Rv1656 is selected from a yeast surface display library based on the reduced-charge Sso7d scaffold (rcSso7d). The yeast library can be generated using trinucleotide oligo synthesis and in vivo homologous recombination with a linearized plasmid, such as the pCTcon2 plasmid. (Traxlmayr et al., 2016). Methods of isolation, such as the highly-avid magnetic bead sorting (Ackerman et al., 2009) (MBS) and fluorescence-activated cell sorting (FACS) (Chao et al., 2006) can be employed to select binders against an antigen of interest, such as Rv1656, and stringency increased over rounds of FACS-based library screening, after which a sub-library can be sequenced and the antigen-binding protein that binds the antigen of interest (e.g., rcSso7d.Rv1656) can be selected for further characterization, such as robust expression in a system, such as a bacterial system, for downstream applications. Additional methods for creating a yeast surface display library include methods known to one of ordinary skill in the art.

In some embodiments, one or more of the target-binding proteins, antigens, etc. disclosed herein are expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (RNA).

A nucleic acid molecule that encodes a bifunctional fusion protein or antigen or any other molecule disclosed herein can be introduced into a cell or cells using methods and techniques that are standard in the art. For example, nucleic acid molecules can be introduced by standard protocols such as transformation including chemical transformation and electroporation, transduction, particle bombardment, etc.

Any type of cell that can be engineered to recombinantly express genes can be used in the methods described herein, including prokaryotic and eukaryotic cells. In some embodiments the cell is a bacterial cell, such as *Escherichia* spp.,

*Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp. (e.g., *S. cerevisiae*), *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other examples of fungi include *Aspergillus* spp., *Penicillium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell.

Antigen Detection

In some aspects, methods for detecting an antigen of interest are also provided herein. In some embodiments, the method includes contacting any of the bifunctional fusion proteins described herein with a cellulose-containing substrate for a time sufficient for the bifunctional fusion protein to bind to the cellulose-containing substrate; contacting the bifunctional fusion protein bound to the cellulose-containing substrate with a sample comprising an antigen of interest; and detecting the antigen of interest bound by the engineered reduced charge Sso7d antigen-binding protein (e.g., rcSso7d).

In some embodiments, the method includes contacting any of the bifunctional fusion proteins described herein with a sample comprising an antigen of interest, wherein the antigen of interest binds to the bifunctional fusion protein and forms a complex; contacting the complex with a cellulose-containing substrate for a time sufficient for the complex to bind to the cellulose-containing substrate; and detecting the antigen of interest bound by the engineered Sso7d antigen-binding protein.

In some embodiments, the method includes contacting any of the bifunctional fusion proteins described herein, such as rcSso7d-CBD, with a cellulose-containing substrate for a time sufficient for bifunctional fusion protein to bind to the cellulose-containing substrate; contacting a sample, such as a biological sample, comprising an antigen or an antigen of interest for a time sufficient to allow the antigen or antigen of interest to bind to the bifunctional fusion protein and form a complex; contacting the complex with an antibody that recognizes the antigen or antigen of interest; and detecting the antibody. In some embodiments, the antibody is directly or indirectly linked to a fluorophore or a molecule that emits a detectable signal to detect the antigen or antigen of interest. In some embodiments, the antibody is biotinylated. In some embodiments, the biotinylated antibody is contacted with a streptavidin molecule that is directly or indirectly linked to a fluorophore or a molecule that emits a detectable signal to detect the antigen or antigen of interest.

In some embodiments, the bifunctional fusion protein comprises more than one rcSso7d antigen-binding protein.

In some embodiments, the bifunctional fusion protein comprises at least or 2, at least or 3, at least or 4, at least or 5, at least or 6, at least or 7, at least or 8, at least or 9, at least or 10, at least or 12, at least or 14, at least or 16, at least or 18, at least or 20, at least or 25, at least or 30, at least or 35, at least or 40, at least or 45, at least or 50, at least or 55, at least or 60, at least or 65, at least or 70, at least or 75, at least or 80, at least or 85, at least or 90, at least or 95, or at least or 100 antigen-binding proteins or domains, such as any of the rcSso7d or its variants disclosed herein.

In some embodiments, the more than one antigen-binding proteins or domains, such as any of the rcSso7d or its variants disclosed herein are genetically fused together. The more than one antigen-binding proteins or domains, such as any of the rcSso7d or its variants disclosed herein are genetically fused together by using an expression vector that includes more than one copy of a nucleic acid sequence that encodes the antigen-binding protein or domain. In some embodiments, the nucleic acid sequences that encodes one antigen-binding protein or domain is separated from another nucleic acid sequence that encodes one antigen-binding protein or domain by a nucleic acid encoding a linker. Non-limiting examples of linkers encoded by a nucleic acid contemplated herein include a protein linker or a peptide linker, such as a Gly-Ser linker (e.g., a linker that includes the amino acid sequence GGGGSGGGGSGGGGS (SEQ ID NO: 125), known as $(G_4S)_3$). The Gly-Ser linker can be replicated n number of times, wherein n=1, 2, 3, 4, 5, 6, 7, 8, 9, 10, 15, 20, 25, or 30, for example. Additional non-limiting examples of linkers disclosed herein and/or known to one of ordinary skill in the art are also contemplated herein. In some embodiments, the more than one antigen-binding proteins or domains, such as any of the rcSso7d or its variants disclosed herein are not genetically fused together. In some embodiments, the more than one antigen-binding proteins or domains, such as any of the rcSso7d or its variants disclosed herein are chemically fused. In some embodiments, the more than one antigen-binding proteins or domains, such as any of the rcSso7d or its variants disclosed herein are chemically fused together. The more than one antigen-binding proteins or domains, such as any of the rcSso7d or its variants disclosed herein are chemically fused by a chemical reagent after the proteins have been expressed from a nucleic acid sequence. In some embodiments, the more than one antigen-binding proteins or domains, such as any of the rcSso7d or its variants disclosed herein are chemically fused after antigen-binding proteins or domains, such as any of the rcSso7d or its variants disclosed herein is expressed, for instance, from an expression vector. In some embodiments, the more than one rcSso7d antigen-binding proteins are chemically fused by a linker, such as a bifunctional linker, or using other methods known to one of ordinary skill in the art. In some embodiments, the more than one antigen-binding proteins or domains, such as any of the rcSso7d or its variants disclosed herein, are chemically fused by a fusion via disulfide linkages between cysteine residues at the N- and C-termini, or via dual-maleimide chemical reagents. In some embodiments, in vivo ligation tags such as HALO or SPY tags to attach orthogonal reactive moieties to the antigen-binding proteins or domains, such as any of the rcSso7d or its variants disclosed herein, allowing separate molecules to react together, are also contemplated herein. In some embodiments, residues of antigen-binding proteins or domains, such as any of the rcSso7d or its variants disclosed herein, could be chemically altered to feature aldehyde moieties, which can be reacted with primary amines to form covalent imine linkages. (See e.g., Tuley et al., *Chemical communications* (2014) 50(56):7424-7426. doi:10.1039/c4cc02000f). In some embodiments, a sortase-based method could be used for in vitro fusion of an antigen-binding protein or domain, such as any of the rcSso7d or its variants disclosed herein.

In some embodiments, the bifunctional fusion protein or the complex is in solution. In some embodiments, the solution includes a buffer, such as a buffer known to one of ordinary skill in the art. The bifunctional protein may be in solution at a desired concentration. In some embodiments, the bifunctional fusion protein is at a desired concentration of or about 5 μM, of or about 10 μM, of or about 15 μM, of or about 20 μM, of or about 25 μM, of or about 30 μM, of or about 35 μM, of or about 40 μM, of or about 45 μM, of or about 50 μM, of or about 60 μM, of or about 70 μM, of or about 80 μM, of or about 90 μM, of or about 100 μM, of or about 200 μM, of or about 300 μM, or of or about 400 μM.

In some embodiments, the bifunctional fusion protein described herein is contacted with the cellulose-containing substrate for about 5 seconds, about 15 seconds, about 20 seconds, about 30 seconds, about 35 seconds, about 40 seconds, about 45 seconds, about 1 minute, about 1.5 minutes, about 2 minutes, about 2.5 minutes, about 3 minutes, about 4 minutes, about 5 minutes, about 7 minutes, about 10 minutes, about 15 minutes, about 20 minutes, about 30 minutes, or about 1 hour.

In some embodiments, the bifunctional fusion protein bound to the cellulose-containing substrate is contacted with a sample that contains an antigen of interest. In some embodiments, the bifunctional fusion protein described herein is contacted with a sample comprising an antigen of interest, wherein the antigen of interest binds to the bifunctional fusion protein and forms a complex; the complex is then contacted with a cellulose-containing substrate for a time sufficient for the complex to bind to the cellulose-containing substrate.

In some embodiments, the sample is a biological sample. The biological sample may be obtained from a subject. As described herein, the term "biological sample" is used to generally refer to any biological material obtained from a subject. The biological sample typically is a fluid sample. Solid tissues may be made into fluid samples using routine methods in the art. In some embodiments, the biological sample is tissue, feces, or a cell obtained from a subject. In some embodiments, the biological sample comprises a bodily fluid from a subject. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid or combinations thereof.

In some embodiments, the cellulose-containing substrate is paper (e.g., chromatography paper) or nitrocellulose. In certain embodiments, the cellulose-containing substrate is modified in an oxidizing chemical bath to yield covalent chemical linkage of the protein to the substrate, passivated with a blocking agent (See e.g., Y. Zhu, et al., *Anal Chem.* (2014) 86:2871-5; M. Vuoriluoto, et al., *ACS Appl. Mater. Interfaces* (2016) 8, 5668-78) to reduce non-specific protein adsorption to the substrate, or pre-incubated with a stabilizing species such as trehalose in order to improve assay functionality and stability. In certain embodiments, the cellulose-containing substrate is not modified (unmodified). In some embodiments, the cellulose-containing substrate is an unmodified chromatography paper, such as unmodified WHATMAN® Grade 1 Qualitative Filtration Paper. Additional non-limiting examples of cellulose-containing substrates also contemplated herein include cellulose powder, cellulose microbeads, cellulosic fabrics/yarns, etc.

In some embodiments, the cellulose-containing substrate is oxidized. In some embodiments, the cellulose-containing substrate is oxidized with sodium metaperiodate to functionalize the cellulose surfaces with aldehyde groups or other methods to oxidize cellulose known to one of ordinary skill in the art. (See e.g., Badu-Tawiah, et al., *Lab Chip*, (2015) 15:655-9).

For instance, a non-limiting example is the use of rcSso7d.Rv1656-CBD bifunctional fusion protein bound to a cellulose-containing substrate, such as a chromatography paper (e.g., WHATMAN® Grade 1 Qualitative Filtration Paper), which is contacted with a sample that contains an antigen of interest, such as an urine-based biomarker of active tuberculosis obtained from a subject that has or is suspected of having tuberculosis, which, in some instances, may be used to determine whether the subject has tuberculosis. In some embodiments, the biomarker for tuberculosis is Rv1656.

Additional non-limiting examples of biomarkers for tuberculosis which could be detected by any of the bifunctional fusion proteins described herein, through any of the methods described herein, include detection of the bacterium that causes tuberculosis (i.e., *Mycobacterium tuberculosis*), detection of specific regions of the genome of *M. tuberculosis*, such as regions detected by the GeneXpert MTB/RIF nucleic acid amplification test. Additional examples of antigens of interest for tuberculosis include antigens that are shed from *M. tuberculosis* into body fluids surrounding the one or more infected tissues, which can reach the blood circulation and be eliminated from the body of the subject, such as in urine. The antigen could be detected from both pulmonary tuberculosis or extrapulmonary tuberculosis. The antigen or antigen of interest could be detected from latent tuberculosis, if they are identified/validated (See e.g., Tucci et al., *Front Microbiol* (2014) 5(549):1-6). For instance, lipoarabinomannan (LAM) is a component of the outer cell wall of all Mycobacteria shed from metabolically active or degrading cells, which is cleared by the kidney and detectable in urine, which can be detected by the bifunctional fusion protein and methods described herein. (See e.g., Hunter et al. *J Biol Chem* (1986) 261(26):12345-51; Chan et al. *Infect Immun* (1991) 59(5): 1755-61).

Additional non-limiting examples of antigens that can be detected using the bifunctional fusion protein and methods described herein to detect and diagnose tuberculosis are listed in Table 2 (See e.g., Tucci et al., *Front Microbiol* (2014) 5(549):1-6).

Other antigens present in a subject with tuberculosis, which can be detected using the bifunctional fusion protein, methods compositions and kits described herein, known to one of ordinary skill in the art are also contemplated herein.

In some embodiments, the antigen of interest is streptavidin.

In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5, at least or about 4 micromoles, at least or about 4.5 micromoles, or at least or about 5 micromoles of any of the bifunctional fusion proteins described herein are attached to a cellulose-containing substrate per gram of cellulose of the cellulose-containing substrate.

In some embodiments, at least or about 1 µM, at least or about 25 µM, at least or about 50 µM, at least or about 60 µM, at least or about 70 µM, at least or about 80 µM, at least or about 90 µM, at least or about 100 µM, at least or about 150 µM, at least or about 200 µM, at least or about 250 µM, at least or about 300 µM, at least or about 350 µM, at least or about 400 µM, at least or about 500 µM, at least or about 550 µM, at least or about 600 µM, at least or about 650 µM, at least or about 700 µM, at least or about 750 µM, at least or about 800 µM, at least or about 850 µM, at least or about 900 µM, at least or about 950 µM, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-average concentrations any of the bifunctional fusion proteins described herein are attached to a cellulose-containing substrate.

In some aspects, the molar abundance or molar excess of the antigen-binding protein in the bifunctional fusion protein, such as a rcSso7d linked to a CBD, relative to the antigen of interest allows the rapid capture and, in some embodiments, efficient and complete depletion of the antigen of interest from a sample.

In some embodiments, at least or about a 10-fold molar excess of bifunctional fusion protein or antigen-binding protein completely depletes an antigen of interest from a sample or solution. In some embodiments, at least or about a 10-fold volume-average concentration excess leads to rapid capture and/or immobilization of a bifunctional fusion protein or antigen-binding protein.

In some embodiments, the bifunctional fusion protein is in molar excess of the antigen of interest. In some embodiments, the bifunctional fusion protein is in at least or about 2-fold molar excess, at least or about 3-fold molar excess, at least or about 4-molar excess, at least or about 5-fold molar excess, at least or about 6-fold molar excess, at least or about 7-fold molar excess, at least or about 8-fold molar excess, at least or about 9-fold molar excess, at least or about 10-fold molar excess, at least or about 15-fold molar excess, at least or about 20-fold molar excess, at least or about 25-fold molar excess, at least or about 30-fold molar excess, at least or about 35-fold molar excess, at least or about 40-fold molar excess, at least or about 45-fold molar excess, at least or about 50-fold molar excess, at least or about 60-fold molar excess, at least or about 65-fold molar excess, at least or about 70-fold molar excess, at least or about 80-fold molar excess, at least or about 90-fold molar excess, at least or about 100-fold molar excess, at least or about 200-fold molar excess, at least or about 300-fold molar excess, at least or about 400-fold molar excess, at least or about 500-fold molar excess, at least or about 600-fold molar excess, at least or about 700-fold molar excess, at least or about 800-fold molar excess, at least or about 900-fold molar excess, at least or about 1000-fold molar excess, at least or about 1500-fold molar excess, or at least or about 2000-fold molar excess relative to the antigen of interest in the sample.

In some embodiments, the bifunctional fusion protein is in such excess that the antigen of interest is depleted from the sample. In some embodiments, about or at least 10%, about or at least 20%, about or at least 30%, about or at least 40%, about or at least 50%, about or at least 55%, about or at least 60%, about or at least 65%, about or at least 70%, about or at least 75%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 95.5%, about or at least 96%, about or at least 96.5%, about or at least 97%, about or at least 97.5%, about or at least 98%, about or at least 98.5%, about or at least 99%, about or at least 99.5%, or about 100% of the antigen of interest is depleted from the sample, such as a biological sample.

In some aspects, standard curves can be prepared given the advantageous properties of the disclosure in which complete or near-complete depletion of an antigen of interest can be achieved from a sample or solution. The abundance of the captured antigen can be detected and measured or determined using a readout, such as a fluorescent readout or a colorimetric readout.

In some embodiments, the surface-immobilized concentration of the antigen-binding protein (e.g., rcSso7d.SA-CBD) is quantified using a protein assay, such as a micro bicinchoninic acid (BCA) assay. A standard curve can be prepared by evaporating known quantities of protein onto cellulose test zones, depositing these test zones into the wells of a micro BCA assay, and quantifying the signal development in this format. The same procedure is followed for the experimental samples (following the substrate washing step), and the associated signal for each sample is then mapped to this standard curve in order to determine the mass of immobilized rcSso7d.SA-CBD.

In some embodiments, the sample is a biological sample from a subject. A subject includes, but is not limited to, any mammal, such as a human, a primate, a mouse, a rat, a dog, a cat, a horse, or agricultural stocks (e.g., fish, pigs, cows, sheep, and birds—particularly chickens). In certain embodiments, the subject is a human. In some embodiments, the sample is a solution, such as a buffer solution.

In some embodiments, the cellulose-containing substrate is rinsed with a buffer solution before detecting the antigen of interest bound to the engineered reduced charge Sso7d antigen-binding protein (e.g., rcSso7d). In some embodiments, the buffer is phosphate buffered saline (PBS) or another buffer known to one of ordinary skill in the art that provides a stable environment for a macromolecule, such as a protein, protein complex, antigen, etc.

In some embodiments, the method further includes detecting the antigen of interest bound by the engineered reduced charge Sso7d antigen-binding protein (e.g., rcSso7d) in the bifunctional fusion protein. In some embodiments, the antigen of interest bound to the bifunctional fusion protein is contacted with a cellulose-containing substrate in which the CBD of the bifunctional fusion protein binds the cellulose-containing substrate (e.g., chromatography paper such as WHATMAN® Grade 1 Qualitative Filtration Paper). The method allows for the separation or isolation of the antigen of interest from any other molecules that may be present in a sample, such as a biological sample (e.g., urine). In some embodiments, the presence or amount of the antigen of interest is determined or measured using a signal-generating reagent that specifically recognizes the antigen of interest and generates a signal.

In some embodiments, the bifunctional fusion protein (e.g., rcSso7d-CBD) would be immobilized on a cellulose substrate (e.g., chromatography paper, cellulose powder, etc.), and would then be brought into contact with the solution/biological sample bearing the antigen of interest (either forced convection to draw the fluid across or through the test zone, or soluble co-incubation of the CBD/substrate and antigen). This immobilized complex would then be contacted with a second, epitope-specific variant of rcSso7d (not fused to CBD, but fused instead to a biotin acceptor sequence, or modified with a fluorophore). The second species (e.g., rcSso7d) would bind to a second epitope of the captured antigen. This second species would be conjugated to a means of transducing this binding reaction; several examples are outlined below. All of these steps could be done directly on the cellulose-containing substrate.

Non-limiting examples of signal-generating that can be fused to the antigen-binding protein (e.g., rcSso7d) include, without limitation, gold nanoparticles, enzymes (expressed as fusion partners or indirectly bound to rcSso7d) which yield a colorimetric response, enzymes which yield an amperometric or impedometric signal (e.g., glucose oxidase), a macrophotoinitiator which can initiate a polymerization reaction, cellulose nanobeads, other metallic nanoparticles, dye-filled liposomes, DNA which can be amplified enzymatically, RNA which can be expressed for the production of a color-producing enzyme, etc. The presence or amount of the signal-generating reagent can be detected using an imaging device, such as a digital imager. Additional non-limiting examples of detecting the signal-generating reagent include gold nanoparticles, which can be used in a point-of-care setting, and are the reagents used in traditional pregnancy tests. The spatial localization of gold nanoparticles, mediated by the antigen-binding interaction, concentrates the optical signal (which is also amplified by the occurrence of surface plasmon resonance). This can be detected by the naked eye. Polymerization-based amplification would use the localization of a macrophotoinitiator in order to yield a rapid, durable polymerization response following incubation with a monomer solution and irradiation with the appropriate wavelength of light. Entrained phenolphthalein yields a high-contrast colorimetric readout following the application of a basic solution, which can be detected with the naked eye. An amperometric method, such as fusing glucose oxidase to the second rcSso7d species and contacting the tests with gold probes and a glucose solution, would allow for smart phone based detection. Enzymatic methods can also be used, and rely upon a fusion of the second species (e.g., rcSso7d) to an enzyme and contacting the tests with a labile substrate which becomes colored following enzymatic cleavage. Impedometric means of detecting the signal generating reagent are also possible, and can be achieved using smartphone-compatible adaptors.

In some aspects, provided herein are also methods for enhancing the sensitivity of an assay. The method includes binding of a target to a target-binding species, which includes fusing a target-binding species that binds to a target of interest to a cellulose binding domain (CBD). Any antigen-binding protein that can be attached to a cellulose-binding domain can benefit from its favorable properties; the high immobilized abundance of bifunctional fusion protein with a CBD results in high molar abundance of the binding species, thereby allowing, in some instances, depletion of an antigen of interest and a high local concentration of this species, thereby allowing, in some instances, rapid capture of an antigen of interest. In some embodiments, the antigen of interest is in solution. In contrast to traditional immunoassays in which the immobilized binding partner is the limiting reagent and the antigen of interest is captured slowly and incompletely, the present disclosure allows for the antigen capture/detection to rapidly proceed to completion. Additionally, because the bifunctional fusion protein, and thus the antigen-binding domain, is at a high local abundance, this allows the use of higher sample volumes containing higher amounts of antigen, which would be captured and depleted, in some instances, to provide high signal over a method previously available in the art in which the antigen-binding species is actually the limiting reagent, reducing the amount of antigen that can be captured and detected at a given point. This could be applied to any binding scaffold by expressing the binding scaffold as a fusion partner to the CBD.

Target-Binding Domain

In some embodiments, any of the target-binding domains or any of its variants described herein are not part of a bifunctional fusion protein described herein. In some embodiments, any of the target-binding domains described herein, such as rcSso7d or any of its variants that is not part of a bifunctional fusion protein (e.g., rcSso7d-CBD), is directly or indirectly linked to or expressed with a molecule or protein that increases the solubility of the target-binding domain. In some embodiments, the molecule or protein that increases solubility is a maltose binding protein (MBP; e.g., Gene ID: 1097664) or an MBP comprising the amino acid sequence:

(SEQ ID NO: 124)
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNSGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQT

In some embodiments, the molecule or protein that increases solubility is small ubiquitin-like modifier (SUMO; e.g., e.g., Gene ID: 7341), glutathione S-transferase (GST; e.g., Gene ID: 101890455), enhanced green fluorescent protein (eGFP; e.g., Gene ID: 20473140), or Thioredoxin (TRX; e.g., Gene ID: 22166). Other molecules or proteins that increase solubility of a protein or protein construct known to one of ordinary skill in the art are also contemplated herein.

In some embodiments, any of the target-binding domains disclosed herein include a biotin acceptor sequence. In some embodiments, any of the target-binding domains disclosed herein are chemically biotinylated. A target-binding domain disclosed herein can be chemically biotinylated by methods known to one of ordinary skill in the art. Non-limiting examples of methods to chemically biotinylate a protein include the use of sulfo-NHS-LC-biotin. In some embodiments, the method to chemically biotinylate a protein is a variation of NHS conjugation with biotin with different linker arms (e.g., Sulfo-NHS-Biotin, Sulfo-NHS-LC-Biotin, Sulfo-NHS-LC-LC-Biotin). Additional non-limiting examples of methods to chemically biotinylate a protein include sulfhydryl conjugation [e.g., BMCC-Biotin (1-biotinamido-4-[4'-(maleimidomethyl)cyclohexane-carboxamido]butane)), Iodoacetyl-Biotin, and pyridyldithiol-biotin].

In some embodiments, the cellulose-containing substrate is oxidized. In some embodiments, the target-binding domain, such as rcSso7d, includes one or more biotin acceptors. In some embodiments, the target binding domain includes at least 1 or 1, at least 2 or 2, at least 3 or 3, at least 4 or 4, at least 5 or 5, at least 6 or 6, at least 7 or 7, at least 8 or 8, at least 9 or 9, at least 10 or 10, at least 15 or 15, at least 20 or 20, at least 25 or 25, at least 30 or 30, at least 35 or 35, at least 40 or 40, at least 45 or 45, at least 50 or 50, or at least 100 or 100 biotin acceptors. In some embodiments, the biotin acceptor is an amino acid sequence. In some embodiments, the biotin acceptor is a biotin molecule. In some embodiments, the biotin molecule is chemically added to any of the target-binding domains described herein, such as rcSso7d or any of its variants.

In some embodiments, the antigen or antigen of interest described herein binds to the oxidized cellulose substrate. In some embodiments, the antigen or antigen of interest is contacted with a target binding domain that includes one or more biotin acceptors and forms a complex. In some embodiments, the target-binding domain that includes one or more biotin acceptors is contacted with a streptavidin molecule. In some embodiments, the streptavidin is labeled or linked to a fluorophore or a molecule that emits a detectable signal.

Diseases and Conditions

The bifunctional fusion proteins, compositions, methods and kits described herein can be used to detect the presence of molecules, such as antigens, that are generated in response to various diseases or conditions. Non-limiting examples of diseases or conditions that generate molecules, such as antigens, which can be detected include a disease or condition that releases an antigen of interest, such as cancer, cardiovascular diseases, infectious diseases, liver diseases, such as liver failure, Alzheimer's disease, Parkinson's disease, or autoimmune diseases. Any condition which has an associated biochemical signature can theoretically be detected.

The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In some embodiments, the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

Infectious diseases can be caused by bacteria, viruses, fungi, or parasites. Bacteria are responsible for illnesses such as strep throat, urinary tract infections and tuberculosis. Viruses cause a multitude of diseases, ranging from the common cold to AIDS. Fungi cause several skin diseases, such as ringworm and athlete's foot, or can also affect the lungs and/or nervous system. Parasites can cause diseases such as malaria.

Autoimmune disease is a class of diseases in which an subject's own antibodies react with host tissue or in which immune effector T cells are autoreactive to endogenous self-peptides and cause destruction of tissue. Thus, an immune response is mounted against a subject's own antigens, referred to as self-antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjôgren's syndrome, insulin resistance, and autoimmune diabetes mellitus.

In some embodiments, the disease or condition is prostate cancer and the antigen that can be detected is PSA. In some embodiments, the disease or condition is cardiac arrest and the antigen of interest that can be detected is troponin. In some embodiments, the disease or condition is Alzheimer's disease and the antigen of interest that can be detected is tau protein. In some embodiments, the disease or condition is HIV and the antigen of interest that can be detected is IP-10. In some embodiments, the disease or condition is Schistomiasis and the antigen of interest that can be detected is Schistosome GST. In some embodiments, the disease or condition is ovarian cancer and the antigen of interest that can be detected is CA-125. In some embodiments, the disease or condition is lyme disease and the antigen of interest that can be detected is ospA.

In some embodiments, antigens or antigens of interest produced by vector-borne diseases (e.g., chikungunya, Chagas, Ebola, bubonic plague, Lyme disease, brucellosis, encephalitis, etc.) are also contemplated herein; by food/water-borne illness (e.g., diarrhea, cholera, schistomiasis, bovine spongiform encephalopathy (prion), etc.) are also contemplated herein; by patient-to-patient transmitted infectious disease (e.g., tuberculosis (ESAT-6/CFP-10/Rv1656/LAM), HIV (CD32a), influenza (HA), rhinitis, pneumonia, bronchitis, syphilis, gonnorhea, hepatitis A/B/C, HPV, etc.) are also contemplated herein; by chronic diseases (diabetes/pre-diabetes (glycated hemogloblin), anemia (hemoglobin), liver cirrhosis, cardiac arrest (troponin), Alzheimer's disease, autoimmune disease, etc.) are also contemplated herein. General health assays (protein urine analysis, etc), livestock assays, companion diagnostics for cancer therapeutics are also contemplated herein.

Compositions

In some aspects, compositions of the bifunctional fusion proteins described herein are also provided. In some embodiments, the composition includes any of the bifunctional fusion proteins described herein bound to a cellulose-containing substrate. In some embodiments, the cellulose-containing substrate is paper (e.g., chromatography paper) or nitrocellulose. In certain embodiments, the cellulose-containing substrate is modified in an oxidizing chemical bath to yield covalent chemical linkage of the protein to the substrate, passivated with a blocking agent to reduce non-specific protein adsorption to the substrate, or pre-incubated with a stabilizing species such as trehalose in order to improve assay functionality and stability. In certain embodiments, the cellulose-containing substrate is not modified (unmodified). In some embodiments, the cellulose-containing substrate is an unmodified chromatography paper, such as unmodified WHATMAN® Grade 1 Qualitative Filtration Paper. Additional non-limiting examples of cellulose-containing substrates also contemplated herein include cellulose powder, cellulose microbeads, or cellulosic fabrics/yams.

In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5 micromoles, at least or about 4 micromoles, at least or about 4.5 micromoles, or at least or about 5 micromoles of any of the bifunctional fusion proteins described herein are attached to a cellulose-containing substrate per gram of cellulose of the cellulose-containing substrate.

In some embodiments, at least or about 1 µM, at least or about 25 µM, at least or about 50 µM, at least or about 60 µM, at least or about 70 µM, at least or about 80 µM, at least or about 90 µM, at least or about 100 µM, at least or about 150 µM, at least or about 200 µM, at least or about 250 µM, at least or about 300 µM, at least or about 350 µM, at least or about 400 µM, at least or about 500 µM, at least or about 550 µM, at least or about 600 µM, at least or about 650 µM, at least or about 700 µM, at least or about 750 µM, at least or about 800 µM, at least or about 850 µM, at least or about 900 µM, at least or about 950 µM, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-average concentration of any of the bifunctional fusion proteins described herein are attached to a cellulose-containing substrate.

Kits

In some aspects, the bifunctional fusion protein and compositions described herein are provided in a kit. In some embodiments, the kit is used to assess the presence or amount of a molecule, such as an antigen or an antigen of interest and includes a container containing any of the bifunctional fusion proteins described herein.

In some embodiments, the kit further comprises a cellulose-containing substrate. In some embodiments, the bifunctional fusion protein is bound to the cellulose-containing substrate. In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5, at least or about 4 micromoles, at least or about 4.5 micromoles, or at least or about 5 micromoles of any of the bifunctional fusion proteins described herein are attached to the cellulose-containing substrate per gram of cellulose of the cellulose-containing substrate.

In some embodiments, at least or about 1 µM, at least or about 25 µM, at least or about 50 µM, at least or about 60 µM, at least or about 70 µM, at least or about 80 µM, at least or about 90 µM, at least or about 100 µM, at least or about 150 µM, at least or about 200 µM, at least or about 250 µM, at least or about 300 µM, at least or about 350 µM, at least or about 400 µM, at least or about 500 µM, at least or about 550 µM, at least or about 600 µM, at least or about 650 µM, at least or about 700 µM, at least or about 750 µM, at least or about 800 µM, at least or about 850 µM, at least or about 900 µM, at least or about 950 µM, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-concentration of any of the bifunctional fusion proteins described herein are attached to the cellulose-containing.

In some embodiments, the bifunctional fusion protein is bound to the cellulose-containing substrate. In some embodiments, the cellulose-containing substrate is paper (e.g., chromatography paper), nitrocellulose or cellulose powder. In certain embodiments, the cellulose-containing substrate is modified in an oxidizing chemical bath to yield covalent chemical linkage of the protein to the substrate, passivated with a blocking agent to reduce non-specific protein adsorption to the substrate, or pre-incubated with a stabilizing species such as trehalose in order to improve assay functionality and stability. In certain embodiments, the cellulose-containing substrate is not modified (unmodified). In some embodiments, the cellulose-containing substrate is an unmodified chromatography paper, such as unmodified WHATMAN® Grade 1 Qualitative Filtration Paper. Additional non-limiting examples of cellulose-containing substrates also contemplated herein include cellulose powder, or cellulose microbeads, cellulosic fabrics/yams.

EXAMPLES

Example 1. Paper-Based Diagnostics in the Antigen-Depletion Regime: High-Density Immobilization of Rcsso7d-Cellulose-Binding Domain Fusion Proteins for Efficient Target Capture Materials and Methods Materials Unless otherwise stated, all chemical reagents, biological materials, and consumables were procured from the same source as outlined in the supplementary information of Reference 1. All DNA cloning enzymes were purchased from New England Biolabs (Ipswich, MA, USA). Streptavidin-eosin conjugate was prepared as previously described (Miller et al., 2016, SI).

Yeast Surface Display Selection and Characterization of rcSso7d-Based Binding Variants The development and selection of rcSso7d.SA was described in previous work. (Miller et al., 2016) The Rv1656-binding variant of rcSso7d was selected in similar fashion, from a yeast surface display library based on the reduced-charge Sso7d scaffold (rcSso7d). This yeast library was generated using trinucleotide oligo synthesis and in vivo homologous recombination with the linearized pCTcon2 plasmid. (Traxlmayr et al., 2016).

Figure 8:
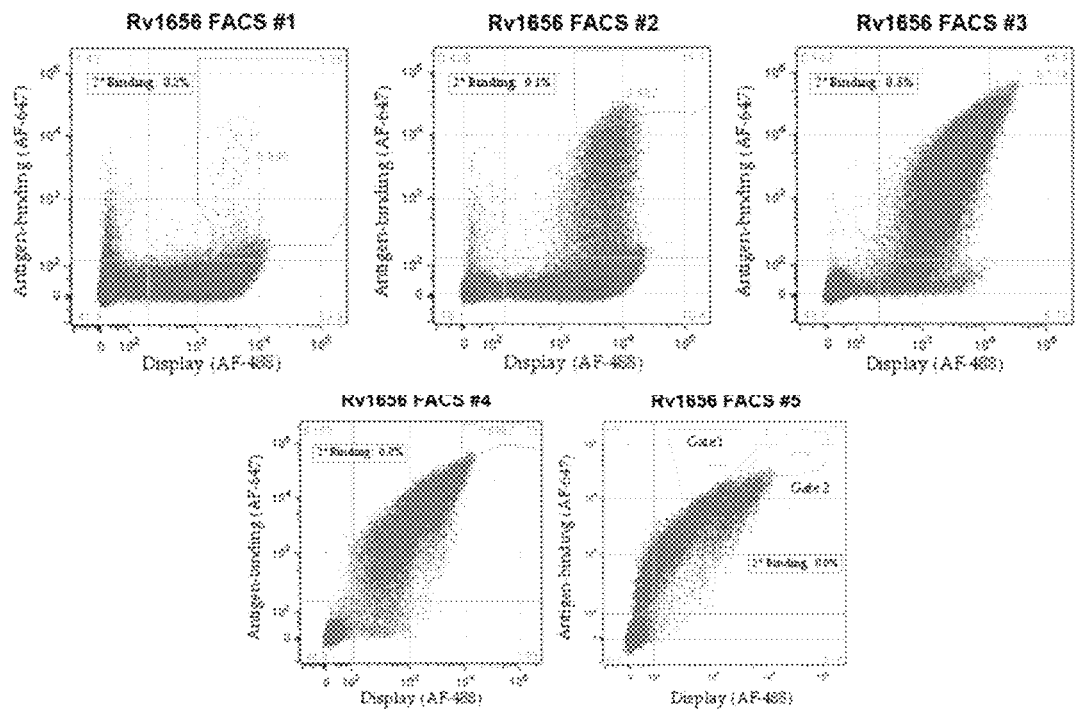
FIG. 8. FACS plots for yeast-surface display selection of Rv1656-binding variants of rcSso7d. Data points represent the measured fluorescence for 20,000 individual yeast cells. Full-length surface display of the rcSso7d scaffold, quantified via the surface localization of the ALEXA FLUOR®488 fluorophore, is presented on the x-axis. Rv1656 binding activity, quantified via the ALEXA FLUOR®64 7 fluorophore, is presented on the y-axis. The corner of each quadrant is labeled with the proportion of the library population falling within those bounds, and the sorting gate used to capture the subsequent sub-library is labeled with the captured percentage of the library population. The secondary binding, corresponding to the population proportion which binds to the secondary reagent (SA-AF647), is also noted. The soluble concentration of Rv1656 was 100 nM for the first three rounds of sorting, 50 nM for the fourth round, and 25 nM for the fifth round.

Both highly-avid magnetic bead sorting (Ackerman et al., 2009) (μMBS) and fluorescence-activated cell sorting (FACS) (Chao et al., 2006) were used to select binders against a biotinylated Rv1656 target (FIG. 8). The sorting stringency was increased over five rounds of FACS-based library screening, after which a sub-library was sequenced and rcSso7d.Rv1656 was selected for further characterization. The affinity of this species was assessed in a yeast surface display format, via a soluble titration of biotinylated Rv1656 against the displayed rcSso7d variant.

Recombinant Protein Expression, Purification, and Characterization

The genes for rcSso7d.SA and rcSso7d.Rv1656 were both cloned from the pCTcon2 yeast display plasmid into the pET28b(+) bacterial expression plasmid as previously described. (Miller et al., 2016) The rcSso7d.SA-CBD gene product was generated by Integrated DNA Technologies (IDT; Coralville, IA, USA) via gene synthesis, and traditional PCR cloning was used to integrate the rcSso7d.Rv1656 module into this rcSso7d-CBD fusion construct. All gene products were modified with an N-terminal hexahistidine tag for purification via immobilized metal affinity chromatography (IMAC). The pET14b-Rv1656 plasmid was provided by the lab of Dr. Antonio Campos-Neto at the Forsyth Institute. (Napolitano et al., 2008)

The heterologous expression of all protein species was conducted in a BL21(DE3) strain of E. coli, and induced via the addition of 0.5 mM isopropyl β-D-1-thiogalactopyranoside (IPTG). Induced cells were lysed by ultrasonification, and the recombinant product was purified from the clarified lysate via IMAC. A 3-kDa Amicon Ultracentrifuge Filter cassette was used to buffer exchange the 9.24-kDa rcSso7d monomer 1,000-fold into the resuspension buffer (40 mM sodium acetate, pH 5.5). Products featuring a CBD fusion partner were buffer-exchanged using a 3.5 kDa MWCO Slide-A-Lyzer Dialysis Cassette (Thermo Fisher Scientific, Waltham, MA, USA), in order to prevent the adsorption of the CBD fusion products to the cellulose acetate membrane of the spin filters.

Rv1656 was expressed in similar fashion using BL21 (DE3) E. coli, and was resuspended in 50 mM HEPES buffer (pH 8.0) using a 10 kDa MWCO Slide-A-Lyzer Dialysis Cassette. Purified Rv1656 was biotinylated using the EZ-Link Sulfo-NHS-LC-Biotin No-Weigh Format labeling kit from Thermo Fisher Scientific, and desalted using Micro G-25 Spin Columns from Santa Cruz Biotech (Dallas, TX, USA).

The concentrations of all purified proteins were assessed using a bicinchoninic acid (BCA) assay, and all standards and purified samples were tested in triplicate for greater accuracy. Protein purity was assessed using a freshly cast 15% sodium dodecyl sulfate polyacrylamide gel electrophoresis (SDS-PAGE) gel, stained using COOMASSIE® Brilliant Blue G-250.

Fabrication and Testing of Biofunctional Cellulose Test Zones

Unmodified WHATMAN® No. 1 chromatography paper was used as shipped for the immobilization of rcSso7d-CBD fusion proteins. In order to enable the covalent immobilization of rcSso7d variants lacking a CBD fusion partner, WHATMAN® No. 1 chromatography paper was functionalized in 30 mM sodium metaperiodate solution as previously described. (Miller et al., 2016) This oxidized, aldehyde-functionalized cellulose was stored under vacuum in a desiccator until use, whereas non-functionalized paper was stored under ambient conditions. As previously described, a solid ink printer was used to produce test zone arrays, and this printed wax was melted through the paper thickness (0.18 mm) to yield test zones with an average area of 2.5±0.1 $mm^2$ (unless otherwise noted).

Stock solutions of purified rcSso7d and rcSso7d-CBD variants were diluted to the desired concentrations in resuspension buffer. For bare rcSso7d species, glycerol was also added to the solution at a final volumetric concentration of 10% in order to prevent evaporation during the extended initial incubation. Unless otherwise stated, all binding protein solutions were prepared at a final concentration of 30 μM. Negative controls for functionalized paper samples consisted of test zones contacted with 1 mg/mL bovine serum albumin (BSA). Bare paper test zones were used as the negative control for unmodified paper samples.

Functionalized test zones were modified with the bare rcSso7d variants, washed, and neutralized in Tris-buffered saline as described in previous work. Both rcSso7d-CBD variants were contacted with unmodified paper in 6 μL aliquots for at least thirty seconds, and then washed twice in 20 μL of 1× phosphate-buffered saline (PBS; pH 7.4).

Figure 14:
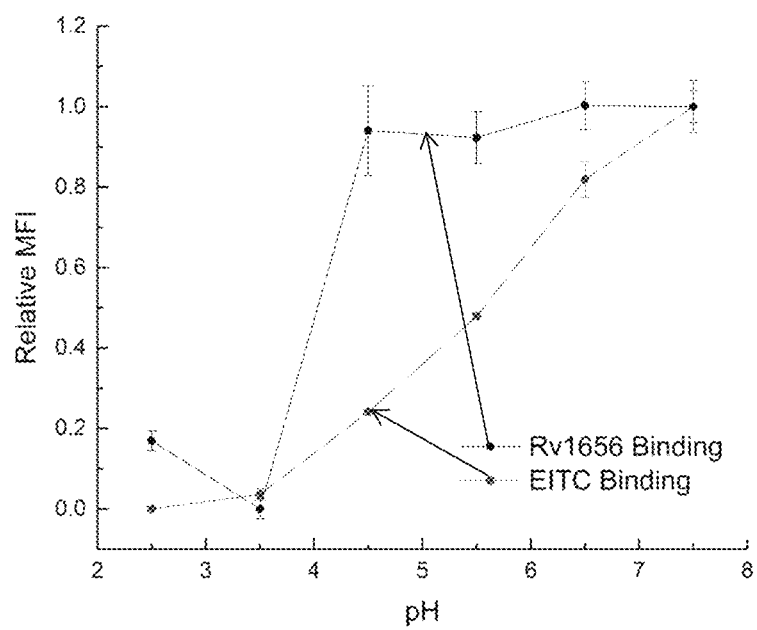

Protein-coated test zones were then contacted with 10 μL of the relevant antigen, diluted to the desired concentration in sterile-filtered 1×PBS/1% w/v BSA. rcSso7d.SA and rcSso7d.SA-CBD species were contacted with either streptavidin eosin (SA-E), prepared as previously described, (Miller et al., 2016) or streptavidin ALEXA FLUOR®647 (SA-AF647) sourced from Invitrogen (Carlsbad, CA, USA). rcSso7d.Rv1656-CBD was contacted with biotinylated recombinant Rv1656. All test zones were incubated with antigen solution for 30 minutes at room temperature, after which they were washed twice with PBS. Negative controls were incubated in PBS in the absence of soluble antigen during this period. Assays incorporating rcSso7d.Rv1656 and rcSso7d.Rv1656-CBD were then subjected to an additional 30-minute incubation with SA-E/SA-AF647 at a concentration of 256 nM. SA-E samples were prepared in a citric acid-sodium phosphate buffer system (50 mM citric acid, 90 mM Na2HPO4, pH 4.5) containing 1% BSA, and washed in the same acidic buffer lacking BSA, in order to reduce non-specific binding of rcSso7d.Rv1656-CBD to the eosin reagent (FIG. 14). Developed samples were blotted dry and stored in the dark in a freezer box until needed for fluorescence microscopy imaging.

Fluorescence Microscopy

All samples were imaged as previously described (Miller et al., 2016), using an Olympus 1X81 Microscope. Unless otherwise noted, all samples developed with SA-E were exposed for 1000 ms using a Semrock TxRed-4040C filter set. Samples developed with SA-AF647 were exposed for either 80 ms or 100 ms (as noted) using a Semrock CY5®-4040C filter set. The ImageJ Auto Threshold function (Default algorithm) was used to identify the bounds of each sample zone, and the mean fluorescence intensity (MFI) of each sample was calculated by averaging the brightness of all pixels within the thresholded area. Four technical replicates were prepared for all experimental conditions, and the resultant MFI values were averaged for all replicates. Error bars represent one standard deviation from this mean intensity value.

Quantification of Surface-Immobilized CBD Fusion Proteins

A micro BCA assay (Thermo Fisher Scientific) was used to determine the immobilized surface density of the engineered rcSso7d.SA-CBD fusion protein on non-functionalized WHATMAN® No. 1 chromatography paper. A series of standards was prepared by contacting test zones with known masses of rcSso7d.SA-CBD and allowing these solutions to evaporate in a vacuum chamber at room temperature for 30 minutes, yielding complete protein adsorption to the cellulosic substrate. Experimental samples were generated by applying a series of known soluble rcSso7d.SA-CBD concentrations to the test zones, followed by a PBS wash step.

All samples were excised from the test strips and deposited into the wells of a 96-well plate pre-filled with 150 µL of 40 mM sodium acetate (pH 5.5). These test zones were vigorously stirred with clean pipette tips, and 150 µL of Working Reagent was then added to each sample well. The plate was incubated at 37° C. for two hours, and after removing the paper test zones (wringing any entrained fluid back into the sample well), the absorbance at 562 nm was quantified for all samples.

The response curve for the evaporated standards was fit to a second-order polynomial, and this standard curve was used to determine the effective quantity of rcSso7d.SA-CBD immobilized on the washed samples. Proportional rcSso7d.SA-CBD retention was calculated by comparing these experimentally determined quantities to the known protein masses applied to the surface. In order to quantify the binding capacity of the cellulose substrate under these processing conditions, the density of WHATMAN® No. 1 chromatography paper was measured in triplicate, and was found to be $0.088 \pm 0.00016$ mg/mm$^2$. The area of the test zones was measured by determining the pixel density at 40× magnification (0.287 megapixels/mm$^2$), and measuring the thresholded test zone area in ImageJ. For this micro BCA experiment, the average area of the test zones was found to be $3.65 \pm 0.25$ mm$^2$, corresponding to a cellulose mass of $0.32 \pm 0.021$ mg.

Combinatorial Library Screening

The pCTcon2-encoded library of rcSso7d variants is expressed and exported to the exterior of the yeast membrane as a C-terminal fusion to the yeast Aga2p mating protein. This permits the selection of yeast carrier cells based on the binding activity of the displayed protein, allowing the population genetics to be biased towards plasmids encoding for functional rcSso7d variants. In order to select binding variants against the recombinant Rv1656b antigen, two rounds of target positive MBS were used to reduce the library diversity from 1.4 billion to approximately 1 million, and one round of target-negative MBS was used to deplete the library of streptavidin-binding variants. This sub-library was then screened via five rounds of FACS, sequentially increasing the sorting stringency by decreasing the concentration of available antigen and the captured proportion of the library population.

A sub-population of yeast was sequenced following the final FACS round, and rcSso7d.Rv1656 was selected based on its superior binding properties. The binding affinity of the rcSso7d.Rv1656 species was assessed in a yeast-surface display format, via a titration of the soluble, biotinylated Rv1656 antigen against the displayed rcSso7d binding species. The antigen concentration was varied from 256 nM to 0.25 nM, and at every concentration of Rv1656 the yeast cells were resuspended in sufficient volume such that the antigen was present in ten-fold molar excess of the displayed binding species (assuming 50,000 displayed copies per cell, and efficient display in 60% of the population). Samples were incubated with continuous mixing for sufficient time to achieve greater than 99% of theoretical equilibrium binding. Following fluorescent labeling with streptavidin ALEXA FLUOR®647, the cell surface fluorescence was analyzed using a BD FACS LSR Fortessa II flow cytometer and the FACSDiva software package. All samples were analyzed using the 488 nm and 640 nm lasers, set to a voltage of 300V. The total geometric mean fluorescence intensity of all rcSso7d-displaying cells was quantified, and a sigmoidal function was fit to these data points to determine the affinity of the rcSso7d.Rv1656 binding species.

Production of Gene Constructs rcSso7d-Rv1656 was cloned from the pCTcon2 yeast display plasmid into the pET28b(+) bacterial expression plasmid as previously described. (Miller et al., 2016) Briefly, polymerase chain reaction (PCR) amplification of the desired gene was conducted using the primers rcSso7d-for and rcSso7d-rev (Table 3), at an annealing temperature of 58.3° C. This PCR amplicon was subjected to an NdeI/XhoI double digest at 37° C. for three hours (adding the NdeI enzyme after two hours to prevent aberrant cleavage), and this cleaved product was subsequently ligated into the digested pET-28b(+) plasmid backbone at room temperature in order to generate the stable rcSso7d.RvI656 construct. All ligation mixtures were purified using the DNA Clean and Concentrator-5 Kit from Zyrno Research (Irvine, CA, USA), and eluted in 12 µL of PCR-grade water. 4 µL of this ligation product was transformed into DH5a E. coli (F-φ801acZΔM15Δ(1acZYA-argF) U169 recA1 end A1 hsdR17 (rk−, mk+) gal-phoA supE44λ-thi-1 gyrA96 relA1) via electroporation. The entirety of this transformation mixture was plated on LB-kan plates and incubated overnight at 37° C. Positive clones were verified via both N- and C-terminal sequencing, using the T7 promoter and T7 terminator sequencing primers.

This general workflow was used for all cloning projects, and all relevant primers can be found in Table 3. Additional cloning projects involved 1) the amplification and integration of the rcSso7d.SA-CBD GeneBlock into the pET28b(+) plasmid (primers: rcSso7d-for/CBD-rev; $T_m$: 58.3° C.), and integration of the rcSso7d.Rv1656 gene into the CBD construct (primers: rcSso7dfor/rcSso7d-BamHI-rev; $T_m$: 58.3° C.). In this latter project, the PCR amplicon and pET28b(+) plasmid were both subjected to an NdeI/BamHI double digest at 37° C. for one hour in order to excise the rcSso7d.SA gene and prepare complementary sticky ends. All sequence-verified plasmids were transformed into BL21 (DE3) (F-ompT gal dcm lon hsdS$_B$ (r$_B$−m$_B$−) λ(DE3)) E. coli by electroporation for expression and purification.

TABLE 3

Oligonucleotide sequences of primers used in sequencing reactions
and plasmid cloning of selected binders rcSso7d.SA and rcSso7d.Rv1656.

| #Oligo Name | SEQ ID NO | DNA Sequence (NdeI, XhoI, and BamHI sites) |
|---|---|---|
| 1 rcSso7d-for | 6 | 5'-AGGCAGTCTCATATGGCAACCGTGAAAT-3' |
| 2 rcSso7d-rev | 7 | 5'-ACCCCTCTCGAGTTATTGCTTTTCCAGCATCTG-3' |
| 3 rcSso7d-BamHI-rev | 8 | 5'-ACCCCTCTCGAGTTATTAGGATCCTTGCTTTTCCAGCATCTG-3' |
| 4 CBD-rev | 9 | 5'-AAGTTACGCTCGAGTTAGGGTTCTTTACCCCATACAAGAACACCG-3' |

Derivation of the Exact Analytical Solution for a Monovalent Binding System

For a monovalent binding system, wherein [L] and [R] represent the volumetric molar concentrations of free ligand and free receptor, respectively, and [LR] represents the concentration of the bound complex, the ligand-capture reaction can be described using the following first-order differential equation:

$$\frac{d[LR]}{dt} = k_{on}[L][R] - k_{off}[LR]$$

It is also noted that:

$$[L]=[L]_0-[LR]$$

and $$[R]=[R]_0-[LR]$$

Thus:

$$\frac{d[LR]}{dt} = k_{on}([L]_0 - [LR])([R]_0 - [LR]) - k_{off}[LR]$$

Multiplying out and rearranging:

$$\frac{d[LR]}{dt} = k_{on}([L]_0[R]_0 - [LR][L]_0 - [LR][R]_0 + [LR]^2) - k_{on}K_D[LR]$$

$$\frac{d[LR]}{dt} = k_{on}([L]_0[R]_0 - [LR]([L]_0 + [R]_0 + K_D) + [LR]^2)$$

For simplicity, these terms shall be referred to as:

$$a=[L]_0[R]_0$$

$$b=-([L]_0+[R]_0+K_D)$$

$$c=1$$

Thus:

$$\frac{d[LR]}{dt} = k_{on}(a + b[LR] + c[LR]^2)$$

Performing separation of variables, an equation of the below form is arrived at:

$$\frac{d[LR]}{(a + b[LR] + c[LR]^2)} = k_{on}dt$$

This is of the Ricatti equation class, and can be solved implicitly. This integral is also tabulated in the CRC Handbook of Chemistry and Physics (Formula 108), in the form:

$$\int \frac{dx}{X} = \frac{1}{\sqrt{-q}} \ln\left(\frac{2cx + b - \sqrt{-q}}{2cx + b + \sqrt{-q}}\right)$$

where $$X=a+bx+cx^2$$

and $$q=4ac-b^2$$

This solution form holds for all $q<0$, which is true for all real solutions of this quadratic equation.

Plugging these values in, the below solution is found:

$$\frac{1}{\sqrt{-([L]_0 + [R]_0 + K_D))^2 - 4[L]_0[R]_0}} \ln\left(\frac{2[LR](t) - ([L]_0 + [R]_0 + K_D) - \sqrt{(-([L]_0 + [R]_0 + K_D))^2 - 4[L]_0[R]_0}}{2[LR](t) - ([L]_0 + [R]_0 + K_D) + \sqrt{(-([L]_0 + [R]_0 + K_D))^2 - 4[L]_0[R]_0}}\right) = k_{on}t + \phi$$

This expression can be simplified via the following definitions (Schafer, 1983):

$$D = [L]_0 - [R]_0$$

$$S = [L]_0 + [R]_0$$

$$F = \sqrt{-q} = \sqrt{D^2 + 2SK_D + K_D^2}$$

$$P = \frac{-b - \sqrt{-q}}{2} = \frac{(S + K_D - F)}{2}$$

$$Q = \frac{-b + \sqrt{-q}}{2} = \frac{(S + K_D + F)}{2}$$

Plugging these expressions in:

$$\frac{1}{F} \ln\left(\frac{[LR] - Q}{[LR] - P}\right) = k_{on}t + \phi$$

Rearranging:

$$\ln\left(\frac{[LR]-Q}{[LR]-P}\right) = -Fk_{on}t + \phi$$

$$\frac{[LR]-Q}{[LR]-P} = w_0 e^{-Fk_{on}t}$$

For simplicity, this exponential term is defined to be $w = w_0 e^{-Fk_{on}t}$ and thus:

$$\frac{[LR]-Q}{[LR]-P} = w$$

$$[LR] - P = w([LR]-Q)$$

$$[LR] - w[LR] = P - wQ$$

$$[LR](t) = \frac{P - wQ}{1 - w}$$

Recognizing that at t=0, [LR]=0, the constant $w_0$ can be solved for:

$$0 = \frac{P - w_0 Q}{1 - w_0}$$

$$w_0 = \frac{P}{Q}$$

$[LR]_{eq}$ can also be solved for by taking the limit as t→∞:

$$[LR]_{eq} = \frac{P - 0}{1 - 0} = P$$

Thus, the proportion of equilibrium binding at any given time is equal to:

$$\frac{[LR](t)}{[LR]_{eq}} = \frac{P - wQ}{P - wP} = \frac{P - wQ}{P - wP}$$

The time $t_{99}$ at which 99% of equilibrium binding has been achieved is:

$$0.99 = \frac{P - wQ}{P - wP}$$

$$0.99P - 0.99wP = P - wQ$$

$$w(Q - 0.99P) = P - 0.99P$$

$$\frac{P}{Q} e^{-Fk_{on}t_{99}} = \frac{0.01P}{Q - 0.99P}$$

$$t_{99} = -\frac{1}{Fk_{on}} \ln\left(\frac{0.01Q}{Q - 0.99P}\right)$$

These findings can also be non-dimensionalized, substituting either:

$$u = \frac{[LR]}{[R]_0} \text{ or}$$

$$v = \frac{[LR]}{[L]_0}$$

and $$\tau = K_{off} t$$

Doing so, the below relative equations are arrived at:

$$u = \frac{P\left(1 - e^{-\frac{F}{K_D}\tau}\right)}{[R]_0 \left(1 - \frac{P}{Q} e^{-\frac{F}{K_D}\tau}\right)}$$

$$\frac{u}{u_{eq}} = \frac{v}{v_{eq}} = \frac{\left(1 - e^{-\frac{F}{K_D}\tau}\right)}{\left(1 - \frac{P}{Q} e^{-\frac{F}{K_D}\tau}\right)}$$

$$v = \frac{P\left(1 - e^{-\frac{F}{K_D}\tau}\right)}{[L]_0 \left(1 - \frac{P}{Q} e^{-\frac{F}{K_D}\tau}\right)}$$

$$\tau_{99} = -\frac{K_D}{F} \ln\left(\frac{0.01Q}{Q - 0.99P}\right)$$

Derivation of Pseudo First-Order Rate Constant Model $$\frac{d[LR]}{dt} = k_{on}[L][R] - k_{off}[LR]$$

Assume that R>>L, so a pseudo first-order rate constant can be established, with $k^* = k_{on}[R]$.

$$\frac{d[LR]}{dt} = k^*[L] - k_{off}[LR]$$

Note that $[L]_{tot} = [L] + [LR]$.

$$\frac{d[LR]}{dt} = k^*([L]_{tot} - [LR]) - k_{off}[LR]$$

$$\frac{d[LR]}{dt} = k^*[L]_{tot} - (k^* + k_{off})[LR]$$

At equilibrium, $$\frac{d[LR]}{dt} = 0.$$

$$0 = k^*[L]_{tot} - (k^* + k_{off})[LR]_{eq}$$

$$k_{off} = \frac{k^*[L]_{tot} - k^*[LR]_{eq}}{[LR]_{eq}}$$

This relation can be used to solve for the theoretical equilibrium binding in this PFORC model:

$$[LR]_{eq} = \frac{k^*[L]_{tot}}{(k^* + k_{off})}$$

Plugging the expression for $k_{off}$ back into the differential equation form:

$$\frac{d[LR]}{dt} = k^*[L]_{tot} - \left(k^* + \frac{k^*[L]_{tot} - k^*[LR]_{eq}}{[LR]_{eq}}\right)[LR]$$

$$\frac{d[LR]}{dt} = k^*[L]_{tot} - \left(\frac{k^*[L]_{tot}}{[LR]_{eq}}\right)[LR]$$

$$\frac{d[LR]}{dt} = k^*[L]_{tot}\left(\frac{[LR]_{eq} - [LR]}{[LR]_{eq}}\right)$$

Integrating:

$$\int_0^{[LR]_t} \frac{d[LR]}{[LR]_{eq} - [LR]} = \int_0^t \left(\frac{k^*[L]_{tot}}{[LR]_{eq}}\right)dt$$

$$-\ln([LR]_{eq} - [LR]_t) + \ln([LR]_{eq}) = \frac{k^*[L]_{tot}}{[LR]_{eq}}t$$

$$\ln\left(\frac{[LR]_{eq} - [LR]_t}{[LR]_{eq}}\right) = -\frac{k^*[L]_{tot}}{[LR]_{eq}}t$$

$$1 - \frac{[LR]_t}{[LR]_{eq}} = e^{-\frac{k^*[L]_{tot}}{[LR]_{eq}}t}$$

$$1 - \frac{[LR]_t}{[LR]_{eq}} = e^{-(k_{off}+k^*)t}$$

$$1 - \frac{[LR]_t}{[LR]_{eq}} = e^{-(k_{off}+k_{on}[R])t}$$

The $t_{99}$, the time at which 99% of equilibrium binding has occurred, was also calculated for each concentration pairing, via the relation:

$$1 - \frac{[LR]_t}{[LR]_{eq}} = e^{-(k_{off}+k_{on}[R])t}$$

$$t_{99} = \frac{-\ln(0.01)}{(k_{off} + k_{on}[R])} \approx \frac{-4.6}{(k_{off} + k_{on}[R])}$$

Cost Calculations

Costs per production run were estimated in similar fashion as in the supplementary information of Reference 1, though the cost of the HisTrap FF Crude column was distributed across five runs, since these columns are reusable. The per-batch cost, then, at a 1000 mL scale, was detemlined to be $18.02. Given a conservative estimate of 100,000 g rcSso7d-CBD/L, and a per-test usage of 5 g (6 μL of 30 μM solution per test, with a MW of 27.88 kDa), a 1-L production run yields enough material for 20,000 tests. This results in a per-test cost of $0.0009/test.

In order to assess the thermal stability of the rcSso7d.SA-CBD fusion species relative to the bare rcSso7d.SA monomer and to a representative SA-binding polyclonal antibody (pAb.SA), all three species were immobilized on the appropriate substrate (aldehyde-functionalized cellulose in the case of the rcSso7d.SA monomer and pAb.SA, unmodified cellulose in the case of rcSso7d.SA-CBD) at a concentration of 20 μM. Following a 16-hour primary incubation and subsequent inactivation in TBS, the samples were incubated in a humid chamber for 10 minutes in 4 μL of 5 w/v % trehalose in 1×PBS. Excess solution was blotted from these samples, and following the application of an additional 2 μL of 5 w/v % trehalose solution, all samples were placed in a vacuum oven at 45° C. until dry (5-7 minutes). These samples were then placed in a Binder oven at 40° C. for varying periods of time, after which they were exposed to a 10 μL aliquot of 330 nM SA-AF647, and imaged via fluorescence microscopy.

Figure 11A:
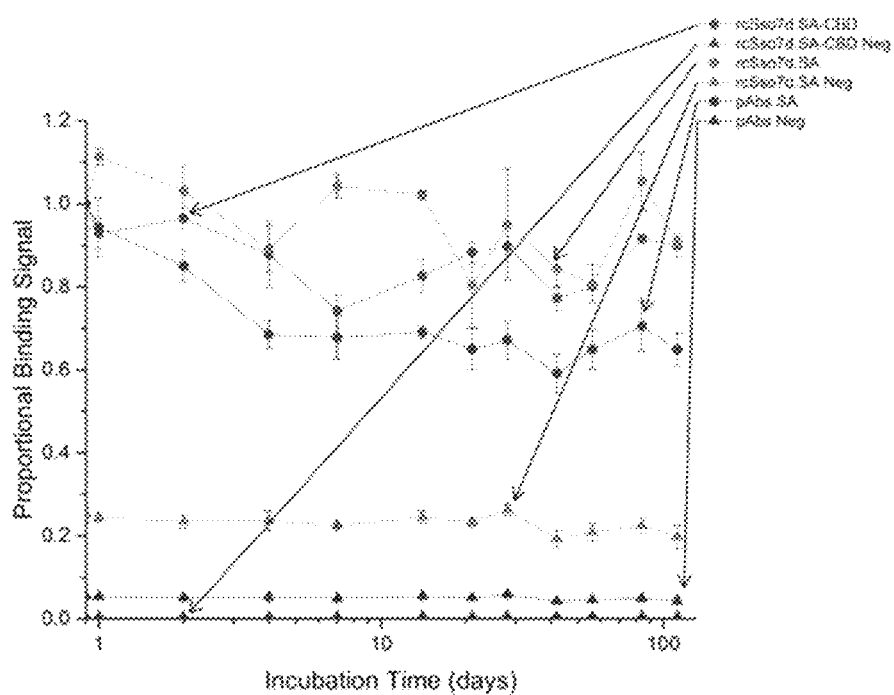
Figure 11B:
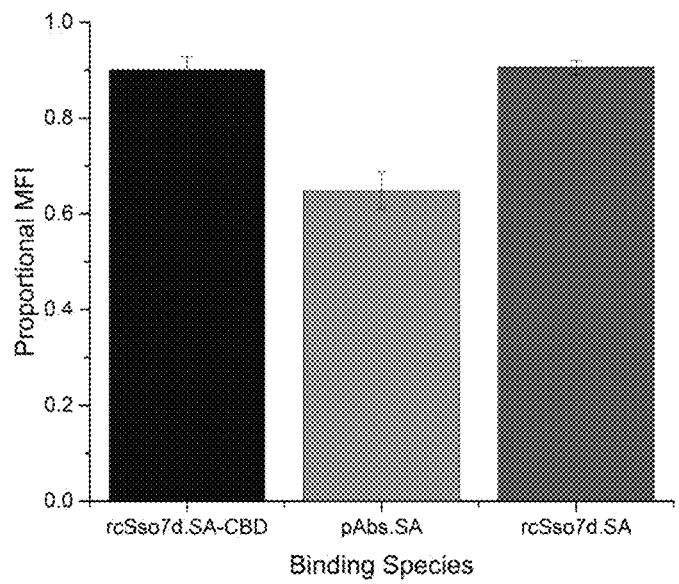

It should be noted that the gain in functionality observed with the rcSso7d-CBD construct does not come at the expense of the thermal stability of this binding species—following four months' dry incubation at 40° C., rcSso7d-CBD was observed to retain activity to the same degree as bare rcSso7d (~90%, compared to ~60% for a representative polyclonal antibody; FIGS. 11A-11B).

Maximal binding signal is observed at 30 μM rcSso7d.SA-CBD, and at higher concentrations, mean fluorescence signal is observed to diminish. This is likely due to fluorophore quenching while the molar quantity of binder immobilized from a 30 μM solution of rcSso7d.SA-CBD is sufficient to capture all antigen in a 10 μL antigen solution at a concentration of 100 nM, the higher surface density of immobilized binder places a subpopulation of the captured target in sufficient proximity that the fluorophores can interact and self-quench. In order to avoid this occurrence, an optimal concentration of 30 μM CBD will be employed. This allows the depletion of antigen from solution, without yielding sufficient surface coverage for quenching to occur.

Example 2. Pseudo First-Order Rate Constant Model

In order to explore the effects of operating within the antigen-limited binding regime, a monovalent binding model based on the principles of mass-action kinetics was developed. This binding system can be described mathematically by a simple first-order differential equation:

$$\frac{d[LR]}{dt} = k_{on}[L][R] - k_{off}[LR]$$

Here, [L] and [R] represent the volumetric molar concentrations of free ligand and free receptor, respectively, and [LR] represents the concentration of the bound complex. By employing the law of molar conservation (e.g. $[L]=[L]_0-[LR]$; $[R]=[R]_0-[LR]$), this monovalent binding system can be solved analytically to yield the expression:

$$\frac{[LR]_t}{[LR]_{eq}} = \frac{1 - e^{-\left(\sqrt{([L]_0-[R]_0)^2 + 2([L]_0+[R]_0)K_D + K_D^2}\,k_{on}t\right)}}{1 - \frac{\left([L]_0 + [R]_0 + K_D - \sqrt{([L]_0-[R]_0)^2 + 2([L]_0+[R]_0)K_D + K_D^2}\right)}{\left([L]_0 + [R]_0 + K_D + \sqrt{([L]_0-[R]_0)^2 + 2([L]_0+[R]_0)K_D + K_D^2}\right)} e^{-\left(\sqrt{([L]_0-[R]_0)^2 + 2([L]_0+[R]_0)K_D + K_D^2}\,k_{on}t\right)}}$$

However, when operating in the antigen-depletion regime, this relation can be simplified by noting that antigen capture does not significantly diminish the pool of free receptor, such that a constant concentration of available binding species can be assumed. This permits the use of a pseudo first-order rate constant (PFORC; units: s$^{-1}$) which incorporates the initial receptor concentration:

$$k^* = k_{on}[R]_0$$

By applying this PFORC in the first-order differential equation describing this binding system (derivation also in SI), the following, more compact expression for the proportion of bound antigen (relative to the equilibrium value) is found. Notably, this relation no longer depends upon the initial concentration of the soluble ligand, given that the receptor concentration alone determines the profile of the approach to binding equilibrium.

$$\frac{[LR]_t}{[LR]_{eq}} = 1 - e^{-(k_{off} + k_{on}[R]_0)t}$$

The binding regime affects not only the thermodynamics and stoichiometry of antigen capture, but also the binding kinetics. These basic models also enable the calculation of the time required for the system to reach 99% of equilibrium binding. The exact analytical expression for this value is:

highly accurate throughout much of the regime where the immobilized receptor is in molar excess to the soluble ligand.

Figure 7A:
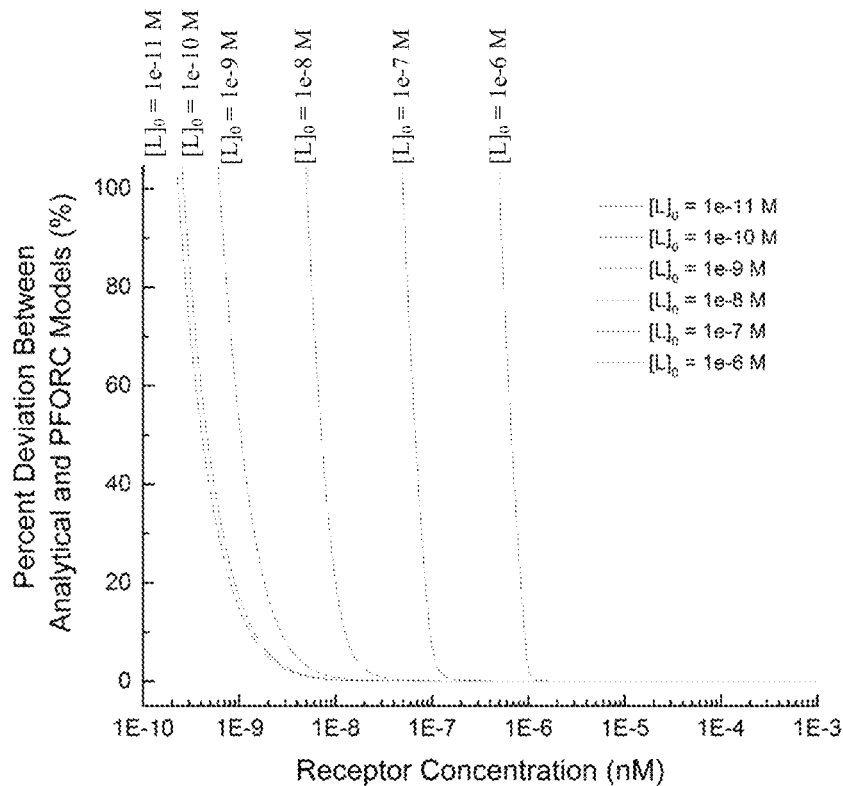
FIGS. 7A-7B. Deviation between the exact analytical solution and PFORC model in the (FIG. 7A) predicted proportional ligand capture at equilibrium and (FIG. 7B) the predicted time required to achieve 99% of equilibrium binding. All plots were generated using Kv=$5.5 \times 10^{-10}$, the measured affinity of the rcSso7d.SA species. Triangles denote the points at which the receptor concentration is equal to the ligand concentration for the curve of the corresponding color.
Figure 7B:
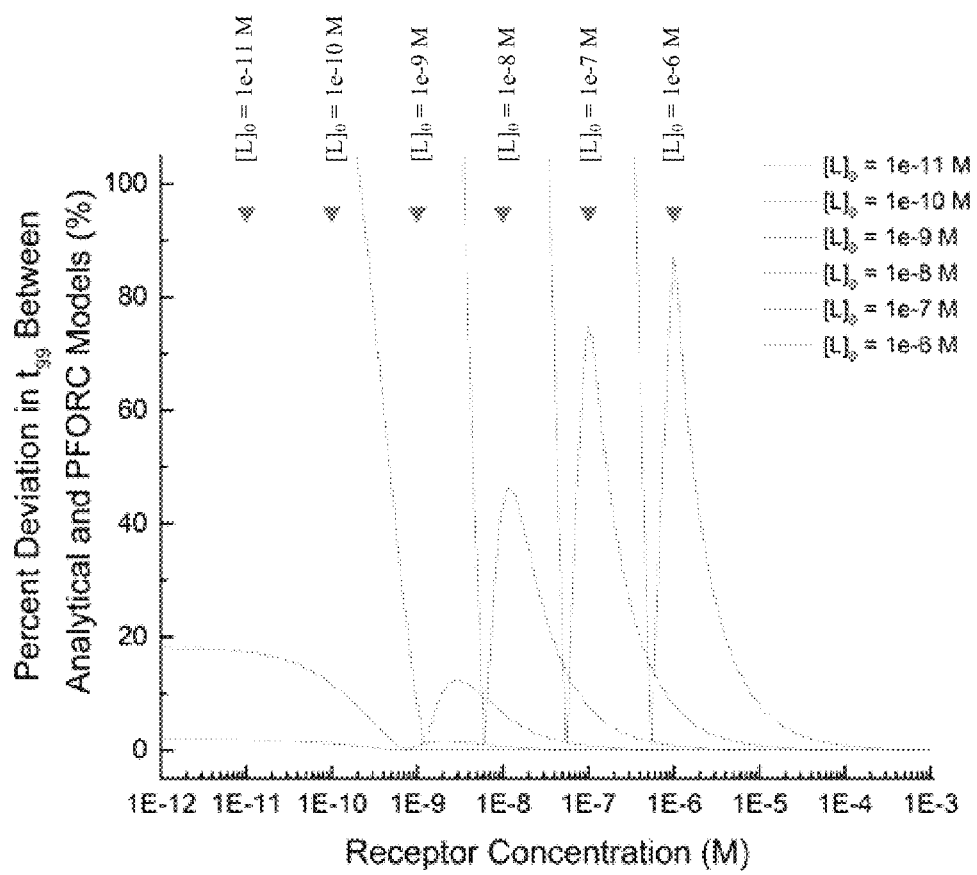

In fact, the PFORC model only appreciably deviates from the analytical solution as the initial receptor concentration either i) approaches the initial concentration of the free ligand, or ii) nears the dissociation constant of the binding pair, whichever value is greater (FIGS. 7A-7B). Generally, the proportional deviation between the analytical solution and the PFORC model only becomes significant for a ligand concentration or a $K_D$ within one order of magnitude of the local concentration of the immobilized receptor. Note that this treatment assumes that all species are present in soluble form in the same volume, thereby establishing a direct link between molar concentration and molar abundance. In the context of a heterogeneous assay, the average local concentration of the immobilized binder within the test zone volume does not directly reflect its molar abundance relative to the soluble target. Thus the molar abundance of the immobilized species must be considered instead of its local concentration, and this quantity must be an order of magnitude greater than the abundance of the soluble target in order to yield antigen depletion as described by the PFORC model.

$$t_{99} = -\frac{1}{k_{on}\sqrt{([L]_0 - [R]_0)^2 + 2([L]_0 + [R]_0)K_D + K_D^2}}$$

$$\ln\left(\frac{0.01\left([L]_0 + [R]_0 + K_D + \sqrt{([L]_0 - [R]_0)^2 + 2([L]_0 + [R]_0)K_D + K_D^2}\right)}{0.01([L]_0 + [R]_0 + K_D) + 1.99\sqrt{([L]_0 - [R]_0)^2 + 2([L]_0 + [R]_0)K_D + K_D^2}}\right)$$

In contrast, the PFORC model permits the calculation of a simplified, effective rate of reaction ($k_{obs} = k_{off} + k_{on}[R]$), which can be incorporated into the following relation to evaluate $t_{99}$:

$$t_{99} = \frac{-\ln(0.01)}{k_{obs}}$$

Figure 2A:
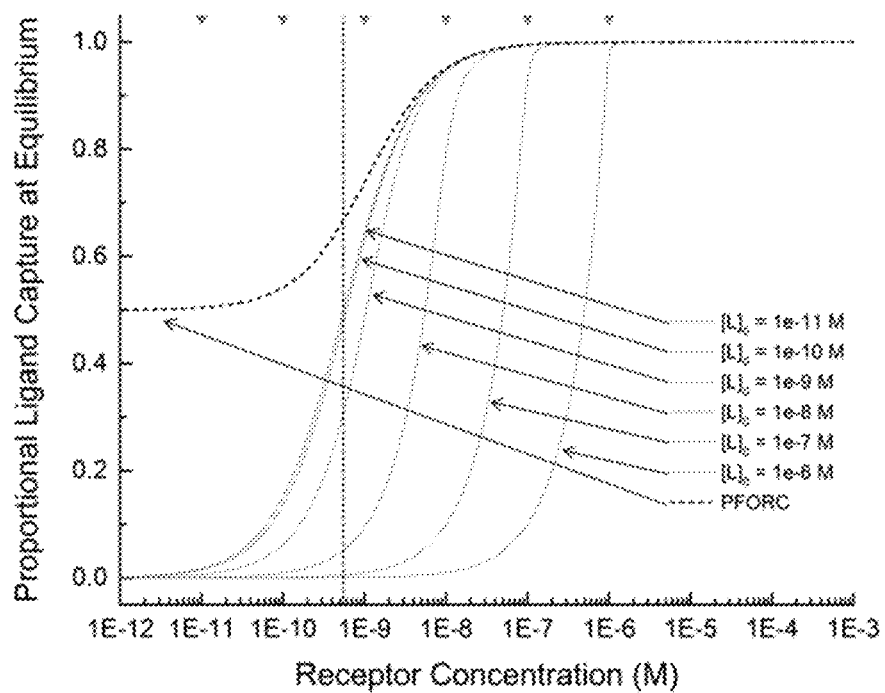
FIGS. 2A-2B. Comparison of analytical solution and PFORC model results.
Figure 2B:
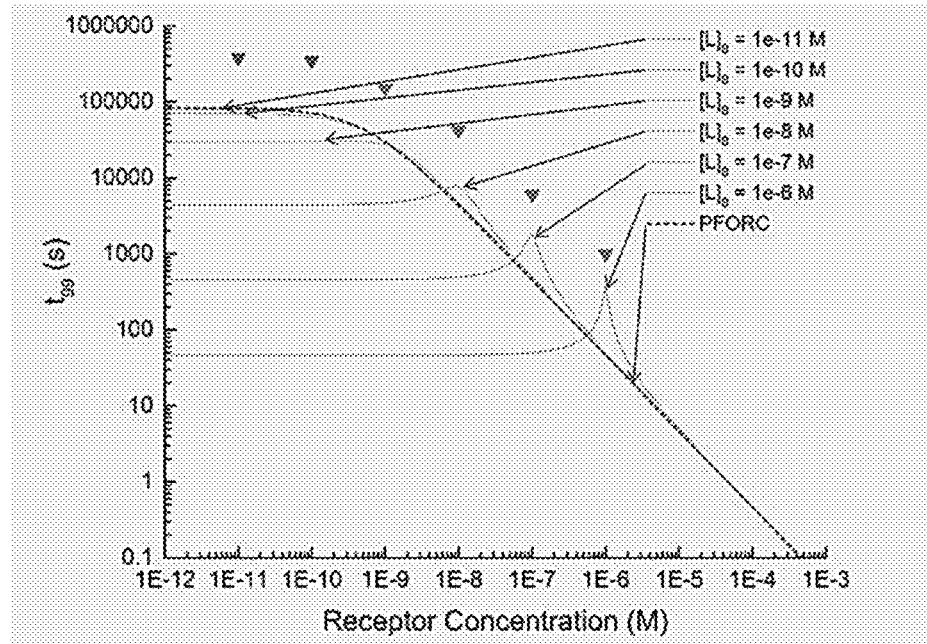

By varying the initial receptor and ligand concentrations, proportional ligand capture at equilibrium and $t_{99}$ values can be plotted for both the analytical solution and PFORC approximation (FIGS. 2A-2B), permitting direct comparison of the models and establishing bounds for the validity of the PFORC approach. It is observed that the PFORC model is Example 3. Selection And Characterization of rcSso7d Binding Variants In order to test the predictions of this basic binding model, two distinct binding variants were developed based on the thermostable rcSso7d scaffold. Both rcSso7d.SA and rcSso7d.Rv1656 were selected from a yeast surface display library of high initial diversity (~1.4 billion library members) via magnetic bead sorting and flow cytometry. The amino acid sequence of these selected binding variants can be seen below (Table 4). As reported by Traxlmayr et al (2016), strong enrichment of the aromatic residues tyrosine and tryptophan was observed. This may serve to impart greater topological diversity and electron density upon the planar rcSso7d binding face, facilitating strong, conformal binding to the target antigen.

TABLE 4

Primary protein structure of selected rcSso7d binders.

| Protein Species | SEQ ID NO | Primary Structure (N → C) (Variable AA residues) | Shorthand Tag |
|---|---|---|---|
| rcSso7d.SA | 4 | MATVKFTYQGEEKQVDISKIK<u>IVARDGQYIDFK</u>YDEGGGA<u>YGYGW</u><br>VSEKDAPKELLQMLEKQ | IADYDKYYW<br>(SEQ ID NO: 29) |
| rcSso7d.Rv1656 | 5 | MATVKFTYQGEEKQVDISKIK<u>WVRRYGQYIGFS</u>YDEGGGA<u>WGKG</u><br><u>Y</u>VSEKDAPKELLQMLEKQ | WRYYGSWKY<br>(SEQ ID NO: 30) |

Figure 9:
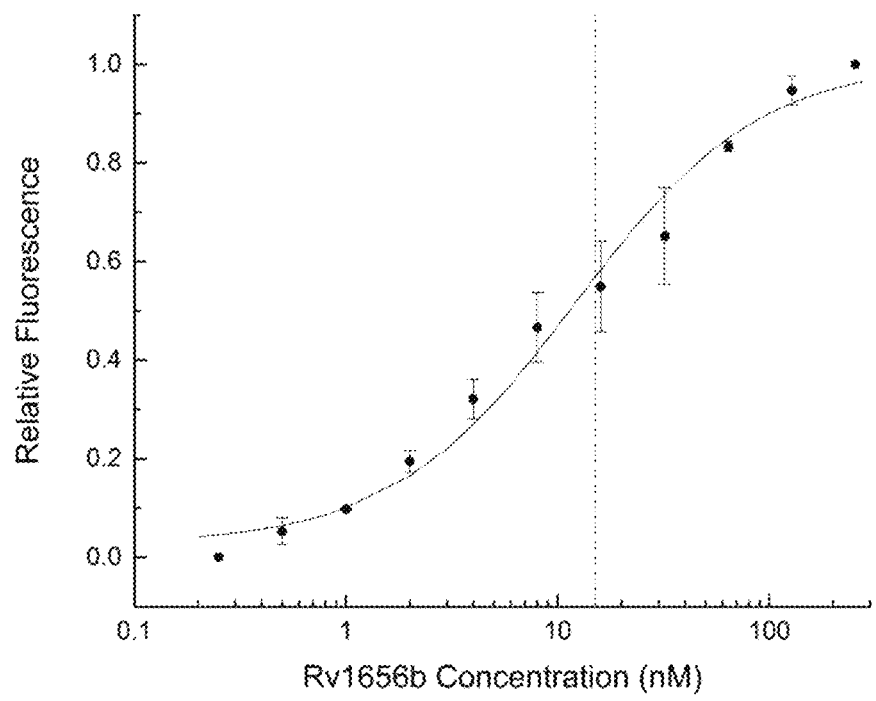
FIG. 9. Affinity determination for rcSso7d.Rv1656 via yeast-surface display titration. For each s

The dissociation constants of the rcSso7d.SA and rcSso7d.Rv1656 modules were both measured in the yeast surface display format by titrating soluble, biotinylated antigen against monoclonal yeast populations expressing these binding species as surface-bound fusion proteins. The affinity of rcSso7d.SA was previously reported to be 556±136 pM, (Miller et al., 2016) and the affinity of rcSso7d.Rv1656 was found to be 15.1±7.0 nM (FIG. 9).

In order to incorporate these binding proteins into the rcSso7d-CBD format, the gene encoding the type 3 cellulose binding domain of the CipA protein from *Clostridium thermocellum* (GenBank: HF912725.1, residues 364-522) was synthesized by IDT as a C-terminal fusion partner to the rcSso7d.SA species. This particular cellulose-binding domain was chosen for its high immobilization density and demonstrated activity in an immunoassay format, (Dai et al., 2016; Holstein et al., 2016; Hussack et al., 2009) as well for its thermal (McBee, 1954) and chemical stability. (Berdichevsky et al., 1999) The two fusion partners are joined by a flexible $(G_4S)_3$-linker sequence (SEQ ID NO: 125), and an internal BamHI site is included at the C-terminal end of the rcSso7d gene.

Figure 10:
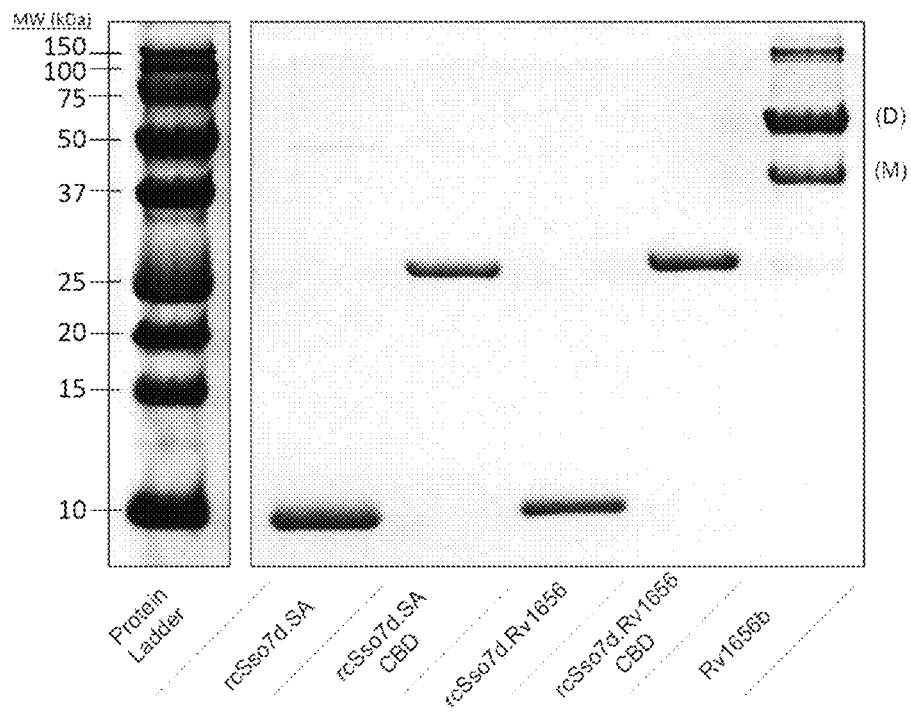

These rcSso7d-CBD constructs were expressed in BL21 (DE3) *E. coli* and purified via a reusable IMAC column, yielding a product of electrophoretic purity within a single purification step (FIG. 10). Protein concentration was quantified via a BCA assay, and the protein yield was determined to range from 131.4 mg/$L_{culture}$ (14.28 mg/g wet cell mass (WCM)) for rcSso7d.SA-CBD to 105.5 mg/$L_{culture}$ (8.55 mg/g WCM) for rcSso7d.Rv1656-CBD. Given a calculated cost basis for a single bacterial production run of $18.02, and a conservative per-test usage of 5 micrograms, a single 36-hour production run at a 1000-mL scale can produce enough material for approximately 20,000 assays, at a cost of $0.0009/device. These favorable bio-manufacturing economics enable the high-throughput production of these paper-based assays, at a price point that is well-suited for low-cost biomedical applications in resource-limited settings.

Example 4. Characterization of rcSso7d.SA-CBD Cellulose-Binding Activity

In order to assess the capture efficiency of bioactive cellulose functionalized with the rcSso7d.SA-CBD fusion species, these binding proteins were immobilized in hydrophilic test zones and subsequently contacted with the soluble antigen, forming an immunocomplex. By using these half-sandwich assay formats, it is possible to decouple the typical immunoassay binding steps, allowing each molecular interaction to be evaluated in isolation and engineered for optimal performance prior to re-integration into a full diagnostic format.

Fluorescence microscopy imaging of developed test zones indicates that the cellulose-binding domain strongly binds to unmodified WHATMAN® No. 1 chromatography paper in high abundance (FIG. 3), removing the need for substrate pre-processing steps. This represents a significant process improvement in the production of these paper-based assays, given that typical procedures require functionalization steps for the activation of inert cellulosic substrates, in order to immobilize diagnostic binding proteins in greater abundance. (Credou and Berthelot, 2014; Nery and Kubota, 2016; Shen et al., 2016; Yu et al., 2012; Zhao et al., 2016) These chemical pre-processing methods limit production throughput, and require efficient surface passivation steps following binder immobilization in order to prevent the non-specific adsorption of patient proteins and free detection reagents. (Vuoriluoto et al., 2016; Zhu et al., 2014) Additionally, stochastic chemical conjugation methods result in the non-oriented immobilization of the binding species, which can reduce the solvent accessibility of the target-binding paratope and result in an inactive sub-population of immobilized binder. (Song et al., 2012)

Figure 3:
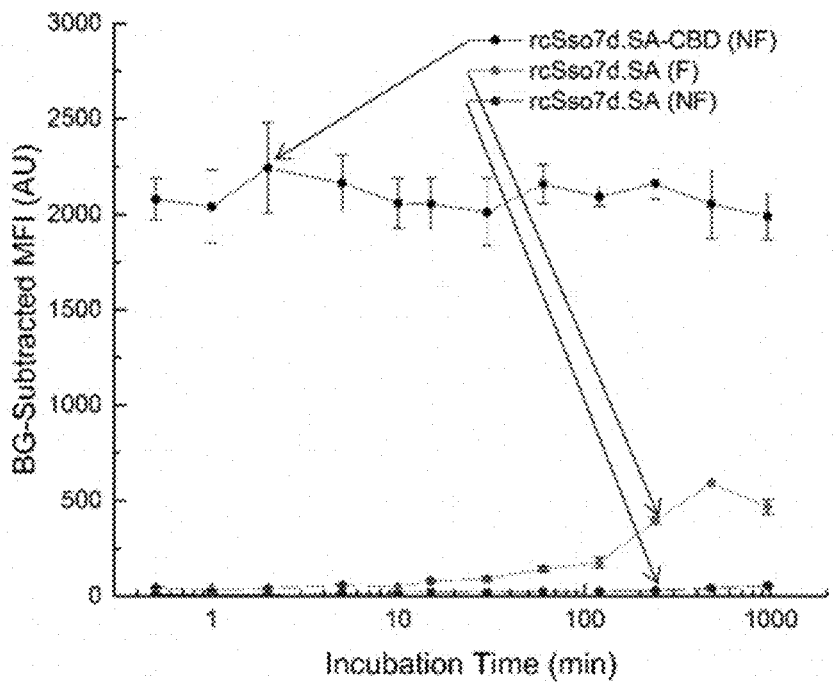
FIG. 3. Time course of primary incubation. rcSso7d.SA-CBD was contacted with non-functionalized paper (NF) and rcSso7d.SA was contacted with both functionalized (F) and non-functionalized (NF) paper for periods of time ranging from 30 seconds to 16 hours, at soluble concentrations of 30 μM (180 picomoles of applied binder). Following washing and substrate neutralization, these samples were subsequently treated with 10 μL of SA-AF647 at a soluble concentration of 256 nM (2.56 picomoles of target). All samples were imaged in the CY5® channel using an exposure time of 80 ms, and background-subtracted using the relevant negative control. Error bars represent the standard deviation of four independent replicates.

Furthermore, given the rate-dependent formation of the imine bond, an extended primary incubation is typically required in order for this covalent immobilization reaction to proceed to completion. Even following this incubation period in the functionalized paper format, this time-dependent process yielded sub-optimal antigen capture for the bare rcSso7d species (FIG. 3).

In contrast, unmodified chromatography paper requires no special pre-treatment, can be stored under ambient conditions, and yields minimal nonspecific protein adsorption both prior to and during immunoassay development. The rcSso7d-CBD fusion also yields oriented display of the antigen-binding rcSso7d module, ensuring maximal paratope accessibility and surface activity. Finally, the CBD fusion rapidly binds to the cellulose substrate in high abundance. Regardless of whether the CBD fusion was contacted with the surface for a primary incubation period of 16 hours or 30 seconds, the binding signal was observed to be roughly equivalent, and significantly greater than that of the bare rcSso7d species (FIG. 3). This drastically reduces the amount of time required to proceed from raw cellulose substrate to fully functional assays, from two days of processing time down to roughly ten minutes.

Example 5. Characterization of Assay Sensitivity Using Cellulose-Immobilized rcSso7d.SA-CBD The greater surface density of the rcSso7d.SA-CBD species also results in the onset of discernible binding signal at lower concentrations of soluble antigen relative to the bare rcSso7d.SA species. Standard definitions of assay sensitivity establish a reliable detection threshold at three standard deviations above the average signal of the negative controls.

Figure 4A:
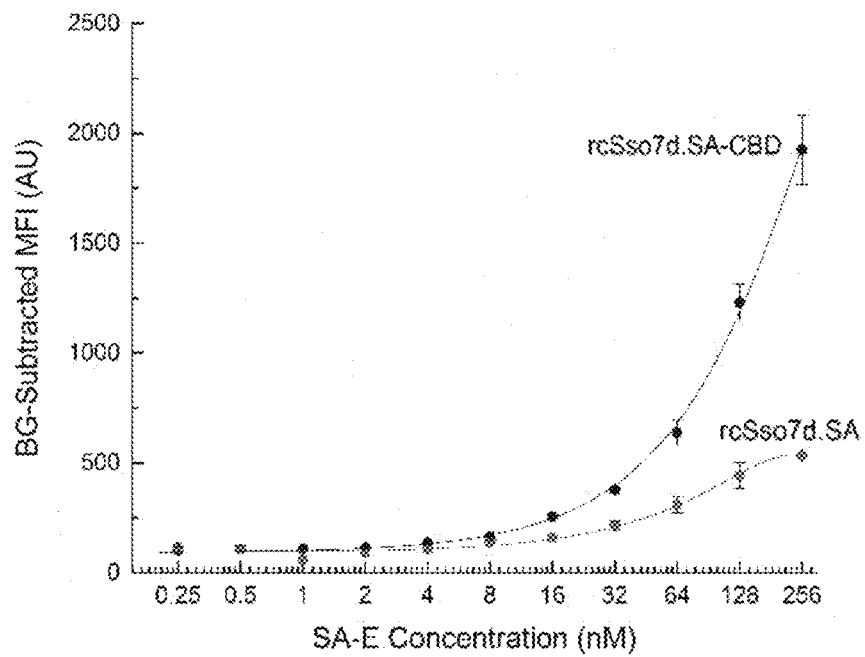
FIGS. 4A-4B. Comparison of antigen titration curves for (FIG. 4A) rcSso7d.SA/rcSso7d.SA-CBD and (FIG. 4B) rcSso7d.Rv1656/rcSso7d.Rv1656-CBD. rcSso7d and rcSso7d-CBD species were contacted with their associated substrates (functionalized and non-functionalized cellulose, respectively) for standard incubation times at a soluble concentration of 20 μM. Sample sets were treated with a serial dilution of (FIG. 4A) SA-E or (FIG. 4B) Rv1656b, at concentrations ranging from 256 nM to 0.25 nM. Samples contacted with Rv1656b were subsequently contacted with SA-E at a concentration of 256 nM. Samples were imaged in the TEXAS RED® channel using an exposure time of 1000 ms. Datasets were fit with a second-order polynomial (rcSso7d.SA: $-0.008362x^2+3.851x+100.0$, $r^2=0.9904$; rcSso7d.SA-CBD: $-0.01059x^2+9.899x+100.0$, $r^2$ 0.9986; rcSso7d.Rv1656: $-0.002774x^2+1.229x+100.0$, $r^2=0.8271$; rcSso7d.Rv1656-CBD: $-0.02791x^2+14.16x+100.0$, $r^2=0.9961$). The baseline for these datasets was adjusted to an arbitrary value of 100 AU in order to enable the comparison of signal onset. Error bars represent the standard deviation of four independent replicates.

By comparing the binding curves obtained by treating these species with a serial dilution of SA-E (FIG. 4A), a conservative limit of detection (LOD) of 8.2 nM (IBG=324.3 AU; σ=41.7 AU) is found for the bare rcSso7d species, and 2.56 nM (IBG=150.1 AU; σ=5.9 AU) for rcSso7d.SA-CBD. The background signal due to non-specific SA-E binding was also lower for unmodified cellulose, yielding better discrimination of genuine binding signal from random fluctuations near the noise threshold. The binding curve for rcSso7d.SA-CBD is also seen to continue to rise at high nanomolar concentrations of the soluble antigen, whereas the binding signal appears to saturate for the rcSso7d.SA species. This suggests a significantly higher degree of rcSso7d.SA-CBD surface immobilization, which has implications for the more rapid and efficient capture of the target from solution.

Figure 4B:
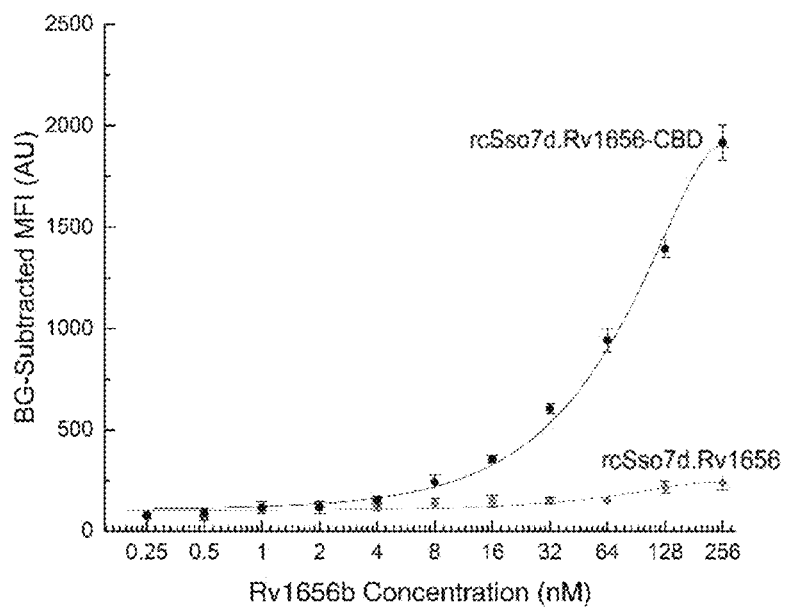

These findings were also validated in a second, orthogonal binding system, using the rcSso7d.Rv1656 binding module (FIG. 4B). In this system, too, a drastically improved binding response was observed with the rcSso7d-CBD fusion species, both in terms of its capture efficiency at high antigen concentrations, and its limit of detection (rcSso7d.Rv1656-CBD: LOD=3.1 nM; IBG=468.8 AU; σ=17.3 AU; rcSso7d.Rv1656: LOD: 48.3 nM; IBG=350.1 AU; σ=32.2 AU). The background signal for the rcSso7d.Rv1656 species is significantly higher on unmodified cellulose, due to a limited degree of nonspecific binding to the aromatic eosin species (see FIG. 14).

It should be noted that the effect of the 30-fold difference in affinity between these two binders can be observed qualitatively in the bare rcSso7d format. However, upon integration of these distinct binding species into the rcSso7d-CBD format, the binding curves are much more similar, suggesting that at higher immobilization densities, the binding affinity has little impact upon the ultimate capture efficiency.

Example 6. Identification of the Antigen-Binding Regime

Figure 12:
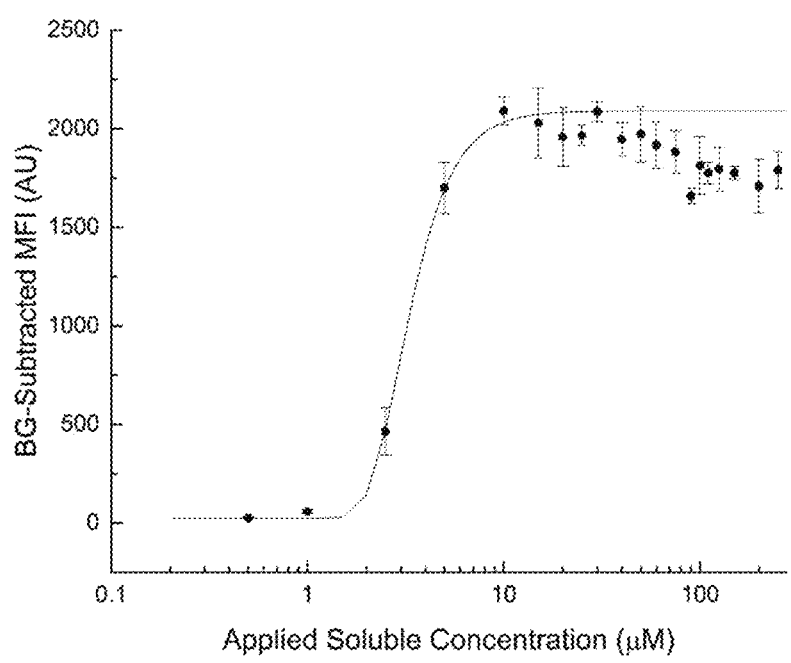

While these observations demonstrate the benefits of incorporating the CBD fusion partner, it is necessary to characterize the binding regime directly in order to confidently validate the predictions of the PFORC model. Given the clear improvement in capture efficiency observed with the rcSso7d.SA-CBD species, it was sought to determine whether this antigen binding could be further enhanced by contacting the cellulose substrate with greater molar quantities of rcSso7d.SA-CBD (FIG. 12). A series of soluble rcSso7d.SA-CBD concentrations, ranging from 0.5 mg/mL to 7 mg/mL (18.3 µM to 256 µM), was applied to the paper test zones. These sample sets were incubated with a serial dilution of SA-E, ranging from 256 nM to 0.25 nM (FIG. 11A).

Figure 5A:
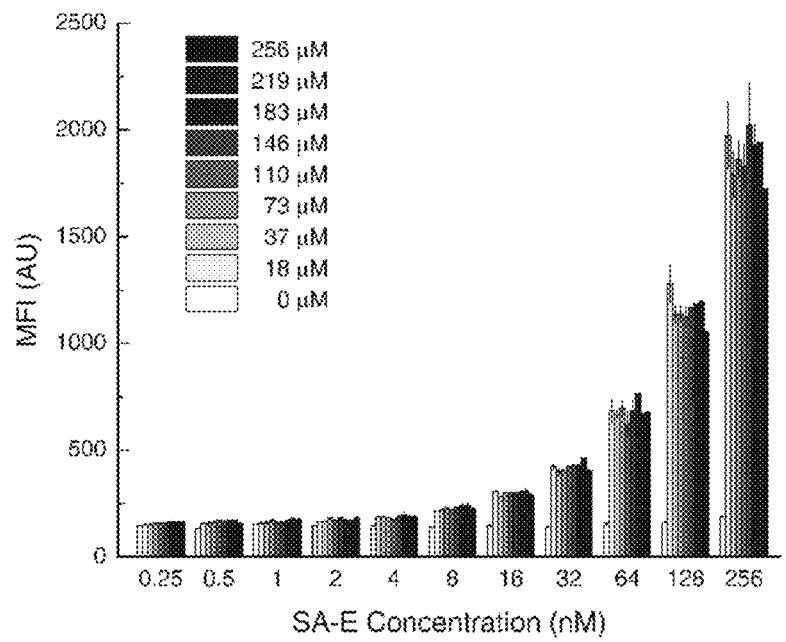
FIGS. 5A-5B.
Figure 5B:
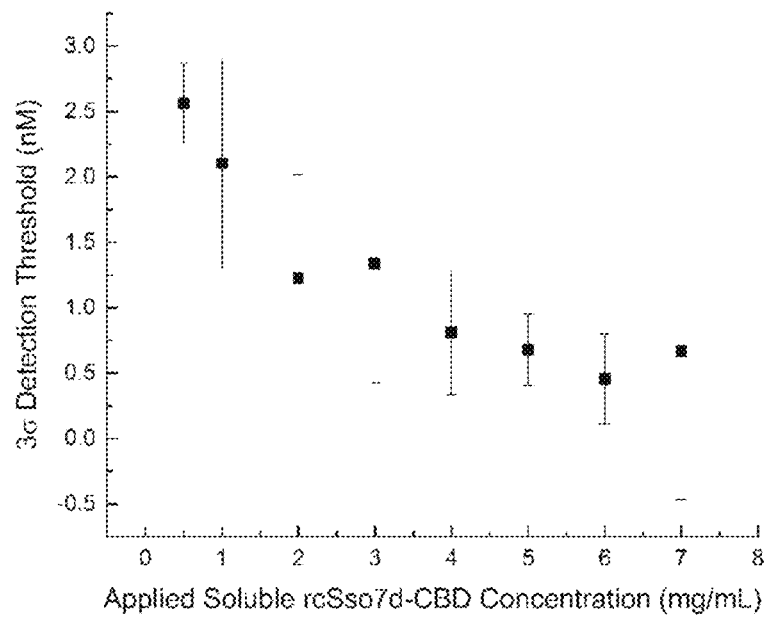

The resulting binding curves for each antigen titration are exceptionally regular, yielding an average $r^2$ value of 0.9994 when fit with a second-order polynomial. These curves generally overlap, but while no large-scale trends are immediately apparent in these clustered data sets, it was found that higher soluble concentrations of applied binder do yield greater capture efficiency at antigen concentrations in the low nanomolar range. Using the negative control dataset from all SA-E concentrations applied to bare cellulose ($I_{BG}$=150.1 AU; σ=5.9 AU), a conservative three-sigma threshold MFI of $I_{th}$=167.8 AU was calculated. Applying the second-order polynomial fit equations for each sample set, it was found that as the applied concentration of rcSso7d.SA-CBD increases, the minimum detectable antigen concentration decreases (FIG. 5B). This finding suggests that additional rcSso7d.SA-CBD binds to the cellulose substrate at higher applied concentrations, and indicates that this greater surface coverage yields improved capture efficiency at dilute antigen concentrations. Given that significantly higher MFI values are observed for more concentrated antigen solutions, this improvement in capture efficiency at low antigen concentrations is likely due to enhanced binding kinetics, rather than due to insufficient molar quantities of the immobilized binder at lower applied concentrations of rcSso7d.SA-CBD.

The general overlap of the rcSso7d.SA-CBD binding curves indicates that this binding system is operating in one of two regimes: either a) the assay is in fact within the antigen-depletion regime, such that there is no additional target to capture at a given soluble antigen concentration, or b) the cellulose substrate is saturated with immobilized rcSso7d.SA-CBD, preventing the adsorption of any additional binder. While these preliminary results suggest that the substrate is not saturated (namely the enhanced capture efficiency observed at dilute antigen concentrations with increased quantities of applied rcSso7d.SA-CBD), this finding was sought to be confirmed experimentally by directly quantifying the abundance of the immobilized rcSso7d.SA-CBD species on the cellulose substrate.

Example 7. Direct Quantification of rcSso7d-CBD Surface Abundance

Figure 6:
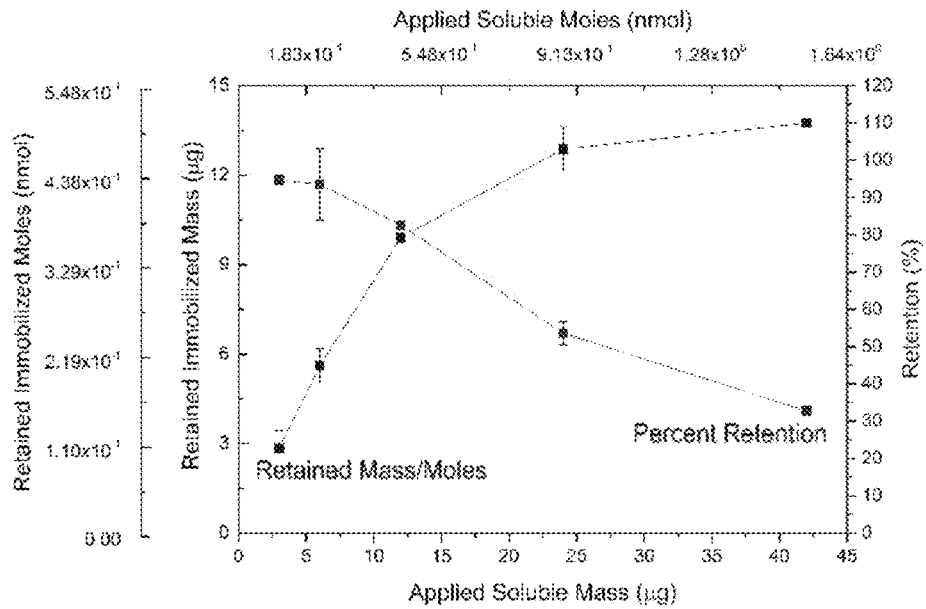
FIG. 6. Micro BCA assay data indicating the adsorption efficiency of rcSso7d.SA-CBD on non-functionalized cellulose. A standard curve of known masses of adsorbed rcSso7d.SA-CBD was used to quantify the immobilization density of rcSso7d.SA-CBD on washed samples. Experimentally determined immobilized masses, assessed via this standard curve, are plotted against the known quantity of applied rcSso7d.SA-CBD, as is the percent retention. Error bars represent the standard deviation of four independent replicates.
Figure 13:
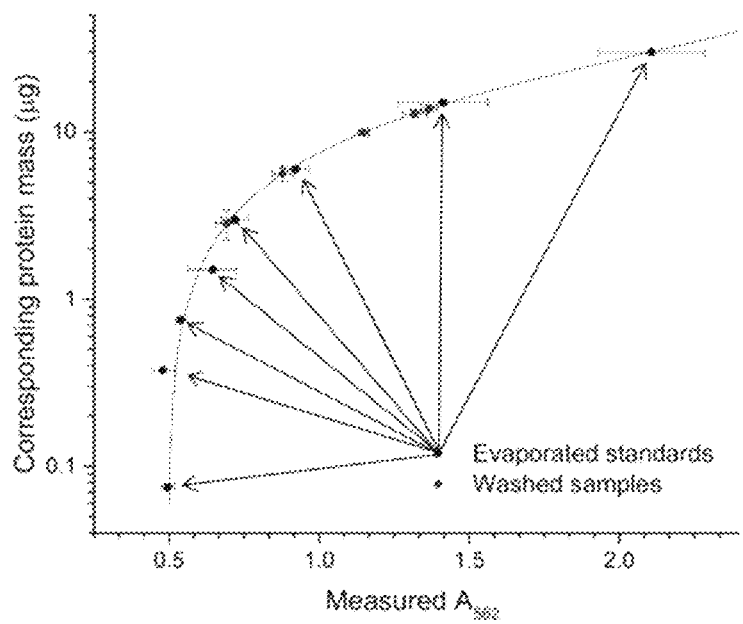

In order to further verify the relevant binding regime for this binding system, a micro BCA assay was used to quantify the immobilized surface concentration of the rcSso7d.SA-CBD species. Known masses of rcSso7d.SA-CBD were evaporated onto test zones in order to generate a standard curve that was directly comparable to the washed experimental samples. A highly regular response curve was observed for all standard samples ($r^2$=0.9978), and all washed samples fell within the bounds of this standard curve (FIG. 13). A clear monotonic increase is observed for these experimental samples, indicating that the substrate is far from saturation under the binding conditions used at the standard concentration of 30 µM (FIG. 6).

This serves to confirm that antigen depletion is responsible for the similar response curves observed at varying soluble rcSso7d-CBD concentrations. The signal development observed for the washed samples indicates a molar abundance of rcSso7d-CBD that ranges from 0.1-0.5 nmol/test zone. Given an average test zone mass of 0.32±0.021 mg, this equates to a surface density that varies from 0.32-1.56 mol of rcSso7d-CBD/g cellulose, which agrees with previously reported values. (Dai et al., 2016; Li et al., 2016)

It should be noted that the efficiency of rcSso7d.SA-CBD immobilization decreases as higher soluble concentrations of protein are applied, indicating that substrate saturation can in fact occur at high immobilized surface density. Whereas the application of 0.1-0.2 nmol of rcSso7d-CBD to the surface results in an immobilized yield of ~90%, this efficiency drops to ~30% at an application of 1.5 nmol. Though higher densities of immobilized binder do allow enhanced capture efficiency at low antigen concentrations, these diminishing returns will necessarily impose practical and economic constraints on how near to saturation the surface coverage can be driven.

Figure 15:
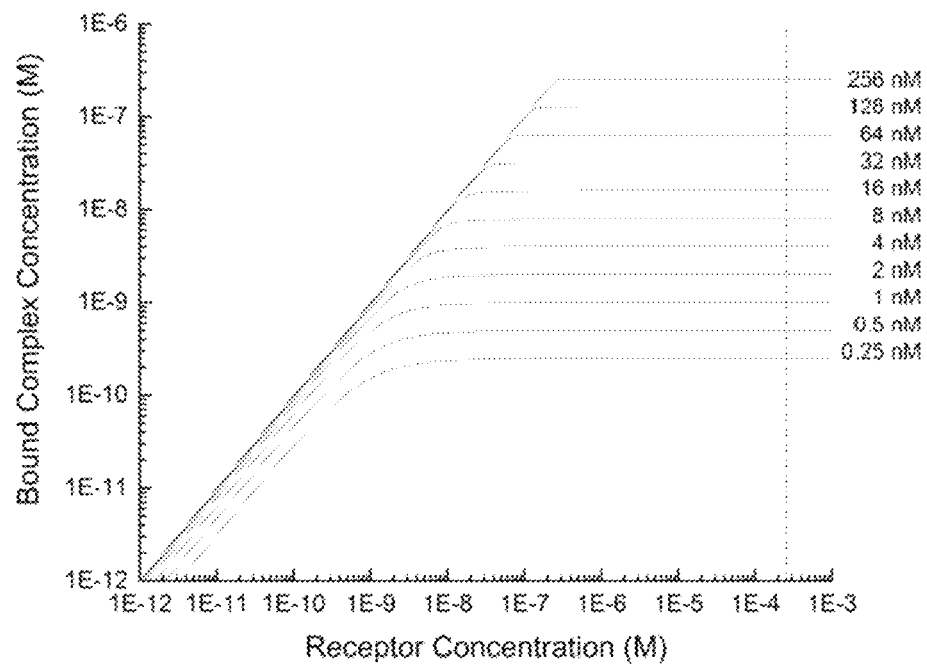

At a standard molar application of 180 picomoles (corresponding to a soluble concentration of 30 µM), the observed immobilization efficiency of 90% yields approximately 162 picomoles immobilized on the test substrate (corresponding to an average local concentration of ~360 µM). At this molar abundance, immobilized rcSso7d.SA-CBD is present in 63.3-fold molar excess relative to the soluble antigen when contacted with a 10 µL sample at the highest titration concentration (256 nM). Under these conditions, the PFORC model predicts that rapid, complete depletion of the soluble ligand will occur (FIG. 15). This approximation will remain valid for all dissociation constants and soluble target concentrations below 1.62 µM (for a 10 µL sample volume).

Figure 16:
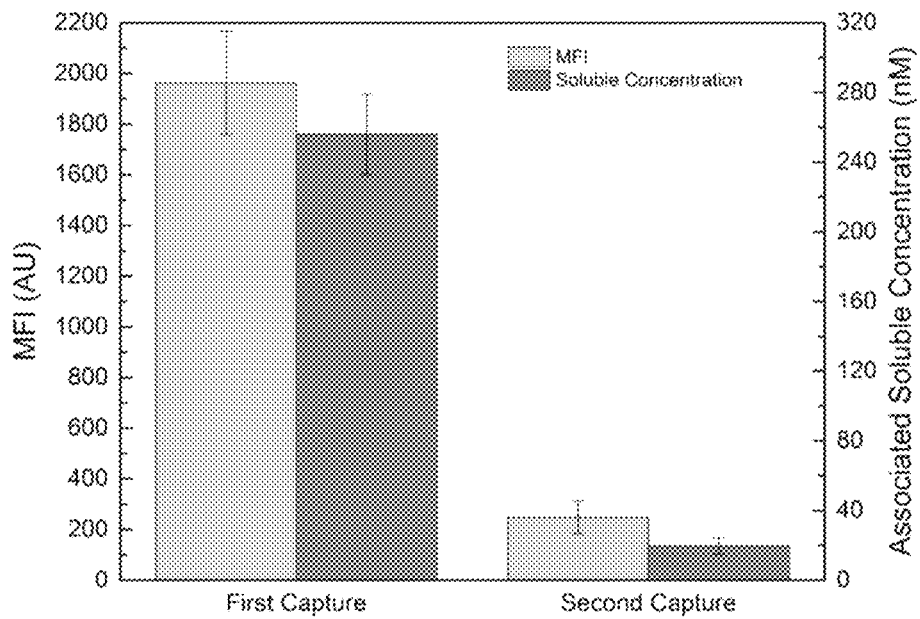
Figure 17:
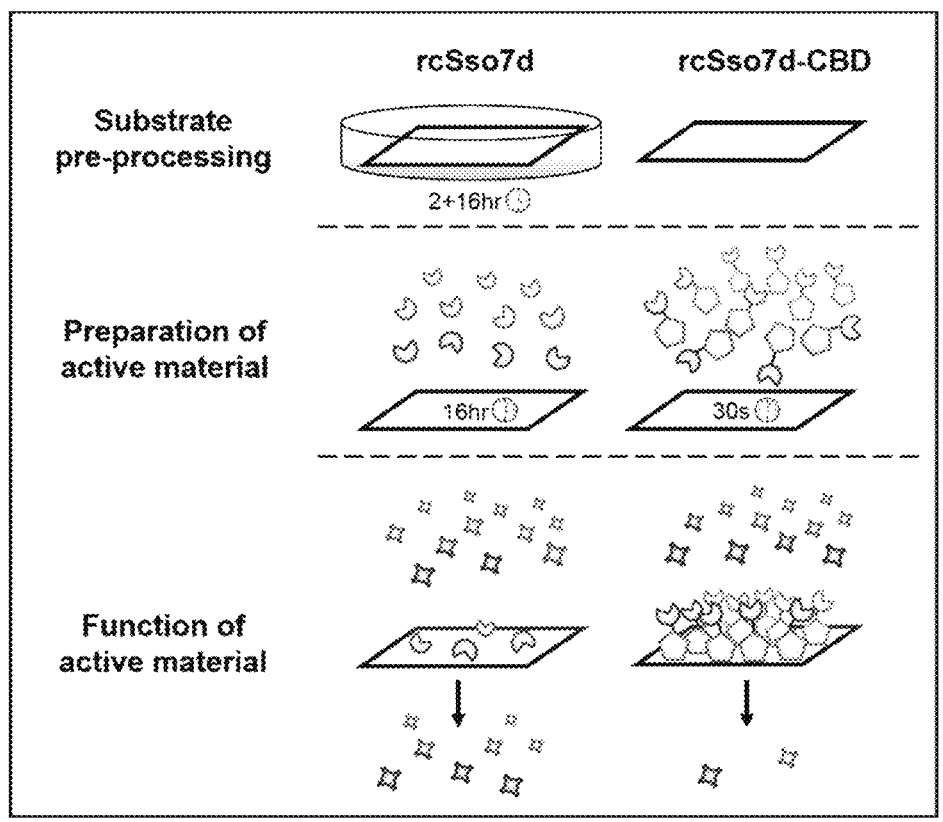
Figure 18:
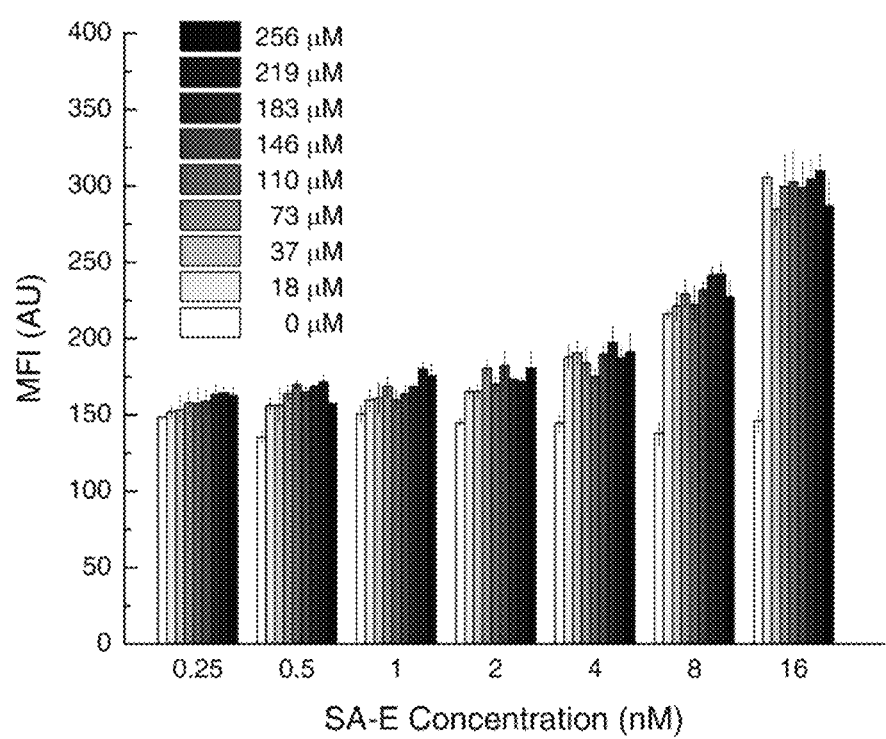
Figure 19:
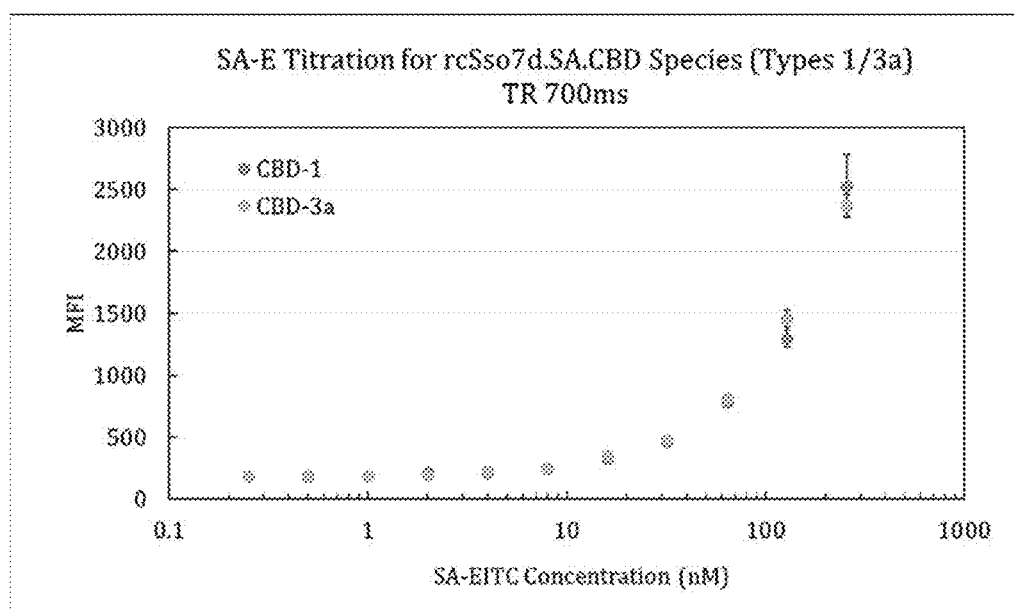
Figure 23:
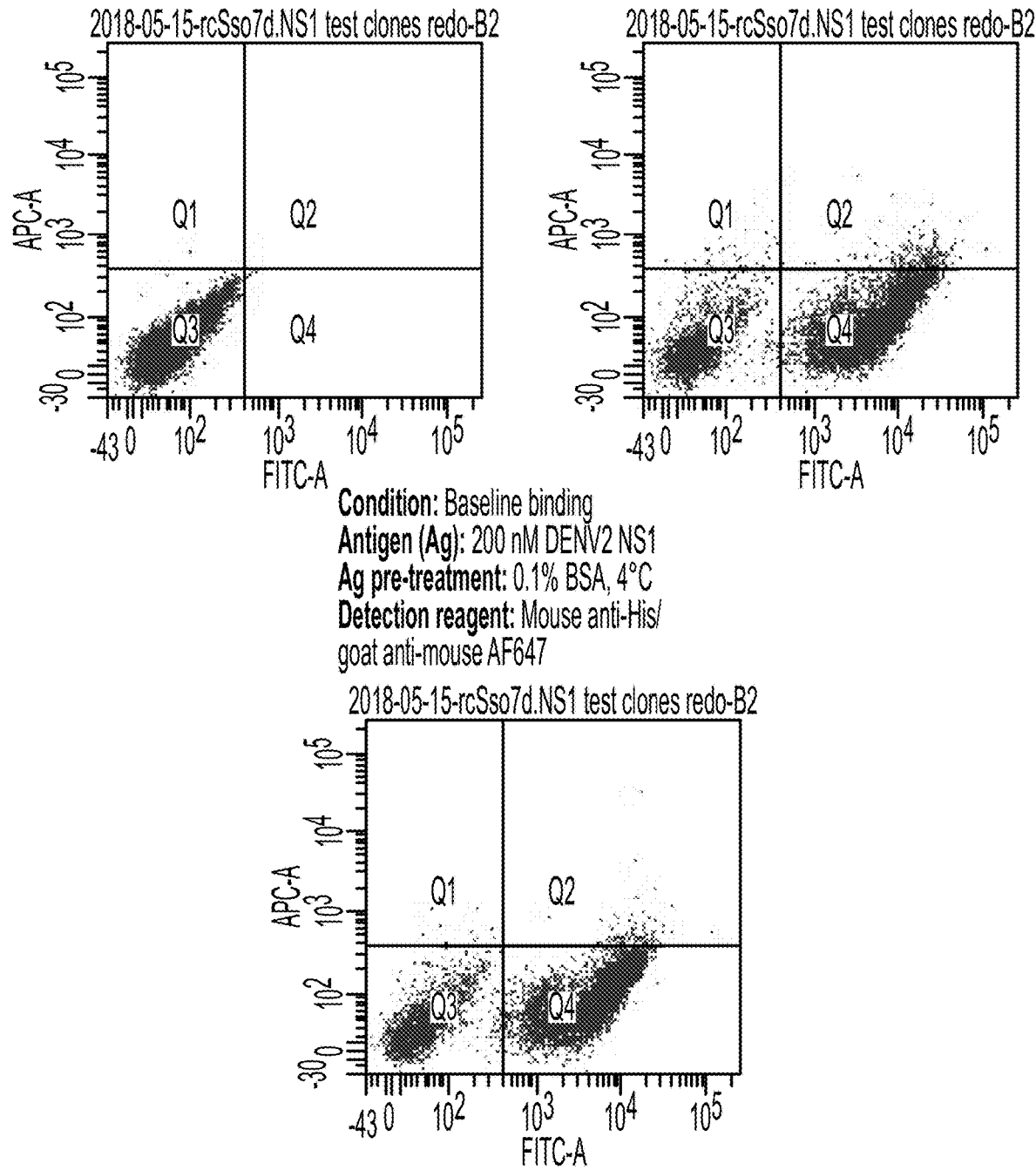
Figure 26:
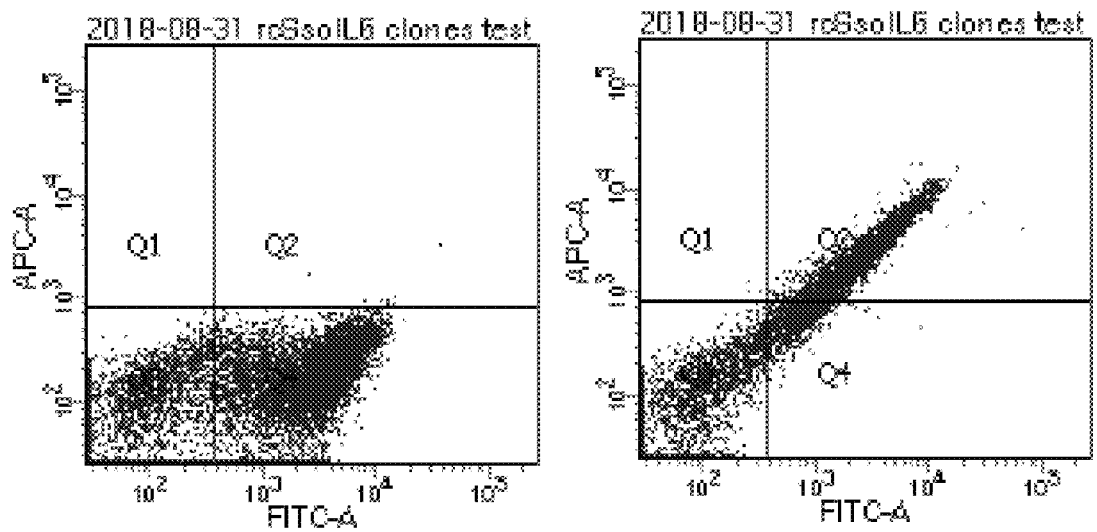
Figure 28:
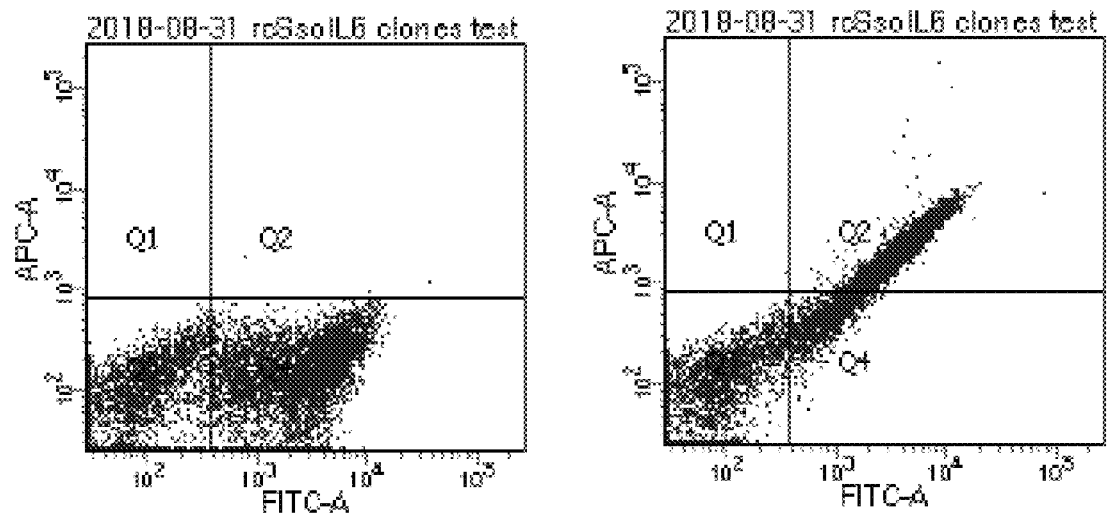
Figure 29:
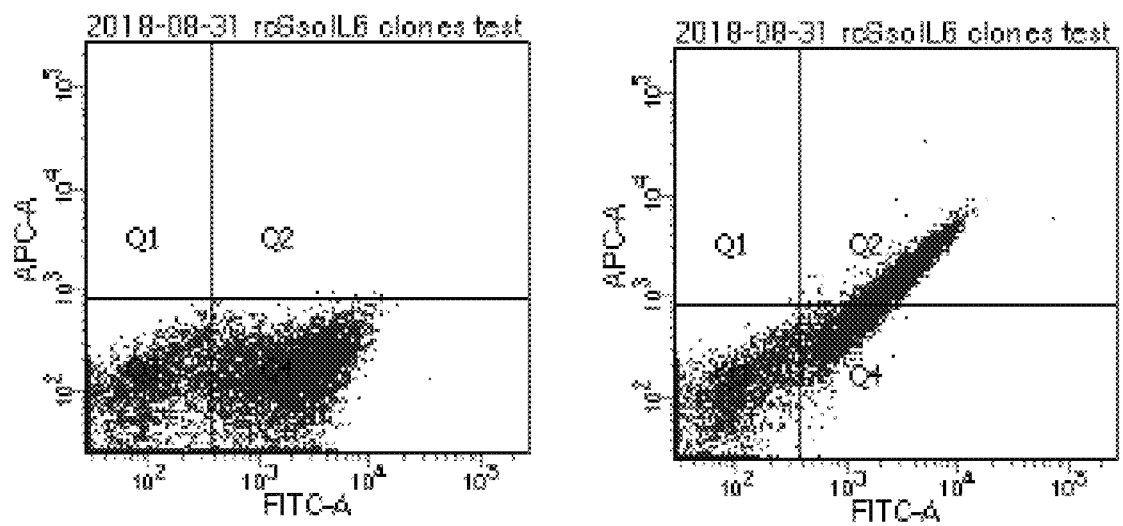
Figure 30:
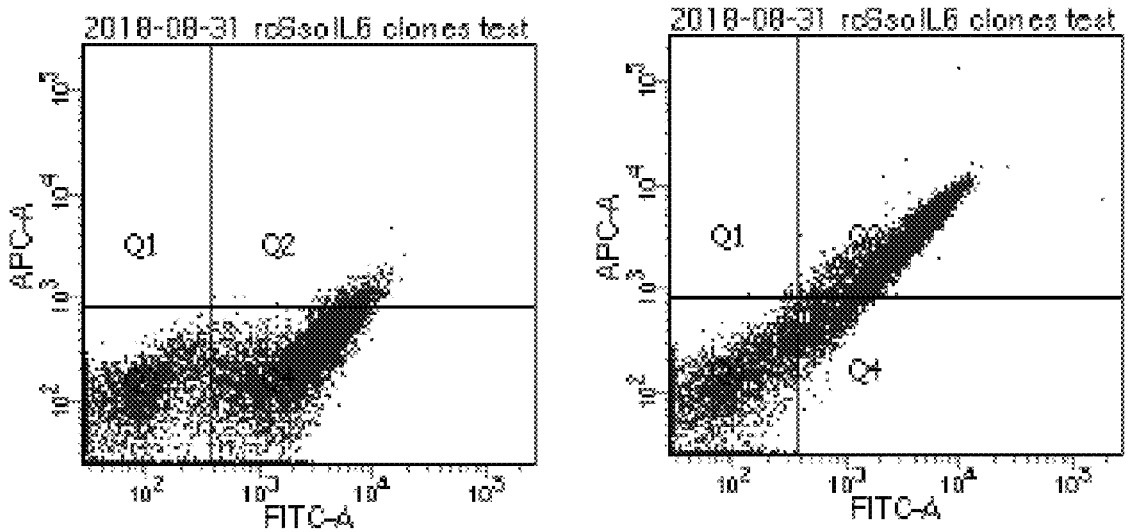
FIG. 30 shows flow cytometry data indicating the specific binding activity of Human IL-6 protein binder rcSso7d.IL6.5.
Figure 32:
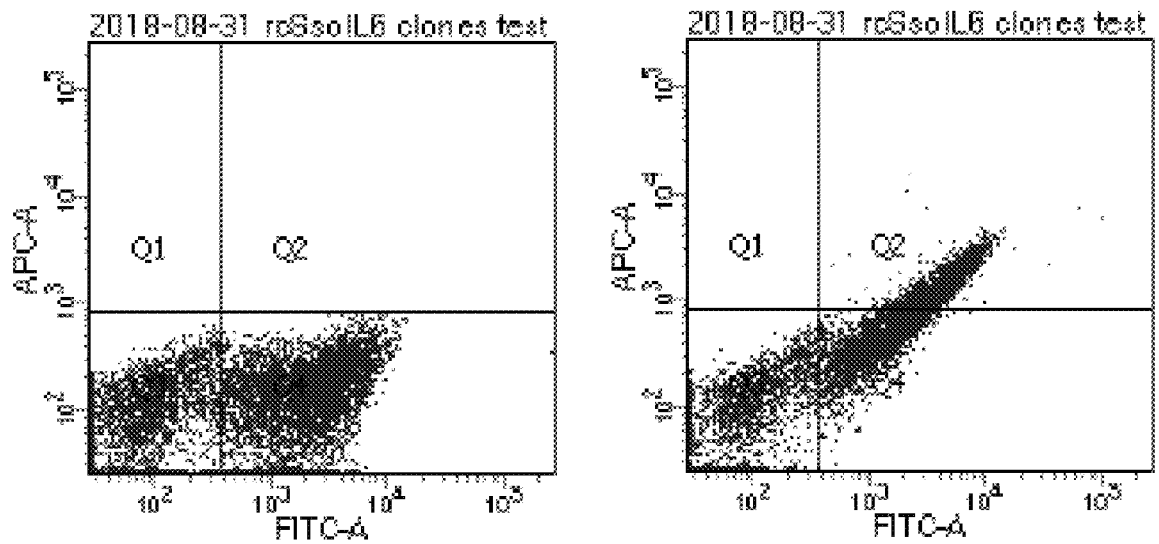
FIG. 32 shows flow cytometry data indicating the specific binding activity of Human IL-6 protein binder rcSso7d.IL6.7.

Finally, in order to directly test this prediction experimentally, the flow-through was collected following a 30-minute incubation of a 256 nM solution of SA-AF647 (10 µL) on rcSso7d.SA-CBD-coated test zones. This flow-through was applied directly to a second set of test zones coated with rcSso7d.SA-CBD, and following an additional 30-minute incubation, these sample sets were washed and imaged in the CY5® channel. By using a standard curve of known concentrations of SA-AF647 applied to rcSso7d.SA-CBD-based assays (data not shown), the resultant fluorescence measurements can be correlated with their associated antigen concentration (FIG. 16). These results indicate that following the initial depletion of SA-AF647 from a 256 nM solution, the concentration of the subsequent solution is 20.7 nM. This represents a capture efficiency of 92.2% during the initial incubation, confirming that rcSso7d.SA-CBD captures the available antigen with high efficiency.

In this study, the effects of operating within the antigen-depletion regime, using a simplified pseudo first-order rate constant model to predict the capture efficiency of immunoassays incorporating a molar excess of an immobilized binder, have been considered. In order to test these predictions, an rcSso7d-CBD fusion protein has been developed which can be readily expressed in bacteria and facilely purified in high molar yields. It has been demonstrated that this species rapidly adsorbs to unmodified cellulose, resulting in a molar abundance of the binding species which is sufficient for the near-complete depletion of a soluble antigen from solution. These findings were validated with two distinct binding systems, and serve to validate the predictions of this simple PFORC model.

By operating within this antigen-depletion regime, it was possible to maximize the analyte capture efficiency of the bioactive cellulose substrate. Given that this captured target is the biological signal which a diagnostic amplification method must render visually discernible, this enhanced capture efficiency guarantees that the maximum possible signal floor for a given biomarker can be achieved for every sample collected from a heterogeneous patient population. This general strategy, which uses a substrate-anchoring moiety for high-abundance surface adsorption of the target-binding species, is expected to be an applicable method of boosting diagnostic sensitivity in a broad array of assay formats.

Example 8. SA-E Titration for rcSso7d-CBD Types 1 and 3a

For both sample sets the bifunctional rcSso7d.SA-CBD fusion protein was contacted with the cellulose test zone at a soluble concentration of 20 µM. These rcSso7d.SA-CBD modified cellulose substrates were then contacted with streptavidin-eosin (SA-E) at a range of different concentrations, from 0.5 nM to 256 nM. Following a thirty-minute incubation, these samples were washed twice in 20 µL of 1×PBS buffer, and the samples were imaged on a fluorescence microscope in the TEXAS RED® channel at an exposure time of 700 ms. Each data point represents the mean fluorescence of the sample, and the error bars indicate the standard deviation about the average of four experimental replicates. The similar binding curves indicate that both the rcSso7d.SA-CBD1 and rcSso7d.SA-CBD3a perform similarly, binding to the cellulose substrate in high abundance and depleting the soluble antigen from solution.

Example 9. Selection and Characterization of rcSso7d Binding Variants that Bind to Flavivirus NS1 Proteins Moderate binding proteins were developed that bind to flavivirus non-structural 1 (NS1) proteins, including Zika virus NS1 and Dengue 2 virus NS1. Zika virus NS1 (Zika.NS1) was recombinantly expressed and purified with an N-terminal hexahistidine tag. A biotinylated version of Zika virus NS1 (Zika.NS1-BA) was cloned, expressed, and purified with an additional biotin acceptor sequence tag on the C-terminus. Dengue 2 virus NS1 (Dengue2.NS1) was recombinantly expressed and purified with an N-terminal hexahistidine tag. A biotinylated version of Zika virus NS1 (Dengue2.NS1-BA) was cloned, expressed, and purified with an additional biotin acceptor sequence tag on the C-terminus.

The amino acid sequence of the selected binding variants can be seen below (Table 5). Flow cytometry data indicating the specific binding activity of each particular rcSso7d clone for the selected rcSso7d binding variants that bind to flavivirus non-structural 1 (NS1) proteins is shown in the FACS plots in FIGS. 20A-20C, 21A-21C, 22A-22C, 23A-23C, 24A-24C, and 25A-25C.

Flow cytometry data was collected using the yeast-surface display platform, in which the particular rcSso7d variant is displayed on the surface of a clonal population of yeast. The target-specific binding activity of each particular rcSso7d variant was assessed using fluorescent reagents specific to epitope fusion tags associated with the target biomarker (either the biotin acceptor tag or the hexahistidine tag).

Datasets include both secondary controls and experimental samples demonstrating baseline binding in an idealized 0.1% BSA/PBS buffer. Secondary controls indicate the extent of off-target binding to the fluorescent reagents used to detect binding activity, and are thus a proximate measure of the binding specificity of the rcSso7d variant. The experimental samples indicate the activity of the surface-displayed rcSso7d variant against the purified Zika.NS1 and Dengue2.NS1 biomarkers, at a concentration denoted in the corresponding figure. The x-axis signifies rcSso7d expression level on the surface of the yeast (using the cMyc or HA tags on the yeast-surface displayed rcSso7d with a biotinylated antibody). The y-axis signifies binding to the antigen of interest (in this case, NS1). Specific binding variants are observed to exhibit an increase in fluorescence signal on the y-axis of the flow cytometry plots.

TABLE 5

Primary protein structure of selected rcSso7d binding variants that bind to Flavivirus NS1 proteins.

| Protein Species | SEQ ID NO | Primary Structure (N → C) (Variable AA residues) | Shorthand Tag | Binding targets | Validated conditions |
|---|---|---|---|---|---|
| rcSso7d.NS1.1 (rcSso7d.NS1.D3) | 31 | MATVKFTYQGEEKQVDISKIKNVHRHGQKIYFIYDEGGGAKGHGKVSEKDAPKELLQMLEKQ | NHHKYIKHK (SEQ ID NO: 37) | ZIKV NS1, DENV2 NS1 | 0.1% BSA/PBS |
| rcSso7d.NS1.2 (rcSso7d.NS1.A4) | 32 | MATVKFTYQGEEKQVDISKIKHVKRHGQWIKFAYDEGGGAKGKGKVSEKDAPKELLQMLEKQ | HKHWKAKK (SEQ ID NO: 38) | ZIKV NS1, DENV2 NS1 | 0.1% BSA/PBS |
| rcSso7d.NS1.3 (rcSso7d.NS1.A6) | 33 | MATVKFTYQGEEKQVDISKIKKVHRKGQIIRFRYDEGGGAWGHGYVSEKDAPKELLQMLEKQ | KHKIRRWHY (SEQ ID NO: 39) | ZIKV NS1, DENV2 NS1 | 0.1% BSA/PBS |
| rcSso7d.NS1.4 (rcSso7d.NS1.B2) | 34 | MATVKFTYQGEEKQVDISKIKHVKRHGQKIYFRYDEGGGAGGRGRVSEKDAPKELLQMLEKQ | HKHKYRGRR (SEQ ID NO: 40) | ZIKV NS1, DENV2 NS1 | 0.1% BSA/PBS |
| rcSso7d.NS1.5 (rcSso7d.NS1.E10) | 35 | MATVKFTYQGEEKQVDISKIKRVYRHGQWIHFRYDEGGGARGHGHVSEKDAPKELLQMLEKQ | RYHWHRRHH (SEQ ID NO: 41) | ZIKV NS1, DENV2 NS1 | 0.1% BSA/PBS |
| rcSso7d.NS1.6 (rcSso7d.NS1.H7) | 36 | MATVKFTYQGEEKQVDISKIKRVSRKGQRIYFRYDEGGGAHGKGKVSEKDAPKELLQMLEKQ | RSKRYRHKK (SEQ ID NO: 42) | ZIKV NS1, DENV2 NS1 | 0.1% BSA/PBS |

Example 10. Selection and Characterization of rcSso7d Binding Variants that Bind to Human Interleukin-6 (IL-6) Protein Binding proteins were developed that bind to human interleukin-6 (IL-6). The amino acid sequence of selected rcSso7d binding variants that bind to human interleukin-6 (IL-6) protein can be seen below (Table 6). Flow cytometry data indicating the specific binding activity of each particular rcSso7d clone for the selected rcSso7d binding variants that bind to human interleukin-6 (IL-6) protein is shown in the FACS plots in FIGS. 26A-26B, 27A-27B, 28A-28B, 29A-29B, 30A-30B, 31A-31B, and 32A-32B.

Flow cytometry data was collected using the yeast-surface display platform, in which the particular rcSso7d variant is displayed on the surface of a clonal population of yeast. The target-specific binding activity of each particular rcSso7d variant was assessed using fluorescent reagents specific to epitope fusion tags associated with the target biomarker (either the biotin acceptor tag or the hexahistidine tag).

Datasets include both three-component negative controls and experimental samples demonstrating baseline binding in an idealized 0.1% BSA/PBS buffer. Three-component negative controls undergo the same conditions as the experimental samples but do not include the target biomarker; thus, they indicate the extent of off-target binding to the fluorescent reagents used to detect binding activity, and are thus a proximate measure of the binding specificity of the rcSso7d variant. The experimental samples indicate the activity of the surface-displayed rcSso7d variant against human IL-6, at a concentration denoted in the corresponding figure. The x-axis signifies rcSso7d expression level on the surface of the yeast (using the cMyc or HA tags on the yeast-surface displayed rcSso7d with a biotinylated antibody). The y-axis signifies binding to the antigen of interest (in this case, IL-6). Specific binding variants are observed to exhibit an increase in fluorescence signal on the y-axis of the flow cytometry plots.

TABLE 6

Primary protein structure of selected rcSso7d binding variants that bind to human interleukin-6 (IL-6) protein.

| Protein Species | SEQ ID NO | Primary Structure (N → C) (Variable AA residues) | Shorthand Tag | Binding targets | Validated conditions |
|---|---|---|---|---|---|
| rcSso7d.IL6.1 | 43 | MATVKFTYQGEEKQVDISKIKIVGRHGQWIYFWYDEGGGANGNGWVSEKDAPKELLQMLEKQ | IGHWYWNNW (SEQ ID NO: 50) | Human IL-6 | 0.1% BSA/PBS |
| rcSso7d.IL6.2 | 44 | MATVKFTYQGEEKQVDISKIKIVGRHGQWIYFWYDEGGGADGNGWVSEKDAPKELLQMLEKQ | IGHWYWDNW (SEQ ID NO: 51) | Human IL-6 | 0.1% BSA/PBS |
| rcSso7d.IL6.3 | 45 | MATVKFTYQGEEKQVDISKIKIVGRHGQWIYFWYDEGGGAYGNGWVSEKDAPKELLQMLEKQ | IGHWYWYNW (SEQ ID NO: 52) | Human IL-6 | 0.1% BSA/PBS |

TABLE 6-continued

Primary protein structure of selected rcSso7d binding variants that bind to human interleukin-6 (IL-6) protein.

| Protein Species | SEQ ID NO | Primary Structure (N → C) (Variable AA residues) | Shorthand Tag | Binding targets | Validated conditions |
|---|---|---|---|---|---|
| rcSso7d.IL6.4 | 46 | MATVKFTYQGEEKQVDISKIKIVG RSGQWIYFWYDEGGGAWGNGW VSEKDAPKELLQMLEKQ | IGSWYWWNW (SEQ ID NO: 53) | Human IL-6 | 0.1% BSA/PBS |
| rcSso7d.IL6.5 | 47 | MATVKFTYQGEEKQVDISKIKIVG RWGQWIYFWYDEGGGASGNGW VSEKDAPKELLQMLEKQ | IGWWYWSNW (SEQ ID NO: 54) | Human IL-6 | 0.1% BSA/PBS |
| rcSso7d.IL6.6 | 48 | MATVKFTYQGEEKQVDISKIKWV RRDGQIIYFNYDEGGGAWGWGD VSEKDAPKELLQMLEKQ | WRDIYNWWD (SEQ ID NO: 55) | Human IL-6 | 0.1% BSA/PBS |
| rcSso7d.IL6.7 | 49 | MATVKFTYQGEEKQVDISKIKWV RRWGQWIYFNYDEGGGAWGWG DVSEKDAPKELLQMLEKQ | WRWWYNWWD (SEQ ID NO: 56) | Human IL-6 | 0.1% BSA/PBS |

Example 11. rcSso7d Protein Fusions rcSso7d.NS1.1-CBD rcSso7d.NS 1.1 (SEQ ID NO: 31) was cloned into a CBD construct, rcSso7d.NS 1.1-CBD.

rcSso7d.NS1.1-CBD
(SEQ ID NO: 57)
*MGSSHHHHHHSSGLVPRGSHM*ATVKFTYQGEEKQVDISKIKNVRHRHGQKI
YFIYDEGGGAKGHGKVSEKDAPKELLQMLEKQGSGGGGSGGGGSGGGGSP
VSGNLKVEFYNSNPSDTTNSINPQFKVTNTGSSAIDLSKLTLRYYYTVDG
QKDQTFWCDHAAIIGSNGSYNGITSNVKGTFVKMSSSTNNADTYLEISFT
GGTLEPGAHVQIQGRFAKNDWSNYTQSNDYSFKSASQFVEWDQVTAYLNG
VLVWGKEP*

The italicized amino acids in the above sequence refer to a Hexahistidine tag, the underlined amino acids refer to the rcSso7d.NS1.1 sequence, and the bolded amino acids refer to the CBD sequence.

Figures 33A, 33B:
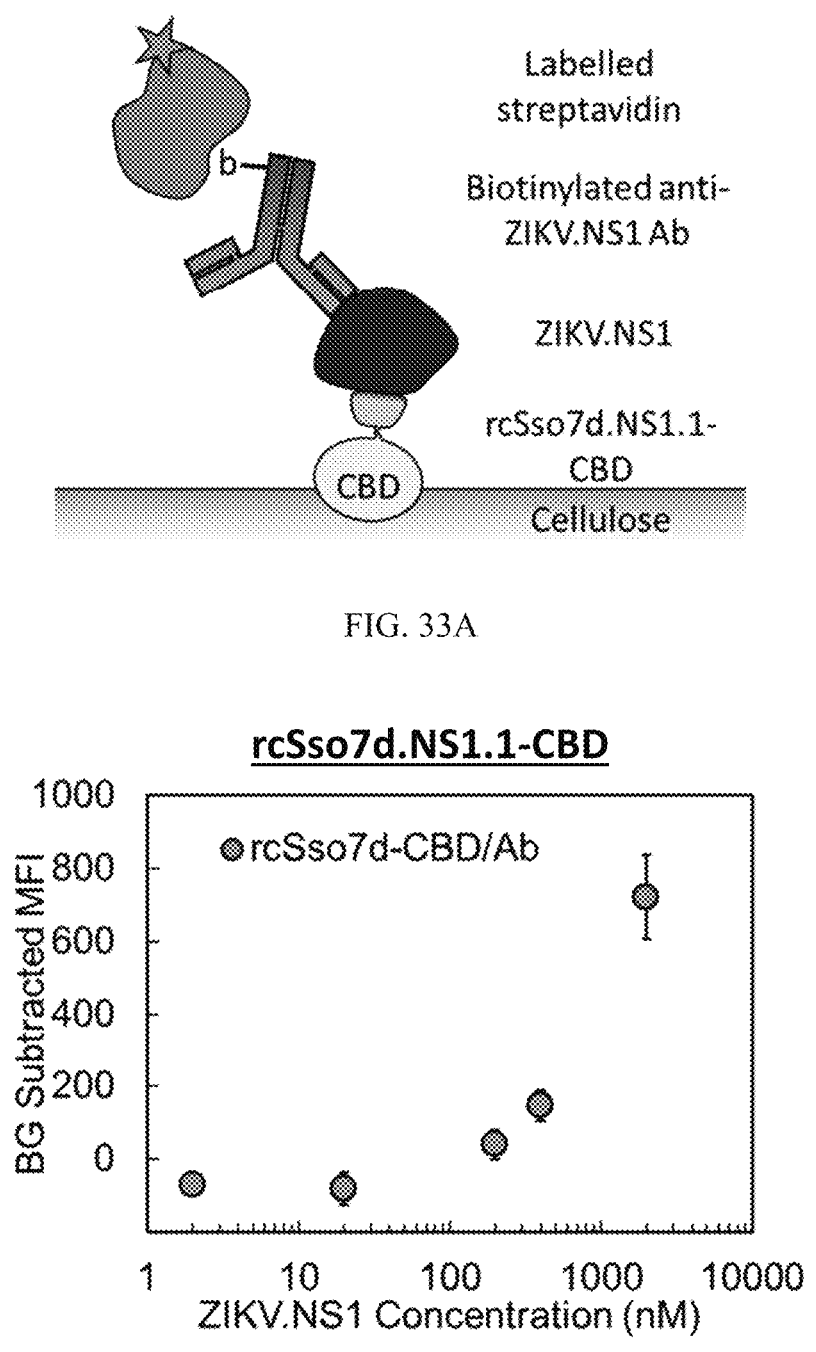

The construct was tested on cellulose paper by first immobilizing rcSso7d.NS1.1-CBD to cellulose and following with incubations of Zika virus NS1 (at various concentrations), biotinylated anti-Zika virus NS1 antibody, and streptavidin-AF 647 (see FIGS. 33A-33B). Negative controls were conducted using the same conditions as the experimental samples but with bovine serum albumin (BSA) instead of NS1 protein. The test zones were then imaged using fluorescent microscopy and analyzed to determine the mean fluorescence intensity of each test zone. The background (fluorescence without presence of antigen) was subtracted from the sample to obtain background subtracted MFI. It was demonstrated that rcSso7d.NS1.1-CBD protein fusion has function detecting Zika virus NS1 protein from solution.

BA-MBP-rcSso7d.H4 and MBP-rcSso7d.H4-bx rcSso7d.H4 was cloned into MBP (maltose binding protein) fusion protein construct with BA (biotin acceptor sequence). rcSso7d.H4 was also cloned into MBP without BA to chemically biotinylate that protein fusion (MBP-rcSso7d.H4-bx). In the following amino acid sequences, the italicized amino acids refer to a Hexahistidine tag, the bolded amino acids refer to the biotin acceptor sequence, the bolded and underlined amino acids refer to the MBP sequence, and the underlined amino acids refer to rcSso7d.H4.

BA-MBP-rcSso7d.H4
(SEQ ID NO: 58)
*MGSSHHHHHHSSGLVPRGSHM*MAGGLNDIFEAQKIEWHELKGGGGSGGGG
SEFKIEEGKLVIWINGDKGYNGLAEVGKKFEKDTGIKVTVEHPDKLEEKE
PQVAATGDGPDIIFWAHDREGGYAQSGLLAEITPDKAFQDKLYPFTWDAV
RYNGKLIAYPIAVEALSLIYNKDLLPNPPKTWEEIPALDKELKAKGKSAL
MFNLQEPYFTWPLIAADGGYAFKYENGKYDIKDVGVDNSGAKAGLTFLVD
LIKNKHMNADTDYSIAEAAFNKGETAMTINGPWAWSNIDTSKVNYGVTVL
PTFKGQPSKPFVGVLSAGINAASPNKELAKEFLENYLLTDEGLEAVNKDK
PLGAVALKSYEEELAKDPRIAATMENAQKGEIMPNIPQMSAFWYAVRTAV
INAASGRQTVDEALKDAQTGSGGGGSGGGGSTATVKFTYQGEEKQVDIS
KIKSVWRRGQRIWFRYDEGGGAWGAGKVSEKDAPKELLQMLEKQ

MBP-rcSso7d.H4
(SEQ ID NO: 59)
*MGSSHHHHHHSSGLVPRGSHM*KIEEGKLVIWINGDKGYNGLAEVGKKFEK
DTGIKVTVEHPDKLEEKEPQVAATGDGPDIIFWAHDRFGGYAQSGLLAEI
TPDKAFQDKLYPFTWDAVRYNGKLIAYPIAVEALSLIYNKDLLPNPPKTW
EEIPALDKELKAKGKSALMENLQEPYFTWPLIAADGGYAFKYENGKYDIK
DVGVDNSGAKAGLTFLVDLIKNKHMNADTDYSIAEAAFNKGETAMTINGP
WAWSNIDTSKVNYGVTVLPTFKGQPSKPFVGVLSAGINAASPNKELAKEF
LENYLLTDEGLEAVNKDKPLGAVALKSYEEELAKDPRIAATMENAQKGEI
MPNIPQMSAFWYAVRTAVINAASGRQTVDEALKDAQTGSGGGGSGGGGSM
ATVKFTYQGEEKQVDISKIKSVWRRGQRIWFRYDEGGGAWGAGKVSEKDA
PKELLQMLEKQ

The MBP fusion proteins were compared to BA-rcSso7d.H4 and rcSso7d.H4-bx, which are the protein sequences that do not contain the MBP fusion proteins, in order to demonstrate the effects of the MBP fusion partner.

BA-rcSso7d.H4
(SEQ ID NO: 60)
*MGSSHHHHHHSSGLVPRGSH*MTSMAGGLNDIFEAQKIEWHEHMATVKFTY

QGEEKQVDISKIKSVWRRGQRIWFRYDEGGGAWGAGKVSEKDAPKELLQM

LEKQGG rcSso7d.H4
(SEQ ID NO: 61)
*MGSSHHHHHHSSGLVPRGSH*MATVKFTYQGEEKQVDISKIKSVWRRGQRI

WFRYDEGGGAWGAGKVSEKDAPKELLQMLEKQ

Figure 34:
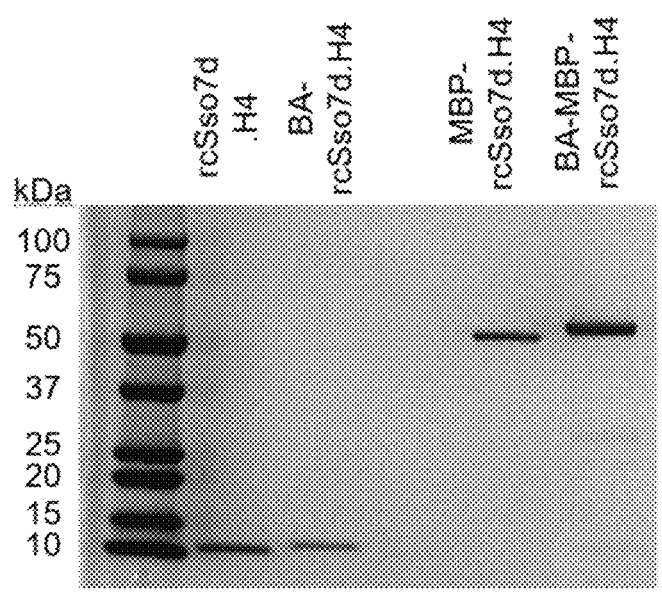
FIG. 34 shows a 12% SDS-PAGE gel image demonstrating the purity of four proteins (rcSso7d.H4, BA-rcSso7d.H4, MBP-rcSso7d.H4, and BA-MBP-rcSso7d.H4) after expression and purification.

All four proteins (rcSso7d.H4, BA-rcSso7d.H4, MBP-rcSso7d.H4, and BA-MBP-rcSso7d.H4) were expressed and purified. rcSso7d.H4 and MBP-rcSso7d.H4 were chemically biotinylated. A portion of the BA-rcSso7d.H4 and BA-MBP-rcSso7d.H4 proteins were purified on a monomeric avidin column to separate out the subpopulations that had biotins on the protein (see FIG. 34).

Biotin efficiency was quantified for both the biotin acceptor sequence (BA), which added biotin to the BA sequence during expression in *E. coli*, and chemical biotinylation using Sulfo-NHS-LC-Biotin to conjugate biotins to free amines on the protein (see Table 7). The purification yield after monomeric avidin column purification indicates issues with biotin accessibility when the BA sequence is directly fused to the protein; however, having the MBP structured protein between the BA and rcSso7d sequences reduce effects of biotin accessibility. Product yield of the proteins after chemical conjugation also indicates that rcSso7d.H4 lost structural integrity as indicated by the majority of the protein precipitating out of solution. The addition of the MBP fusion improved protein solubility and stability, as indicated by the much higher product yields.

TABLE 7

| Protein | Approx. Biotins per Protein | Approx. Avidin Column Purification Yield | Approx. Chemical Conjugation Product Yield |
|---|---|---|---|
| rcSso7d.H4-$b_x$ | —† | —‡ | <1% |
| BA-rcSso7d.H4 | 0.35 | 5% | —§ |
| BA-MBP-rcSso7d.H4 | 0.60 | 50% | —§ |
| MBP-rcSso7d.H4-$b_x$ | 11 | —‡ | 50% |

Figure 35:
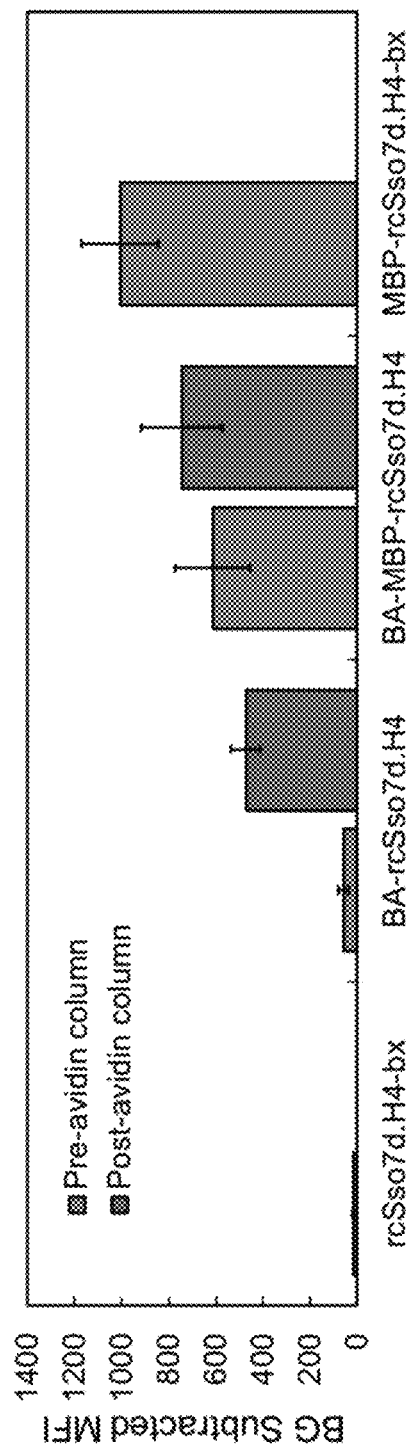
FIG. 35 shows binder performance of four protein constructs, including both pre-avidin purified and post-avidin purified subpopulations for BA-rcSso7d.H4 and BA-MBP-rcSso7d.H4.

All protein constructs (and both pre-avidin purified and post-avidin purified subpopulations for BA-rcSso7d.H4 and BA-MBP-rcSso7d.H4) were tested by first immobilizing TB antigen Rv1656 on oxidized cellulose and following with incubations with the rcSso7d.H4 construct and streptavidin-AF 647. Negative controls were conducted using the same conditions as the experimental samples but with immobilized bovine serum albumin (BSA) instead of TB antigen protein. The test zones were then imaged using fluorescent microscopy and analyzed to determine the mean fluorescence intensity of each test zone. The background (fluorescence without presence of antigen) was subtracted from the sample to obtain background subtracted MFI.

rcSso7d.H4-bx resulted in reduced signal (in addition to the low product yield after conjugation). The addition of MBP for MBP-rcSso7d.H4-bx demonstrated a much higher signal, part of which can be attributed to the increased biotin valency (multiple biotins per protein). For BA-rcSso7d.H4, the performance after avidin column purification was much higher than the theoretical increase from 35% to 100% biotinylation. This significant increase—about an order of magnitude increase in background-subtracted MFI—may be attributed to the inaccessibility of biotins on BA-rcSso7d.H4. Through avidin column purification, only the proteins with biotins that were accessible to avidin were collected; therefore, the post-avidin column purified populations reflected the proteins with accessible biotins while the pre-avidin column purified population contained mainly proteins with inaccessible biotins (see FIG. 35). For BA-MBP-Sso.TB, the post-avidin column fraction demonstrated an increase in signal intensity as compared to the pre-avidin column population; this can be attributed to the increase in proportional biotinylation since this variant did not appear to have biotin accessibility issues. Compared to BA-rcSso7d.H4, BA-MBP-rcSso7d.H4 demonstrated an increase in signal, which may be a result of the intrinsic improved accessibility of biotins on BA-MBP-rcSso7d.H4 and also potentially diminished steric hindrance effects, which may have caused the smaller rcSso7d.H4 to dissociate from the TB antigen as a result of streptavidin binding.

Protein fusions of rcSso7d.H4 and MBP (maltose binding protein) were developed as a structure protein mass with improved solubility characteristics to demonstrate improved signal detection when used as the detection reagent.

Multimerized BA-(rcSso7d.H4)$_n$ rcSso7d.H4 multimers (1×, 2×, 3×) were cloned into BA (biotin acceptor sequence) constructs BA-rcSso7d.H4(1×), BA-rcSso7d.H4(2×), and BA-rcSso7d.H4(3×). In the following amino acid sequences, the italicized amino acids refer to a Hexahistidine tag, the bolded amino acids refer to the biotin acceptor sequence, and the underlined amino acids refer to rcSso7d.H4.

BA-rcSso7d.H4(1x)
(SEQ ID NO: 62)
*MGSSHHHHHHSSGLVPRGSH*MTSMAGGLNDIFEAQKIEWHEHMATVKFTY

QGEEKQVDISKIKSVWRRGQRIWFRYDEGGGAWGAGKVSEKDAPKELLQM

LEKQGG

BA-rcSso7d.H4(2x)
(SEQ ID NO: 63)
*MGSSHHHHHHSSGLVPRGSH*MTSMAGGLNDIFEAQKIEWHEHMATVKFTY

QGEEKQVDISKIKSVWRRGQRIWFRYDEGGGAWGAGKVSEKDAPKELLQM

LEKQGGGGSGGGGSMATVKFTYQGEEKQVDISKIKSVWRRGQRIWFRYDE

GGGAWGAGKVSEKDAPKELLQMLEKQGG

BA-rcSso7d.H4(3x)
(SEQ ID NO: 64)
*MGSSHHHHHHSSGLVPRGSH*MTSMAGGLNDIFEAQKIEWHEHMATVKFTY

QGEEKQVDISKIKSVWRRGQRIWFRYDEGGGAWGAGKVSEKDAPKELLQM

LEKQGGGGSGGGGSMATVKFTYQGEEKQVDISKIKSVWRRGQRIWFRYDE

GGGAWGAGKVSEKDAPKELLQMLEKQGGGGSGGGGSMATVKFTYQGEEKQ

VDISKIKSVWRRGQRIWFRYDEGGGAWGAGKVSEKDAPKELLQMLEKQGG

Figure 36A:
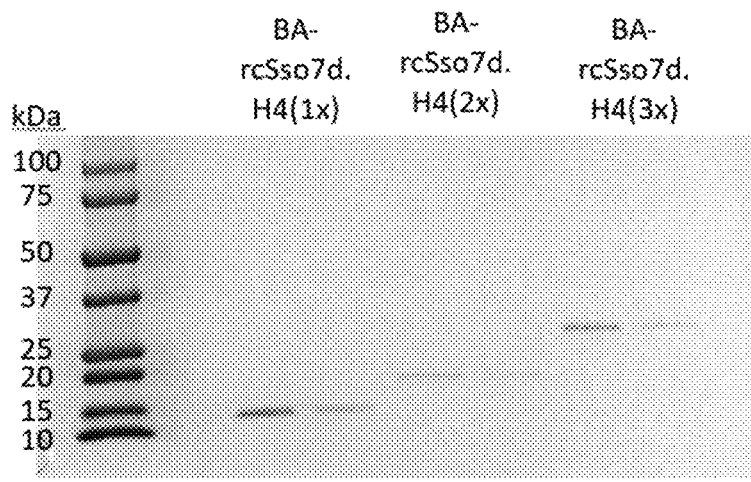
FIG. 36A shows a 12% SDS-PAGE image demonstrating the purity of three multimerized proteins (BA-(rcSso7d.H4)$_1$, BA-(rcSso7d.H4)$_2$, and BA-(rcSso7d.H4)$_3$) after expression and purification.
Figure 36B:
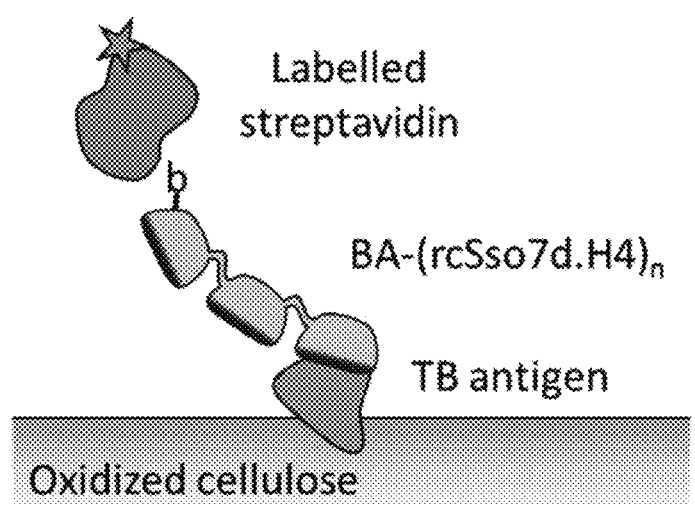
FIG. 36B shows a schematic representation of TB antigen Rv1656 immobilized to cellulose followed by incubations of the BA-(rcSso7d.H4)$_n$ and streptavidin-AF 647.
Figure 36C:
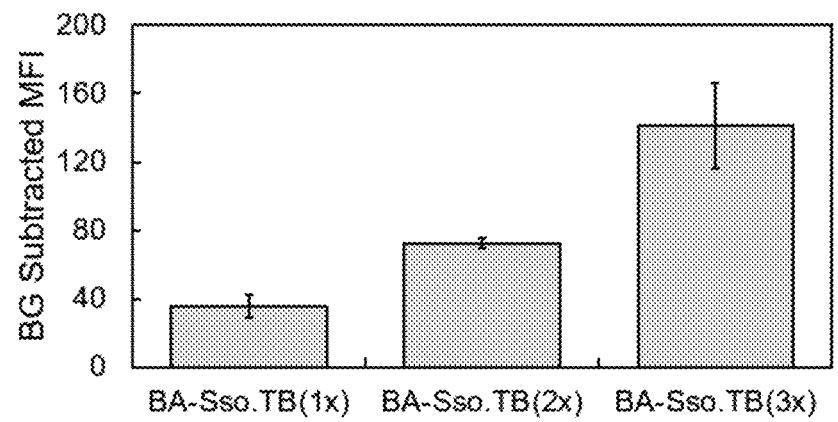
FIG. 36C shows binder performance of BA-(rcSso7d.H4)$_n$ constructs in cellulose paper-based assay.

Preliminary tests were conducted using BA-(rcSso7d.H4)$_1$, BA-(rcSso7d.H4)$_2$, and BA-(rcSso7d.H4)$_3$ after expression and purification. SDS-PAGE shows purity of each protein (each protein run at two different dilutions) (see FIG. 36A). Each multimerized protein was then tested by first immobilizing TB antigen Rv1656 to oxidized cellulose paper and following with incubations of the BA-(rcSso7d.H4)$_n$ and streptavidin-AF 647 (see FIGS. 36B-36C). Negative controls were conducted using the same conditions as the experimental samples but with immobilized bovine serum albumin (BSA) instead of TB antigen protein. The test zones were then imaged using fluorescent microscopy and analyzed to determine the mean fluorescence intensity of each test zone. The background (fluorescence without presence of antigen) was subtracted from the sample to obtain background subtracted MFI.

The multimers of rcSso7d.H4 with biotin acceptor sequence (BA) were developed to be used as detection reagent.

Example 12. Selection and Characterization of rcSso7d Binding Variants that Bind to Urine-based TB Biomarkers Biotinylation In some cases, the biomarker has been expressed with an in vivo biotinylation tag (termed BA), which provides a chemical handle by which the capture of the biomarker can be detected, using a fluorescent streptavidin reagent. This biotinylated species can be further purified using a monomeric avidin column, in order to yield a preparation with 100% biotinylation efficiency.

Magnetic-Bead Sorting and Fluorescence-Activated Cell Sorting (FACS)

Binding variants of rcSso7d were developed using the yeast-surface display platform, in which a combinatorial library of rcSso7d variants is displayed on the surface of a population of yeast cells. This library was screened using magnetic-bead sorting and fluorescence activated cell sorting in order to enrich the population for rcSso7d variants binding to the target of interest. Briefly, the biotinylated target was incubated with streptavidin-coated magnetic Dynabeads in order to coat these beads with the target. Target-covered beads were incubated with the combinatorial yeast library for a sufficient period of time for analyte-specific rcSso7d-variants to bind to the beads. These clones were then drawn from solution using a magnetic rack. In instances where urine-based biomarkers were the target of interest, the biomarker could be incubated in a urine sample for 4-16 hours at 25-37° C., in order to bias selection toward binding variants which interact with the urine-treated form of the analyte.

The library was also screened using fluorescence-activated cell sorting. Soluble biotinylated analyte was incubated with the yeast library after it was screened with magnetic beads. A fluorophore was associated with analyte-bound rcSso7d variants, either using fluorophore-conjugated streptavidin, or by using an epitope-specific antibody (e.g. mouse anti-hexahistidine/goat anti-mouse ALEXA FLUOR®647). In order to prevent the selection of binders against fluorescent reagents, orthogonal sets were used in alternating rounds (e.g. streptavidin phycoerythrin, and mouse anti-hexahistidine/goat anti-mouse ALEXA FLUOR®647). Yeast cells bearing binding variants of the rcSso7d molecule (as evidenced by fluorescent signal) were sorted into culture media for expansion and further sorting.

Flow Cytometry Analysis

Flow cytometry data was collected using the yeast-surface display platform, in which the particular rcSso7d variant is displayed on the surface of a clonal population of yeast. The target-specific binding activity of each particular rcSso7d variant was assessed using fluorescent reagents specific to epitope fusion tags associated with the target biomarker (either the BA tag or the hexahistidine tag).

Figure 38:
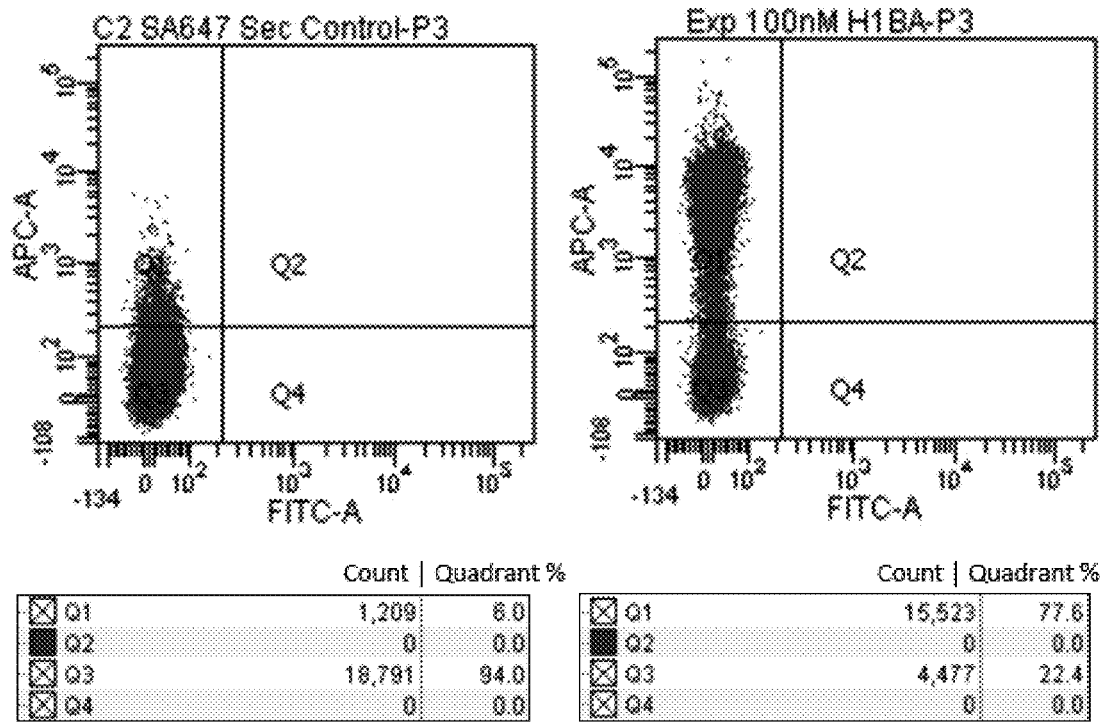
FIG. 38 shows flow cytometry data indicating the specific binding activity of H1 binder rcSso7d.H1BA.1.
Figure 39:
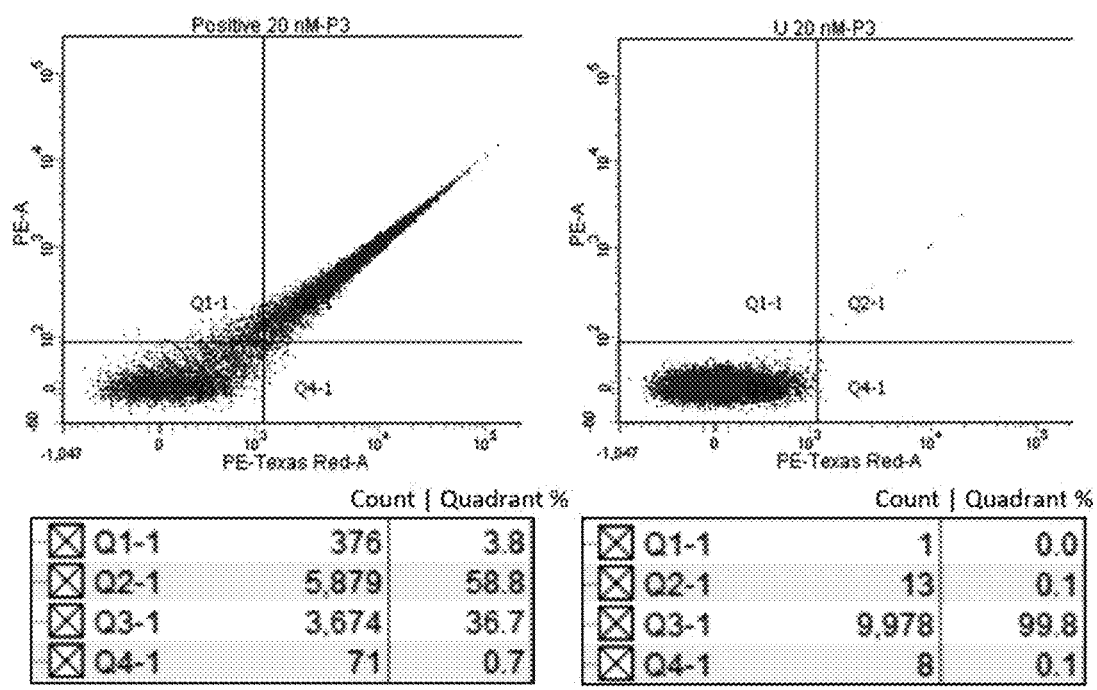
FIG. 39 shows flow cytometry data indicating the specific binding activity of H1 binder rcSso7d.H1BA.2.

Datasets discussed below include both secondary controls and experimental samples demonstrating baseline binding in an idealized 0.1% BSA/PBS buffer. Secondary controls indicate the extent of off-target binding to the fluorescent reagents used to detect binding activity, and are thus a proximate measure of the binding specificity of the rcSso7d variant. The experimental samples indicate the activity of the surface-displayed rcSso7d variant against the purified TB biomarker, at a concentration denoted in the corresponding figure. Specific binding variants are observed to exhibit a large difference in proportional binding between the secondary control and the experimental sample (observed in the tables below the FACS plots). Generally, high binding signal correlates with a significant population of labeled yeast in the positive quadrants (Q1 and Q2)—differences in the orientation/layout of these plots are due to the use of different fluorophores (ALEXA FLUOR®647 and streptavidin-phycoerythrin, e.g. FIGS. 38 and 39), or the orthogonal labeling of yeast cells to quantify rcSso7d display (e.g. FIGS. 40A-40C).

H1 Binders

Antigen name: H1

Protein ID: Rv1681

Gene ID: MT1721

(See e.g., Kashino et al. *Clin Exp Immunol* (2008) 153: 56-62; Pollock et al., *J Clin Microbiol* (2013) 51:1367-73)

Figure 37:
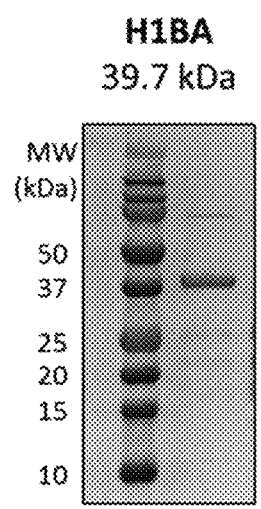
FIG. 37 shows a 12% SDS-PAGE gel showing purified protein preparation of H1BA.

H1BA (see FIG. 37)

(SEQ ID NO: 65)

*MGSSHHHHHHSSGLVPRGSH*MVIIELMRRVVGLAQGATAEVAVYGDRDRD

LAERWCANTGNTLVRADVDQTGVGTLVVRRGHPPDPASVLGPDRLPGVRL

WLYTNFHCNLCCDYCCVSSSPSTPHRELGAERIGRIVGEAARWGVRELFL

TGGEPFLLPDIDTIIATCVKQLPTTVLTNGMVFKGRGRRALESLPRGLAL

QISLDSATPELHDAHRGAGTWVKAVAGIRLALSLGFRVRVAATVASPAPG

ELTAFHDFLDGLGIAPGDQLVRPIALEGAASQGVALTRESLVPEVTVTAD

GVYWHPVAATDERALVTRTVEPLTPALDMVSRLFAEQWTRAAEEAALFPC

A(GSMAGGLNDIFEAQKIEWHE)*

The italicized amino acids in the above sequence refer to a Hexahistidine tag and the underlined amino acids in parentheseses refer to a (Biotin acceptor sequence).

The amino acid sequence of selected rcSso7d binding variants that bind to H1 can be seen below (Table 8). Flow cytometry data indicating the specific binding activity of each particular rcSso7d clone for the selected rcSso7d binding variants that bind to H1 is shown in the FACS plots in FIGS. 38-43. For example, flow cytometry data indicating the specific binding activity ofrcSso7d.H1BA.1 is shown in the FACS plots in FIG. 38. Flow cytometry data indicating the specific binding activity of rcSso7d.H1BA.2 is shown in the FACS plots in FIG. 39. Flow cytometry data indicating the specific binding activity of rcSso7d.H1BA.3 is shown in the FACS plots in FIGS. 40A-40C. Flow cytometry data indicating the specific binding activity of rcSso7d.H1BA.4 is shown in the FACS plots in FIG. 41. Flow cytometry data indicating the specific binding activity of rcSso7d.H1BA.5 is shown in the FACS plots in FIG. 42. Flow cytometry data indicating the specific binding activity ofrcSso7d.H1BA.6 is shown in the FACS plots in FIG. 43.

TABLE 8

Primary protein structure of selected rcSso7d binding variants that bind to H1.

| Protein Species | SEQ ID NO | Primary Structure (N → C) (Variable AA residues) | Shorthand Tag | Binding targets | Validated conditions |
|---|---|---|---|---|---|
| reSso7d.H1BA.1 (1.4.1) | 66 | MATVKFTYQGEEKQVDIS KIKHVRRWGQYIIFAYDE GGGAYGGGWVSEKDAP KELLQMLEKQ | HRWYIAYGW (SEQ ID NO: 72) | H1BA | 0.1% BSA/PBS |
| reSso7d.H1BA.2 (1.E2.1) | 67 | MATVKFTYQGEEKQVDIS KIKHVIRNGQYIIFAYDEG GGAYGGGWVSEKDAPKE LLQMLEKQ | RAYYIAYAW (SEQ ID NO: 73) | H1BA | 0.1% BSA/PBS, heat, urine |
| reSso7d.H1BA.3 (1.E2.2) | 68 | MATVKFTYQGEEKQVDIS KIKHVIRNGQYIIFAYDEG GGAYGGGWVSEKDAPKE LLQMLEKQ | HINYIAYGW (SEQ ID NO: 74) | H1-bx | 0.1% BSA/PBS |
| reSso7d.H1BA.4 (1.E2.3) | 69 | MATVKFTYQGEEKQVDIS KIKNVYRWGQYIIFSYDE GGGAYGWGWVSEKDAP KELLQMLEKQ | NYWYISYWW (SEQ ID NO: 75) | H1-bx | 0.1% BSA/PBS |
| reSso7d.H1BA.5 (1.E2.4) | 70 | MATVKFTYQGEEKQVDIS KIKYVRRYGQYIGFIYDE GGGAWGKGYVSEKDAP KELLQMLEKQ | YRYYGIWKY (SEQ ID NO: 76) | H1BA | 0.1% BSA/PBS |
| reSso7d.H1BA.6 (H1BA.PF5.1) | 71 | MATVKFTYQGEEKQVDIS KIKDVWRWGQWIDFIYD EGGGADGWGRVSEKDAP KELLQMLEKQ | DWWWDIDWR (SEQ ID NO: 77) | H1BA | 0.1% BSA/PBS |

Figure 40B:
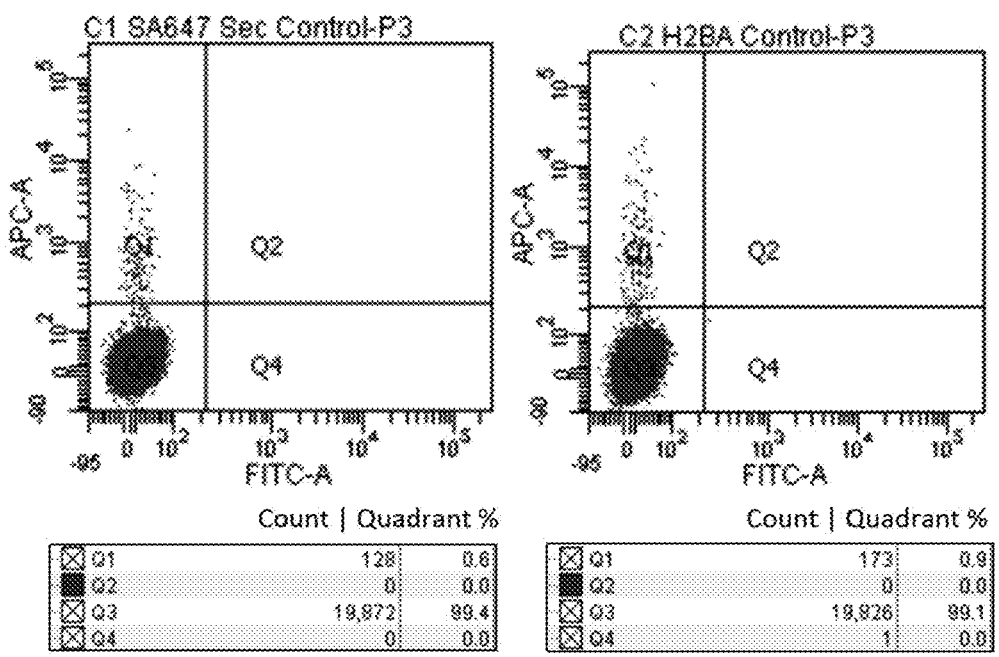

FIGS. 40B and 40C show the binding specificity of clone H1BA.3 to the H1BA antigen, demonstrating the marked difference between its binding activity against H1BA (71.5% positive) and its binding activity against the antigens H2BA, H6BA, and H7BA (0.9%, 0.9%, and 1.3%, respectively).

H2 Binders

Antigen name: H2
Protein ID: Rv2392
Gene ID: MT2462

Figure 44:
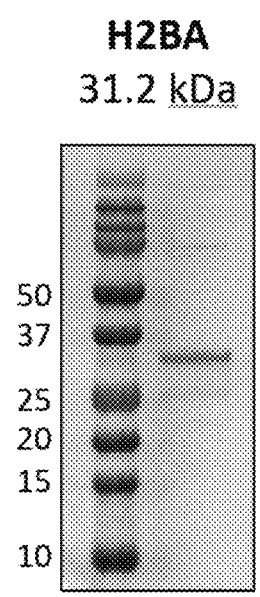
FIG. 44 shows a 12% SDS-PAGE gel image showing purified protein preparation of H2BA.

H2BA (see FIG. 44)
(SEQ ID NO: 78)
*MGSSHHHHHHSSGLVPRGSH*MSGETTRLTEPQLRELAARGAAELDGATAT
DMLRWTDETFGDIGGAGGGVSGHRGWTTCNYVVASNMADAVLVDLAAKVR
PGVPVIFLDTGYHFVETIGTRDAIESVYDVRVLNVTPEHTVAEQDELLGK
DLFARNPHECCRLRKVVPLGKTLRGYSAWVTGLRRVDAPTRANAPLVSFD
ETFKLVKVNPLAAWTDQDVQEYIADNDVLVNPLVREGYPSIGCAPCTAKP
AEGADPRSGRWQGLAKTECGLHAS(GSMAGGLNDIFEAQKIEWHE)*

The italicized amino acids in the above sequence refer to a Hexahistidine tag and the underlined amino acids in parentheseses refer to a (Biotin acceptor sequence).

The amino acid sequence of selected rcSso7d binding variants that bind to H2 can be seen below (Table 9). Flow cytometry data indicating the specific binding activity of rcSso7d.H2BA.1 is shown in the FACS plots in FIG. 45.

TABLE 9

Primary protein structure of selected rcSso7d binding variants that bind to H2.

| Protein Species | SEQ ID NO | Primary Structure (N → C) (Variable AA residues) | Shorthand Tag | Binding targets | Validated conditions |
|---|---|---|---|---|---|
| reSso7d.H2BA.1 (H2BA.PF5.1) | 79 | MATVKFTYQGEEKQV DISKIKRVIRYGQAIAF AYDEGGGARGYGWVS EKDAPKELLQMLEKQ | RIYAAARYW (SEQ ID NO: 81) | H2BA | 0.1% BSA/PBS, heat, urine (limited) |

TABLE 9-continued

Primary protein structure of selected rcSso7d binding variants that bind to H2.

| Protein Species | SEQ ID NO | Primary Structure (N → C) (Variable AA residues) | Shorthand Tag | Binding targets | Validated conditions |
|---|---|---|---|---|---|
| re5so7d.H2BA.2 (H2BA.PUF5.2) | 80 | MATVKFTYQGEEKQV DISKIKYVGRWGQNIG FAYDEGGGAYGYGGV SEKDAPKELLQMLEKQ | YGWNGAYYG (SEQ ID NO: 82) | H2BA | |

H4 Binders
 Antigen name: H4
 Protein ID: Rv1656
 Gene ID: MT1694
 (See e.g., Napolitano et al., 2008)

Figure 46:
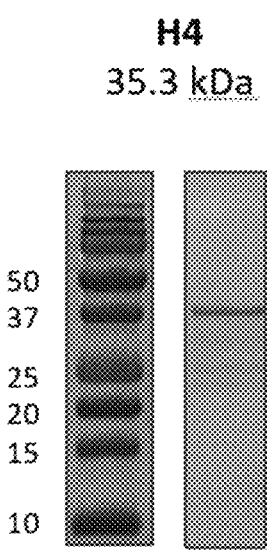
FIG. 46 shows a 12% SDS-PAGE gel showing purified protein preparation of H4.

H4 (see FIG. 46)
(SEQ ID NO: 83)
*MGSSHHHHHHSSGLVPRGSH*MVIRHFLRDDDLSPAEQAEVLELAAELKKD

PVSRRPLQGPRGVAVIFDKNSTRTRFSFELGIAQLGGHAVVVDSGSTQLG

RDETLQDTAKVLSRYVDAIVWRTFGQERLDAMASVATVPVINALSDEFHP

CQVLADLQTIAERKGALRGLRLSYFGDGANNMAHSLLLGGVTAGIHVTVA

APEGFLPDPSVRAAAERRAQDTGASVTVTADAHAAAAGADVLVTDTWTSM

GQENDGLDRVKPFRPFQLNSRLLALADSDAIVLHCLPAHRGDEITDAVMD

GPASAVWDEAENRLHAQKALLVWLLERS*

The italicized amino acids in the above sequence refer to a Hexahistidine tag.

The amino acid sequence of selected rcSso7d binding variants that bind to H4 can be seen below (Table 10). Flow cytometry data indicating the specific binding activity of each particular rcSso7d clone for the selected rcSso7d binding variants that bind to H4 is shown in the FACS plots in FIGS. 47-55. For example, flow cytometry data indicating the specific binding activity of rcSso7d.H4.1 is shown in the FACS plots in FIG. 47. Flow cytometry data indicating the specific binding activity of rcSso7d.H4.2 is shown in the FACS plots in FIG. 48. Flow cytometry data indicating the specific binding activity of rcSso7d.H4.3 is shown in the FACS plots in FIG. 49. Flow cytometry data indicating the specific binding activity of rcSso7d.H4.4 is shown in the FACS plots in FIG. 50. Flow cytometry data indicating the specific binding activity of rcSso7d.H4.5 is shown in the FACS plots in FIG. 51. Flow cytometry data indicating the specific binding activity of rcSso7d.H4.6 is shown in the FACS plots in FIG. 52. Flow cytometry data indicating the specific binding activity of rcSso7d.H4.7 is shown in the FACS plots in FIG. 53. Flow cytometry data indicating the specific binding activity of rcSso7d.H4.8 is shown in the FACS plots in FIG. 54. Flow cytometry data indicating the specific binding activity of rcSso7d.H4.9 is shown in the FACS plots in FIG. 55. Flow cytometry data indicating the specific binding activity of rcSso7d.H4.2/H4/BA-MBP-rcSso7d.H4.1 is shown in the FACS plots in FIGS. 56A-56B.

FIGS. 56A-56B indicate the performance of binders H4.1 and H4.2 in a full sandwich assay format, wherein H4.1 has been solubly expressed in the BA-MBP-rcSso7d fusion construct, and biotinylated variants have been purified via a monomeric avidin column. In these samples, the yeast-surface displayed rcSso7d.H4.2 variant has been sequentially incubated with the H4 antigen at 100 nM (except for in the case of the secondary control), the purified BA-MBP-rcSso7d.H4.1 protein, and streptavidin ALEXA FLUOR®647. FIG. 56A shows baseline binding signal for the full immunocomplex (with H4 incubated in buffer) is compared to the full immunocomplex binding signal with H4 incubated in urine overnight at 37° C. FIG. 56B compares similar samples, except the H4 antigen has been incubated in urine for one week at 37° C.

TABLE 10

Primary protein structure of selected rcSso7d binding variants that bind to H4.

| Protein Species | SEQ ID NO | Primary Structure (N → C) (Variable AA residues) | Shorthand Tag | Binding targets | Validated conditions |
|---|---|---|---|---|---|
| rcSso7d.H4.1 (H4.1, 4.4.2) | 84 | MATVKFTYQGEEKQVDIS KIKSVWRRGQRIWFRYD EGGGAWGAGKVSEKDAP KELLQMLEKQ | SWRRWRWAK (SEQ ID NO: 93) (close variant: SWRRWRWAR (SEQ ID NO: 94) | H4 | 0.1% BSA/PBS, heat, urine |
| rcSso7d.H4.2 (H4.2, 4.5) | 85 | MATVKFTYQGEEKQVDIS KIKWVRRYGQYIGFSYDE GGGAWGKGYVSEKDAP KELLQMLEKQ | WRYYGSWKY (SEQ ID NO: 95) | H4 | 0.1% BSA/PBS, heat, urine |

TABLE 10-continued

Primary protein structure of selected rcSso7d
binding variants that bind to H4.

| Protein Species | SEQ ID NO | Primary Structure (N → C) (Variable AA residues) Shorthand Tag | Binding targets | Validated conditions |
|---|---|---|---|---|
| rcSso7d.H4.3 (P4-10, C2) | 86 | MATVKFTYQGEEKQVDIS HWRNYRWAA KIKHVWRRGQNIYFRYD (SEQ ID NO: 96) EGGGAWGAGAVSEKDAP KELLQMLEKQ | H4 | 0.1% BSA/PBS |
| rcSso7d.H4.4 (P4-12, C3) | 87 | MATVKFTYQGEEKQVDIS SKNSDDAEK KIKSVKRNGQSIDFDYDE (SEQ ID NO: 97) GGGAAGEGKVSEKDAPK ELLQMLEKQ | H4 | 0.1% BSA/PBS |
| rcSso7d.H4.5 (P4-17, C5) | 88 | MATVKFTYQGEEKQVDIS GYHSWRWWI KIKGVYRHGQSIWFRYD (SEQ ID NO: 98) EGGGAWGWGIVSEKDAP KELLQMLEKQ | H4 | 0.1% BSA/PBS |
| rcSso7d.H4.6 (P5-4, C6) | 89 | MATVKFTYQGEEKQVDIS SHYKYDIKH KIKSVHRYGQKIYFDYDE (SEQ ID NO: 99) GGGAIGKGHVSEKDAPK ELLQMLEKQ | H4 | 0.1% BSA/PBS |
| rcSso7d.H4.7 (P5-5, C7) | 90 | MATVKFTYQGEEKQVDIS YWHHARHWS KIKYVWRHGQHIAFRYD (SEQ ID NO: EGGGAHGWGSVSEKDAP 100) KELLQMLEKQ | H4 | 0.1% BSA/PBS |
| rcSso7d.H4.8 (P5-8, C8) | 91 | MATVKFTYQGEEKQVDIS DWHHISYAH KIKDVWRHGQHIIFSYDE (SEQ ID NO: GGGAYGAGHVSEKDAPK 101) ELLQMLEKQ | H4 | 0.1% BSA/PBS |
| rcSso7d.H4.9 (P5-10, C9) | 92 | MATVKFTYQGEEKQVDIS YKIYSNHHI KIKYVKRIGQYISFNYDE (SEQ ID NO: GGGAHGHGIVSEKDAPK 102) ELLQMLEKQ | H4 | 0.1% BSA/PBS |
| rcSso7d.H4.2/H4/ BA-MBP- rcSso7d.H4.1 | | | H4 | 0.1% BSA/PBS, heat, urine (1 week) |

H6 Binders
Antigen name: H6
Protein ID: Rv1729c
Gene ID: MT1770

Figure 57:
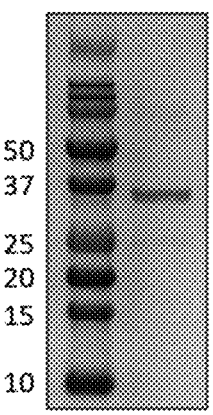
FIG. 57 shows a 12% SDS-PAGE gel showing purified protein preparation of H6BA.

H6BA (see FIG. 57)

(SEQ ID NO: 103)

*MGSSHHHHHHSSGLVRGSH*MVARTDDDNWDLTSSVGVTATIVAVGRALAT

KDPRGLINDPFAEPLVRAVGLDLFTKMMDGELDMSTIADVSPAVAQAMVY

GNAVRTKYFDDYLLNATAGGIRQVAILASGLDSRAYRLPWPTRTVVYEID

QPKVMEFKTTTLADLGAEPSAIRRAVPIDLRADWPTALQAAGFDSAAPTA

WLAEGLLIYLKPQTQDRLFDNITALSAPGSMVATEFVTGIADFSAERART

ISNPFRCHGVDVDLASLVYTGPRNHVLDYLAAKGWQPEGVSLAELFRRSG

LDVRAADDDTIFISGCLTDHSSISPPTAAGWREF<u>(GSMAGGLNDIFEAQK

IEWHE)</u>*

The italicized amino acids in the above sequence refer to a Hexahistidine tag and the underlined amino acids in parentheseses refer to a (Biotin acceptor sequence).

Figure 58A:
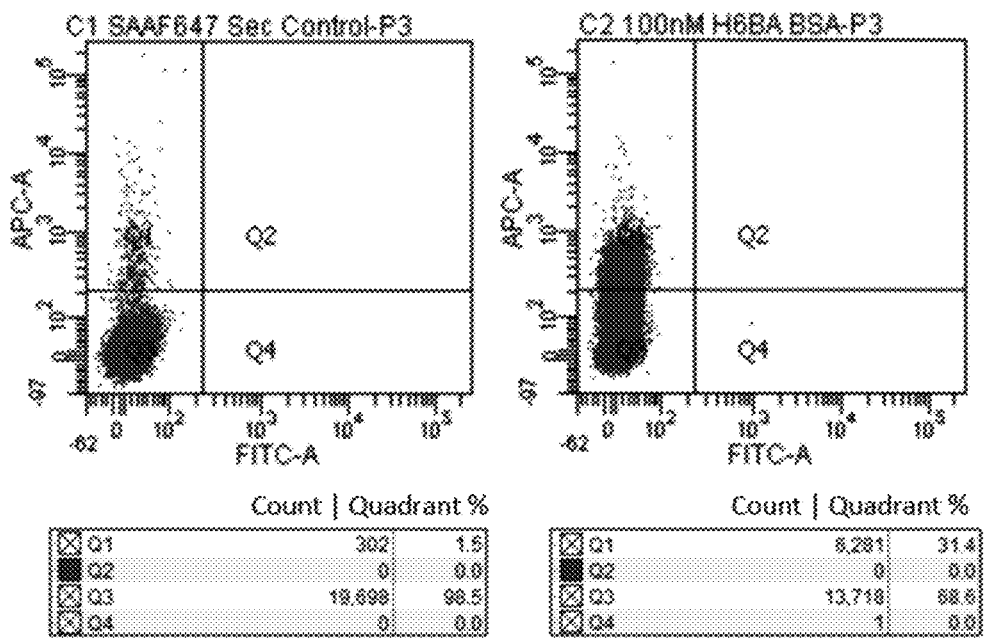
Figure 59A:
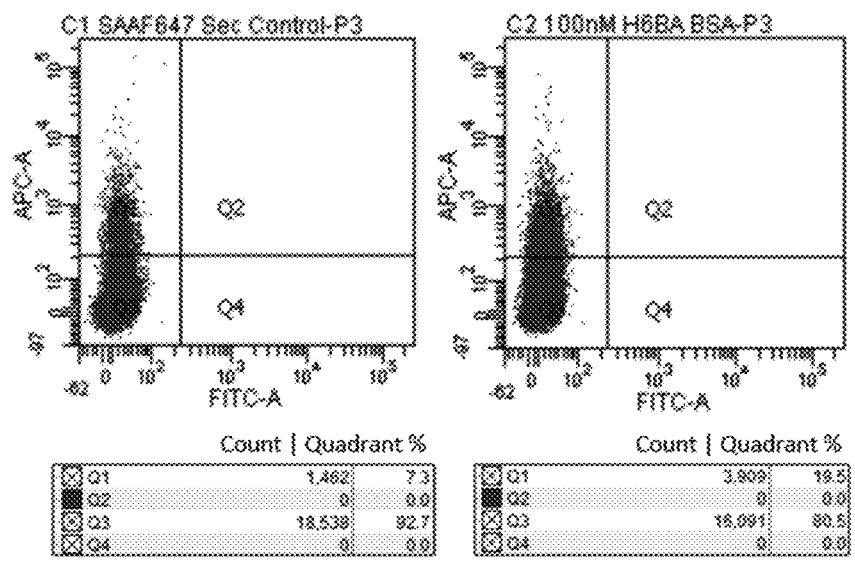
Figure 60A:
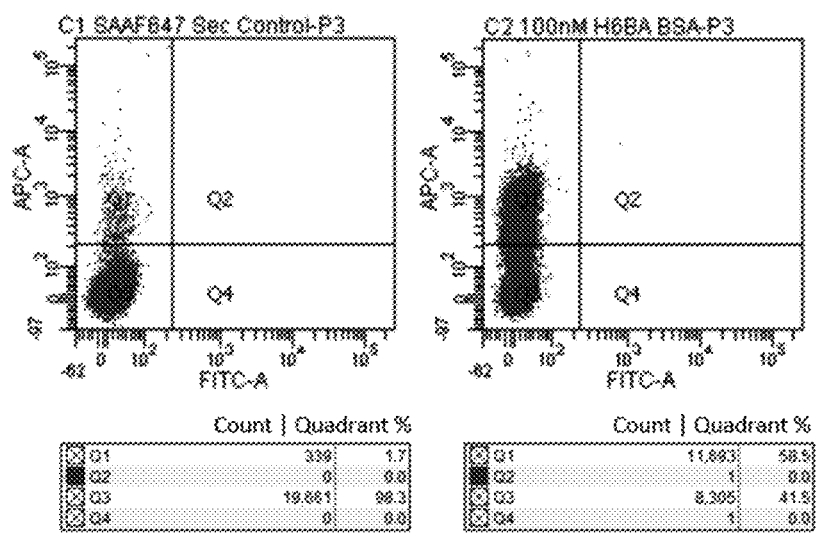

The amino acid sequence of selected rcSso7d binding variants that bind to H6 can be seen below (Table 11). Flow cytometry data indicating the specific binding activity of each particular rcSso7d clone for the selected rcSso7d binding variants that bind to H6 is shown in the FACS plots in FIGS. 58-60. For example, flow cytometry data indicating the specific binding activity of rcSso7d.H6BA.1 is shown in the FACS plots in FIGS. 58A-58B. Flow cytometry data indicating the specific binding activity of rcSso7d.H6BA.2 is shown in the FACS plots in FIGS. 59A-59B. Flow cytometry data indicating the specific binding activity of rcSso7d.H6BA.3 is shown in the FACS plots in FIGS. 60A-60B.

TABLE 11

Primary protein structure of selected rcSso7d binding variants that bind to H6.

| Protein Species | SEQ ID NO | Primary Structure (N → C) (Variable AA residues) | Shorthand Tag | Binding targets | Validated conditions |
|---|---|---|---|---|---|
| rcSso7d.H6BA.1 (6.PF2.2) | 104 | MATVKFTYQGEEKQV DISKIKWVYRYGQYIIF GYDEGGGAKGNGYVS EKDAPKELLQMLEKQ | WYYYIGKNY (SEQ ID NO: 107) | H6BA | 0.1% BSA/PBS, heat, urine |
| rcSso7d.H6BA.2 (6.PF2.4) | 105 | MATVKFTYQGEEKQV DISKIKWVYRWGQYIIF AYDEGGGAAGKGSVS EKDAPKELLQMLEKQ | WYWYIAAKS (SEQ ID NO: 108) | H6BA | 0.1% BSA/PBS |
| rcSso7d.H6BA.3 (6.PF2.5) | 106 | MATVKFTYQGEEKQV DISKIKRVIRAGQSIIFS YDEGGGAIGHGWVSE KDAPKELLQMLEKQ | RIASISIHW (SEQ ID NO: 109) | H6BA | 0.1% BSA/PBS, heat, urine |

H7 Binders
  Antigen name: H7
  Protein ID: TBCG_03312
  Gene ID: ZP_04927296.1

Figure 61:
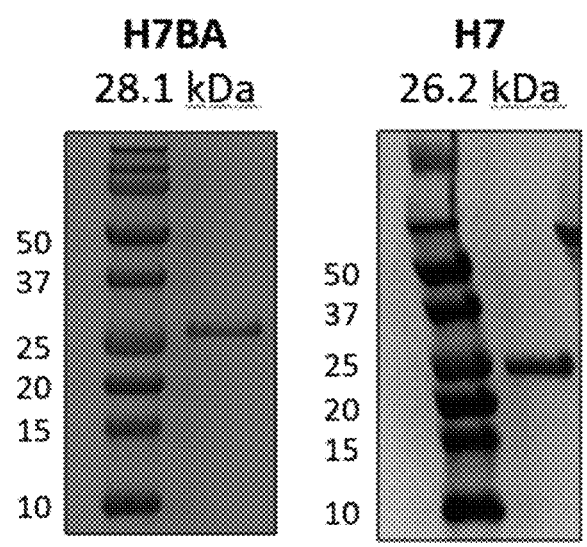
FIG. 61 shows a 12% SDS-PAGE gel showing purified protein preparation of H7BA and H7.

H7BA (see FIG. 61)
(SEQ ID NO: 110)
*MGSSHHHHHHSSGLVPRGSH*MTLNLSVDEVLTTTRSVRKRLDFDKPVPRD
VLMECLELALQAPTGSNSQGWQWVFVEDAAKKKAIADVYLANARGYLSGP
APEYPDGDTRGERMGRVRDSATYLAEHMHRAPVLLIPCLKGREDESAVGG
VSFWASLFPAVWSFCLALRSRGLGSCWTTLHLLDNGEHKVADVLGIPYDE
YSQGGLLPIAYTQGIDFRPAKRLPAESVTHWNGW<u>(GSMAGGLNDIFEAQK
IEWHE)</u>*

The italicized amino acids in the above sequence refer to a Hexahistidine tag and the underlined amino acids in parentheseses refer to a (Biotin acceptor sequence).

The amino acid sequence of selected rcSso7d binding variants that bind to H7 can be seen below (Table 12). Flow cytometry data indicating the specific binding activity of rcSso7d.H7.1 is shown in the FACS plots in FIG. 62.

TABLE 12

Primary protein structure of selected rcSso7d binding variants that bind to H7.

| Protein Species | SEQ ID NO | Primary Structure (N → C) (Variable AA residues) | Shorthand Tag | Binding targets | Validated conditions |
|---|---|---|---|---|---|
| rcSso7d.H7.1 (7.B10) | 111 | MATVKFTYQGEEKQVDIS KIKYVYRWGQRIWFRYD EGGGAIGRGRVSEKDAP KELLQMLEKQ | YYWRWRIRR (SEQ ID NO: 112) (close variant: YYWRWRSYR (SEQ ID NO: 113) | H7, H7BA | 0.1% BSA/PBS, heat, urine |

Figure 64:
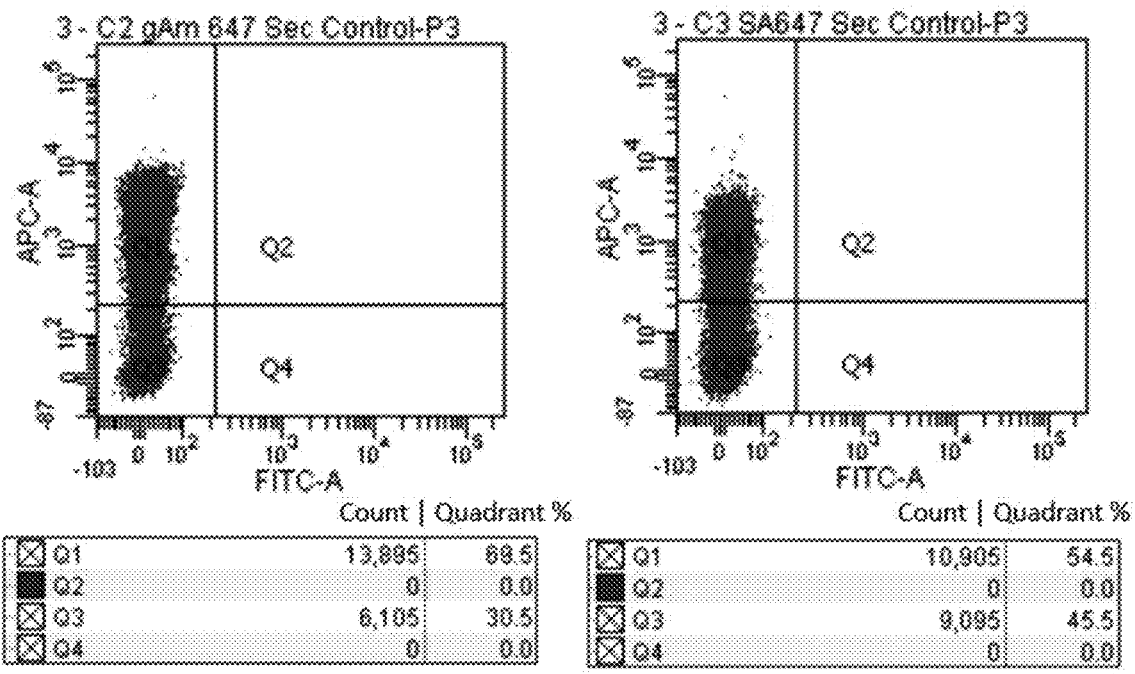
FIG. 64 shows flow cytometry data indicating the specific binding activity of AF647 binder rcSso7d.AF647.2.

ALEXA FLUOR®647 (AF647) Binders
Antigen name: ALEXA FLUOR®647
Classification: Small molecule The amino acid sequence of selected rcSso7d binding variants that bind to ALEXA FLUOR®647 (AF647) can be seen below (Table 13). FIGS. 63 and 64 detail binding variants that have been found to bind to two distinct reagents which have been labeled with the ALEXA FLUOR®647 fluorophore (a goat anti-mouse antibody and streptavidin). Flow cytometry data indicating the specific binding activity of rcSso7d.AF647.1 is shown in the FACS plots in FIG. 63. Flow cytometry data indicating the specific binding activity ofrcSso7d.AF647.2 is shown in the FACS plots in FIG. 64.

TABLE 13

Primary protein structure of selected rcSso7d binding variants that bind to Alexa Fluor ® 647 (AF647).

| Protein Species | SEQ ID NO | Primary Structure (N → C) (Variable AA residues) | Shorthand Tag | Binding targets | Validated conditions |
|---|---|---|---|---|---|
| rcSso7d.AF647.1 (6.PF2.1) | 114 | MATVKFTYQGEEKQVDISKIKWVIR YGQKIAFGYDEGGGAKGAGAVSEK DAPKELLQMLEKQ | WIYKAGKAA (SEQ ID NO: 116) | Alexa Fluor ® 647 | 0.1% BSA/PBS |
| rcSso7d.AF647.2 (6.PF2.3) | 115 | MATVKFTYQGEEKQVDISKIKKVW RYGQWIYFIYDEGGGAKGRGWVS EKDAPKELLQMLEKQ | KWYWYIKRW (SEQ ID NO: 117) | Alexa Fluor ® 647 | 0.1% BSA/PBS |

The binder performance of selected rcSso7d binding variants is summarized below in Table 14.

TABLE 14

TB Antigen Binder Performance

| Clone | Secondary control signal | Baseline binding | Geometric MFI | Antigen concentration (nM) | Urine-based binding (overnight) | Geometric MFI | Antigen concentration (nM) |
|---|---|---|---|---|---|---|---|
| H1BA.1 | 6% | 77.60% | | 100 | N/A | | N/A |
| H1BA.2 | N/A | 62.60% | 267 | 100 | 0.10% | 3.95 | 100 |
| H1BA.3 | 0.40% | 74.10% | 1396 | 100 | 8.10% | 48.1 | 100 |
| H1BA.4 | 0% | 31.40% | | 100 | N/A | | N/A |
| H1BA.5 | 0.90% | 32.50% | | 100 | N/A | | N/A |
| H1BA.6 | 0.50% | 70.40% | 1920 | 100 | 1.30% | 40.1 | 100 |
| H2BA.1 | 3.20% | 55.10% | 474 | 100 | 8.20% | 73.2 | 100 |
| H4.1 | 0% | 69.30% | | 100 | 68.20% | | 100 |
| H4.2 | 0% | 60.40% | | 100 | 63.60% | | 100 |
| H4.3 | 0% | 25.80% | | 100 | N/A | | N/A |
| H4.4 | 0% | 7.80% | | 100 | N/A | | N/A |
| H4.5 | 0.60% | 30.80% | | 100 | N/A | | N/A |
| H4.6 | 0% | 15.30% | | 100 | N/A | | N/A |
| H4.7 | 0% | 13.40% | | 100 | N/A | | N/A |
| H4.8 | 0% | 3.50% | | 100 | N/A | | N/A |
| H4.9 | 0% | 19.60% | | 100 | N/A | | N/A |
| H4.1/H4.2 Full Sandwich | 0.60% | 70.90% | 1108 | 100 | 69% | 828 | 100 |
| H4.1/H4.2 Full Sandwich (1 w) | 2.30% | 62.20% | 486 | 100 | 57.40% | 366 | 100 |
| H6BA.1 | 1.50% | 31.40% | | 100 | 2% | | 100 |
| H6BA.2 | 7.30% | 19.50% | | 100 | 6.60% | | 100 |
| H6BA.3 | 1.70% | 58.50% | | 100 | 13.50% | | 100 |
| H7.1 | 1.80% | 70% | | 100 | 68.40% | | 100 |

Cloning and Purification of rcSso7d.H4.5-CBD and rcSso7d.H4.9-CBD

Several of the H-4-binding rcSso7d variants have been cloned into the rcSso7d-CBD construct. These include the H4.2 clone, discussed herein above, as well as, H4.5, and H4.9. rcSso7d.H4.5 and rcSso7d.H4.9 were cloned into CBD constructs rcSso7d.H4.5-CBD and rcSso7d.H4.9-CBD, respectively, and purified. FIGS. 65A-65B illustrate the plasmid maps for rcSso7d.H4.5-CBD and rcSso7d.H4.9-CBD, as well as the purification chromatograms associated with these binding species.

Immunoassay Performance of rcSso7d.H4.5-CBD and rcSso7d.H4.9-CBD

Figure 66A:
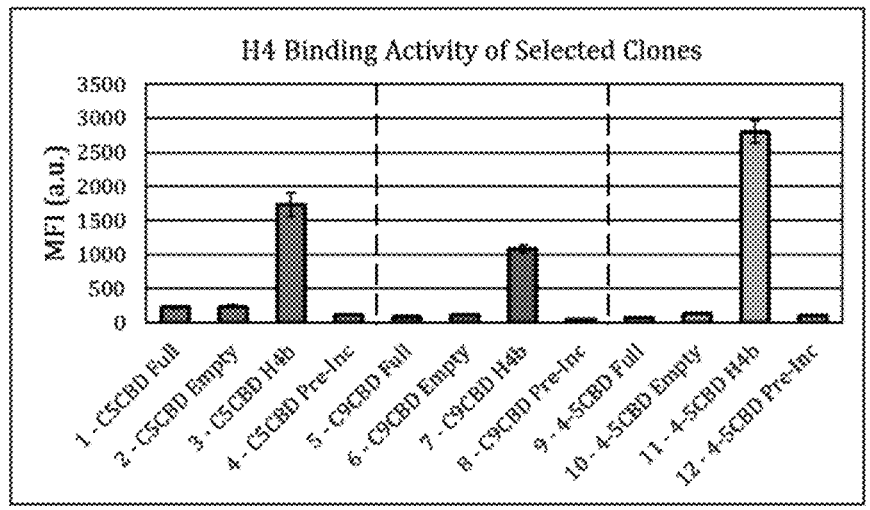
FIGS. 66A-66D show immunoassay performance of rcSso7d.H4.5-CBD, rcSso7d.H4.9-CBD, and rcSso7d.H4.2-CBD.
Figure 66B:
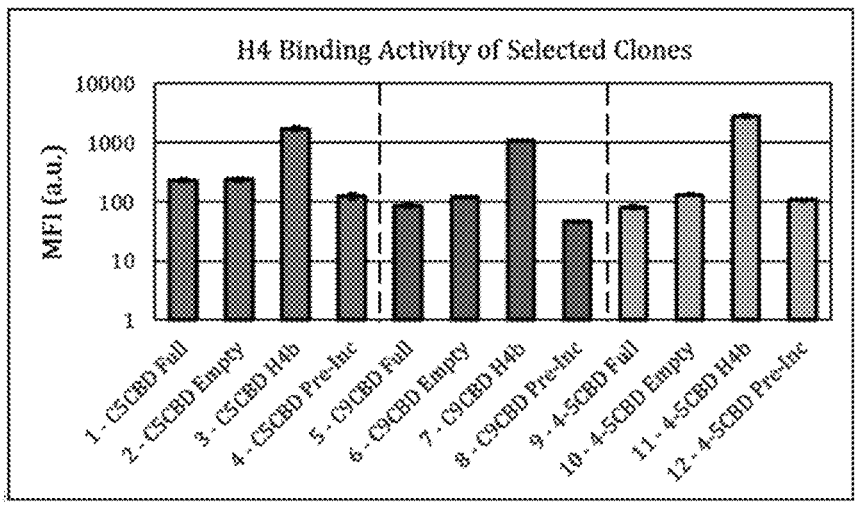
Figure 66C:
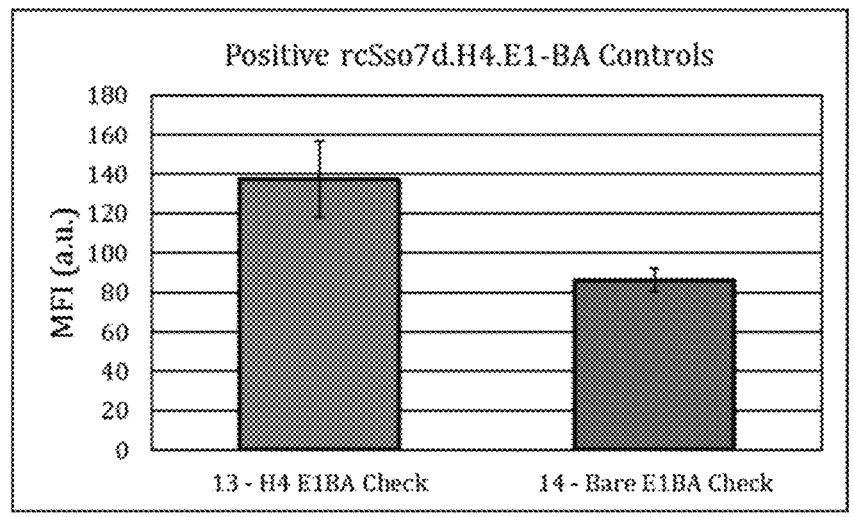
Figure 66D:
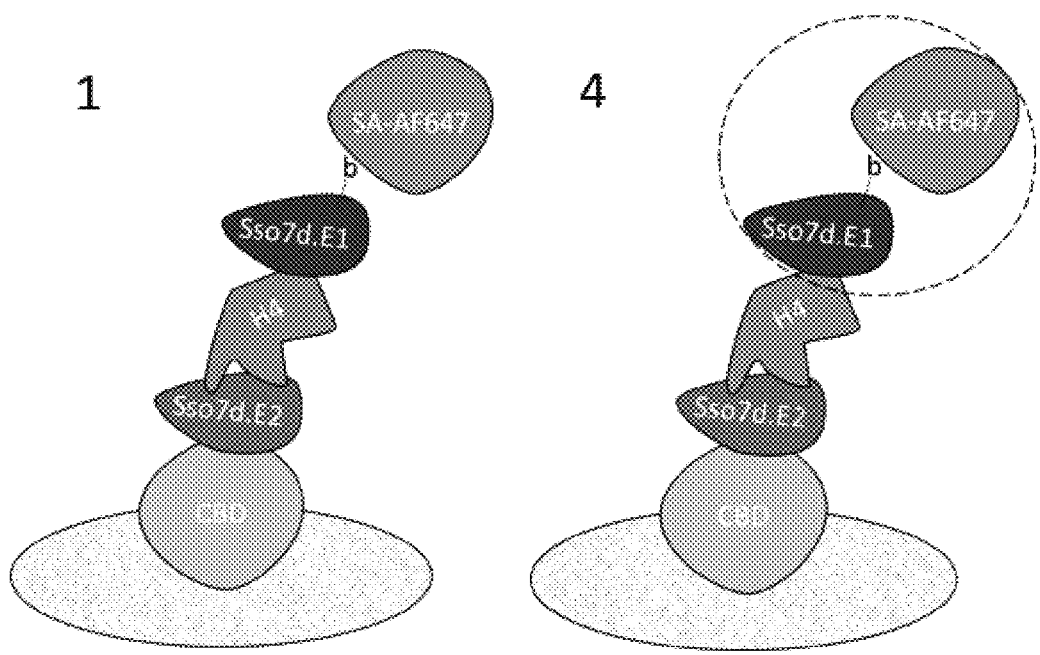

Binding activity of purified variants rcSso7d.H4.5-CBD, rcSso7d.H4.9-CBD, and rcSso7d.H4.2-CBD, is shown in FIGS. 66A-66D and are denoted as C5-CBD, C9-CBD, and 4-5CBD, respectively. FIG. 66A indicates the performance of each of these species in a full sandwich (with the H4.1-BA construct), an empty sandwich, a half sandwich with a biotinylated H4 variant, and with the H4.1-BA and H4 pre-incubated prior to being brought into contact with the rcSso7d.H4-CBD variant. In the full sandwich format, 180 picomoles of the rcSso7d-CBD fusion is immobilized on a cellulose test spot. Following two 20 μL wash steps in phosphate-buffered saline, 10 μL of soluble H4 at 256 nM is contacted with the spot. Following another wash step, the surface is contacted with 10 μL of soluble H4.E1-BA at 256 nM, and after an additional wash step the surface is contacted with 10 μL of streptavidin ALEXA FLUOR®647 at 256 nM. In the case of the empty sandwich, all steps are identical except instead of contacting the surface with H4, the surface is incubated in PBS for an equivalent period of time. The half-sandwich experiment uses a chemically biotinylated form of H4, which is brought into contact with the rcSso7d-CBD-coated surface. Following a wash step, the surface is contacted with streptavidin ALEXA FLUOR®647. The pre-incubation samples are identical to the full sandwich, except the H4.E1-BA and streptavidin ALEXA FLUOR®647 are pre-incubated together in the bulk solution, at a 1:1 molar ratio.

The half-sandwich data (the large bars in FIGS. 66A and 66B) indicates that the selected variants retain their function in the CBD format. The full sandwiches yield no signal, due to the limited accessibility of the directly attached biotin species, demonstrated in FIG. 66C.

Demonstration of the principle using a different CBD variant: dCBD Data

```
rcSso7d.SA-dCBD
                                        (SEQ ID NO: 118)
MGSSHHHHHHSSGLVPRGSHMATVKFTYQGEEKQVDISKIKIVARDGQYI

DFKYDEGGGAYGYGWVSEKDAPKELLQMLEKQGSAGPGANPPGTTTTSRP

ATTTGSSPGPQACSSVWGQCGGQNWSGPTCCASGSTCVYSNDYYSQCLPG

ANPPGTTTTSRPATTTGSSPGPTQSHYGQCGGIGYSGPTVCASGTTCQVL

Figure 67:
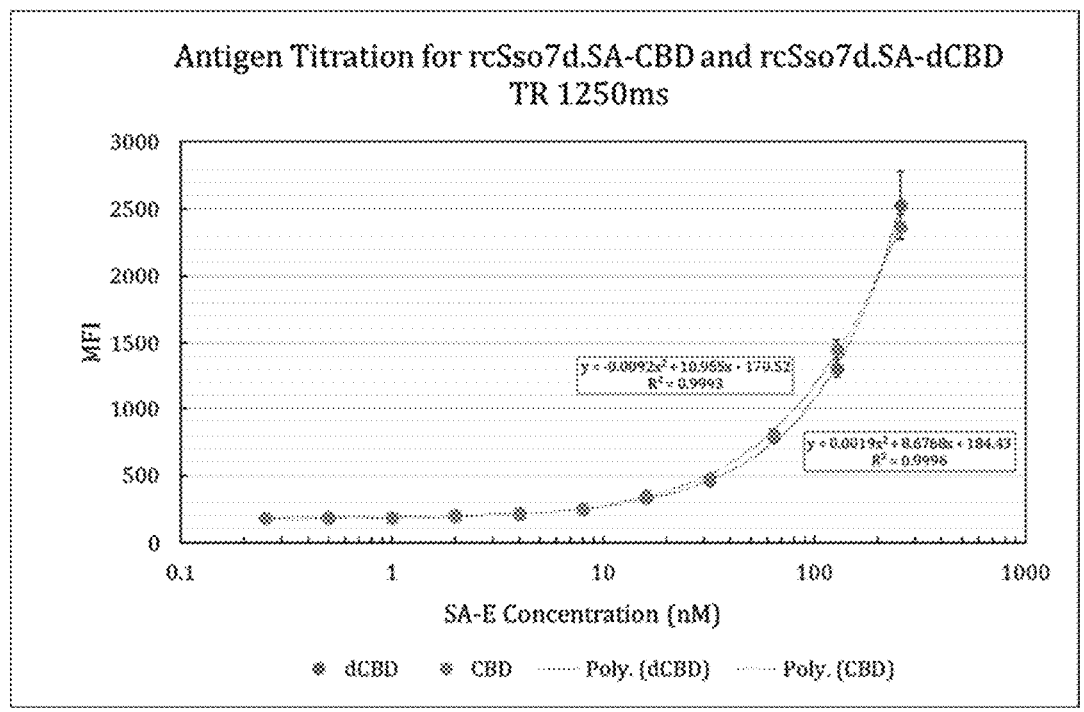
FIG. 67 shows the results of antigen titration for rcSso7d.SA-CBD and rcSso7d.SA-dCBD and demonstrates the principle of using a different CBD variant (dCBD).

NPYYSQCL*
``` dCBD is a member of the Carbohydrate-binding module family 1 (CBM-1). Similar performance is observed with this dCBD variant as with the CBM-3 variant (CBD) previously reported (see FIG. 67). There is a 30 second primary incubation time. 6 μL of 30 μM applied protein and rapid depletion of soluble analyte from solution. FIG. 67 demonstrates proof that the approach of using an rcSso7d-CBD fusion construct is relevant for other members of the carbohydrate-binding module family. Here, the sequence for the rcSso7d.SA-dCBD construct has been included, and a representative titration of a fluorescent streptavidin-eosin reagent has been prepared for two distinct sample sets, produced using rcSso7d.SA-CBD and rcSso7d.SA-dCBD. These data sets indicate similar performance between the Type 3 CBD and the Type 1 dCBD species.

Example 13. Multimerized rcSso7d-CBD Variants

Multimerized (rcSso7d.SA)n-CBD for Further Enhancement of Surface Abundance

Figure 68A:
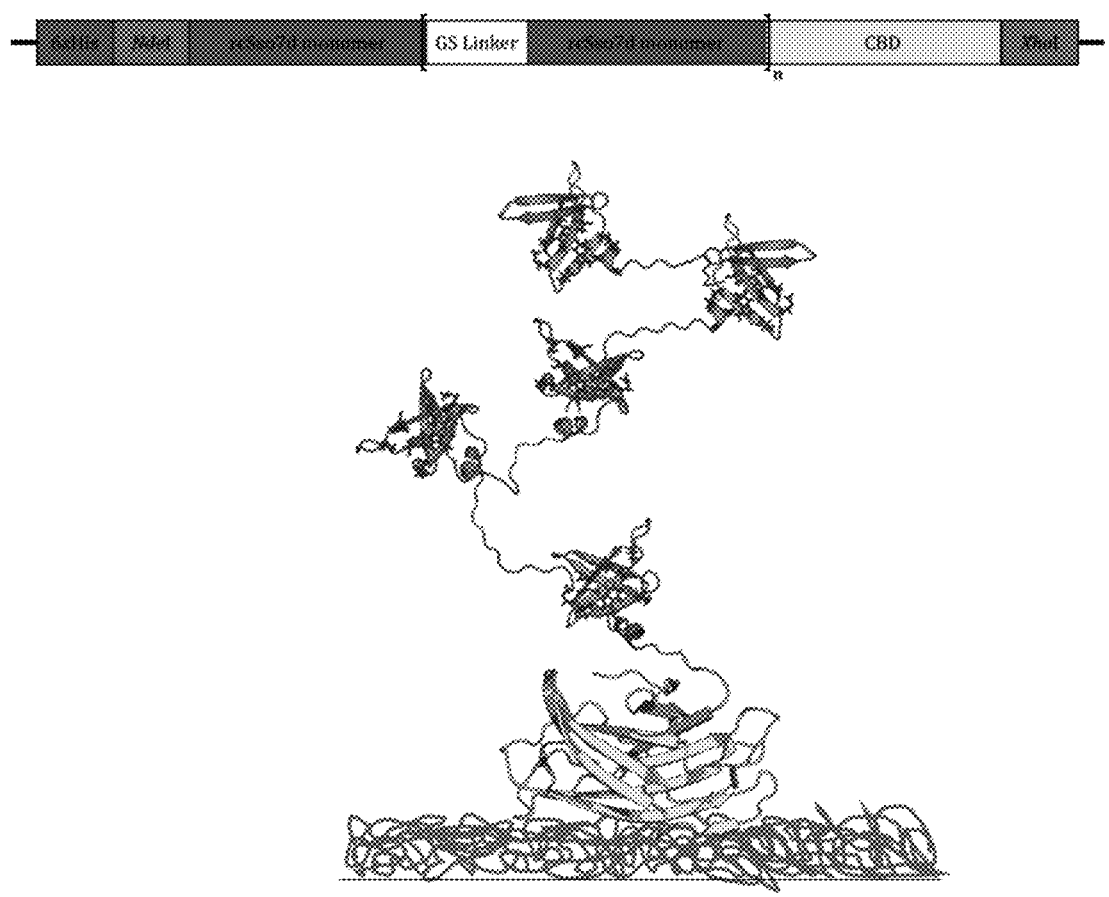
FIGS. 68A-68C show multimerized (rcSso7d.SA)n-CBD for further enhancement of surface abundance.

Multimerized rcSso7d-CBD variants 1×-rcSso7d.SA-CBD, 2×-rcSso7d.SA-CBD, and 3×-rcSso7d.SA-CBD, were created, with one, two, or three independent rcSso7d.SA binding modules genetically fused together and integrated into the CBD binding construct (see FIG. 68A). An approach for producing multimerized species has been documented, for instance, in Paloni, et al. *Biomacromolecules* (2018) 19(9):3814-24). The sequences for these variants are shown below. A general schematic for this fusion construct is illustrated in FIG. 68A, indicating that a $(G_4S)_3$ linker sequence (SEQ ID NO: 125) is included between each rcSso7d binding variant, as well as between the final rcSso7d module and the CBD fusion partner.

```
1x-rcSso7d.SA-CBD
                                        (SEQ ID NO: 119)
MGSSHHHHHHSSGLVPRGSHMATVKFTYQGEEKQVDISKIKIVARDGQYI

DFKYDEGGGAYGYGWVSEKDAPKELLQMLEKQGSGGGGSGGGGSGGGGSP

VSGNLKVEFYNSNPSDTTNSINPQFKVTNTGSSAIDLSKLTLRYYYTVDG

QKDQTFWCDHAAIIGSNGSYNGITSNVKGTFVKMSSSTNNADTYLEISFT

GGTLEPGAHVQIQGRFAKNDWSNYTQSNDYSFKSASQFVEWDQVTAYLNG

VLVWGKEP*

2x-rcSso7d.SA-CBD
                                        (SEQ ID NO: 120)
MGSSHHHHHHSSGLVPRGSHMATVKFTYQGEEKQVDISKIKIVARDGQYI

DFKYDEGGGAYGYGWVSEKDAPKELLQMLEKQGGGGSGGGGSMATVKFTY

QGEEKQVDISKIKIVARDGQYIDFKYDEGGGAYGYGWVSEKDAPKELLQM

LEKQGSGGGGSGGGGSGGGGSPVSGNLKVEFYNSNPSDTTNSINPQFKVT

NTGSSAIDLSKLTLRYYYTVDGQKDQTFWCDHAAIIGSNGSYNGITSNVK

GTFVKMSSSTNNADTYLEISFTGGTLEPGAHVQIQGRFAKNDWSNYTQSN

DYSFKSASQFVEWDQVTAYLNGVLVWGKEP*

3x-rcSso7d.SA-CBD
                                        (SEQ ID NO: 121)
MGSSHHHHHHSSGLVPRGSHMATVKFTYQGEEKQVDISKIKIVARDGQYI

DFKYDEGGGAYGYGWVSEKDAPKELLQMLEKQGGGGSGGGGSMATVKFTY

QGEEKQVDISKIKIVARDGQYIDFKYDEGGGAYGYGWVSEKDAPKELLQM

LEKQGGGGSGGGGSMATVKFTYQGEEKQVDISKIKIVARDGQYIDFKYDE

GGGGAYGYGWVSEKDAPKELLQMLEKQGSGGGGSGGGGSGGGGSPVSGNL

KVEFYNSNPSDTTNSINPQFKVTNTGSSAIDLSKLTLRYYYTVDGQKDQT
```

-continued

FWCDHAAIIGSNGSYNGITSNVKGTFVKMSSSTNNADTYLEISFTGGTLE

PGAHVQIQGRFAKNDWSNYTQSNDYSFKSASQFVEWDQVTAYLNGVLVWG

KEP*

Figure 68B:
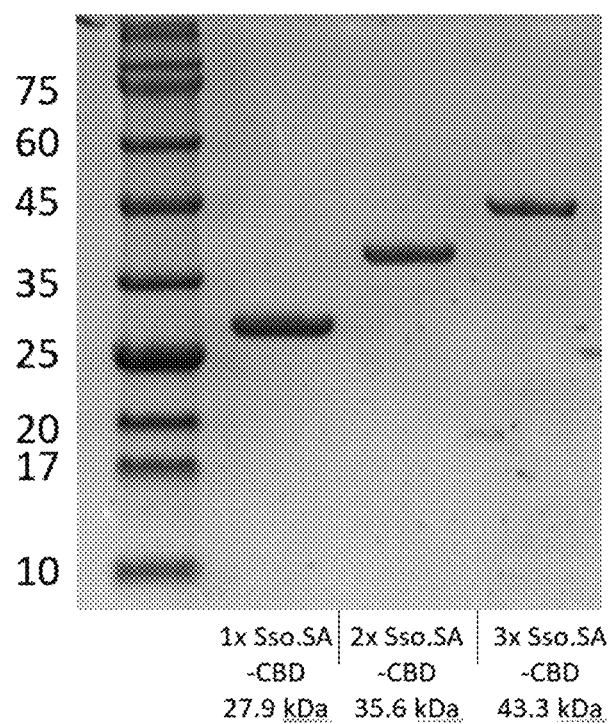
Figure 68C:
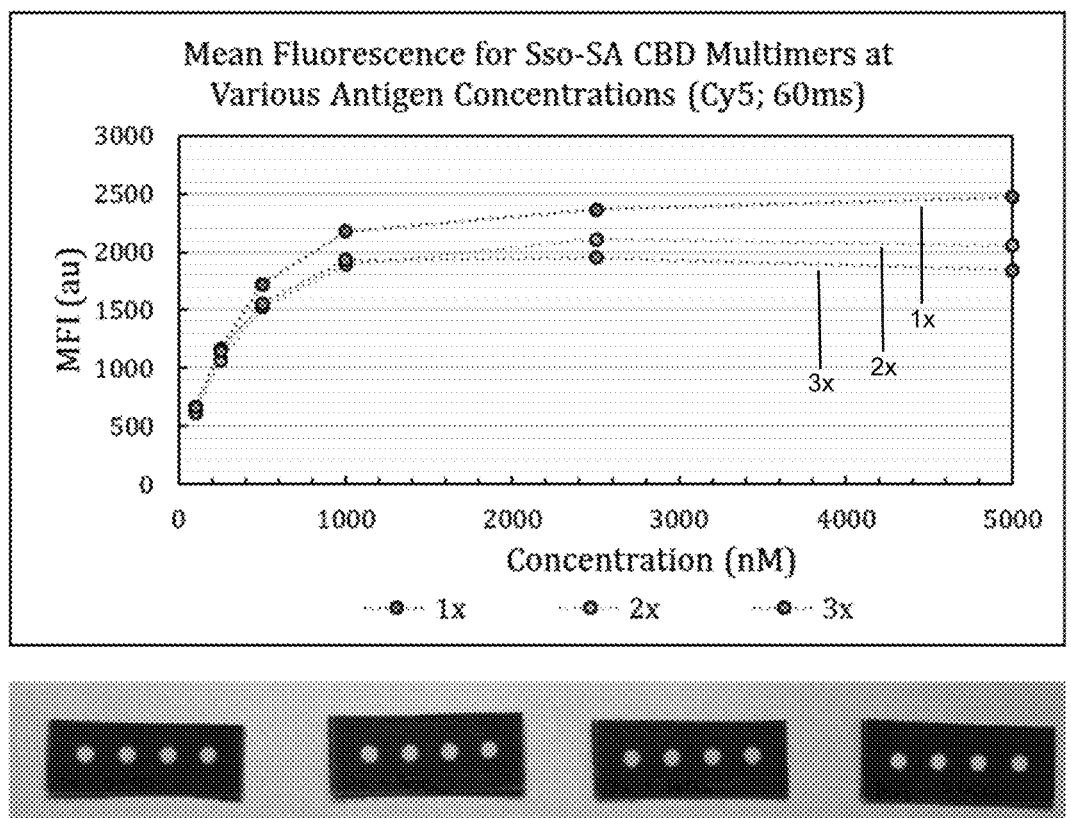

A 12% SDS-PAGE gel shown in FIG. 68B demonstrates the purity of the 1×-, 2×-, and 3×-CBD variants following purification with immobilized metal affinity chromatography. The performance of these immobilized rcSso7d-CBD variants in antigen-capture assays is indicated in FIG. 68C, using streptavidin ALEXA FLUOR®647 as the analyte. Notably, the signal appears to drop off for the higher rcSso7d-CBD multimers at high analyte concentrations, which runs counter to the expected trend—as the surface-immobilized 1×-rcSso7d-CBD species is saturated, it would be expected that there would be additional free rcSso7d modules for the 2× and 3× variants, and that the binding signal would continue to increase for those constructs. Upon visual inspection of the 5 μM samples (depicted beneath the graph), it appears that the 2× and 3× are both darker than the 1× variant, suggesting that additional analyte is in fact being captured for these samples. This suggests that the decrease in the mean fluorescence signal may actually be due to fluorescent quenching, as the higher-order binding constructs sequester a greater molar quantity of the fluorescent analyte in close proximity. This indicates that the use of multimeric (rcSso7d)x-CBD constructs may indeed serve to more efficiently capture analyte, and may yield significant benefits in the large-volume processing format, where the timescale for analyte capture must match the short timescale during which the analyte is in contact with the test zone.

Immobilization of rcSso7d.SA-CBD on Cellulose Powder for Combing Through Large Volumes It was demonstrated that the rcSso7d.SA-CBD protein can be immobilized on cellulose powder, which can be mixed into a large volume sample for the efficient capture of a soluble analyte. 180 picomoles of rcSso7d.SA-CBD was applied to a circular test zone (see the positive control in FIG. 69) or to an equivalent mass of cellulose powder (represented in the experimental sample). Two 10 mL aliquots of a 2 nM solution of streptavidin ALEXA FLUOR®647 were prepared. One was forced across the paper test zone by pressure-driven flow, using a syringe pump, and was circulated back and forth across the test zone for 40 minutes at a volumetric flowrate of 5 mL/min. The rcSso7d.SA-CBD-coated cellulose powder was spiked into the other aliquot, which was incubated with mixing for an equivalent time period. Following the analyte incubation step, this powder was retained by flowing the analyte solution across a paper test zone, concentrating the powder and captured analyte in a relatively small region for detection and quantification. The analyte signal seems more disperse, but the average intensity is roughly equivalent, suggesting that a more robust method for concentrating the powder may allow the sensitive detection of a chemical species captured by the cellulose powder reagent.

Example 14. Large-Volume Processing Data

The high-abundance immobilization enabled by rcSso7d-CBD constructs is uniquely enabling for the enhancement of analytical sensitivity via large-volume processing.

Figure 70:
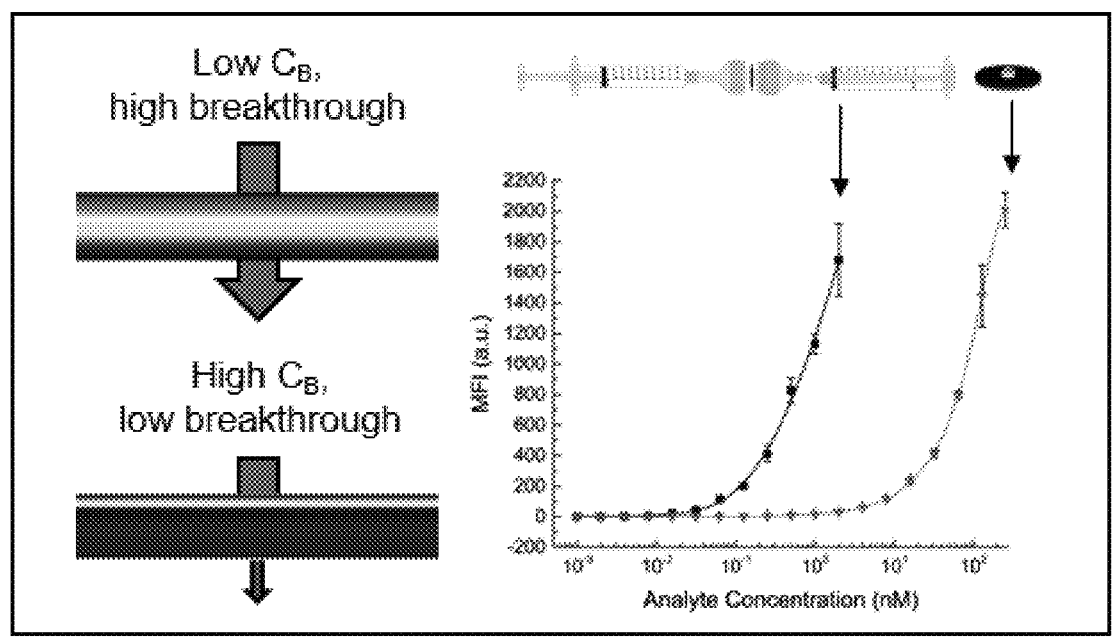
FIG. 70 is a schematic showing large-volume processing.

Large-volume processing data was previously disclosed, (see Miller et al., *Anal Chem* (2018) 90(15):9472-9) and demonstrates the enabling nature of the concentration domain achieved by using the CBD fusion species. The higher immobilized concentration of the binder enables capture of dilute analyte from a flowing system within the brief period that the analyte is in contact with the test zone. This permits the processing of large sample volumes within a clinically relevant timescale, and the capture of greater quantities of analyte even at lower concentrations, increasing analytical sensitivity (see FIG. 70).

Figure 71:
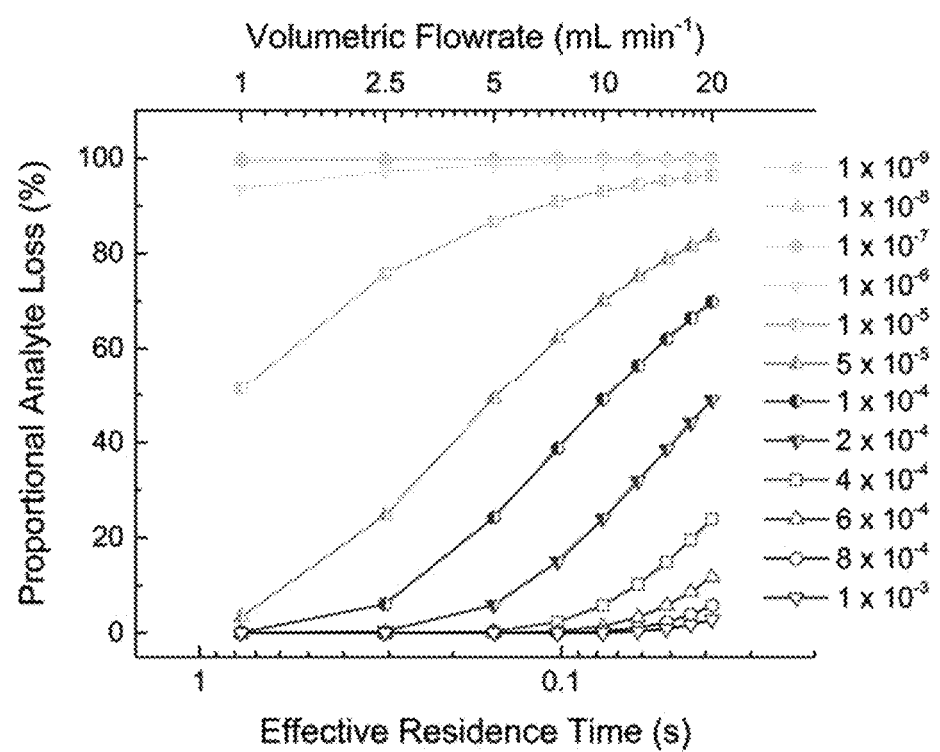
FIG. 71 shows finite-element modeling data demonstrating proportional analyte breakthrough at varying volumetric flow rates and with varying concentrations of binding reagents. These curves depict how analyte capture is influenced by the relationship between the kinetics of the binding reaction and the rates of transport processes within cellulose. Each curve represents a single 10 mL recirculation at a different local binder concentration (mol L−1; denoted in the legend). The inlet analyte concentration is 1 nM.

Finite-element modeling data demonstrating proportional analyte breakthrough at varying volumetric flow rates and with varying concentrations of binding reagents is shown in FIG. 71. These curves depict how analyte capture is influenced by the relationship between the kinetics of the binding reaction and the rates of transport processes within cellulose. Each curve represents a single 10 mL recirculation at a different local binder concentration (mol $L^{-1}$; denoted in the legend). The inlet analyte concentration is 1 nM.

Figure 72:
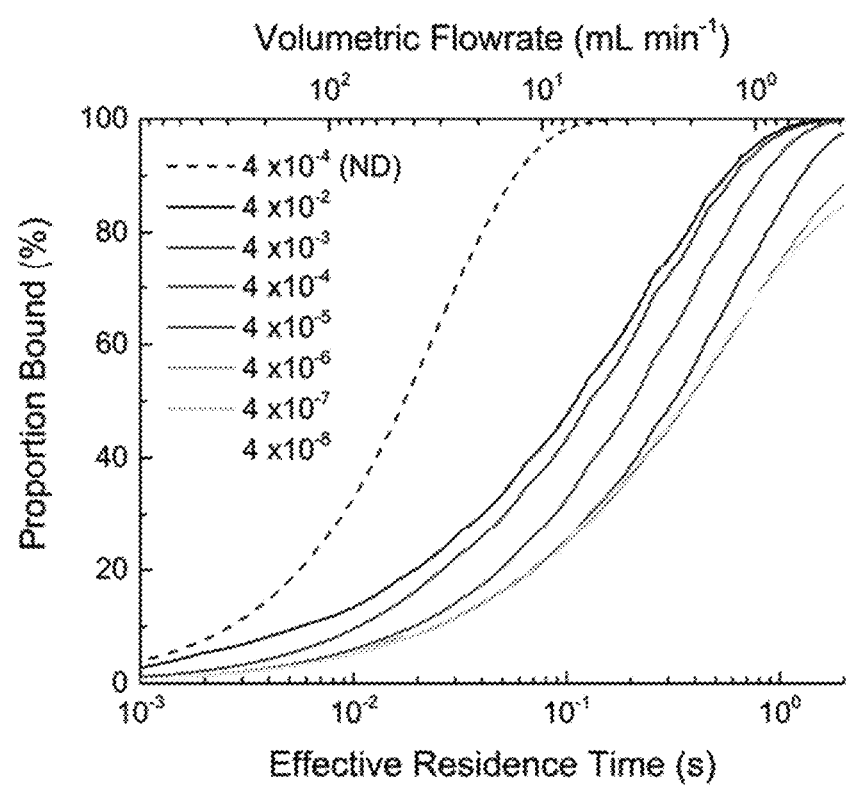
FIG. 72 shows proportional binding curves predicted by the finite-element model in the diffusive limit. In this scenario, the rate of diffusion to the cellulose fibers is the rate-limiting process, as the immobilized binder is localized to the pore walls and the rate of analyte capture is assumed to be rapid relative to diffusion. The dashed curve (ND) represents the binding performance predicted by the non-diffusive, homogeneous distribution model at standard rcSso7d-CBD concentration (400 µM). Solid curves represent binding in the diffusion-limited case at varying local concentrations of the immobilized binder (mol L$^{-1}$). The leftmost diffusive curve (black) corresponding to a local surface concentration of 40 mM was used to simulate instantaneous capture; no appreciable increase in the binding proportion is seen for higher local concentrations.

Proportional binding curves predicted by the finite-element model in the diffusive limit are shown in FIG. 72. In this scenario, the rate of diffusion to the cellulose fibers is the rate-limiting process, as the immobilized binder is localized to the pore walls and the rate of analyte capture is assumed to be rapid relative to diffusion. The dashed curve (ND) represents the binding performance predicted by the non-diffusive, homogeneous distribution model at standard rcSso7d-CBD concentration (400 μM). Solid curves represent binding in the diffusion-limited case at varying local concentrations of the immobilized binder (mol $L^{-1}$). The leftmost diffusive curve (black) corresponding to a local surface concentration of 40 mM was used to simulate instantaneous capture; no appreciable increase in the binding proportion is seen for higher local concentrations.

Figure 73:
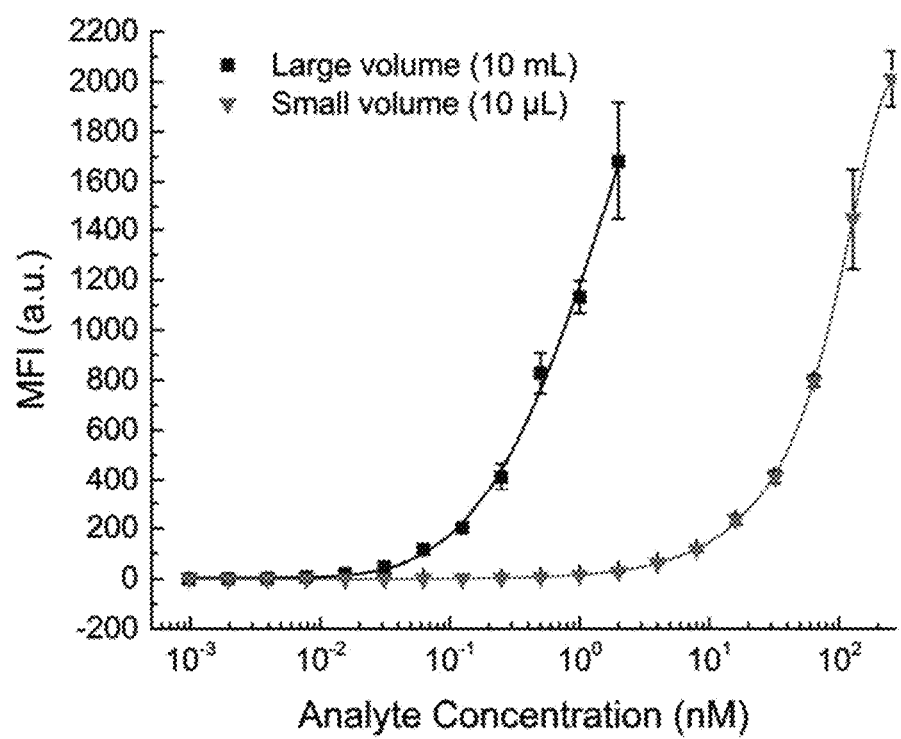
FIG. 73 shows sensitivity enhancement through large-volume processing. Mean fluorescence intensity (MFI) observed at varying analyte concentrations for large-(10 mL; 5 mL min-1; 20 recirculations) and small-volume (10 µL; 40 min) samples. Lines of best fit were generated using a five-point sigmoidal curve (Eq. S10). (Miller et al. *Anal Chem* (2018) 90(15):9472-9). Error bars represent the standard deviation of three (large-volume) or four (small-volume) independent replicates.

Sensitivity enhancement through large-volume processing is shown in FIG. 73. Mean fluorescence intensity (MFI) observed at varying analyte concentrations for large-(10 mL; 5 mL min-1; 20 recirculations) and small-volume (10 μL; 40 min) samples. Lines of best fit were generated using a five-point sigmoidal curve (eq S10). Error bars represent the standard deviation of three (large-volume) or four (small-volume) independent replicates.

A comparison between analyte titration curves for rcSso7d-CBD at varying local concentrations is shown in FIGS. 74A-74B. Mean fluorescence intensity (MFI) observed at varying analyte concentrations for large-(10 mL) and small-volume (10 μL) samples using test zones with local rcSso7d-CBD concentrations of 400 and 40 μM (see FIG. 74A). Data points corresponding to the 400 μM/10 μL samples directly overlap with those corresponding to the 40 μM/10 μL samples (FIG. 87). Fluorescence ratios comparing the corresponding large- and small-volume samples at local rcSso7d-CBD concentrations of 400 and 40 μM are shown in FIG. 74B. Large-volume samples consist of 10 mL of analyte solution (5 mL $min^{-1}$, 20 recirculations). Small-volume samples consisted of 10 μL incubated on the test zones for an equivalent 40 min period. Error bars represent the standard deviation of three (large-volume) or four (small-volume) independent replicates.

Assay performance for varying flow rates and total processing times is shown in FIGS. 75A-75D. Absolute mean fluorescence intensity (MFI) is shown in FIG. 75A, proportional MFI (relative to samples processed for the same period of time at 1 mL $min^-$) is shown in FIG. 75B, and signal development efficiency (MFI $min^-$) for varying single-pass residence times and total processing times is shown in FIG. 75C. Signal development as a function of the number of recirculations is depicted in FIG. 75D. Linear trend lines indicate the performance of samples produced using a common volumetric flow rate (denoted in the legend). Sample specifications: 10 mL and 1 nM SA-AF647. Error bars represent the standard deviation of three independent replicates.

Syringe-based assay format is depicted in FIG. 76. Paper samples were excised and secured in a 13 mm Swinnex filter holder. A 10-mL syringe was connected upstream and used to pre-fill the filter holder with the analyte solution. A Qosina Female-to-Female Luer-Lok connector was used to join this cassette to a second syringe downstream, and any remaining air is bled from the system. In all cases, the top of the test zone (the surface to which the rcSso7d.SA-CBD solution was applied) was oriented so as to be the first side contacted by the analyte solution.

Set-up of COMSOL proportional analyte capture model is depicted in FIGS. 77A-77D. The test zone was modeled as a two dimensional reactor volume, throughout which the immobilized binder was homogeneously distributed. Depth=L=180 µm; width=2rtz=1.8 mm. Analyte concentration at the inlet (at left) was 1 nM. The binder concentration and volumetric flow rate for the sample sets were varied across the different subfigures: 1 µM, 1 mL min-1 (FIG. 77A), 1 µM, 20 mL min-1 (FIG. 77B), 400 µM, 1 mL min-1 (FIG. 77C), and 400 µM, 20 mL mini (FIG. 77D). Within each sub-figure, the rows of test snapshots correspond to the soluble analyte, free binder, and the occupied binder (from top to bottom). Test zone snapshots were captured every sixty seconds, at timepoints denoted along the top of each sub-figure. Legends at right denote the concentrations of the relevant species for the corresponding row of cross-sectional snapshots. In order to capture system dynamics, color-bars were scaled relative to the relevant species for each set of operating conditions, rather than representing a universal concentration scale.

Set-up of COMSOL diffusion model is shown in FIG. 78. An idealized circular pore (r=5.5 µm) was initialized with an analyte concentration of 1 nM. The surrounding matrix represents a binder-functionalized fibrous network, at an average binder concentration of 40 mM. Analyte diffusion and capture was allowed to proceed over the course of 2 seconds, to model diffusive capture over a range of different sample residence times. Each snapshot represents a different time-point, denoted above the pore image, and the color-bar represents the concentration of the soluble analyte.

Confirmation of fluid flow across the entire assay cross-sectional area is shown in FIG. 79. Insoluble cellulose powder (50 µm diameter) was added to the sample volume in order to track the fluid flow as the sample was recirculated across the test zone. Rather than focusing solely within the hydrophilic region, the powder distributes across the entire cross-sectional area, indicating that the hydrophobic region permits fluid flow once it becomes sufficiently wetted. Thus, the relevant flow volume is 12.81 µL, rather than that associated strictly with the binder-functionalized region (0.45 µL).

Proportional binder occupancy at varying concentrations and volumetric flow rates is shown in FIG. 80. Each line plot represents operation at a different local binder concentration (denoted in the legend). For all data sets, analyte was introduced at a concentration of 1 nM, and data was collected immediately following a single simulated 10-mL recirculation.

Correlation of flow rate, binder concentration, analyte capture, and DaI is shown in FIGS. 81A-81B. Standard curves correlating volumetric flow rate, binder concentration (mol L−1), and Damköhler number, as well as rates of proportional analyte capture predicted by the pseudo first-order rate model are shown in FIG. 81A. Predicted proportional binding curves for varying local concentrations of immobilized binder are shown in FIG. 81B.

Deviation between finite-element analysis and PFORC model is shown in FIGS. 82A-82B. A comparison of the finiteelement model of analyte binding in the non-diffusive limit (dashed lines) and the pseudo first-order rate constant model (solid lines) is shown in FIG. 82A. Absolute basis point deviation between the FEA model and PFORC model for all processing conditions is shown in FIG. 82B. The greatest deviation between the predictive models is observed in regions of dynamic signal change.

A Damköhler master curve is shown in FIG. 83. All dimensional binding curves generated via the pseudo first-order rate model collapse onto a single dimensionless binding curve describing system performance. This relation is valid for all cases in which the immobilized binder is in significant molar excess (>10x) of the soluble analyte. Dashed lines highlight the value of the Damköhler number at which 50% of the analyte is captured.

Binding isotherms are shown in FIG. 84. Curves denote the theoretical proportional analyte capture observed for a given volumetric flow rate (or residence time) at varying concentrations of immobilized binder. The dashed line indicates the operating regime of the standard rcSso7d-CBD system (CB=400 µM).

Titration curves near the point of signal onset are shown in FIG. 85. All large-volume samples consisted of 10 mL sample volumes, driven across the test zone at 5 mL min-1 for 20 recirculations. All small-volume samples consisted of 10 µL sample volumes, applied directly to the test zones and allowed to incubate for an equivalent 40-minute period. Dataset is identical to that seen in FIG. 73. Error bars represent the standard deviation of three (large-volume) or four (small-volume) independent replicates.

A calculation of immobilized protein abundance on functionalized paper is shown in FIGS. 86A-86B. Titration data is shown in FIG. 86A for rcSso7d.SA-CBD applied to non-functionalized paper (black) and rcSso7d.SA applied to aldehyde functionalized paper (red), for streptavidin-eosin (SA-E) concentrations ranging from 0.25 nM to 256 nM and 10 µL sample volumes. Proportional analyte capture at varying applied analyte concentrations is shown in FIG. 86B. Analysis is conducted for all applied concentrations wherein there is an appreciable difference between signals observed for the functionalized and non-functionalized samples. All tests were incubated with the analyte solution for thirty minutes. Error bars represent the standard deviation of four independent replicates.

A comparison between small-volume titration curves for rcSso7d-CBD at local concentrations of 400 µM and 40 µM is shown in FIG. 87. Dataset is identical to that seen in FIG. 74A. Small-volume samples consisted of 10 µL incubated on the test zones for a 40-minute period. Error bars represent the standard deviation of four independent replicates.

Linear regression slopes, which correlate the number of recirculations and the degree of signal development, decline with increasing volumetric flow rate (see FIG. 88). In nearly all cases, linear regression curves are observed to correlate well with the experimental data, as indicated by Pearson coefficients near ±1.

A representative manual titration curve using streptavidin-eosin as the soluble analyte is shown in FIG. 89. Samples were processed for 20 recirculations each. Each data point represents a single assay replicate. Manual samples were processed at a flow rate that could be sustained without physical discomfort (~25 mL min-1). Samples were exposed for 1000 ms using a TXRED®-4040C filter set.

Example 15. Binder Activity in Urine Samples

The binding activity of various binders against urine-treated analytes, quantified using the geometric mean fluorescence intensity, rather than population proportions is shown in FIGS. 90, 91, 93, 94 and 95A-95B. The binding specificity of rcSso7d.H1BA.3, quantified with the geometric mean fluorescence intensity is shown in FIG. 92. The performance of the BA-MBP-rcSso7d.H4.1 and rcSso7d.H4.2-CBD species in a paper-based immunoassay format are shown in FIGS. 96-103.

FIG. 96 includes a schematic of the full sandwich immunoassay (as well as the empty versions used to assess binding specificity). FIG. 97 documents the performance of these binding reagents in various formats (the full immunocomplex and empty immunocomplexes), indicating significant analyte-specific activity for the full sandwich. FIG. 98 demonstrates that this analyte-specific activity is specific to the complementary binding species rcSso7d.H4.1 and rcSso7d.H4.2—other H4-binding variants yield no discernible signal in the full sandwich format. FIG. 99 demonstrates the limited cross-reactivity of the H4.1-CBD and H4.2-CBD species against other tuberculosis antigens in the paper-based format. Where high signal is seen, this is likely due to a) inadequate surface passivation, b) the high abundance of the CBD binding species, and c) the near-permanent nature of the streptavidin-based detection method. When the same rcSso7d.H4.1/rcSso7d.H4.2 species are challenged with other TB antigens in the yeast-surface display format, the only appreciable signal is observed with the H4 species. FIGS. 100 and 101 document efforts to reduce non-specific binding of detection reagents to reduce background signal, both by passivating the surface in bovine serum albumin for empty sandwich assays (FIG. 100) and by varying the pH of the solution in which the BA-MBP-rcSso7d.H4.1 species is applied/washed (FIG. 101). These findings were applied to produce the titration curve seen in FIG. 102. The limit of detection, determined as the fluorescence value three standard deviations above the mean negative signal, was observed to be approximately 8 nM. FIG. 103 documents further efforts to enhance assay sensitivity, demonstrating that by boosting the applied concentration of BA-MBP-rcSso7d.H4.1, the analyte-specific signal can be greatly increased for a given applied concentration of H4.

REFERENCES

Ackerman, M., Levary, D., Tobon, G., Hackel, B., Orcutt, K. D., Wittrup, K. D., 2009. Biotechnol. Prog. 25, 774-783.
Ahmed, S., Bui, M.-P. P. N., Abbas, A., 2016. Biosens. Bioelectron. 77, 249-263.
Baumann, H., Knapp, S., Lundback, T., Ladenstein, R., Hard, T., 1994. Nat. Struct. Biol. 1, 808-819.
Berdichevsky, Y., Lamed, R., Frenkel, D., Gophna, U., Bayer, E. A., Yaron, S., Shoham, Y., Benhar, I., 1999. Protein Expr. Purif 17, 249-259.
Care, A., Bergquist, P. L., Sunna, A., 2015. Trends Biotechnol. 33, 259-268.
Care, A., Petroll, K., Gibson, E. S. Y., Bergquist, P. L., Sunna, A., 2017. Biotechnol. Biofuels 10, 1-16.
Chao, G., Lau, W. L., Hackel, B. J., Sazinsky, S. L., Lippow, S. M., Wittrup, K. D., 2006. Nat. Protoc. 1, 755-68.
Credou, J., Berthelot, T., 2014. J. Mater. Chem. B 2, 4767-4788.
Dai, G., Hu, J., Zhao, X., Wang, P., 2016. Sensors Actuators B Chem. 238, 138-144.
Esteban, B., De, A., Watkins, H. M., Pingarro, J. M., Plaxco, K. W., Palleschi, G., Ricci, F., 2013. Anal. Chem. 1-5.
Giri, B., Pandey, B., Neupane, B., Ligler, F. S., 2016. TrAC—Trends Anal. Chem. 79, 326-334.
Holstein, C. A., Chevalier, A., Bennett, S., Anderson, C. E., Keniston, K., Olsen, C., Li, B., Bales, B., Moore, D. R., Fu, E., Baker, D., Yager, P., 2016. Anal. Bioanal. Chem. 408, 1335-1346.
Hussack, G., Luo, Y., Veldhuis, L., Hall, J. C., Tanha, J., MacKenzie, R., 2009. Sensors 9, 5351-5367.
Hyre, D. E., Le Trong, I., Merritt, E. A., Eccleston, J. F., Green, N. M., Stenkamp, R. E., Stayton, P. S., 2006. Protein Sci. 15, 459-467.
Kaastrup, K., Chan, L., Sikes, H. D., 2013. Anal. Chem. 85, 8055-8060.
Kelley, S. O., Mirkin, C. A., Walt, D. R., Ismagilov, R. F., Toner, M., Sargent, E. H., 2014. Nat. Nanotechnol. 9, 969-980.
Kim, H. D., Choi, S. L., Kim, H., Sohn, J. H., Lee, S. G., 2013. Biotechnol. Bioprocess Eng. 18, 575-580.
Kumada, Y., 2014. Biochim. Biophys. Acta—Proteins Proteomics 1844, 1960-1969.
Levy, I., Shoseyov, O., 2002. Biotechnol. Adv. 20, 191-213.Li, M., Yue, Y., Zhang, Z. J., Wang, Z. Y., Tan, T. W., Fan, L. H., 2016. Bioconjug. Chem. 27, 1579-1583.
McBee, R. H., 1954. J. Bacteriol. 67, 505-6.
Miller, E. A., Traxlmayr, M. W., Shen, J., Sikes, H. D., 2016. Mol. Syst. Des. Eng. 1, 377-381.
Napolitano, D. R., Pollock, N., Kashino, S. S., Rodrigues, V., Campos-Neto, A., 2008. Clin. Vaccine Immunol. 15, 638-43.
Nery, E. W., Kubota, L. T., 2016. J. Pharm. Biomed. Anal. 117, 551-559.
Parsa, H., Chin, C. D., Mongkolwisetwara, P., Lee, B. W., Wang, J. J., Sia, S. K., 2008. Lab Chip 8, 2062.
Peluso, P., Wilson, D. S., Do, D., Tran, H., Venkatasubbaiah, M., Quincy, D., Heidecker, B., Poindexter, K., Tolani, N., Phelan, M., Witte, K., Jung, L. S., Wagner, P., Nock, S., 2003. Anal. Biochem. 312, 113-24.
Ricci, F., Valldée-Bélisle, A., Simon, A. J., Porchetta, A., Plaxco, K. W., 2016. Ace. Chem. Res. 49, 1884-1892.
Rissin, D. M., Wilson, D. H., Duffy, D. C., 2013. Chapter 2.13: Measurement of Single Protein Molecules Using Digital ELISA, in: The Immunoassay Handbook. Elsevier, pp. 223-242.
Rosa, A. M. M., Louro, A. F., Martins, S. A. M., Inácio, J., Azevedo, A. M., Prazeres, D. M. F., 2014. Anal. Chem. 86, 4340-4347.
Seker, U. O. S., Demir, H. V., 2011. Molecules 16, 1426-1451.
Shen, M., Rusling, J., Dixit, C. K., 2016. Methods 116, 95-111.
Song, H. Y., Zhou, X., Hobley, J., Su, X., 2012. Langmuir 28, 997-1004.
Sugimoto, N., Igarashi, K., Samejima, M., 2012. Protein Expr. Purif. 82, 290-296.
Tang, R., Yang, H., Choi, J. R., Gong, Y., Hu, J., Feng, S., Pingguan-Murphy, B., Mei, Q., Xu, F., 2016. Talanta 152, 269-276.
Tomme, P., Boraston, A., McLean, B., Kormos, J., Creagh, A. L., Sturch, K., Gilkes, N. R., Haynes, C. A., Warren, R. A. J., Kilburn, D. G., 1998. J. Chromatogr. B Biomed. Appl. 715, 283-296.

Traxlmayr, M. W., Kiefer, J. D., Srinivas, R. R., Lobner, E., Tisdale, A. W., Mehta, N. K., Yang, N. J., Tidor, B., Wittrup, K. D., 2016. J. Biol. Chem. 291, 22496-22508.

Vuoriluoto, M., Orelma, H., Zhu, B., Johansson, L.-S. S., Rojas, O. J., 2016. ACS Appl. Mater. Interfaces 8, 5668-5678.

Yaniv, O., Morag, E., Borovok, I., Bayer, E. A., Lamed, R., Frolow, F., Shimon, L. J. W., 2013. Acta Cryst 69, 733-737.

Yu, A., Shang, J., Cheng, F., Paik, B. A., Kaplan, J., Andrade, R. B., Ratner, D. M., 2012. Langmuir 28, 11265-11273.

Zhao, M., Li, H., Liu, W., Guo, Y., Chu, W., 2016. Biosens. Bioelectron. 79, 581-588.

Zhu, Y., Xu, X., Brault, N. D., Keefe, A. J., Han, X., Deng, Y., Xu, J., Yu, Q., Jiang, S., 2014. Anal. Chem. 86, 2871-2875.

Miller, E. A., Traxlmayr, M. W., Shen, J., Sikes, H. D., 2016. Mol. Syst. Des. Eng. 1, 377-381.

Schafer, D. E., 1983. Measurement of Receptor-Ligand Binding: Theory and Practice, in: Lambrecht, R. M., Rescigno, A. (Eds.), Springer Berlin Heidelberg, Berlin, Heidelberg, pp. 445-507.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

SEQUENCE LISTING

```
Sequence total quantity: 135
SEQ ID NO: 1          moltype = AA   length = 1674
FEATURE               Location/Qualifiers
source                1..1674
                      mol_type = protein
                      organism = Clostridium thermocellum
SEQUENCE: 1
MRKVISMLLV VAMLTTIFAA MIPQTVSAAT MTVEIGKVTA AVGSKVEIPI TLKGVPSKGM   60
ANCDFVLGYD PNVLEVTEVK PGSIIKDPDP SKSFDSAIYP DRKMIVFLFA EDSGRGTYAI  120
TQDGVFATIV ATVKSAAAAP ITLLEVGAFA DNDLVEISTT FVAGGVNLGS SVPTTQPNVP  180
SDGVVVEIGK VTGSVGTTVE IPVYFRGVPS KGIANCDFVF RYDPNVLEII GIDPGDIIVD  240
PNPTKSFDTA IYPDRKIIVF LFAEDSGTGA YAITKDGVFA KIRATVKSSA PGYITFDEVG  300
GFADNDLVEQ KVSFIDGGVN VGNATPTKGA TPTNTATPTK SATATPTRPS VPTNTPTNTP  360
ANTPVSGNLK VEFYNSNPSD TTNSINPQFK VTNTGSSAID LSKLTLRYYY TVDGQKDQTF  420
WCDHAAIIGS NGSYNGVTSN VKGTFVKMSS STNNADTYLE ISFTGGTLEP GAHVQIQGRF  480
AKNDWSNYTQ SNDYSFKSAS QFVEWDQVTA YLNGVLVWGK EPGGSVVPST QPVTTPPATT  540
KPPATTIPPS DDPNAIKIKV DTVNAKPGDT VNIPVRFSGI PSKGIANCDF VYSYDPNVLE  600
IIEIKPGELI VDPNPDKSFD TAVYPDRKII VFLFAEDSGT GAYAITKDGV FATIVAKVKS  660
GAPNGLSVIK FVEVGGFANN DLVEQKTQFS DGGVNVGGTT VPTTPPASTT PTDDPNAIKI  720
KVDTVNAKPG DTVNIPVRFS GIPSKGIANC DFVYSYDPNV LEIIEIKPGE LIVDPNPDKS  780
FDTAVYPDRK IIVFLLTEDS GTGAYAITKD GVFATIVAKV KSGAPNGLSV IKFVEVGGFA  840
NNDLVEQKTQ FFDGGVNVGD TTVPTTPTTP VTTPTDDPNA VRIKVDTVNA KTGDTVRIPV  900
RFSGIPSKGI ANCDFVYSYD PNVLEIIEIE PGDIIVDPNP DKSFDTAVYP DRKIIVFLFA  960
EDSGTGAYAI TKDGVFATIV AKVKSGAPNG LSVIKFVEVG GFANNDLVEQ KTQFFDGGVN 1020
VGDTTEPATP TTPVTTPTTT DGLDAVRIKV DTVNAKPGDT VRIPVRFSGI PSKGIANCDF 1080
VYSYDPNVLE IIEIEPGDII VDPNPDKSFD TAVYPDRKII VFLFAEDSGT GAYAITKDGV 1140
FATIVAKVKS GAPNGLSVIK FVEVGGFANN DLVEQRTQFF DGGVNVGDTT VPTTPTTPVT 1200
TPTDDSNAVR IKVDTVNAKP GDTVRIPVRF SGIPSKGIAN CDFVYSYDPN VLEIIEIEPG 1260
DIIVDPNPDK SFDTAVYPDR KIIVFLFAED SGTGAYAITK DGVFATIVAK VKSGAPNGLS 1320
VIKFVEVGGF ANNDLVEQKT QFFDGGVNVG DTTVPTTSPT TTPPEPTIAP NKLTLKIGRA 1380
EGRPGDTVEI PVNLYGVPQK GIASGDFVVS YDPNVLEIIE IEPGELIVDP NPTKSFDTAV 1440
YPDRKMIVFL FAEDSGTGAY AITEDGVFAT IVAKVKEGAP EGFSAIEISE FGAFADNDLV 1500
EVETDLINGG VLVTNKTVIE GYKVSGYILP DFSFDATVAP LVKAGFKVEI VGTELYAVTD 1560
ANGYFEITGV PANASGYTLK ISRATYLDRV IANVVVTGDT SVSTSQAPIM MWVGDIVKDN 1620
SINLLDVAEV IRCFNATKGS ANYVEELDIN RNGAINMQDI MIVHKHFGAT SSDY       1674

SEQ ID NO: 2          moltype = AA   length = 159
FEATURE               Location/Qualifiers
source                1..159
                      mol_type = protein
                      organism = Clostridium thermocellum
SEQUENCE: 2
PVSGNLKVEF YNSNPSDTTN SINPQFKVTN TGSSAIDLSK LTLRYYYTVD GQKDQTFWCD   60
HAAIIGSNGS YNGVTSNVKG TFVKMSSSTN NADTYLEISF TGGTLEPGAH VQIQGRFAKN  120
DWSNYTQSND YSFKSASQFV EWDQVTAYLN GVLVWGKEP                         159

SEQ ID NO: 3          moltype = AA   length = 62
FEATURE               Location/Qualifiers
source                1..62
                      mol_type = protein
                      organism = Sulfolobus solfataricus
SEQUENCE: 3
MATVKFTYQG EEKQVDISKI KKVWRVGQMI SFTYDEGGGA TGRGAVSEKD APKELLQMLE   60
KQ                                                                  62

SEQ ID NO: 4          moltype = AA   length = 62
FEATURE               Location/Qualifiers
REGION                1..62
                      note = Synthetic Polypeptide
source                1..62
```

```
                        mol_type = protein
                        organism = synthetic construct
SEQUENCE: 4
MATVKFTYQG EEKQVDISKI KIVARDGQYI DFKYDEGGGA YGYGWVSEKD APKELLQMLE      60
KQ                                                                    62

SEQ ID NO: 5            moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 5
MATVKFTYQG EEKQVDISKI KWVRRYGQYI GFSYDEGGGA WGKGYVSEKD APKELLQMLE      60
KQ                                                                    62

SEQ ID NO: 6            moltype = DNA  length = 28
FEATURE                 Location/Qualifiers
misc_feature            1..28
                        note = Synthetic Polynucleotide
source                  1..28
                        mol_type = other DNA
                        organism = synthetic construct
SEQUENCE: 6
aggcagtctc atatggcaac cgtgaaat                                         28

SEQ ID NO: 7            moltype = DNA  length = 33
FEATURE                 Location/Qualifiers
misc_feature            1..33
                        note = Synthetic Polynucleotide
source                  1..33
                        mol_type = other DNA
                        organism = synthetic construct
SEQUENCE: 7
acccctctcg agttattgct tttccagcat ctg                                   33

SEQ ID NO: 8            moltype = DNA  length = 42
FEATURE                 Location/Qualifiers
misc_feature            1..42
                        note = Synthetic Polynucleotide
source                  1..42
                        mol_type = other DNA
                        organism = synthetic construct
SEQUENCE: 8
acccctctcg agttattagg atccttgctt ttccagcatc tg                         42

SEQ ID NO: 9            moltype = DNA  length = 45
FEATURE                 Location/Qualifiers
misc_feature            1..45
                        note = Synthetic Polynucleotide
source                  1..45
                        mol_type = other DNA
                        organism = synthetic construct
SEQUENCE: 9
aagttacgct cgagttaggg ttctttaccc catacaagaa caccg                      45

SEQ ID NO: 10           moltype = AA  length = 124
FEATURE                 Location/Qualifiers
REGION                  1..124
                        note = Synthetic Polypeptide
source                  1..124
                        mol_type = protein
                        organism = synthetic construct
SEQUENCE: 10
AGPGANPPGT TTTSRPATTT GSSPGPQACS SVWGQCGGQN WSGPTCCASG STCVYSNDYY      60
SQCLPGANPP GTTTTSRPAT TTGSSPGPTQ SHYGQCGGIG YSGPTVCASG TTCQVLNPYY     120
SQCL                                                                 124

SEQ ID NO: 11           moltype = AA  length = 64
FEATURE                 Location/Qualifiers
source                  1..64
                        mol_type = protein
                        organism = Sulfolobus solfataricus
SEQUENCE: 11
MATVKFKYKG EEKQVDISKI KKVWRVGKMI SFTYDEGGGK TGRGAVSEKD APKELLQMLE      60
KQKK                                                                  64

SEQ ID NO: 12           moltype = AA  length = 64
```

| FEATURE | Location/Qualifiers |
|---|---|
| source | 1..64 |
| | mol_type = protein |
| | organism = Sulfolobus solfataricus |

SEQUENCE: 12
```
MATVKFKYKG EEKEVDISKI KKVWRVGKMI SFTYDEGGGK TGRGAVSEKD APKELLQMLE    60
KQKK                                                                64
```

```
SEQ ID NO: 13          moltype = AA   length = 66
FEATURE                Location/Qualifiers
source                 1..66
                       mol_type = protein
                       organism = Sulfolobus acidocaldarius
```

SEQUENCE: 13
```
MVKVKFKYKG EEKEVDTSKI KKVWRVGKMV SFTYDDNGKT GRGAVSEKDA PKELLDMLAR    60
AEREKK                                                              66
```

```
SEQ ID NO: 14          moltype = AA   length = 253
FEATURE                Location/Qualifiers
REGION                 1..253
                       note = Synthetic Polypeptide
source                 1..253
                       mol_type = protein
                       organism = synthetic construct
```

SEQUENCE: 14
```
MGSSHHHHHH SSGLVPRGSH MATVKFTYQG EEKQVDISKI KIVARDGQYI DFKYDEGGGA    60
YGYGWVSEKD APKELLQMLE KQGGGGSGGG GSGGGGSPVS GNLKVEFYNS NPSDTTNSIN   120
PQFKVTNTGS SAIDLSKLTL RYYYTVDGQK DQTFWCDHAA IIGSNGSYNG ITSNVKGTFV   180
KMSSSTNNAD TYLEISFTGG TLEPGAHVQI QGRFAKNDWS NYTQSNDYSF KSASQFVEWD   240
QVTAYLNGVL VWG                                                     253
```

```
SEQ ID NO: 15          moltype = AA   length = 1674
FEATURE                Location/Qualifiers
source                 1..1674
                       mol_type = protein
                       organism = Clostridium thermocellum
```

SEQUENCE: 15
```
MRKVISMLLV VAMLTTIFAA MIPQTVSAAT MTVEIGKVTA AVGSKVEIPI TLKGVPSKGM    60
ANCDFVLGYD PNVLEVTEVK PGSIIKDPDP SKSFDSAIYP DRKMIVFLFA EDSGRGTYAI   120
TQDGVFATIV ATVKSAAAAP ITLLEVGAFA DNDLVEISTT FVAGGVNLGS SVPTTQPNVP   180
SDGVVVEIGK VTGSVGTTVE IPVYFRGVPS KGIANCDFVF RYDPNVLEII GIDPGDIIVD   240
PNPTKSFDTA IYPDRKIIVF LFAEDSGTGA YAITKDGVFA KIRATVKSSA PGYITFDEVG   300
GFADNDLVEQ KVSFIDGGVN VGNATPTKGA TPTNTATPTK SATATPTRPS VPTNTPTNTP   360
ANTPVSGNLK VEFYNSNPSD TTNSINPQFK VTNTGSSAID LSKLTLRYYY TVDGQKDQTF   420
WCDHAAIIGS NGSYNGITSN VKGTFVKMSS STNNADTYLE ISFTGGTLEP GAHVQIQGRF   480
AKNDWSNYTQ SNDYSFKSAS QFVEWDQVTA YLNGVLVWGK EPGGSVVPST QPVTTPPATT   540
KPPATTIPPS DDPNAIKIKV DTVNAKPGDT VNIPVRFSGI PSKGIANCDF VYSYDPNVLE   600
IIEIKPGELI VDPNPDKSFD TAVYPDRKII VFLFAEDSGT GAYAITKDGV FATIVAKVKS   660
GAPNGLSVIK FVEVGGFANN DLVEQKTQFS DGGVNVGGTT VPTTPPASTT PTDDPNAIKI   720
KVDTVNAKPG DTVNIPVRFS GIPSKGIANC DFVYSYDPNV LEIIEIKPGE LIVDPNPDKS   780
FDTAVYPDRK IIVFLLTEDS GTGAYAITKD GVFATIVAKV KSGAPNGLSV IKFVEVGGFA   840
NNDLVEQKTQ FFDGGVNVGD TTVPTTPTTP VTTPTDDPNA VRIKVDTVNA KTGDTVRIPV   900
RFSGIPSKGI ANCDFVYSYD PNVLEIIEIE PGDIIVDPNP DKSFDTAVYP DRKIIVFLFA   960
EDSGTGAYAI TKDGVFATIV AKVKSGAPNG LSVIKFVEVG GFANNDLVEQ KTQFFDGGVN  1020
VGDTTEPATP TTPVTTPTTT DGLDAVRIKV DTVNAKPGDT VRIPVRFSGI PSKGIANCDF  1080
VYSYDPNVLE IIEIEPGDII VDPNPDKSFD TAVYPDRKII VFLFAEDSGT GAYAITKDGV  1140
FATIVAKVKS GAPNGLSVIK FVEVGGFANN DLVEQRTQFF DGGVNVGDTT VPTTPTTPVT  1200
TPTDDSNAVR IKVDTVNAKP GDTVRIPVRF SGIPSKGIAN CDFVYSYDPN VLEIIEIEPG  1260
DIIVDPNPDK SFDTAVYPDR KIIVFLFAED SGTGAYAITK DGVFATIVAK VKSGAPNGLS  1320
VIKFVEVGGF ANNDLVEQKT QFFDGGVNVG DTTVPTTSPT TTPPEPTIAP NKLTLKIGRA  1380
EGRPGDTVEI PVNLYGVPQK GIASGDFVVS YDPNVLEIIIE IEPGELIVDP NPTKSFDTAV  1440
YPDRKMIVFL FAEDSGTGAY AITEDGVFAT IVAKVKEGAP EGFSAIEISE FGAFADNDLV  1500
EVETDLINGG VLVTNKTVIE GYKVSGYILP DFSFDATVDF LVKAGFKVEI VGTELYAVTD  1560
ANGYFEITGV PANASGYTLK ISRATYLDRV IANVVTGDT SVSTSQAPIM MWVGDIVKDN  1620
SINLLDVAEV IRCFNATKGS ANYVEELDIN RNGAINMQDI MIVHKHFGAT SSDY        1674
```

```
SEQ ID NO: 16          moltype = AA   length = 159
FEATURE                Location/Qualifiers
source                 1..159
                       mol_type = protein
                       organism = Clostridium thermocellum
```

SEQUENCE: 16
```
PVSGNLKVEF YNSNPSDTTN SINPQFKVTN TGSSAIDLSK LTLRYYYTVD GQKDQTFWCD    60
HAAIIGSNGS YNGITSNVKG TFVKMSSSTN NADTYLEISF TGGTLEPGAH VQIQGRFAKN   120
DWSNYTQSND YSFKSASQFV EWDQVTAYLN GVLVWGKEP                         159
```

```
SEQ ID NO: 17          moltype = AA   length = 57
FEATURE                Location/Qualifiers
REGION                 1..57
```

```
                       note = Synthetic Polypeptide
source                 1..57
                       mol_type = protein
                       organism = synthetic construct
SEQUENCE: 17
MATVKFTYQG EEKQVDISKI KYVYRWGHYI YFWYDEGGGA SGWGWVSEKD APKELLQ         57

SEQ ID NO: 18          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 18
MATVKFTYQG EEKQVDISKI KHVRRWGQWI YFIYDEGGGA RGNGYVSEKD APKELLQ         57

SEQ ID NO: 19          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 19
MATVKFTYQG EEKQVDISKI KRVRRYGQWI AFHYDEGGGA AGWGYVSEKD APKELLQ         57

SEQ ID NO: 20          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 20
MATVKFTYQG EEKQVDISKI KWVWRGGQGI IFWYDEGGGA RGYGRVSEKD APKELLQ         57

SEQ ID NO: 21          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 21
MATVKFTYQG EEKQVDISKI KRVIRIGQYI YFWYDEGGGA RGWGYVSEKD APKELLQ         57

SEQ ID NO: 22          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 22
MATVKFTYQG EEKQVDISKI KWVHRWGQRI RFWYDEGGGA AGNGKVSEKD APKELLQ         57

SEQ ID NO: 23          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 23
MATVKFTYQG EEKQVDISKI KWVIRWGQWI WFKYDEGGGA SGWGYVSEKD APKELLQ         57

SEQ ID NO: 24          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 24
MATVKFTYQG EEKQVDISKI KRVRRWGQWI YFRYDEGGGA YGSGYVSEKD APKELLQ         57

SEQ ID NO: 25          moltype = AA  length = 57
FEATURE                Location/Qualifiers
```

```
REGION                  1..57
                        note = Synthetic Polypeptide
source                  1..57
                        mol_type = protein
                        organism = synthetic construct
SEQUENCE: 25
MATVKFTYQG EEKQVDISKI KYVYRWGQWI YFWYDEGGGA WGRGYVSEKD APKELLQ     57

SEQ ID NO: 26           moltype = AA  length = 57
FEATURE                 Location/Qualifiers
REGION                  1..57
                        note = Synthetic Polypeptide
source                  1..57
                        mol_type = protein
                        organism = synthetic construct
SEQUENCE: 26
MATVKFTYQG EEKQVDISKI KYVRRYGQYI GFIYDEGGGA WGKGYVSEKD APKELLQ     57

SEQ ID NO: 27           moltype = AA  length = 57
FEATURE                 Location/Qualifiers
REGION                  1..57
                        note = Synthetic Polypeptide
source                  1..57
                        mol_type = protein
                        organism = synthetic construct
SEQUENCE: 27
MATVKFTYQG EEKQVDISKI KHVRRYGQWI RFRYDEGGGA SGWGIVSEKD APKELLQ     57

SEQ ID NO: 28           moltype = AA  length = 57
FEATURE                 Location/Qualifiers
REGION                  1..57
                        note = Synthetic Polypeptide
source                  1..57
                        mol_type = protein
                        organism = synthetic construct
SEQUENCE: 28
MATVKFTYQG EEKQVDISKI KSVKRSGQGI KFIYDEGGGA YGHGRVSEKD APKELLQ     57

SEQ ID NO: 29           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 29
IADYDKYYW                                                          9

SEQ ID NO: 30           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 30
WRYYGSWKY                                                          9

SEQ ID NO: 31           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 31
MATVKFTYQG EEKQVDISKI KNVHRHGQKI YFIYDEGGGA KGHGKVSEKD APKELLQMLE  60
KQ                                                                 62

SEQ ID NO: 32           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 32
MATVKFTYQG EEKQVDISKI KHVKRHGQWI KFAYDEGGGA KGKGKVSEKD APKELLQMLE  60
KQ                                                                 62
```

```
SEQ ID NO: 33           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 33
MATVKFTYQG EEKQVDISKI KKVHRKGQII RFRYDEGGGA WGHGYVSEKD APKELLQMLE   60
KQ                                                                 62

SEQ ID NO: 34           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 34
MATVKFTYQG EEKQVDISKI KHVKRHGQKI YFRYDEGGGA GGRGRVSEKD APKELLQMLE   60
KQ                                                                 62

SEQ ID NO: 35           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 35
MATVKFTYQG EEKQVDISKI KRVYRHGQWI HFRYDEGGGA RGHGHVSEKD APKELLQMLE   60
KQ                                                                 62

SEQ ID NO: 36           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 36
MATVKFTYQG EEKQVDISKI KRVSRKGQRI YFRYDEGGGA HGKGKVSEKD APKELLQMLE   60
KQ                                                                 62

SEQ ID NO: 37           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 37
NHHKYIKHK                                                          9

SEQ ID NO: 38           moltype = AA  length = 8
FEATURE                 Location/Qualifiers
REGION                  1..8
                        note = Synthetic Polypeptide
source                  1..8
                        mol_type = protein
                        organism = synthetic construct
SEQUENCE: 38
HKHWKAKK                                                           8

SEQ ID NO: 39           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 39
KHKIRRWHY                                                          9

SEQ ID NO: 40           moltype = AA  length = 9
FEATURE                 Location/Qualifiers
REGION                  1..9
                        note = Synthetic Polypeptide
```

```
source                          1..9
                                mol_type = protein
                                organism = synthetic construct
SEQUENCE: 40
HKHKYRGRR                                                                    9

SEQ ID NO: 41                   moltype = AA   length = 9
FEATURE                         Location/Qualifiers
REGION                          1..9
                                note = Synthetic Polypeptide
source                          1..9
                                mol_type = protein
                                organism = synthetic construct
SEQUENCE: 41
RYHWHRRHH                                                                    9

SEQ ID NO: 42                   moltype = AA   length = 9
FEATURE                         Location/Qualifiers
REGION                          1..9
                                note = Synthetic Polypeptide
source                          1..9
                                mol_type = protein
                                organism = synthetic construct
SEQUENCE: 42
RSKRYRHKK                                                                    9

SEQ ID NO: 43                   moltype = AA   length = 62
FEATURE                         Location/Qualifiers
REGION                          1..62
                                note = Synthetic Polypeptide
source                          1..62
                                mol_type = protein
                                organism = synthetic construct
SEQUENCE: 43
MATVKFTYQG EEKQVDISKI KIVGRHGQWI YFWYDEGGGA NGNGWVSEKD APKELLQMLE           60
KQ                                                                          62

SEQ ID NO: 44                   moltype = AA   length = 62
FEATURE                         Location/Qualifiers
REGION                          1..62
                                note = Synthetic Polypeptide
source                          1..62
                                mol_type = protein
                                organism = synthetic construct
SEQUENCE: 44
MATVKFTYQG EEKQVDISKI KIVGRHGQWI YFWYDEGGGA DGNGWVSEKD APKELLQMLE           60
KQ                                                                          62

SEQ ID NO: 45                   moltype = AA   length = 62
FEATURE                         Location/Qualifiers
REGION                          1..62
                                note = Synthetic Polypeptide
source                          1..62
                                mol_type = protein
                                organism = synthetic construct
SEQUENCE: 45
MATVKFTYQG EEKQVDISKI KIVGRHGQWI YFWYDEGGGA YGNGWVSEKD APKELLQMLE           60
KQ                                                                          62

SEQ ID NO: 46                   moltype = AA   length = 62
FEATURE                         Location/Qualifiers
REGION                          1..62
                                note = Synthetic Polypeptide
source                          1..62
                                mol_type = protein
                                organism = synthetic construct
SEQUENCE: 46
MATVKFTYQG EEKQVDISKI KIVGRSGQWI YFWYDEGGGA WGNGWVSEKD APKELLQMLE           60
KQ                                                                          62

SEQ ID NO: 47                   moltype = AA   length = 62
FEATURE                         Location/Qualifiers
REGION                          1..62
                                note = Synthetic Polypeptide
source                          1..62
                                mol_type = protein
                                organism = synthetic construct
SEQUENCE: 47
MATVKFTYQG EEKQVDISKI KIVGRWGQWI YFWYDEGGGA SGNGWVSEKD APKELLQMLE           60
```

```
SEQ ID NO: 48          moltype = AA  length = 62
FEATURE                Location/Qualifiers
REGION                 1..62
                       note = Synthetic Polypeptide
source                 1..62
                       mol_type = protein
                       organism = synthetic construct
SEQUENCE: 48
MATVKFTYQG EEKQVDISKI KWVRRDGQII YFNYDEGGGA WGWGDVSEKD APKELLQMLE    60
KQ                                                                   62

SEQ ID NO: 49          moltype = AA  length = 62
FEATURE                Location/Qualifiers
REGION                 1..62
                       note = Synthetic Polypeptide
source                 1..62
                       mol_type = protein
                       organism = synthetic construct
SEQUENCE: 49
MATVKFTYQG EEKQVDISKI KWVRRWGQWI YFNYDEGGGA WGWGDVSEKD APKELLQMLE    60
KQ                                                                   62

SEQ ID NO: 50          moltype = AA  length = 9
FEATURE                Location/Qualifiers
REGION                 1..9
                       note = Synthetic Polypeptide
source                 1..9
                       mol_type = protein
                       organism = synthetic construct
SEQUENCE: 50
IGHWYWNNW                                                             9

SEQ ID NO: 51          moltype = AA  length = 9
FEATURE                Location/Qualifiers
REGION                 1..9
                       note = Synthetic Polypeptide
source                 1..9
                       mol_type = protein
                       organism = synthetic construct
SEQUENCE: 51
IGHWYWDNW                                                             9

SEQ ID NO: 52          moltype = AA  length = 9
FEATURE                Location/Qualifiers
REGION                 1..9
                       note = Synthetic Polypeptide
source                 1..9
                       mol_type = protein
                       organism = synthetic construct
SEQUENCE: 52
IGHWYWYNW                                                             9

SEQ ID NO: 53          moltype = AA  length = 9
FEATURE                Location/Qualifiers
REGION                 1..9
                       note = Synthetic Polypeptide
source                 1..9
                       mol_type = protein
                       organism = synthetic construct
SEQUENCE: 53
IGSWYWWNW                                                             9

SEQ ID NO: 54          moltype = AA  length = 9
FEATURE                Location/Qualifiers
REGION                 1..9
                       note = Synthetic Polypeptide
source                 1..9
                       mol_type = protein
                       organism = synthetic construct
SEQUENCE: 54
IGWWYWSNW                                                             9

SEQ ID NO: 55          moltype = AA  length = 9
FEATURE                Location/Qualifiers
REGION                 1..9
                       note = Synthetic Polypeptide
source                 1..9
```

```
                        mol_type = protein
                        organism = synthetic construct
SEQUENCE: 55
WRDIYNWWD                                                               9

SEQ ID NO: 56           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 56
WRWWYNWWD                                                               9

SEQ ID NO: 57           moltype = AA   length = 258
FEATURE                 Location/Qualifiers
REGION                  1..258
                        note = Synthetic Polypeptide
source                  1..258
                        mol_type = protein
                        organism = synthetic construct
SEQUENCE: 57
MGSSHHHHHH SSGLVPRGSH MATVKFTYQG EEKQVDISKI KNVHRHGQKI YFIYDEGGGA        60
KGHGKVSEKD APKELLQMLE KQGSGGGGSG GGGSGGGGSP VSGNLKVEFY NSNPSDTTNS       120
INPQFKVTNT GSSAIDLSKL TLRYYYTVDG QKDQTFWCDH AAIIGSNGSY NGITSNVKGT       180
FVKMSSSTNN ADTYLEISFT GGTLEPGAHV QIQGRFAKND WSNYTQSNDY SFKSASQFVE       240
WDQVTAYLNG VLVWGKEP                                                    258

SEQ ID NO: 58           moltype = AA   length = 494
FEATURE                 Location/Qualifiers
REGION                  1..494
                        note = Synthetic Polypeptide
source                  1..494
                        mol_type = protein
                        organism = synthetic construct
SEQUENCE: 58
MGSSHHHHHH SSGLVPRGSH MMAGGLNDIF EAQKIEWHEL KGGGGSGGGG SEFKIEEGKL        60
VIWINGDKGY NGLAEVGKKF EKDTGIKVTV EHPDKLEEKF PQVAATGDGP DIIFWAHDRF       120
GGYAQSGLLA EITPDKAFQD KLYPFTWDAV RYNGKLIAYP IAVEALSLIY NKDLLPNPPK       180
TWEEIPALDK ELKAKGKSAL MFNLQEPYFT WPLIAADGGY AFKYENGKYD IKDVGVDNSG       240
AKAGLTFLVD LIKNKHMNAD TDYSIAEAAF NKGETAMTIN GPWAWSNIDT SKVNYGVTVL       300
PTFKGQPSKP FVGVLSAGIN AASPNKELAK EFLENYLLTD EGLEAVNKDK PLGAVALKSY       360
EEELAKDPRI AATMENAQKG EIMPNIPQMS AFWYAVRTAV INAASGRQTV DEALKDAQTG       420
SGGGGSGGGG STSATVKFTY QGEEKQVDIS KIKSVWRRGQ RIWFRYDEGG GAWGAGKVSE       480
KDAPKELLQM LEKQ                                                        494

SEQ ID NO: 59           moltype = AA   length = 461
FEATURE                 Location/Qualifiers
REGION                  1..461
                        note = Synthetic Polypeptide
source                  1..461
                        mol_type = protein
                        organism = synthetic construct
SEQUENCE: 59
MGSSHHHHHH SSGLVPRGSH MKIEEGKLVI WINGDKGYNG LAEVGKKFEK DTGIKVTVEH        60
PDKLEEKFPQ VAATGDGPDI IFWAHDRFGG YAQSGLLAEI TPDKAFQDKL YPFTWDAVRY       120
NGKLIAYPIA VEALSLIYNK DLLPNPPKTW EEIPALDKEL KAKGKSALMF NLQEPYFTWP       180
LIAADGGYAF KYENGKYDIK DVGVDNSGAK AGLTFLVDLI KNKHMNADTD YSIAEAAFNK       240
GETAMTINGP WAWSNIDTSK VNYGVTVLPT FKGQPSKPFV GVLSAGINAA SPNKELAKEF       300
LENYLLTDEG LEAVNKDKPL GAVALKSYEE ELAKDPRIAA TMENAQKGEI MPNIPQMSAF       360
WYAVRTAVIN AASGRQTVDE ALKDAQTGSG GGGSGGGGSM ATVKFTYQGE EKQVDISKIK       420
SVWRRGQRIW FRYDEGGGAW GAGKVSEKDA PKELLQMLEK Q                          461

SEQ ID NO: 60           moltype = AA   length = 106
FEATURE                 Location/Qualifiers
REGION                  1..106
                        note = Synthetic Polypeptide
source                  1..106
                        mol_type = protein
                        organism = synthetic construct
SEQUENCE: 60
MGSSHHHHHH SSGLVPRGSH MTSMAGGLND IFEAQKIEWH EHMATVKFTY QGEEKQVDIS        60
KIKSVWRRGQ RIWFRYDEGG GAWGAGKVSE KDAPKELLQM LEKQGG                     106

SEQ ID NO: 61           moltype = AA   length = 82
FEATURE                 Location/Qualifiers
REGION                  1..82
                        note = Synthetic Polypeptide
```

```
source                          1..82
                                mol_type = protein
                                organism = synthetic construct
SEQUENCE: 61
MGSSHHHHHH SSGLVPRGSH MATVKFTYQG EEKQVDISKI KSVWRRGQRI WFRYDEGGGA    60
WGAGKVSEKD APKELLQMLE KQ                                             82

SEQ ID NO: 62                   moltype = AA   length = 106
FEATURE                         Location/Qualifiers
REGION                          1..106
                                note = Synthetic Polypeptide
source                          1..106
                                mol_type = protein
                                organism = synthetic construct
SEQUENCE: 62
MGSSHHHHHH SSGLVPRGSH MTSMAGGLND IFEAQKIEWH EHMATVKFTY QGEEKQVDIS    60
KIKSVWRRGQ RIWFRYDEGG GAWGAGKVSE KDAPKELLQM LEKQGG                  106

SEQ ID NO: 63                   moltype = AA   length = 178
FEATURE                         Location/Qualifiers
REGION                          1..178
                                note = Synthetic Polypeptide
source                          1..178
                                mol_type = protein
                                organism = synthetic construct
SEQUENCE: 63
MGSSHHHHHH SSGLVPRGSH MTSMAGGLND IFEAQKIEWH EHMATVKFTY QGEEKQVDIS    60
KIKSVWRRGQ RIWFRYDEGG GAWGAGKVSE KDAPKELLQM LEKQGGGGSG GGGSMATVKF   120
TYQGEEKQVD ISKIKSVWRR GQRIWFRYDE GGGAWGAGKV SEKDAPKELL QMLEKQGG     178

SEQ ID NO: 64                   moltype = AA   length = 250
FEATURE                         Location/Qualifiers
REGION                          1..250
                                note = Synthetic Polypeptide
source                          1..250
                                mol_type = protein
                                organism = synthetic construct
SEQUENCE: 64
MGSSHHHHHH SSGLVPRGSH MTSMAGGLND IFEAQKIEWH EHMATVKFTY QGEEKQVDIS    60
KIKSVWRRGQ RIWFRYDEGG GAWGAGKVSE KDAPKELLQM LEKQGGGGSG GGGSMATVKF   120
TYQGEEKQVD ISKIKSVWRR GQRIWFRYDE GGGAWGAGKV SEKDAPKELL QMLEKQGGGG   180
SGGGGSMATV KFTYQGEEKQ VDISKIKSVW RRGQRIWFRY DEGGGAWGAG KVSEKDAPKE   240
LLQMLEKQGG                                                         250

SEQ ID NO: 65                   moltype = AA   length = 371
FEATURE                         Location/Qualifiers
REGION                          1..371
                                note = Synthetic Polypeptide
source                          1..371
                                mol_type = protein
                                organism = synthetic construct
SEQUENCE: 65
MGSSHHHHHH SSGLVPRGSH MVIIELMRRV VGLAQGATAE VAVYGDRDRD LAERWCANTG    60
NTLVRADVDQ TGVGTLVVRR GHPPDPASVL GPDRLPGVRL WLYTNFHCNL CCDYCCVSSS   120
PSTPHRELGA ERIGRIVGEA ARWGVRELFL TGGEPFLLPD IDTIIATCVK QLPTTVLTNG   180
MVFKGRGRRA LESLPRGLAL QISLDSATPE LHDAHRGAGT WVKAVAGIRL ALSLGFRVRV   240
AATVASPAPG ELTAPHDFLD GLGIAPGDQL VRPIALEGAA SQGVALTRES LVPEVTVTAD   300
GVYWHPVAAT DERALVTRTV EPLTPALDMV SRLFAEQWTR AAEEEAALFPC AGSMAGGLND   360
IFEAQKIEWH E                                                       371

SEQ ID NO: 66                   moltype = AA   length = 62
FEATURE                         Location/Qualifiers
REGION                          1..62
                                note = Synthetic Polypeptide
source                          1..62
                                mol_type = protein
                                organism = synthetic construct
SEQUENCE: 66
MATVKFTYQG EEKQVDISKI KHVRRWGQYI IFAYDEGGGA YGGGWVSEKD APKELLQMLE    60
KQ                                                                   62

SEQ ID NO: 67                   moltype = AA   length = 62
FEATURE                         Location/Qualifiers
REGION                          1..62
                                note = Synthetic Polypeptide
source                          1..62
                                mol_type = protein
                                organism = synthetic construct
SEQUENCE: 67
```

```
MATVKFTYQG EEKQVDISKI KHVIRNGQYI IFAYDEGGGA YGGGWVSEKD APKELLQMLE    60
KQ                                                                  62

SEQ ID NO: 68           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 68
MATVKFTYQG EEKQVDISKI KHVIRNGQYI IFAYDEGGGA YGGGWVSEKD APKELLQMLE    60
KQ                                                                  62

SEQ ID NO: 69           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 69
MATVKFTYQG EEKQVDISKI KNVYRWGQYI IFSYDEGGGA YGWGWVSEKD APKELLQMLE    60
KQ                                                                  62

SEQ ID NO: 70           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 70
MATVKFTYQG EEKQVDISKI KYVRRYGQYI GFIYDEGGGA WGKGYVSEKD APKELLQMLE    60
KQ                                                                  62

SEQ ID NO: 71           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 71
MATVKFTYQG EEKQVDISKI KDVWRWGQWI DFIYDEGGGA DGWGRVSEKD APKELLQMLE    60
KQ                                                                  62

SEQ ID NO: 72           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 72
HRWYIAYGW                                                            9

SEQ ID NO: 73           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 73
RAYYIAYAW                                                            9

SEQ ID NO: 74           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 74
HINYIAYGW                                                            9

SEQ ID NO: 75           moltype = AA   length = 9
FEATURE                 Location/Qualifiers
```

```
REGION                  1..9
                        note = Synthetic Polypeptide
source                  1..9
                        mol_type = protein
                        organism = synthetic construct
SEQUENCE: 75
NYWYISYWW                                                                     9

SEQ ID NO: 76           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 76
YRYYGIWKY                                                                     9

SEQ ID NO: 77           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 77
DWWWDIDWR                                                                     9

SEQ ID NO: 78           moltype = AA  length = 294
FEATURE                 Location/Qualifiers
REGION                  1..294
                        note = Synthetic Polypeptide
source                  1..294
                        mol_type = protein
                        organism = synthetic construct
SEQUENCE: 78
MGSSHHHHHH SSGLVPRGSH MSGETTRLTE PQLRELAARG AAELDGATAT DMLRWTDETF    60
GDIGGAGGGV SGHRGWTTCN YVVASNMADA VLVDLAAKVR PGVPVIFLDT GYHFVETIGT   120
RDAIESVYDV RVLNVTPEHT VAEQDELLGK DLFARNPHEC CRLRKVVPLG KTLRGYSAWV   180
TGLRRVDAPT RANAPLVSFD ETFKLVKVNP LAAWTDQDVQ EYIADNDVLV NPLVREGYPS   240
IGCAPCTAKP AEGADPRSGR WQGLAKTECG LHASGSMAGG LNDIFEAQKI EWHE         294

SEQ ID NO: 79           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 79
MATVKFTYQG EEKQVDISKI KRVIRYGQAI AFAYDEGGGA RGYGWVSEKD APKELLQMLE    60
KQ                                                                           62

SEQ ID NO: 80           moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 80
MATVKFTYQG EEKQVDISKI KYVGRWGQNI GFAYDEGGGA YGYGGVSEKD APKELLQMLE    60
KQ                                                                           62

SEQ ID NO: 81           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 81
RIYAAARYW                                                                     9

SEQ ID NO: 82           moltype = AA  length = 9
FEATURE                 Location/Qualifiers
REGION                  1..9
                        note = Synthetic Polypeptide
source                  1..9
```

```
                        mol_type = protein
                        organism = synthetic construct
SEQUENCE: 82
YGWNGAYYG                                                                     9

SEQ ID NO: 83           moltype = AA   length = 328
FEATURE                 Location/Qualifiers
REGION                  1..328
                        note = Synthetic Polypeptide
source                  1..328
                        mol_type = protein
                        organism = synthetic construct
SEQUENCE: 83
MGSSHHHHHH SSGLVPRGSH MVIRHFLRDD DLSPAEQAEV LELAAELKKD PVSRRPLQGP            60
RGVAVIFDKN STRTRFSFEL GIAQLGGHAV VVDSGSTQLG RDETLQDTAK VLSRYVDAIV           120
WRTFGQERLD AMASVATVPV INALSDEFHP CQVLADLQTI AERKGALRGL RLSYFGDGAN           180
NMAHSLLLGG VTAGIHVTVA APEGFLPDPS VRAAAERRAQ DTGASVTVTA DAHAAAAGAD           240
VLVTDTWTSM GQENDGLDRV KPFRPFQLNS RLLALADSDA IVLHCLPAHR GDEITDAVMD           300
GPASAVWDEA ENRLHAQKAL LVWLLERS                                              328

SEQ ID NO: 84           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 84
MATVKFTYQG EEKQVDISKI KSVWRRGQRI WFRYDEGGGA WGAGKVSEKD APKELLQMLE            60
KQ                                                                           62

SEQ ID NO: 85           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 85
MATVKFTYQG EEKQVDISKI KWVRRYGQYI GFSYDEGGGA WGKGYVSEKD APKELLQMLE            60
KQ                                                                           62

SEQ ID NO: 86           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 86
MATVKFTYQG EEKQVDISKI KHVWRRGQNI YFRYDEGGGA WGAGAVSEKD APKELLQMLE            60
KQ                                                                           62

SEQ ID NO: 87           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 87
MATVKFTYQG EEKQVDISKI KSVKRNGQSI DFDYDEGGGA AGEGKVSEKD APKELLQMLE            60
KQ                                                                           62

SEQ ID NO: 88           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 88
MATVKFTYQG EEKQVDISKI KGVYRHGQSI WFRYDEGGGA WGWGIVSEKD APKELLQMLE            60
KQ                                                                           62

SEQ ID NO: 89           moltype = AA   length = 62
FEATURE                 Location/Qualifiers
REGION                  1..62
                        note = Synthetic Polypeptide
```

```
                        source          1..62
                                        mol_type = protein
                                        organism = synthetic construct
SEQUENCE: 89
MATVKFTYQG EEKQVDISKI KSVHRYGQKI YFDYDEGGGA IGKGHVSEKD APKELLQMLE    60
KQ                                                                  62

SEQ ID NO: 90           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 90
MATVKFTYQG EEKQVDISKI KYVWRHGQHI AFRYDEGGGA HGWGSVSEKD APKELLQMLE    60
KQ                                                                  62

SEQ ID NO: 91           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 91
MATVKFTYQG EEKQVDISKI KDVWRHGQHI IFSYDEGGGA YGAGHVSEKD APKELLQMLE    60
KQ                                                                  62

SEQ ID NO: 92           moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 92
MATVKFTYQG EEKQVDISKI KYVKRIGQYI SFNYDEGGGA HGHGIVSEKD APKELLQMLE    60
KQ                                                                  62

SEQ ID NO: 93           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 93
SWRRWRWAK                                                            9

SEQ ID NO: 94           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 94
SWRRWRWAR                                                            9

SEQ ID NO: 95           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 95
WRYYGSWKY                                                            9

SEQ ID NO: 96           moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 96
HWRNYRWAA                                                            9
```

```
SEQ ID NO: 97              moltype = AA   length = 9
FEATURE                    Location/Qualifiers
REGION                     1..9
                           note = Synthetic Polypeptide
source                     1..9
                           mol_type = protein
                           organism = synthetic construct
SEQUENCE: 97
SKNSDDAEK                                                                    9

SEQ ID NO: 98              moltype = AA   length = 9
FEATURE                    Location/Qualifiers
REGION                     1..9
                           note = Synthetic Polypeptide
source                     1..9
                           mol_type = protein
                           organism = synthetic construct
SEQUENCE: 98
GYHSWRWWI                                                                    9

SEQ ID NO: 99              moltype = AA   length = 9
FEATURE                    Location/Qualifiers
REGION                     1..9
                           note = Synthetic Polypeptide
source                     1..9
                           mol_type = protein
                           organism = synthetic construct
SEQUENCE: 99
SHYKYDIKH                                                                    9

SEQ ID NO: 100             moltype = AA   length = 9
FEATURE                    Location/Qualifiers
REGION                     1..9
                           note = Synthetic Polypeptide
source                     1..9
                           mol_type = protein
                           organism = synthetic construct
SEQUENCE: 100
YWHHARHWS                                                                    9

SEQ ID NO: 101             moltype = AA   length = 9
FEATURE                    Location/Qualifiers
REGION                     1..9
                           note = Synthetic Polypeptide
source                     1..9
                           mol_type = protein
                           organism = synthetic construct
SEQUENCE: 101
DWHHISYAH                                                                    9

SEQ ID NO: 102             moltype = AA   length = 9
FEATURE                    Location/Qualifiers
REGION                     1..9
                           note = Synthetic Polypeptide
source                     1..9
                           mol_type = protein
                           organism = synthetic construct
SEQUENCE: 102
YKIYSNHHI                                                                    9

SEQ ID NO: 103             moltype = AA   length = 355
FEATURE                    Location/Qualifiers
REGION                     1..355
                           note = Synthetic Polypeptide
source                     1..355
                           mol_type = protein
                           organism = synthetic construct
SEQUENCE: 103
MGSSHHHHHH SSGLVPRGSH MVARTDDDNW DLTSSVGVTA TIVAVGRALA TKDPRGLIND            60
PPAEPLVRAV GLDLFTKMMD GELDMSTIAD VSPAVAQAMV YGNAVRTKYF DDYLLNATAG           120
GIRQVAILAS GLDSRAYRLP WPTRTVVYEI DQPKVMEFKT TTLADLGAEP SAIRRAVPID           180
LRADWPTALQ AAGFDSAAPT AWLAEGLLIY LKPQTQDRLF DNITALSAPG SMVATEFVTG           240
IADFSAERAR TISNPFRCHG VDVDLASLVY TGPRNHVLDY LAAKGWQPEG VSLAELFRRS           300
GLDVRAADDD TIFISGCLTD HSSISPPTAA GWREFGSMAG GLNDIFEAQK IEWHE                355

SEQ ID NO: 104             moltype = AA   length = 62
FEATURE                    Location/Qualifiers
REGION                     1..62
```

```
                        note = Synthetic Polypeptide
source                  1..62
                        mol_type = protein
                        organism = synthetic construct
SEQUENCE: 104
MATVKFTYQG EEKQVDISKI KWVYRYGQYI IFGYDEGGGA KGNGYVSEKD APKELLQMLE    60
KQ                                                                  62

SEQ ID NO: 105          moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 105
MATVKFTYQG EEKQVDISKI KWVYRWGQYI IFAYDEGGGA AGKGSVSEKD APKELLQMLE    60
KQ                                                                  62

SEQ ID NO: 106          moltype = AA  length = 62
FEATURE                 Location/Qualifiers
REGION                  1..62
                        note = Synthetic Polypeptide
source                  1..62
                        mol_type = protein
                        organism = synthetic construct
SEQUENCE: 106
MATVKFTYQG EEKQVDISKI KRVIRAGQSI IFSYDEGGGA IGHGWVSEKD APKELLQMLE    60
KQ                                                                  62

SEQ ID NO: 107          moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 107
WYYYIGKNY                                                            9

SEQ ID NO: 108          moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 108
WYWYIAAKS                                                            9

SEQ ID NO: 109          moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 109
RIASISIHW                                                            9

SEQ ID NO: 110          moltype = AA  length = 254
FEATURE                 Location/Qualifiers
REGION                  1..254
                        note = Synthetic Polypeptide
source                  1..254
                        mol_type = protein
                        organism = synthetic construct
SEQUENCE: 110
MGSSHHHHHH SSGLVPRGSH MTLNLSVDEV LTTTRSVRKR LDFDKPVPRD VLMECLELAL    60
QAPTGSNSQG WQWVFVEDAA KKKAIADVYL ANARGYLSGP APEYPDGDTR GERMGRVRDS   120
ATYLAEHMHR APVLLIPCLK GREDESAVGG VSFWASLFPA VWSFCLALRS RGLGSCWTTL   180
HLLDNGEHKV ADVLGIPYDE YSQGGLLPIA YTQGIDFRPA KRLPAESVTH WNGWGSMAGG   240
LNDIFEAQKI EWHE                                                    254

SEQ ID NO: 111          moltype = AA  length = 62
FEATURE                 Location/Qualifiers
REGION                  1..62
                        note = Synthetic Polypeptide
source                  1..62
```

```
                    mol_type = protein
                    organism = synthetic construct
SEQUENCE: 111
MATVKFTYQG EEKQVDISKI KYVYRWGQRI WFRYDEGGGA IGRGRVSEKD APKELLQMLE    60
KQ                                                                  62

SEQ ID NO: 112          moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 112
YYWRWRIRR                                                            9

SEQ ID NO: 113          moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 113
YYWRWRSYR                                                            9

SEQ ID NO: 114          moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 114
MATVKFTYQG EEKQVDISKI KWVIRYGQKI AFGYDEGGGA KGAGAVSEKD APKELLQMLE    60
KQ                                                                  62

SEQ ID NO: 115          moltype = AA   length = 62
FEATURE                 Location/Qualifiers
REGION                  1..62
                        note = Synthetic Polypeptide
source                  1..62
                        mol_type = protein
                        organism = synthetic construct
SEQUENCE: 115
MATVKFTYQG EEKQVDISKI KKVWRYGQWI YFIYDEGGGA KGRGWVSEKD APKELLQMLE    60
KQ                                                                  62

SEQ ID NO: 116          moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 116
WIYKAGKAA                                                            9

SEQ ID NO: 117          moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 117
KWYWYIKRW                                                            9

SEQ ID NO: 118          moltype = AA   length = 208
FEATURE                 Location/Qualifiers
REGION                  1..208
                        note = Synthetic Polypeptide
source                  1..208
                        mol_type = protein
                        organism = synthetic construct
SEQUENCE: 118
MGSSHHHHHH SSGLVPRGSH MATVKFTYQG EEKQVDISKI KIVARDGQYI DFKYDEGGGA    60
YGYGWVSEKD APKELLQMLE KQGSAGPGAN PPGTTTTSRP ATTTGSSPGP QACSSVWGQC   120
GGQNWSGPTC CASGSTCVYS NDYYSQCLPG ANPPGTTTTS RPATTTGSSP GPTQSHYGQC   180
```

```
GGIGYSGPTV CASGTTCQVL NPYYSQCL                                            208

SEQ ID NO: 119          moltype = AA  length = 258
FEATURE                 Location/Qualifiers
REGION                  1..258
                        note = Synthetic Polypeptide
source                  1..258
                        mol_type = protein
                        organism = synthetic construct
SEQUENCE: 119
MGSSHHHHHH SSGLVPRGSH MATVKFTYQG EEKQVDISKI KIVARDGQYI DFKYDEGGGA          60
YGYGWVSEKD APKELLQMLE KQGSGGGGSG GGGSGGGGSP VSGNLKVEFY NSNPSDTTNS         120
INPQFKVTNT GSSAIDLSKL TLRYYYTVDG QKDQTFWCDH AAIIGSNGSY NGITSNVKGT         180
FVKMSSSTNN ADTYLEISFT GGTLEPGAHV QIQGRFAKND WSNYTQSNDY SFKSASQFVE         240
WDQVTAYLNG VLVWGKEP                                                       258

SEQ ID NO: 120          moltype = AA  length = 330
FEATURE                 Location/Qualifiers
REGION                  1..330
                        note = Synthetic Polypeptide
source                  1..330
                        mol_type = protein
                        organism = synthetic construct
SEQUENCE: 120
MGSSHHHHHH SSGLVPRGSH MATVKFTYQG EEKQVDISKI KIVARDGQYI DFKYDEGGGA          60
YGYGWVSEKD APKELLQMLE KQGGGGSGGG GSMATVKFTY QGEEKQVDIS KIKIVARDGQ         120
YIDFKYDEGG GAYGYGWVSE KDAPKELLQM LEKQGSGGGG SGGGGSGGGG SPVSGNLKVE         180
FYNSNPSDTT NSINPQFKVT NTGSSAIDLS KLTLRYYYTV DGQKDQTFWC DHAAIIGSNG         240
SYNGITSNVK GTFVKMSSST NNADTYLEIS FTGGTLEPGA HVQIQGRFAK NDWSNYTQSN         300
DYSFKSASQF VEWDQVTAYL NGVLVWGKEP                                          330

SEQ ID NO: 121          moltype = AA  length = 402
FEATURE                 Location/Qualifiers
REGION                  1..402
                        note = Synthetic Polypeptide
source                  1..402
                        mol_type = protein
                        organism = synthetic construct
SEQUENCE: 121
MGSSHHHHHH SSGLVPRGSH MATVKFTYQG EEKQVDISKI KIVARDGQYI DFKYDEGGGA          60
YGYGWVSEKD APKELLQMLE KQGGGGSGGG GSMATVKFTY QGEEKQVDIS KIKIVARDGQ         120
YIDFKYDEGG GAYGYGWVSE KDAPKELLQM LEKQGGGGSG GGGSMATVKF TYQGEEKQVD         180
ISKIKIVARD GQYIDFKYDE GGGAYGYGWV SEKDAPKELL QMLEKQGSGG GGSGGGGSGG         240
GGSPVSGNLK VEFYNSNPSD TTNSINPQFK VTNTGSSAID LSKLTLRYYY TVDGQKDQTF         300
WCDHAAIIGS NGSYNGITSN VKGTFVKMSS STNNADTYLE ISFTGGTLEP GAHVQIQGRF         360
AKNDWSNYTQ SNDYSFKSAS QFVEWDQVTA YLNGVLVWGK EP                            402

SEQ ID NO: 122          moltype = AA  length = 25
FEATURE                 Location/Qualifiers
REGION                  1..25
                        note = Synthetic Polypeptide
source                  1..25
                        mol_type = protein
                        organism = synthetic construct
SEQUENCE: 122
KGVYRHGQSI WFRYDEGGGA WGWGI                                               25

SEQ ID NO: 123          moltype = AA  length = 25
FEATURE                 Location/Qualifiers
REGION                  1..25
                        note = Synthetic Polypeptide
source                  1..25
                        mol_type = protein
                        organism = synthetic construct
SEQUENCE: 123
KYVKRIGQYI SFNYDEGGGA HGHGI                                               25

SEQ ID NO: 124          moltype = AA  length = 367
FEATURE                 Location/Qualifiers
REGION                  1..367
                        note = Synthetic Polypeptide
source                  1..367
                        mol_type = protein
                        organism = synthetic construct
SEQUENCE: 124
MKIEEGKLVI WINGDKGYNG LAEVGKKFEK DTGIKVTVEH PDKLEEKFPQ VAATGDGPDI          60
IFWAHDRFGG YAQSGLLAEI TPDKAFQDKL YPFTWDAVRY NGKLIAYPIA VEALSLIYNK         120
DLLPNPPKTW EEIPALDKEL KAKGKSALMF NLQEPYFTWP LIAADGGYAF KYENGKYDIK         180
DVGVDNSGAK AGLTFLVDLI KNKHMNADTD YSIAEAAFNK GETAMTINGP WAWSNIDTSK         240
```

```
VNYGVTVLPT FKGQPSKPFV GVLSAGINAA SPNKELAKEF LENYLLTDEG LEAVNKDKPL    300
GAVALKSYEE ELAKDPRIAA TMENAQKGEI MPNIPQMSAF WYAVRTAVIN AASGRQTVDE    360
ALKDAQT                                                              367

SEQ ID NO: 125          moltype = AA   length = 15
FEATURE                 Location/Qualifiers
REGION                  1..15
                        note = Synthetic Polypeptide
source                  1..15
                        mol_type = protein
                        organism = synthetic construct
SEQUENCE: 125
GGGGSGGGGS GGGGS                                                     15

SEQ ID NO: 126          moltype = AA   length = 6
FEATURE                 Location/Qualifiers
REGION                  1..6
                        note = Synthetic Polypeptide
source                  1..6
                        mol_type = protein
                        organism = synthetic construct
SEQUENCE: 126
GGGGGG                                                               6

SEQ ID NO: 127          moltype = AA   length = 8
FEATURE                 Location/Qualifiers
REGION                  1..8
                        note = Synthetic Polypeptide
source                  1..8
                        mol_type = protein
                        organism = synthetic construct
SEQUENCE: 127
GGGGGGGG                                                             8

SEQ ID NO: 128          moltype = AA   length = 15
FEATURE                 Location/Qualifiers
REGION                  1..15
                        note = Synthetic Polypeptide
source                  1..15
                        mol_type = protein
                        organism = synthetic construct
SEQUENCE: 128
EAAAKEAAAK EAAAK                                                     15

SEQ ID NO: 129          moltype = AA   length = 46
FEATURE                 Location/Qualifiers
REGION                  1..46
                        note = Synthetic Polypeptide
source                  1..46
                        mol_type = protein
                        organism = synthetic construct
SEQUENCE: 129
AEAAAKEAAA KEAAAKEAAA KALEAEAAAK EAAAKEAAAK EAAAKA                   46

SEQ ID NO: 130          moltype = AA   length = 5
FEATURE                 Location/Qualifiers
REGION                  1..5
                        note = Synthetic Polypeptide
source                  1..5
                        mol_type = protein
                        organism = synthetic construct
SEQUENCE: 130
PAPAP                                                                5

SEQ ID NO: 131          moltype = AA   length = 17
FEATURE                 Location/Qualifiers
REGION                  1..17
                        note = Synthetic Polypeptide
source                  1..17
                        mol_type = protein
                        organism = synthetic construct
SEQUENCE: 131
VSQTSKLTRA ETVFPDV                                                   17

SEQ ID NO: 132          moltype = AA   length = 6
FEATURE                 Location/Qualifiers
REGION                  1..6
                        note = Synthetic Polypeptide
source                  1..6
```

-continued

```
                        mol_type = protein
                        organism = synthetic construct
SEQUENCE: 132
RVLAEA                                                             6

SEQ ID NO: 133          moltype = AA  length = 10
FEATURE                 Location/Qualifiers
REGION                  1..10
                        note = Synthetic Polypeptide
source                  1..10
                        mol_type = protein
                        organism = synthetic construct
SEQUENCE: 133
EDVVCCSMSY                                                         10

SEQ ID NO: 134          moltype = AA  length = 8
FEATURE                 Location/Qualifiers
REGION                  1..8
                        note = Synthetic Polypeptide
source                  1..8
                        mol_type = protein
                        organism = synthetic construct
SEQUENCE: 134
GGIEGRGS                                                           8

SEQ ID NO: 135          moltype = AA  length = 4
FEATURE                 Location/Qualifiers
REGION                  1..4
                        note = Synthetic Polypeptide
source                  1..4
                        mol_type = protein
                        organism = synthetic construct
SEQUENCE: 135
GFLG                                                               4
```

What is claimed is:

1. A bifunctional fusion protein comprising a cellulose binding domain (CBD) and an engineered reduced-charge Sso7d (rcSso7d) antigen-binding protein, wherein the rcSso7d antigen-binding protein comprises an amino acid sequence that is at least 85% identical to SEQ ID NO: 3 and has a reduced charge relative to SEQ ID NO: 12, and wherein the CBD comprises an amino acid sequence that is at least 85% identical to SEQ ID NO: 2, SEQ ID NO: 16, or SEQ ID NO: 10.

2. The bifunctional fusion protein of claim 1, wherein the C-terminus of the engineered rcSso7d antigen-binding protein is linked to the N-terminus of the CBD.

3. The bifunctional fusion protein of claim 1, wherein the engineered rcSso7d antigen-binding protein is linked to the CBD through a linker.

4. The bifunctional fusion protein of claim 3, wherein the linker is a Gly-Ser linker.

5. The bifunctional fusion protein of claim 1, wherein the engineered rcSso7d antigen-binding protein comprises a streptavidin-binding domain.

6. The bifunctional fusion protein of claim 1, wherein the rcSso7d antigen-binding protein comprises a tuberculosis antigen-binding domain, a Flavivirus non-structural 1 (NS1) binding domain, an interleukin-6 (IL-6) binding domain, or a fluorophore binding domain.

7. The bifunctional fusion protein of claim 6, wherein the tuberculosis antigen-binding domain comprises a Rv1656-binding domain, a Rv1681-binding domain, a Rv2392-binding domain, a Rv1729c-binding domain, or a TBCG_03312-binding domain.

8. The bifunctional fusion protein of claim 1, wherein the CBD is a type 3a CBD, or the type 1 dimerized CBD (dCBD).

9. The bifunctional fusion protein of claim 8, wherein the type 3a CBD is a domain of the protein CipA from *Clostridium thermocellum*.

10. The bifunctional fusion protein of claim 1, wherein the bifunctional fusion protein comprises at least 2, 3, 4, 5, 6, 7, 8, 9 or 10 rcSso7d antigen-binding proteins.

11. The bifunctional fusion protein of claim 10, wherein the at least 2, 3, 4, 5, 6, 7, 8, 9 or 10 rcSso7d antigen-binding proteins are genetically fused together.

12. A kit for assessing a presence or amount of an antigen, the kit comprising a container containing the bifunctional fusion protein of claim 1.

13. The kit of claim 12, further comprising a cellulose-containing substrate.

14. The kit of claim 13, wherein the bifunctional fusion protein is bound to the cellulose-containing substrate.

15. The kit of claim 13, wherein the bifunctional fusion protein is not bound to the cellulose-containing substrate.

16. The kit of claim 13, wherein the cellulose-containing substrate is paper or nitrocellulose.

17. The kit of claim 13, wherein the cellulose-containing substrate is chromatography paper.

18. The kit of claim 17, wherein the chromatography paper is unmodified.

* * * * *